United States Patent
Angell et al.

(10) Patent No.: US 12,415,798 B2
(45) Date of Patent: Sep. 16, 2025

(54) PROCESSES FOR MAKING MODULATORS OF CYSTIC FIBROSIS TRANSMEMBRANE CONDUCTANCE REGULATOR

(71) Applicant: Vertex Pharmaceuticals Incorporated, Boston, MA (US)

(72) Inventors: Paul T. Angell, Carlsbad, CA (US); Cristian Harrison, Beverly, MA (US); Robert M. Hughes, San Diego, CA (US); Berenice Lewandowski, Braintree, MA (US); Benjamin J. Littler, Carlsbad, CA (US); Vito Melillo, Escondido, CA (US); William A. Nugent, Noblesville, IN (US); David Andrew Siesel, San Diego, CA (US); David Smith, Newton, MA (US); John Studley, Witney (GB)

(73) Assignee: Vertex Pharmaceuticals Incorporated, Boston, MA (US)

( * ) Notice: Subject to any disclaimer, the term of this patent is extended or adjusted under 35 U.S.C. 154(b) by 436 days.

(21) Appl. No.: 17/899,672

(22) Filed: Aug. 31, 2022

(65) Prior Publication Data
US 2024/0025877 A1      Jan. 25, 2024

Related U.S. Application Data

(62) Division of application No. 16/769,047, filed as application No. PCT/US2018/064522 on Dec. 7, 2018, now Pat. No. 11,465,985.

(60) Provisional application No. 62/649,970, filed on Mar. 29, 2018, provisional application No. 62/623,725, filed on Jan. 30, 2018, provisional application No. 62/596,452, filed on Dec. 8, 2017.

(51) Int. Cl.
C07D 401/14      (2006.01)

(52) U.S. Cl.
CPC ................. C07D 401/14 (2013.01)

(58) Field of Classification Search
CPC ................................... C07D 401/14
See application file for complete search history.

(56) References Cited

U.S. PATENT DOCUMENTS

| | | | |
|---|---|---|---|
| 5,410,061 A | 4/1995 | Gilmore et al. |
| 6,441,004 B1 | 8/2002 | Faull et al. |
| 6,787,651 B2 | 9/2004 | Stolle et al. |
| 6,949,572 B2 | 9/2005 | Bertinato et al. |
| 6,979,692 B2 | 12/2005 | Bertinato et al. |
| 7,368,573 B2 | 5/2008 | Bertinato et al. |
| 8,058,299 B2 | 11/2011 | Bolin et al. |
| 9,663,508 B2 | 5/2017 | Bregman et al. |
| 9,782,408 B2 | 10/2017 | Miller et al. |
| 9,981,910 B2 | 5/2018 | Altenbach et al. |
| 10,118,916 B2 | 11/2018 | Altenbach et al. |
| 10,131,670 B2 | 11/2018 | Strohbach et al. |
| 10,138,227 B2 | 11/2018 | Altenbach et al. |
| 10,208,053 B2 | 2/2019 | Strohbach et al. |
| 10,258,624 B2 | 4/2019 | Miller et al. |
| 10,570,115 B2 | 2/2020 | Alcacio et al. |
| 10,654,829 B2 | 5/2020 | Dhamankar et al. |
| 10,758,534 B2 | 9/2020 | Miller et al. |
| 10,793,547 B2 | 10/2020 | Abela et al. |
| 11,155,533 B2 | 10/2021 | Dhamankar et al. |
| 11,179,367 B2 | 11/2021 | Chu et al. |
| 11,186,566 B2 | 11/2021 | Alcacio et al. |
| 11,253,509 B2 | 2/2022 | Chen et al. |
| 11,414,439 B2 | 8/2022 | Abela et al. |
| 11,426,407 B2 | 8/2022 | Miller et al. |
| 11,434,201 B2 | 9/2022 | Angell et al. |
| 11,453,655 B2 | 9/2022 | Abela et al. |
| 11,465,985 B2 | 10/2022 | Angell et al. |
| 11,517,564 B2 | 12/2022 | Chen et al. |
| 2002/0055631 A1 | 5/2002 | Augeri et al. |
| 2002/0086887 A1 | 7/2002 | Augeri et al. |
| 2004/0006237 A1 | 1/2004 | Dolitzky et al. |
| 2005/0171185 A1 | 8/2005 | Yamasaki et al. |
| 2005/0197376 A1 | 9/2005 | Kayakiri et al. |

(Continued)

FOREIGN PATENT DOCUMENTS

| | | |
|---|---|---|
| AU | 2013231151 A1 | 10/2013 |
| AU | 2013270464 A1 | 1/2014 |

(Continued)

OTHER PUBLICATIONS

Anilkumar, G.N. et al. (2011) "II. Novel HCV NS5B polymerase inhibitors: Discovery of indole C2 acyl sulfonamides" *Biogranic & Medicinal Chemistry Letters*, 22(1):713-717.

(Continued)

*Primary Examiner* — Joseph K McKane
*Assistant Examiner* — Quincy McKoy
(74) *Attorney, Agent, or Firm* — Finnegan, Henderson, Farabow, Garrett & Dunner, LLP

(57) ABSTRACT

The disclosure provides processes for preparing a compound of Formula (I):

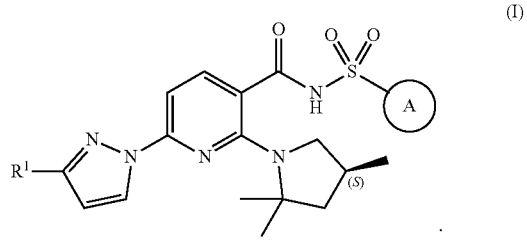

5 Claims, 7 Drawing Sheets
Specification includes a Sequence Listing.

(56) References Cited

U.S. PATENT DOCUMENTS

| | | |
|---|---|---|
| 2007/0105833 A1 | 5/2007 | Ruah et al. |
| 2010/0160322 A1 | 6/2010 | Bruncko et al. |
| 2010/0227888 A1 | 9/2010 | Hadida Ruah et al. |
| 2011/0165118 A1 | 7/2011 | Chan et al. |
| 2013/0072483 A1 | 3/2013 | Wenge et al. |
| 2013/0267493 A1 | 10/2013 | Bhattacharya et al. |
| 2013/0317000 A1 | 11/2013 | Chowdhury et al. |
| 2013/0317001 A1 | 11/2013 | Andrez et al. |
| 2014/0080825 A1 | 3/2014 | Hadida-Ruah et al. |
| 2014/0296200 A1 | 10/2014 | Brown et al. |
| 2015/0320736 A1 | 11/2015 | Phenix et al. |
| 2015/0322002 A1 | 11/2015 | Dehnhardt et al. |
| 2016/0098585 A1 | 4/2016 | Sempere et al. |
| 2018/0099932 A1 | 4/2018 | Altenbach et al. |
| 2018/0141954 A1 | 5/2018 | Strohbach et al. |
| 2018/0170938 A1 | 6/2018 | Strohbach et al. |
| 2018/0244611 A1 | 8/2018 | Altenbach et al. |
| 2018/0244640 A1 | 8/2018 | Altenbach et al. |
| 2019/0055220 A1 | 2/2019 | Bear et al. |
| 2019/0077784 A1 | 3/2019 | Altenbach et al. |
| 2019/0153000 A1 | 5/2019 | Munoz et al. |
| 2019/0240197 A1 | 8/2019 | Chu et al. |
| 2019/0269683 A1 | 9/2019 | Miller et al. |
| 2020/0171015 A1 | 6/2020 | Haseltine et al. |
| 2021/0032272 A1 | 2/2021 | Abela et al. |
| 2021/0069174 A1 | 3/2021 | Chu et al. |
| 2021/0113547 A1 | 4/2021 | Chen et al. |
| 2021/0139514 A1 | 5/2021 | Abela et al. |
| 2021/0228489 A1 | 7/2021 | Dokou et al. |
| 2022/0257564 A1 | 8/2022 | Chu et al. |
| 2022/0306606 A1 | 9/2022 | Alcacio et al. |
| 2023/0233560 A1 | 7/2023 | Miller et al. |
| 2023/0241045 A1 | 8/2023 | Chen et al. |

FOREIGN PATENT DOCUMENTS

| | | |
|---|---|---|
| CA | 2145473 A1 | 9/1995 |
| CN | 101087781 A | 12/2007 |
| CN | 102458122 A | 5/2012 |
| CN | 103946221 A | 7/2014 |
| EA | 011074 B1 | 12/2008 |
| EA | 28378 B1 | 11/2017 |
| EP | 0 194 599 A2 | 9/1986 |
| EP | 0 673 930 A1 | 9/1995 |
| EP | 1 318 978 B1 | 2/2006 |
| GB | 967177 A | 8/1964 |
| IN | 201917015614 | 7/2019 |
| IN | 201917024177 | 8/2019 |
| JP | 10-114654 A | 5/1998 |
| JP | 2007-511530 A | 5/2007 |
| JP | 2008-524233 A | 7/2008 |
| JP | 2011-520785 A | 7/2011 |
| KR | 10-2005-0061501 A | 6/2005 |
| RU | 2463303 C2 | 10/2012 |
| RU | 2608610 C2 | 1/2017 |
| TW | 201713617 A | 4/2017 |
| WO | WO 96/03380 A1 | 2/1996 |
| WO | WO 96/22022 A1 | 7/1996 |
| WO | WO 97/18712 A1 | 5/1997 |
| WO | WO 97/22586 A1 | 6/1997 |
| WO | WO 98/08818 A1 | 3/1998 |
| WO | WO 98/31226 A1 | 7/1998 |
| WO | WO 99/07351 A2 | 2/1999 |
| WO | WO 99/16744 A1 | 4/1999 |
| WO | WO 99/37153 A1 | 7/1999 |
| WO | WO 99/41238 A1 | 8/1999 |
| WO | WO 00/76969 A1 | 12/2000 |
| WO | WO 01/08487 A1 | 2/2001 |
| WO | WO 01/15533 A1 | 3/2001 |
| WO | WO 01/39597 A2 | 6/2001 |
| WO | WO 02/15902 A1 | 2/2002 |
| WO | WO 02/24636 A2 | 3/2002 |
| WO | WO 02/30895 A1 | 4/2002 |
| WO | WO 02/085120 A2 | 10/2002 |
| WO | WO 02/096883 A1 | 12/2002 |
| WO | WO 03/002533 A1 | 1/2003 |
| WO | WO 03/022050 A1 | 3/2003 |
| WO | WO 03/028458 A1 | 4/2003 |
| WO | WO 03/043423 A1 | 5/2003 |
| WO | WO 03/043655 A1 | 5/2003 |
| WO | WO 03/101959 A1 | 12/2003 |
| WO | WO 03/103394 A2 | 12/2003 |
| WO | WO 2004/021788 A1 | 3/2004 |
| WO | WO 2004/021987 A2 | 3/2004 |
| WO | WO 2004/037798 A1 | 5/2004 |
| WO | WO 2004/039753 A2 | 5/2004 |
| WO | WO 2004/043939 A1 | 5/2004 |
| WO | WO 2004/046141 A1 | 6/2004 |
| WO | WO 2004/056775 A1 | 7/2004 |
| WO | WO 2004/056777 A1 | 7/2004 |
| WO | WO 2004/078114 A2 | 9/2004 |
| WO | WO 2004/085420 A2 | 10/2004 |
| WO | WO 2004/111014 A1 | 12/2004 |
| WO | WO 2005/049018 A1 | 6/2005 |
| WO | WO 2005/054191 A1 | 6/2005 |
| WO | WO 2005/070006 A2 | 8/2005 |
| WO | WO 2005/075435 A1 | 8/2005 |
| WO | WO 2005/080373 A1 | 9/2005 |
| WO | WO 2005/085216 A1 | 9/2005 |
| WO | WO 2005/099705 A2 | 10/2005 |
| WO | WO 2005/108369 A1 | 11/2005 |
| WO | WO 2006/002421 A2 | 1/2006 |
| WO | WO 2006/030807 A1 | 3/2006 |
| WO | WO 2006/039212 A2 | 4/2006 |
| WO | WO 2006/065204 A1 | 6/2006 |
| WO | WO 2006/066968 A1 | 6/2006 |
| WO | WO 2006/067392 A2 | 6/2006 |
| WO | WO 2007/019397 A2 | 2/2007 |
| WO | WO 2007/021982 A2 | 2/2007 |
| WO | WO 2007/053641 A2 | 5/2007 |
| WO | WO 2007/075946 A1 | 7/2007 |
| WO | WO 2007/079139 A2 | 7/2007 |
| WO | WO 2007/087066 A2 | 8/2007 |
| WO | WO 2007/113327 A2 | 10/2007 |
| WO | WO 2007/117715 A2 | 10/2007 |
| WO | WO 2007/134279 A2 | 11/2007 |
| WO | WO 2008/005457 A2 | 1/2008 |
| WO | WO 2008/100867 A2 | 8/2008 |
| WO | WO 2008/127399 A2 | 10/2008 |
| WO | WO 2008/141385 A1 | 11/2008 |
| WO | WO 2009/006315 A1 | 1/2009 |
| WO | WO 2009/027730 A1 | 3/2009 |
| WO | WO 2009/032116 A1 | 3/2009 |
| WO | WO 2009/038683 A2 | 3/2009 |
| WO | WO 2009/064848 A1 | 5/2009 |
| WO | WO 2009/071947 A2 | 6/2009 |
| WO | WO 2009/073757 A1 | 6/2009 |
| WO | WO 2009/076142 A2 | 6/2009 |
| WO | WO 2009/127822 A2 | 10/2009 |
| WO | WO 2009/138758 A2 | 11/2009 |
| WO | WO 2010/003444 A2 | 1/2010 |
| WO | WO 2010/007116 A2 | 1/2010 |
| WO | WO 2010/019239 A2 | 2/2010 |
| WO | WO 2010/022307 A2 | 2/2010 |
| WO | WO 2010/025295 A2 | 3/2010 |
| WO | WO 2010/048526 A2 | 4/2010 |
| WO | WO 2010/053471 A1 | 5/2010 |
| WO | WO 2010/054138 A2 | 5/2010 |
| WO | WO 2010/065824 A2 | 6/2010 |
| WO | WO 2010/078103 A1 | 7/2010 |
| WO | WO 2010/083441 A2 | 7/2010 |
| WO | WO 2010/102758 A1 | 9/2010 |
| WO | WO 2010/108155 A1 | 9/2010 |
| WO | WO 2010/108162 A1 | 9/2010 |
| WO | WO 2010/110231 A1 | 9/2010 |
| WO | WO 2010/123822 A1 | 10/2010 |
| WO | WO 2010/138588 A2 | 12/2010 |
| WO | WO 2011/019413 A2 | 2/2011 |
| WO | WO 2011/068560 A1 | 6/2011 |
| WO | WO 2011/072241 A1 | 6/2011 |
| WO | WO 2011/102514 A1 | 8/2011 |
| WO | WO 2011/113894 A1 | 9/2011 |
| WO | WO 2011/116397 A1 | 9/2011 |
| WO | WO 2011/119984 A1 | 9/2011 |

(56) References Cited

FOREIGN PATENT DOCUMENTS

| | | | |
|---|---|---|---|
| WO | WO 2011/127241 A2 | 10/2011 | |
| WO | WO 2011/127290 A2 | 10/2011 | |
| WO | WO 2011/128251 A1 | 10/2011 | |
| WO | WO 2011/133751 A2 | 10/2011 | |
| WO | WO 2011/133951 A1 | 10/2011 | |
| WO | WO 2011/150016 A1 | 12/2011 | |
| WO | WO 2012/027247 A2 | 3/2012 | |
| WO | WO 2012/027731 A2 | 3/2012 | |
| WO | WO 2012/052540 A1 | 4/2012 | |
| WO | WO 2012/087938 A1 | 6/2012 | |
| WO | WO 2012/089721 A1 | 7/2012 | |
| WO | WO 2012/089722 A2 | 7/2012 | |
| WO | WO 2012/102297 A1 | 8/2012 | |
| WO | WO 2012/110519 A1 | 8/2012 | |
| WO | WO 2012/116960 A1 | 9/2012 | |
| WO | WO 2012/139891 A1 | 10/2012 | |
| WO | WO 2012/166415 A1 | 12/2012 | |
| WO | WO 2012/170061 A1 | 12/2012 | |
| WO | WO 2013/033068 A1 | 3/2013 | |
| WO | WO 2013/037955 A1 | 3/2013 | |
| WO | WO 2013/038373 A1 | 3/2013 | |
| WO | WO 2013/041602 A1 | 3/2013 | |
| WO | WO 2013/070961 A1 | 5/2013 | |
| WO | WO 2013/082102 A1 | 6/2013 | |
| WO | WO 2013/112804 A1 | 8/2013 | |
| WO | WO 2013/118805 A1 | 8/2013 | |
| WO | WO 2013/130669 A1 | 9/2013 | |
| WO | WO 2013/158121 A1 | 10/2013 | |
| WO | WO 2013/177224 A1 | 11/2013 | |
| WO | WO 2013/185112 A1 | 12/2013 | |
| WO | WO 2013/185202 A1 | 12/2013 | |
| WO | WO 2014/008458 A2 | 1/2014 | |
| WO | WO 2014/014841 A1 | 1/2014 | |
| WO | WO 2014/017093 A1 | 1/2014 | |
| WO | WO 2014/028381 A1 | 2/2014 | |
| WO | WO 2014/028968 A2 | 2/2014 | |
| WO | WO 2014/039714 A2 | 3/2014 | |
| WO | WO 2014/047427 A2 | 3/2014 | |
| WO | WO 2014/071122 A1 | 5/2014 | |
| WO | WO 2014/071247 A1 | 5/2014 | |
| WO | WO 2014/071378 A1 | 5/2014 | |
| WO | WO 2014/086723 A1 | 6/2014 | |
| WO | WO 2014/086739 A1 | 6/2014 | |
| WO | WO 2014/086751 A1 | 6/2014 | |
| WO | WO 2014/096388 A2 | 6/2014 | |
| WO | WO 2014/109858 A1 | 7/2014 | |
| WO | WO 2014/144100 A2 | 9/2014 | |
| WO | WO 2014/152013 A1 | 9/2014 | |
| WO | WO 2014/152018 A1 | 9/2014 | |
| WO | WO 2014/180562 A1 | 11/2014 | |
| WO | WO 2014/181287 A1 | 11/2014 | |
| WO | WO 2014/190199 A1 | 11/2014 | |
| WO | WO 2015/010832 A1 | 1/2015 | |
| WO | WO 2015/031608 A1 | 3/2015 | |
| WO | WO-2015052264 A1 * | 4/2015 | ......... A61K 31/4025 |
| WO | WO 2015/069287 A1 | 5/2015 | |
| WO | WO 2015/073231 A1 | 7/2015 | |
| WO | WO 2015/160787 A1 | 10/2015 | |
| WO | WO 2016/057730 A1 | 2/2016 | |
| WO | WO 2016/057572 A1 | 4/2016 | |
| WO | WO 2016/081556 A1 | 5/2016 | |
| WO | WO 2016/105484 A1 | 6/2016 | |
| WO | WO 2016/105485 A2 | 6/2016 | |
| WO | WO 2016/128529 A1 | 8/2016 | |
| WO | WO 2016/160945 A1 | 10/2016 | |
| WO | WO 2017/053455 A1 | 3/2017 | |
| WO | WO 2017/172802 A1 | 10/2017 | |
| WO | WO 2017/173274 A1 | 10/2017 | |
| WO | WO 2017/177124 A1 | 10/2017 | |
| WO | WO 2017/187321 A1 | 11/2017 | |
| WO | WO 2017/223188 A1 | 12/2017 | |
| WO | WO 2018/064632 A1 | 4/2018 | |
| WO | WO 2018/081377 A1 | 5/2018 | |
| WO | WO 2018/081378 A1 | 5/2018 | |
| WO | WO 2018/081381 A1 | 5/2018 | |
| WO | WO 2018/107100 A1 | 6/2018 | |
| WO | WO 2018/116185 A1 | 6/2018 | |
| WO | WO 2018/127130 A1 | 7/2018 | |
| WO | WO 2018/183367 A1 | 10/2018 | |
| WO | WO 2018/201126 A1 | 11/2018 | |
| WO | WO 2018/227049 A1 | 12/2018 | |
| WO | WO 2019/010092 A1 | 1/2019 | |
| WO | WO 2019/018353 A1 | 1/2019 | |
| WO | WO 2019/018395 A1 | 1/2019 | |
| WO | WO 2019/028228 A1 | 2/2019 | |
| WO | WO 2019/071078 A1 | 4/2019 | |
| WO | WO 2019/079760 A1 | 4/2019 | |
| WO | WO 2019/113089 A1 | 6/2019 | |
| WO | WO 2019/113476 A1 | 6/2019 | |
| WO | WO 2019/152940 A1 | 8/2019 | |
| WO | WO 2019/026075 A1 | 10/2019 | |
| WO | WO 2019/191620 A1 | 10/2019 | |
| WO | WO 2019/195739 A1 | 10/2019 | |
| WO | WO 2019/200246 A1 | 10/2019 | |
| WO | WO 2020/214921 A1 | 10/2020 | |
| WO | WO 2020/242935 A1 | 12/2020 | |
| WO | WO 2021/030552 A1 | 2/2021 | |
| WO | WO 2021/030554 A1 | 2/2021 | |
| WO | WO 2021/030555 A1 | 2/2021 | |
| WO | WO 2021/030556 A1 | 2/2021 | |

OTHER PUBLICATIONS

Atzrodt J, Derdau V, Fey T, Zimmermann J. "The Renaissance of H/D Exchange" Angew. Chem. Int. Ed. 2007: 46, 7744-7765.

Atzrodt J, Derdau V, Kerr W, Reid M. "C—H functionalization for hydrogen isotope exchange" Angew. Chem. Int. Ed. 2018: 57, 3022-3047.

Belikov, V.G., (2007) *Farmatsevticheskaya khimiya (Pharmaceutical Chemistry)*, Moscow: MEDpress-inform, pp. 27-29.

Bhattacharya, S. et al. (2009) Polymorphism in Pharmaceutical Solids: Thermoanalytical and Crystallographic Methods (Brittain H. ed., 2d ed. Informa Healthcare USA, Inc. 2009) 318-335.

Borhade, S.R. et al. (2013) "Synthesis of Novel Aryl and Heteroaryl Acyl Sulfonimidamides via Pd-Catalyzed Carbonylation Using a Nongaseous Precursor" *Organic Lett*, 15(5):1056-1059.

Boyle, M. "A CFTR corrector (lumacaftor) and a CFTR potentiator (ivacaftor) for treatment of patients with cystic fibrosis who have a phe508del CFTR mutation: a phase 2 randomised controlled trial," The Lancet Respiratory Medicine (Jul. 1, 2014) Retrieved from the Internet: https://www-clinicalkeycom-ez03.infotrieve.com/#!/content/playContent/1-s2.0S2213260014701328?returnurl=null&referrer=null.

Braman, V.; Liu, J. F.; Harbeson, S.; Uttamsingh, V.; Bridson, G.; Wu, L.; Shipley, J. E. "Preliminary Clinical Outcomes for CTP-354, a Novel Subtype-Selective GABA(A) Modulator" Presented at the American Neurological Association (ANA) 2014 Annual Meeting, Baltimore, MD, Oct. 12-14, 2014.

Brown et al. (2006) "On scaffolds and hopping in medicinal Chemistry," Mini-reviews in medicinal chemistry, vol. 6, 11(13), 1217-1229.

Byrn, S. et al. (1995) "Pharmaceutical solids: A strategic approach to regulatory considerations," (12): 945-954.

Caira, M. R. (1998) "Crystalline Polymorphism of Organic Compounds," *Topics in Current Chemistry*, 163-208.

Cargnin S, Serafini M, Pirali T. "A primer of deuterium in drug design" Future Med. Chem. 2019; 11(16): 2039-2042.

Chemical Abstracts Service, CAS Registry No. 204017-11-8. CA Index Name: 1H-Indole-2-carboxamide, 1-[[2,4-bis(trifluoromethyl)phenyl]methyl]-2,3-dihydro-N-(phenylsulfonyl)-. Entered STN: Apr. 12, 1998.

Chemical Abstracts Service, CAS Registry No. 220678-97-7. CA Index Name: 1H-Indole-2-carboxamide, 1-[(3,4-dichlorophenyl)methyl]-N-(phenylsulfonyl)-. Entered STN: Mar. 24, 1999.

Chemical Abstracts Service, CAS Registry No. 220678-99-9. CA Index Name: 1H-Indole-2-carboxamide, 1-[(3,4-dichlorophenyl)methyl]-N-[(3,5-dimethyl-4-isoxazolyl)sulfonyl]-. Entered STN: Mar. 24, 1999.

(56) References Cited

OTHER PUBLICATIONS

Chemical Abstracts Service, CAS Registry No. 412005-98-2. CA Index Name: 1H-Indole-2-carboxamide, 3-(4-methoxyphenyl)-N-(phenylsulfonyl)-1-[[3-(trifluoromethyl)phenyl]methyl]-. Entered STN: May 7, 2002.
Chemical Abstracts Service, CAS Registry No. 895575-67-4. CA Index Name: 1H-Indole-2-carboxamide, 1-[(3-chlorophenyl)methyl]-4-nitro-N-(2-thienylsulfonyl)-. Jun. 30, 2006.
Chemical Abstracts Service, CAS Registry No. 895575-68-5. CA Index Name: 1H-Indole-2-carboxamide, 4-amino-1-[(3-chlorophenyl)methyl]-N-(2-thienylsulfonyl)-. Jul. 23, 2006.
Chen, Y. (Jan. 2, 20166) "*N*-Monoacylation of Sulfonimidamides" *Synthesis*, 48(7):1019-1028.
Czeskis B, Elmore, CS, Haight A, Hesk D, Maxwell BD, Miller SA, Raglione T, Schildknegt K, Traverse JF, Wang P. "Deuterated active pharmaceutical ingredients: A science-based proposal for synthesis, analysis, and control. Part 1: Framing the problem" J. Label. Compd. Radiopharm. 2019, 62: 690-694. DOI: 10.1002/jlcr.3743.
Dao HT, Li C, Michaudel Q, Maxwell BD, Baran PS. J. Am. Chem. Soc. 2015; 137, 8046-8049.
Database Caplus, Accession No. 1965:51408. Abstract of French Patent No. FR M2868, filed Nov. 23, 1964, by Roussel-Uclaf [online]. Retrieved Jan. 6, 2017 (1 page).
Database Caplus, Accession No. 1965:51409. Abstract of German Patent No. DE 1182243, filed Nov. 26, 1964, by Badische Anilin & Soda-Fabrik A.G. [online]. Retrieved Jan. 6, 2017 (2 pages).
Database ChemSpider, CSID:17283620 (CAS: RN 1026625-71-7), http://www.chemspider.com/Chemical-Structure.17283620.html (accessed 16:40, Mar. 30, 2023).
Database Pubchem, CID: 44419393. Compound Summary, *CHEMBL374189*. NIH, U.S. National Library of Medicine, National Center for Biotechnology Information; Modify Date: Jan. 16, 2016. [online]. Retrieved from https://pubchem.ncbi.nlm.nih.gov/compound/44419393, on Jan. 22, 2016 (11 pages).
Database Pubchem, CID: 49774135. Compound Summary, *SCHEMBL13395127*. NIH, U.S. National Library of Medicine, National Center for Biotechnology Information; Modify Date: Jan. 16, 2016 [online]. Retrieved from https://pubchem.ncbi.nlm.nih.gov/compound/49774135, on Jan. 22, 2016 (10 pages).
Database Pubchem, CID: 58132855. Compound Summary, *SCHEMBL831192*. NIH, U.S. National Library of Medicine, National Center for Biotechnology Information, PubChem Open Chemistry Database; Modify Date: Jan. 16, 2016 [online]. Retrieved from: https://pubchem.ncbi.nlm.nih.gov/compound/58132855, on Jan. 22, 2016 (10 pages).
Database Pubchem, CID: 20050716. Compound Summary, 1-[2-[[2-[(2-*Amino*-3-*methylbutanoyl*)*amino*]-3-*methylpentanoyl*]*amino*]-3-*phenylpropanoyl*]*pyrrolidine*-2-*carboxylic acid*. NIH, U.S. National Library of Medicine, National Center for Biotechnology Information; Modify Date: Nov. 30, 2019. [online]. Retrieved from https://pubchem.ncbi.nlm.nih.gov/compound/20050716, on Dec. 3, 2019 (7 pages).
Database Pubchem, CID: 20091118. Compound Summary, [4-(5-*Hexylpyrimidin*-2-*yl*)*phenyl*] 2-*methoxypropanoate*. NIH, U.S. National Library of Medicine, National Center for Biotechnology Information; Modify Date: Nov. 30, 2019. [online]. Retrieved from https://pubchem.ncbi.nlm.nih.gov/compound/20091118, on Dec. 3, 2019 (9 pages).
Database Pubchem, CID: 20120819. Compound Summary, 4-(*Cyclopentyloxy*)-3-*fluorobenzene*-1-*sulfonyl chloride*. NIH, U.S. National Library of Medicine, National Center for Biotechnology Information; Modify Date: Nov. 30, 2019. [online]. Retrieved from https://pubchem.ncbi.nlm.nih.gov/compound/20120819, on Dec. 3, 2019 (8 pages).
Database Pubchem, CID: 2545578. Compound Summary, *T5339296*. NIH, U.S. National Library of Medicine, National Center for Biotechnology Information; Modify Date: Jan. 16, 2016. [online]. Retrieved from https://pubchem.ncbi.nlm.nih.gov/compound/2545578, on Jan. 22, 2016 (9 pages).
Dorwald, F. A. (2006) "Side Reactions in Organic Synthesis" Wiley: VCH, Weinheim p. IX of Preface p. 1-15.
European Patent Application No. 15849396.5 (Patent No. 3203840): Notice of Opposition by Elkington and Fife, LLP, May 5, 2021 (19 pages).
Gant TG. "Using Deuterium in Drug Discovery: Leaving the Label in the Drug" J Med. Chem. 2014; 57(9): 3595-3611.
Garg, V. et al. "Pharmacokinetic and Drug-Drug Interaction Profiles of the Combination of Tezacaftor/Ivacaftor", Clinical and Translational Science—CTS, vol. 12, No. 3, Jan. 29, 2019 (Jan. 29, 2019), pp. 267-275, XP055719490, US ISSN: 1752-8054, DOI: 10.1111/cts.12610.
Ghose et al. (1999) Knowledge-based approach in designing combinatorial or medicinal chemistry libraries for drug discovery—qualitive and quantitative characterization of known drug databases, *J. Comb. Chem.* 1(1), 55-68.
Halford B. "The deuterium switcheroo" Chemical & Engineering News 2016; 94(27), 32-36.
Hopkins, C.R. et al. (2006) "Design and synthesis of novel N-sulfonyl-2-indole carboxamides as potent PPAR-gamma binding agents with potential application to the treatment of osteoporosis" Bioorganic & Medicinal Chemistry Letters, 16(21):5659-5663.
International Patent Application No. PCT/US2018/064522: International Search Report and Written Opinion, mailed Jun. 25, 2019 (21 pages).
International Patent Application No. PCT/US2015/54316: International Search Report and Written Opinion, mailed Feb. 5, 2016 (11 pages).
International Patent Application No. PCT/US2017/025381: International Search Report and Written Opinion, mailed Jun. 6, 2017 (11 pages).
International Patent Application No. PCT/US2017/054611: International Search Report and Written Opinion, mailed Jan. 3, 2018 (10 pages).
International Patent Application No. PCT/US2017/065425: International Search Report and Written Opinion, mailed Feb. 27, 2018 (10 pages).
International Patent Application No. PCT/US2018/036610: International Search Report and Written Opinion, mailed Sep. 19, 2018 (9 pages).
International Patent Application No. PCT/US2018/040427: International Search Report and Written Opinion, mailed Oct. 9, 2018 (15 pages).
International Patent Application No. PCT/US2018/042415: International Search Report and Written Opinion, mailed Oct. 31, 2018 (12 pages).
International Patent Application No. PCT/US2018/042486: International Search Report and Written Opinion, mailed Nov. 7, 2018 (13 pages).
International Patent Application No. PCT/US2018/044963: International Search Report and Written Opinion, mailed Sep. 25, 2018 (15 pages).
International Patent Application No. PCT/US2018/056772: International Search Report and Written Opinion, mailed Jan. 29, 2019 (13 pages).
International Patent Application No. PCT/US2018/063871: International Search Report and Written Opinion, mailed Feb. 25, 2019 (16 pages).
International Patent Application No. PCT/US2019/016537: International Search Report and Written Opinion, mailed Apr. 23, 2019 (13 pages).
International Patent Application No. PCT/US2019/018042: International Search Report and Written Opinion, mailed Apr. 17, 2019 (10 pages).
International Patent Application No. PCT/US2019/024890: International Search Report and Written Opinion, mailed Jun. 17, 2019 (13 pages).
International Patent Application No. PCT/US2019/026075: International Search Report and Written Opinion, mailed Jun. 17, 2019 (13 pages).
International Patent Application No. PCT/US2019/027202: International Search Report and Written Opinion, mailed Jun. 17, 2019 (10 pages).

(56) References Cited

OTHER PUBLICATIONS

International Patent Application No. PCT/US2020/028699: International Search Report and Written Opinion, mailed Jul. 20, 2020 (9 pages).
International Patent Application No. PCT/US2020/034199: International Search Report and Written Opinion, mailed Aug. 11, 2020 (15 pages).
Ivanisevic, I. (2011) "Uses of X-Ray Powder Diffraction in the Pharmaceutical Industry," Pharm. Form. Qual. 30-33.
Jain, B.C. et al. (1947) "Studies in Sulphanilamides. Part XIII. Reaction With Dicarboxylic Acids. Some New N1- and N4-ACYL and Heterocyclic Derivatives" *Journal of the Indian Chemical Society*, 24:173-176.
Kettle, J.G. et al. (2004) "N-Benzylindole-2-carboxylic acids: potent functional antagonists of the CCR2b chemokine receptor" *Bioorganic & Medicinal Chemistry Letters*, 14(2): 405-408.
Kieltsch, I. et al. Laureates: Awards and Honors SCS Fall Meeting 2007 260 Recent Advances in Electrophilic CF 3—Transfer Using Hypervalent Iodine(III) Reagents 11, A Chimia Chimia Schweizerische Chemische Gesellschaft ISSN, vol. 62, No. 62, Jan. 1, 2008 (Jan. 1, 2008), pp. 260-263, XP055591571, DOI: 10.2533/chimia.2008.260.
Kholodov, L.E. et al., Klinicheskaya farmakokinetika (Clinical Pharmacokinetics), M., Meditsina, 1985, pp. 83-98, 134-138, 160, 378-380.
Kola et al. (2004) "Can the pharmaceutical industry reduce attrition rates?" Nature Reviews Drug Discovery, 3(8), 711-715.
Kratkiy kurs molekulyarnoy biologii (A Concise Course in Molecular Biology), edited by P.V. Sergeev, M., 1975, p. 10.
Lai, J.T. et al. (1980) "Rearrangement of 2,2,6,6-tetramethyl-4-piperidone in phase-transfer catalyzed reactions," *Journal of Organic Chemistry*, 45(8):1513-1514.
Liu, J. F. et al. "CTP-354: A Novel Deuterated Subtype-Selective GABA(A) Modulator for Treatment of Neuropathic Pain, Spasticity and Anxiety Disorders" Presented at the American College of Neuropsychopharmacology (ACNP) 51st Annual Meeting, Hollywood, FL, Dec. 2-6, 2012.
Matter, H. et al. (2002) "Design and Quantitative Structure—Activity Relationship of 3-Amidinobenzyl-1H-indole-2-carboxamides as Potent, Nonchiral, and Selective Inhibitors of Blood Coagulation Factor Xa" *Journal of Medicinal Chemistry*, 45(13):2749-2769.
Maxwell BD, Tran SB, Lago M, Li J, and Bonacorsi Jr SJ. "The syntheses of [14C]BMS-823778 for use in a human ADME clinical study and of [13CD313CD2]BMT-094817, a stable-isotope labeled standard of a newly detected human metabolite" J. Label. Compd. Radiopharm. 2016; 59, 255-259.
Montemayor, Kristina et al. "Unmasking catamenial hemoptysis in the era of CFTR modulator therapy", Journal of Cystic Fibrosis, Elsevier, NL, vol. 19, No. 4, Jan. 24, 2020 (Jan. 24, 2020), XP086202454, ISSN: 1569-1993, DOI: 10.1016/J.JCF.2020.01.005 [retrieved on Jan. 24, 2020].
NCT03029455 "A Study to Evaluate Safety and Pharmacokinetics of VX-659 in Healthy Subjects and in Adults With Cystic Fibrosis". Vertex Pharmaceuticals Incorporated, Retrieved from the Internet: https://clinicaltrials.gov/ct2/show/study/NCT03029455.
Norman, P. (2014) "Novel picolinamide-based cystic fibrosis transmembrane regulator modulators: evaluation of WO2013038373, WO2013038376, WO2013038381, WO2013038386, and WO2013038390," *Expert Opinion on Therapeutic Patents*, 24(7):829-837.
Notman, N. (2016) "2Heavy drugs gaining momentum" [online] Retrieved from the internet: https://www.chemistryworld.com/features/2heavy-drugs-gaining-momentum/1010186.article, on Oct. 7, 2019.
Passarella, D. et al. (2001) "Cyclodimerization of indol-2-ylacetylenes. An example of intermolecular enyne-alkyne cycloaddition" *Journal of the Chemical Society, Perkin Transactions 1*, 127-129.
Pham, P. et al. (2011) "Photoredox Catalysis: A Mild, Operationally Simple Approach to the Synthesis of alpha-Trifluoromethyl Carbonyl Compounds" Angew. Chem. Int. Ed. 2011:50 6119-6122.
Pirali T, Serafini M, Cargnin S, Genazzani AA. "Applications of Deuterium in Medicinal Chemistry" J Med. Chem. 2019; 62(11): 5276-5297.
Qun, C. et al. "Synthesis of 3,3,3-trifluoro-2,2-dimethylpropionic acid", Huaxue Shiji—Chemical Reagents, Beijing : Huaxue Huaxue Shiji Keji Qingbao Zhongxinzhan, CN, vol. 38, No. 4, Jan. 1, 2016 (Jan. 1, 2016), pp. 386-388, XP009513488, ISSN: 0258-3283, DOI: 10.13822/J.CNKI.HXSJ.2016.04.026.
Rosebraugh, C.J. (2015) "Highlights of Prescribing Information for Orkambi," [online] Retrieved from the Internet: https://www.accessdata.fda.gov/drugsatfda_docs/label/2015/206038Orig1s000lbl.pdf, on Aug. 24, 2017.
Rossiiskii terapeuticheskii spravochnik [Russian therapeutic reference book], second edition, ed. Acad. RAMS A.G. Chuchalina, M. 2008, p. 144.
Schmidt C. "First deuterated drug approved" Nat. Biotechnol. 2017, 35, 493-494.
Shih et al. (2010) "Pyrazole compound BPR1P0034 with potent and selective anti-influenza virus activity" Journal of Biomedical Science, 17:13.
Silverman, R. (2004) The Organic Chemistry of Drug Design and Drug Action, Elsevier, pp. 29-32.
Soloducho, J. (1989) "Synthesis of Some Pyrido [2,3-c][1,2,6]triazinone Derivatives" *Journal für Pracktische Chemie*, 331(3):503-506.
Soloducho, J. et al. "Synthesis of Some Pyrido[3,2g][1,2,5]triazocine Derivatives," *Polish Journal of Chemistry*, vol. 59, No. 10-12, Jan. 1, 1985, pp. 1115-1120.
Table 2 : List of the mutations or SNP tested in this study (https://www.jmdjournal.org/cms/10.2353/jmoldx.2008.080056/attachment/2286a276-d0b2-4a8a-83f8-8273bef9a761/mmc1.doc). Accessed Jan. 25, 2021.
Tsong-Long H. et al. "Synthesis and pharmacological characterization of 2-aminobenzaldehyde oxime analogs as dual inhibitors of neutrophil elastase and proteinase 3", Bioorganic & Medicinal Chemistry, vol. 23, No. 5, Jan. 16, 2015, pp. 1123-1134, XP029199003.
Tullis, E. et al. (2018) "Preliminary safety and efficacy of triple-combination CFTR modulator regimens," Respirology, 23(51):33.
U.S. Appl. No. 17/880,720, filed Aug. 4, 2022, by Abela et al.
Uttamsingh, V. et al. (2016) "WS13.6 CTP-656 tablet confirmed superiority of pharmacokinetic profile relative to Kalydeco in Phase I clinical studies" *Journal of Cystic Fibrosis*, 15:S22.
Venkatesh, S. et al. (2000) "Role of the development scientist in compound lead selection and optimization" *J. Pharm. Sci.* 89(2), 145-154.
Verado, G. et al. (1999) "Reductive One Batch Synthesis of N-Substituted Pyrrolidines from Primary Amines and 2,5-Dimethoxytetrahydrofuran" *Synthesis*, (1):74-79.
Vertex Pharmaceuticals, Inc. (Jul. 18, 2017) "Vertex Announces Positive Phase 1 & Phase 2 Data from Three Different Triple Combination Regimens in People with Cystic Fibrosis Who Have One F508del Mutation and One Minimal Function Mutation (F508del/Min)", Retrieved from the Internet: URL: http://investors.vrtx.com/news-releases/news-release-details/vertex/announces-positive-phase-1-phase-2-data-three-different [retrieved on Mar. 27, 2019].
Vertex Pharmaceuticals, Inc. (Mar. 2, 20178) "Two Phase 3 Studies of the Tezacaftor/Ivacaftor Combination Treatment Met Primary Endpoints with Statistically Significant Improvements in Lung Function (FEV1) in People With Cystic Fibrosis" [online] Retrieved from the Internet: http://investors.vrtx.com/static-files/f15217ac-4a8b-436a-9215-79144ec2e59b, on Oct. 10, 2019.
Vertex Pharmaceuticals, Inc. (Nov. 3, 2017) "Vertex announces presentations of data at North American Cystic Fibrosis Conference that Demonstrate Important Progress Toward Goal of Helping All People with CF," Health and Medicine Week, vol. 3, p. 196.
"Vertex Provides Update on Ongoing Phase 3 Program for VX-661 in Combination with Ivacaftor for the Treatment of Cystic Fibrosis" (Aug. 15, 2016) Retrieved from the Internet: https://www.businesswire.com/news/home/20160815006099/en/Vertex-Update-Ongoing-Phase-3-Program-VX-661.

(56) References Cited

OTHER PUBLICATIONS

Vodak, D. (2014) "Design and Development of HPMCAS-Based Spray-Dried Dispersions," 303-322.
Wainwright, C.E. et al. (2015) "Lumacaftor-Ivacaftor in Patients with Cystic Fibrosis Homozygous for Phe508del CFTR," *The New England Journal of Medicine*, 373(3):220-231.
Walters et al. (2002) "Prediction of 'drug-likeness'," Advanced Drug Delivery Reviews, 54(3), 255-271.
Willson T. M. et al. (1996) "Bone targeted drugs 2. Synthesis of estrogens with hydroxyapatite affinity," Bioorg. & Med. Chem. Lett., (6):1047-1050.
Winn, M. et al. (1993) "2-(Alkylamino)nicotinic Acid and Analogs. Potent Angiotensin II Antagonists" *Journal of Medicinal Chemistry*, 36(18):2676-2688.
Yarnell AT. "Heavy-Hydrogen Drugs Turn Heads, Again" Chemical & Engineering News 2009; 87(25), 36-39.

* cited by examiner

FIG. 1

| Mutation cDNA Name | Mutation Protein Name | Mutation Legacy Name |
|---|---|---|
| c.1A>G | | M1V |
| c.54-5940_273+10250de l21kb | p.Ser18ArgfsX16 | CFTRdele2,3 |
| c.91C>T | p.Arg31Cys | R31C |
| c.115C>T | p.Gln39X | Q39X |
| c.137C>A | p.Ala46Asp | A46D |
| c.165-1G>A | No protein name | 297-1G->A |
| c.166G>A | p.Glu56Lys | E56K |
| c.174_175insA | p.Arg59LysfsX10 | 306insA |
| c.178G>T | p.Glu60X | E60X |
| c.200C>T | p.Pro67leu | P67L |
| c.220C>T | p.Arg74Trp | R74W |
| c.223C>T | p.Arg75X | R75X |
| c.224G>A | p.Arg75Gln | R75Q |
| c.254G>A | p.Gly85Glu | G85E |
| c.262_263delTT | p.Leu88IlefsX22 | 394delTT |
| c.273+1G>A | No protein name | 405+1G->A |
| c.274-1G>A | No protein name | 406-1G->A |
| c.274G>A | p.Glu92Lys | E92K |
| c.274G>T | p.Glu92X | E92X |
| c.292C>T | p.Gln98X | Q98X |
| c.313delA | p.Ile105SerfsX2 | 444delA |
| c.325_327delTATins G | p.Tyr109GlyfsX4 | 457TAT->G |
| c.328G>C | p.Asp110His | D110H |
| c.349C>T | p.Arg117Cys | R117C |
| c.350G>A | p.Arg117His | R117H |
| c.366T>A | p.Tyr122X | Y122X |
| c.442delA | p.Ile148LeufsX5 | 574delA |
| c.443T>C | p.Ile148Thr | I148T |
| c.489+1G>T | No protein name | 621+1G->T |
| c.531delT | p.Ile177MetfsX12 | 663delT |
| c.532G>A | p.Gly178Glu | G178R |

FIG. 1 (continued)

| Mutation cDNA Name | Mutation Protein Name | Mutation Legacy Name |
|---|---|---|
| c.543_546delTAGT | p.Leu183PhefsX5 | 675del4 |
| c.579+1G>T | No protein name | 711+1G->T |
| c.579+3A>G | No protein name | 711+3A->G |
| c.579+5G>A | No protein name | 711+5G->A |
| c.580-1G>T | No protein name | 712-1G->T |
| c.595C>T | p.His199Tyr | H199Y |
| c.613C>T | p.Pro205Ser | P205S |
| c.617T>G | p.Leu206Trp | L206W |
| c.658C>T | p.Gln220X | Q220X |
| c.680T>G | p.Leu227Arg | L227R |
| c.720_741delAGGGAGAATGATGATGAAGTAC | p.Gly241GlufsX13 | 852del22 |
| c.828C>A | p.Cys276X | C276X |
| c.948delT | p.Phe316LeufsX12 | 1078delT |
| c.988G>T | p.Gly330X | G330X |
| c.1000C>T | p.Arg334Trp | R334W |
| c.1007T>A | p.Ile336Lys | I336K |
| c.1013C>T | p.Thr338Ile | T338I |
| c.1021T>C | p.Ser341Pro | S341P |
| c.1022_1023insTC | p.Phe342HisfsX28 | 1154insTC |
| c.1040G>A | p.Arg347His | R347H |
| c.1040G>C | p.Arg347Pro | R347P |
| c.1055G>A | p.Arg352Gln | R352Q |
| c.[1075C>A; 1079C>A] | p.[Gln359Lys;Thr360Lys] | Q359K/T360K |
| c.1081delT | p.Trp361GlyfsX8 | 1213delT |
| c.1116+1G>A | No protein name | 1248+1G->A |
| c.1127_1128insA | p.Gln378AlafsX4 | 1259insA |
| c.1153_1154insAT | p.Asn386IlefsX3 | 1288insTA |
| c.1202G>A or c.1203G>A | p.Trp401X | W401X |
| c.1209+1G>A | No protein name | 1341+1G->A |
| c.1210-12[5] | No protein name | 5T |

FIG. 1 (continued)

| Mutation cDNA Name | Mutation Protein Name | Mutation Legacy Name |
|---|---|---|
| c.1210-12(7) | No protein name | 7T |
| c.1240C>T | p.Gln414X | Q414X |
| c.1329_1330insAGAT | p.Ile444ArgfsX3 | 1461ins4 |
| c.1340delA | p.Lys447ArgfsX2 | 1471delA |
| c.1364C>A | p.Ala455Glu | A455E |
| c.1393-1G>A | No protein name | 1525-1G->A |
| c.1397C>A or c.1397C>G | p.Ser466X | S466X |
| c.1400T>C | p.Leu467Pro | L467P |
| c.1408A>G | p.Met470Val | M470V |
| c.1418delG | p.Gly473GlufsX54 | 1548delG |
| c.1466C>A | p.Ser489X | S489X |
| c.1475C>T | p.Ser492Phe | S492F |
| c.1477C>T | p.Gln493X | Q493X |
| c.1519_1521delATC | p.Ile507del | I507del |
| c.1521_1523delCTT | p.Phe508del | F508del |
| c.1545_1546delTA | p.Tyr515X | 1677delTA |
| c.1558G>T | p.Val520Phe | V520F |
| c.1573C>T | p.Gln525X | Q525X |
| c.1585-8G>A | No protein name | 1717-8G->A |
| c.1585-1G>A | No protein name | 1717-1G->A |
| c.1624G>T | p.Gly542X | G542X |
| c.1645A>C or c.1647T>G | p.Ser549Arg | S549R |
| | | |
| c.1646G>A | p.Ser549Asn | S549N |
| c.1650delA | p.Gly551ValfsX8 | 1782delA |
| c.1651G>A | p.Gly551Ser | G551S |
| c.1652G>A | p.Gly551Asp | G551D |
| c.1654C>T | p.Gln552X | Q552X |
| c.1657C>T | p.Arg553X | R553X |
| c.1673T>C | p.Leu558Ser | L558S |
| c.1675G>A | p.Ala559Thr | A559T |

FIG. 1 (continued)

| Mutation cDNA Name | Mutation Protein Name | Mutation Legacy Name |
|---|---|---|
| c.1679G>A | p.Arg560Lys | R560K |
| c.1679G>C | p.Arg560Thr | R560T |
| c.1679+1G>C | No protein name | 1811+1G->C |
| c.1679+1.6kbA>G | No protein name | 1811+1.6kbA->G |
| c.1680-1G>A | No protein name | 1812-1G->A |
| c.1682C>A | p.Ala561Glu | A561E |
| c.1692delA | p.Asp565MetfsX7 | 1824delA |
| c.1705T>G | p.Tyr569Asp | Y569D |
| c.1727G>C | p.Gly576Ala | G576A |
| c.1736A>G | p.Asp579Gly | D579G |
| c.1753G>T | p.Glu585X | E585X |
| c.1766+1G>A | No protein name | 1898+1G->A |
| c.1766+1G>C | No protein name | 1898+1G->C |
| c.1766+3A>G | No protein name | 1898+3A->G |
| c.1841A>G | p.Asp614Gly | D614G |
| c.1923_1931del9ins | p.Ser641ArgfsX5 | 2055del9->A |
| c.1973_1985del13insAGAAA | p.Arg658_LysfsX4 | 2105-2117del13insAGAAA |
| c.1986_1989delAACT | p.Thr663ArgfsX8 | 2118del4 |
| c.2002C>T | p.Arg668Cys | R668C |
| c.2012delT | p.Leu671X | 2143delT |
| c.2051_2052delAAinsG | p.Lys684SerfsX38 | 2183AA->G+ |
| c.2051_2052delAAinsG | p.Lys684SerfsX38 | 2183delAA->G# |
| c.2052_2053insA | p.Gln685ThrfsX4 | 2184insA |
| c.2052delA | p.Lys684AsnfsX38 | 2184delA |
| c.2125C>T | p.Arg709X | R709X |
| c.2128A>T | p.Lys710X | K710X |
| c.2175_2176insA | p.Glu726ArgfsX4 | 2307insA |
| c.2195T>G | p.Leu732X | L732X |
| c.2215delG | p.Val739TyrfsX16 | 2347delG |
| c.2260G>A | p.Val754Met | V754M |

FIG. 1 (continued)

| Mutation cDNA Name | Mutation Protein Name | Mutation Legacy Name |
|---|---|---|
| c.2290C>T | p.Arg764X | R764X |
| c.2353C>T | p.Arg785X | R785X |
| c.2374C>T | p.Arg792X | R792X |
| c.2424_2425insAT | p.Ser809IlefsX13 | 2556insAT |
| c.2453delT | p.Leu818TrpfsX3 | 2585delT |
| c.3462_2463delGT | p.Ser821ArgfsX4 | No legacy name |
| c.2464G>T | p.Glu822X | E822X |
| c.2490+1G>A | No protein name | 2622+1G->A |
| c.2491G>T | p.Glu831X | E831X |
| c.2537G>A or c.2538G>A | p.Trp846X | W846X |
| c.2547C>A | p.Tyr849X | Y849X |
| c.2551C>T | p.Arg851X | R851X |
| c.2583delT | p.Phe861LeufsX3 | 2711delT |
| c.2657+2_2657+3insA | No protein name | 2789+2insA |
| c.2657+5G>A | No protein name | 2789+5G->A |
| c.2658-1G>C | No protein name | 2790-1G->C |
| c.2668C>T | p.Gln890X | Q890X |
| c.2735C>A | p.Ser912X | S912X |
| c.2737_2738insG |  | 2869insG |
| c.2739T>A | p.Tyr913X | Y913X |
| c.2764_2765insAG | p.Val922GlufsX2 | 2896insAG |
| c.2780T>C | p.Leu927Pro | L927P |
| c.2834C>T | p.Ser945Leu | S945L |
| c.2875delG | p.Ala959HisfsX9 | 3007delG |
| c.2908G>C | p.Gly970Arg | G970R |
| c.2930C>T | p.Ser977Phe | S977F |
| c.2988G>A | No protein name | 3120G->A |
| c.2988+1G>A | No protein name | 3120+1G->A |
| c.2989-977_3367+248del | No protein name | 3121-977_3499+248del2515 |
| c.2989-1G>A | No protein name | 3121-1G->A |
| c.2991G>C | p.Leu997Phe | L997F |

FIG. 1 (continued)

| Mutation cDNA Name | Mutation Protein Name | Mutation Legacy Name |
|---|---|---|
| c.3002_3003delTG | p.Val1001AspfsX45 | 3132delTG |
| c.3080T>C | p.Ile1027Thr | I1027T |
| c.3140-26A>G | No protein name | 3272-26A->G |
| c.3154T>G | p.Phe1052Val | F1052V |
| c.3160C>G | p.His1054Asp | H1054D |
| c.3181G>C | p.Gly1061Arg | G1061R |
| c.3194T>C | p.Leu1065Pro | L1065P |
| c.3196C>T | p.Arg1066Cys | R1066C |
| c.3197G>A | p.Arg1066His | R1066H |
| c.3205G>A | p.Gly1069Arg | G1069R |
| c.3208C>T | p.Arg1070Trp | R1070W |
| c.3209G>A | p.Arg1070Gln | R1070Q |
| c.3222T>A | p.Phe1074Leu | F1074L |
| c.3230T>C | p.Leu1077Pro | L1077P |
| c.3266G>A | p.Trp1089X | W1089X |
| c.3276C>A or c.3276C>G | p.Tyr1092X | Y1092X |
| c.3302T>A | p.Met1101Lys | M1101K |
| c.3310G>T | p.Glu1104X | E1104X |
| c.3454G>C | p.Asp1152His | D1152H |
| c.3472C>T | p.Arg1158X | R1158X |
| c.3484C>T | p.Arg1162X | R1162X |
| c.3485G>T | p.Arg1162Leu | R1162L |
| c.3528delC | p.Lys1177SerfsX15 | 3659delC |
| c.3535_3536insTCAA | p.Thr1179IlefsX7 | 3667ins4 |
| c.3587C>G | p.Ser1196X | S1196X |
| c.3605delA | p.Asp1202AlafsX9 | 3737delA |
| c.3611G>A or c.3612G>A | p.Trp1204X | W1204X |
| c.3659delC | p.Thr1220LysfsX8 | 3791delC |
| c.3691delT | p.Ser1231ProfsX4 | 3821delT |

FIG. 1 (continued)

| Mutation cDNA Name | Mutation Protein Name | Mutation Legacy Name |
|---|---|---|
| c.3700A>G | p.Ile1234Val | I1234V |
| c.3705T>G | p.Ser1235Arg | S1235R |
| c.3717+12191C>T | No protein name | 3849+10kbC->T |
| c.3718-1G>A | No protein name | 3850-1G->A |
| c.3731G>A | p.Gly1244Glu | G1244E |
| c.3744delA | p.Lys1250ArgfsX9 | 3876delA |
| c.3752G>A | p.Ser1251Asn | S1251N |
| c.3763T>C | p.Ser1255Pro | S1255P |
| c.3764C>A | p.Ser1255X | S1255X |
| c.3773_3774insT | p.Leu1258PhefsX7 | 3905insT |
| c.3808G>A | p.Asp1270Asn | D1270N |
| c.3846G>A | p.Trp1282X | W1282X |
| c.3873+1G>A | No protein name | 4005+1G->A |
| c.3883delA | p.Ile1295PhefsX33 | 4015delA |
| c.3884_3885insT | p.Ser1297PhefsX5 | 4016insT |
| c.3909C>G | p.Asn1303Lys | N1303K |
| c.3937C>T | p.Gln1313X | Q1313X |
| c.3964-78_4242+577del | NULL | CFTRdele22,23 |
| c.4046G>A | p.Gly1349Asp | G1349D |
| c.4077_4080delTGTTinsAA | No protein name | 4209TGTT->AA |
| c.4111G>T | p.Glu1371X | E1371X |
| c.4196_4197delTC | p.Cys1400X | 4326delTC |
| c.4234C>T | p.Gln1412X | Q1412X |
| c.4242+1G>T | No protein name | 4374+1G->T |
| c.4251delA | p.Glu1418ArgfsX14 | 4382delA |
| c.4296_4297insGA | p.Ser1435GlyfsX14 | 4428insGA |

PROCESSES FOR MAKING MODULATORS OF CYSTIC FIBROSIS TRANSMEMBRANE CONDUCTANCE REGULATOR

This application claims the benefit of U.S. Provisional Application No. 62/596,452, filed Dec. 8, 2017, U.S. Provisional Application No. 62/623,725, filed Jan. 30, 2018, and U.S. Provisional Application No. 62/649,970, filed Mar. 29, 2018, all of which are incorporated herein by reference in their entirety.

SEQUENCE LISTING

The instant application contains a sequence listing which has been submitted electronically in XML format and is hereby incorporated by reference in its entirety. The Sequence Listing XML, created on Mar. 6, 2023, is named 10275.0133-01000 SL.xml and is 716 bytes in size.

The invention provides processes for preparing compounds useful for treating a cystic fibrosis transmembrane conductance regulator ("CFTR") mediated disease such as cystic fibrosis, intermediates useful in those processes, and processes for making those intermediates.

Cystic fibrosis (CF) is a recessive genetic disease that affects approximately 70,000 children and adults worldwide. Despite progress in the treatment of CF, there is no cure.

In patients with CF, mutations in CFTR endogenously expressed in respiratory epithelia lead to reduced apical anion secretion causing an imbalance in ion and fluid transport. The resulting decrease in anion transport contributes to enhanced mucus accumulation in the lung and accompanying microbial infections that ultimately cause death in CF patients. In addition to respiratory disease, CF patients typically suffer from gastrointestinal problems and pancreatic insufficiency that, if left untreated, result in death. In addition, the majority of males with cystic fibrosis are infertile, and fertility is reduced among females with cystic fibrosis.

Sequence analysis of the CFTR gene has revealed a variety of disease-causing mutations (Cutting, G. R. et al. (1990) Nature 346:366-369; Dean, M. et al. (1990) Cell 61:863:870; and Kerem, B-S. et al. (1989) Science 245: 1073-1080; Kerem, B-S et al. (1990) Proc. Natl. Acad. Sci. USA 87:8447-8451). To date, greater than 2000 mutations in the CF gene have been identified; currently, the CFTR2 database contains information on only 322 of these identified mutations, with sufficient evidence to define 281 mutations as disease causing. The most prevalent disease-causing mutation is a deletion of phenylalanine at position 508 of the CFTR amino acid sequence and is commonly referred to as the F508del mutation. This mutation occurs in approximately 70% of the cases of cystic fibrosis and is associated with severe disease.

The deletion of residue 508 in CFTR prevents the nascent protein from folding correctly. This results in the inability of the mutant protein to exit the endoplasmic reticulum (ER) and traffic to the plasma membrane. As a result, the number of CFTR channels for anion transport present in the membrane is far less than observed in cells expressing wild-type CFTR, i.e., CFTR having no mutations. In addition to impaired trafficking, the mutation results in defective channel gating. Together, the reduced number of channels in the membrane and the defective gating lead to reduced anion and fluid transport across epithelia. (Quinton, P. M. (1990), FASEB J. 4: 2709-2727). The channels that are defective because of the F508del mutation are still functional, albeit less functional than wild-type CFTR channels. (Dalemans et al. (1991), Nature Lond. 354: 526-528; Pasyk and Foskett (1995), J. Cell. Biochem. 270: 12347-50). In addition to F508del, other disease-causing mutations in CFTR that result in defective trafficking, synthesis, and/or channel gating could be up- or down-regulated to alter anion secretion and modify disease progression and/or severity.

CFTR is a cAMP/ATP-mediated anion channel that is expressed in a variety of cell types, including absorptive and secretory epithelia cells, where it regulates anion flux across the membrane, as well as the activity of other ion channels and proteins. In epithelial cells, normal functioning of CFTR is critical for the maintenance of electrolyte transport throughout the body, including respiratory and digestive tissue. CFTR is composed of approximately 1480 amino acids that encode a protein which is made up of a tandem repeat of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

Chloride transport takes place by the coordinated activity of ENaC and CFTR present on the apical membrane and the Na+-K+-ATPase pump and Cl– channels expressed on the basolateral surface of the cell. Secondary active transport of chloride from the luminal side leads to the accumulation of intracellular chloride, which can then passively leave the cell via Cl– channels, resulting in a vectorial transport. Arrangement of Na+/2Cl–/K+ co-transporter, Na+-K+-ATPase pump and the basolateral membrane K+ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

Accordingly, there is a need for therapeutics to treat CFTR mediated diseases and improved methods of making those compounds.

There is also a need for efficient processes for the synthesis of compounds useful as CFTR modulators that deliver these compounds in for example, higher yield, higher selectivity, or with higher purity relative to known processes. Accordingly, this disclosure provides processes for the synthesis of a compound of Formula (I):

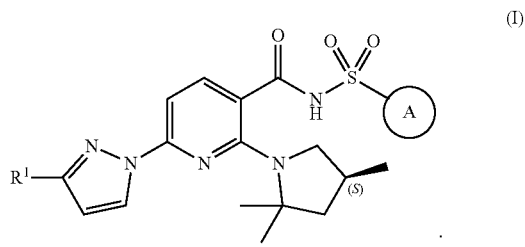

In some embodiments, the compound of Formula I is a N-(1,3-dimethylpyrazol-4-yl)sulfonyl-6-[3-(3,3,3-trifluoro-2,2-dimethyl-propoxy)pyrazol-1-yl]-2-[(4S)-2,2,4-trimethylpyrrolidin-1-yl]pyridine-3-carboxamide (Compound 1), having the structure:

(Compound 1)

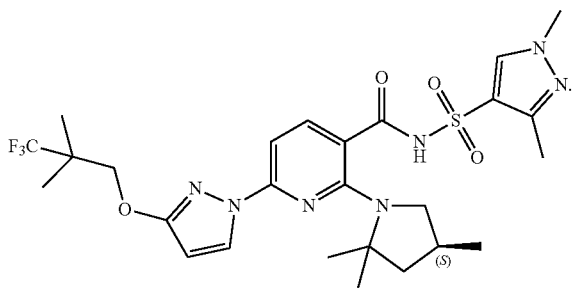

In some embodiments, the compound of Formula (I) is a N-(benzenesulfonyl)-6-[3-[2-[1-(trifluoromethyl)cyclopropyl]ethoxy]pyrazol-1-yl]-2-[(4(S))-2,2,4-trimethylpyrrolidin-1-yl]pyridine-3-carboxamide (Compound 2), having the structure:

(Compound 2)

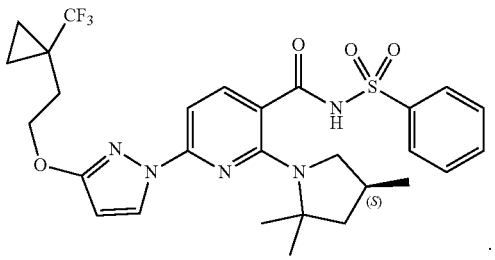

BRIEF DESCRIPTION OF THE DRAWING

FIG. 1 is a representative list of CFTR genetic mutations.

DEFINITIONS

The term "CFTR" as used herein means cystic fibrosis transmembrane conductance regulator or a mutation thereof capable of regulator activity, including, but not limited to, the CFTR gene mutations listed in FIG. 1.

Compounds described herein may optionally be substituted with one or more substituents, such as are illustrated generally above, or as exemplified by particular classes, subclasses, and species of the disclosure. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent.

Unless otherwise indicated, an optionally substituted group may have a substituent at each substitutable position of the group, and when more than one position in any given structure may be substituted with more than one substituent chosen from a specified group, the substituent may be either the same or different at every position. Combinations of substituents envisioned by this disclosure are preferably those that result in the formation of stable or chemically feasible compounds.

The term "stable," as used herein, refers to compounds that are not substantially altered when subjected to conditions to allow for their production, detection, and preferably their recovery, purification, and use for one or more of the purposes disclosed herein.

The term "stable compounds," as used herein, refers to compounds which possess stability sufficient to allow for their manufacture and which maintain the integrity of the compounds for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle", "cycloaliphatic", or "cycloalkyl"), that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. In some embodiments, "cycloaliphatic" (or "carbocycle" or "cycloalkyl") refers to a monocyclic $C_{3-8}$ hydrocarbon or bicyclic or tricyclic $C_{8-14}$ hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl. Suitable cycloaliphatic groups include cycloalkyl, bicyclic cycloalkyl (e.g., decalin), bridged bicycloalkyl such as norbornyl or [2.2.2]bicyclo-octyl, or bridged tricyclic such as adamantyl.

The term "heteroaliphatic", as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle", "heterocyclyl", "heterocycloaliphatic", or "heterocyclic" groups.

The term "heterocycle", "heterocyclyl", "heterocycloaliphatic", or "heterocyclic" as used herein means non-aromatic, monocyclic, bicyclic, or tricyclic ring systems in which one or more ring members is an independently chosen heteroatom. In some embodiments, the "heterocycle", "heterocyclyl", "heterocycloaliphatic", or "heterocyclic" group has three to fourteen ring members in which one or more ring members is a heteroatom independently chosen from oxygen, sulfur, nitrogen, or phosphorus, and each ring in the system contains 3 to 7 ring members.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloaliphatic" and "haloalkoxy" means aliphatic or alkoxy, as the case may be, substituted with one or more halo atoms. The term "halogen" or means F, Cl, Br, or I. Examples of haloaliphatic include —CHF$_2$, —CH$_2$F, —CF$_3$, —CF$_2$—, or perhaloalkyl, such as, —CF$_2$CF$_3$.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" also refers to heteroaryl ring systems as defined herein below.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members.

An aryl (including aralkyl, aralkoxy, aryloxyalkyl and the like) or heteroaryl (including heteroaralkyl and heteroarylalkoxy and the like) group may contain one or more substituents.

An aliphatic or heteroaliphatic group, or a non-aromatic heterocyclic ring may contain one or more substituents.

Examples of useful protecting groups for nitrogen include, for example, t-butyl carbamate (Boc), benzyl (Bn), tetrahydropyranyl (THP), 9-fluorenylmethyl carbamate (Fmoc), benzyl carbamate (Cbz), acetamide, trifluoroacetamide, triphenylmethylamine, benzylideneamine, and p-toluenesulfonamide.

Methods of adding (a process generally referred to as "protecting") and removing (process generally referred to as "deprotecting") such amine protecting groups are well-known in the art and available, for example, in P. J. Kocienski, Protecting Groups, Thieme, 1994, which is hereby incorporated by reference in its entirety and in Greene and Wuts, *Protective Groups in Organic Synthesis, 3rd Edition* (John Wiley & Sons, New York, 1999).

Examples of suitable solvents that may be used in this disclosure include, but not limited to, water, methanol (MeOH), methylene chloride (CH$_2$Cl$_2$), acetonitrile, dimethyl sulfoxide (DMSO), dimethylformamide (DMF), methyl acetate (MeOAc), ethyl acetate (EtOAc), isopropyl acetate (IPAc), tert-butyl acetate (t-BuOAc), isopropyl alcohol (IPA), tetrahydrofuran (THF), 2-methyl tetrahydrofuran (2-Me THF), methyl ethyl ketone (MEK), tert-butanol, diethyl ether (Et$_2$O), methyl-tert-butyl ether (MTBE), 1,4-dioxane, and N-methyl pyrrolidone (NMP).

Examples of suitable bases that may be used in this disclosure include, but not limited to, 1,8-diazabicyclo [5.4.0]undec-7-ene (DBU), potassium tert-butoxide (KOtBu), potassium carbonate (K$_2$CO$_3$), N-methylmorpholine (NMM), triethylamine (Et$_3$N; TEA), diisopropyl-ethyl amine (i-Pr$_2$EtN; DIPEA), pyridine, potassium hydroxide (KOH), sodium hydroxide (NaOH), and sodium methoxide (NaOMe; NaOCH$_3$). In some embodiments, the base is a non-nucleophilic base.

Unless otherwise stated, structures depicted herein are also meant to include all isomeric forms of the structure, e.g., geometric (or conformational), such as (Z) and (E) double bond isomers, and (Z) and (E) conformational isomers. Therefore, geometric and conformational mixtures of the present compounds are within the scope of the disclosure. Unless otherwise stated, all tautomeric forms of the compounds of the disclosure are within the scope of the disclosure.

"Stereoisomer" refers to both enantiomers and diastereomers.

"Tert" and "t-" each refer to tertiary.

The disclosure also provides processes for preparing salts of the compounds of the disclosure.

A salt of a compound of this disclosure is formed between an acid and a basic group of the compound, such as an amino functional group, or a base and an acidic group of the compound, such as a carboxyl functional group. According to another embodiment, the compound is a pharmaceutically acceptable salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this disclosure. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and preferably those formed with organic acids such as maleic acid.

The term "derivative" as used herein refers to a collection of molecules having an chemical structure identical to a compound of this disclosure, except that one or more atoms of the molecule may have been substituted with another atom.

In some embodiments, the derivative is a deuterated derivative of a disclosed compound. A deuterated derivative results from substitution of one or more hydrogen atoms in a disclosed molecule with an equal number of deuterium atoms. It will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this disclosure will depend upon a number of factors including the isotopic purity of deuterated reagents used to make the compound and the efficiency of incorporation of deuterium in the various synthesis steps used to prepare the compound. However, as set forth above the relative amount of such isotopologues in toto will be less than 49.9% of the compound. In other embodiments, the relative amount of such isotopologues in toto will be less than 47.5%, less than 40%, less than 32.5%, less than 25%, less than 17.5%, less than 10%, less than 5%, less than 3%, less than 1%, or less than 0.5% of the compound.

The term "isotopologue" refers to a species in which the chemical structure differs from a specific compound of this disclosure only in the isotopic composition thereof. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$ or $^{14}C$ are within the scope of this disclosure.

In some embodiments, the derivative is a silicon derivative in which at least one carbon atom in a disclosed compound has been replaced by silicon. In some embodiments, the derivative is a boron derivative, in which at least one carbon atom in a disclosed compound has been replaced by boron. In other embodiments, the derivative is a phosphate derivative, in which at least one carbon atom in a disclosed compound has been replaced by phosphorus. Because the general properties of silicon, boron, and phosphorus are similar to those of carbon, replacement of carbon by silicon, boron, or phosphorus can result in compounds with similar biological activity to a carbon containing original compound.

In some embodiments, the derivative is a silicon derivative in which one carbon atom replaced by silicon may is a non-aromatic carbon. In some embodiments an aromatic carbon may be replaced by silicon. In certain embodiments, the silicon derivatives of the invention may also have one or more hydrogen atoms replaced by deuterium.

One aspect of the invention provides processes for the synthesis of N-(1,3-dimethylpyrazol-4-yl)sulfonyl-6-[3-(3,3,3-trifluoro-2,2-dimethyl-propoxy)pyrazol-1-yl]-2-[(4S)-2,2,4-trimethylpyrrolidin-1-yl]pyridine-3-carboxamide (Compound 1), a pharmaceutically acceptable salt of Compound 1, or a derivative thereof. Another aspect of the invention provides processes for the synthesis of N-(benzenesulfonyl)-6-[3-[2-[1-(trifluoromethyl)cyclopropyl]-ethoxy]pyrazol-1-yl]-2-[(4(S))-2,2,4-trimethylpyrrolidin-1-yl]pyridine-3-carboxamide (Compound 2) or a pharmaceutically acceptable salt of Compound 2, or a derivative thereof.

Synthesis of Starting Materials

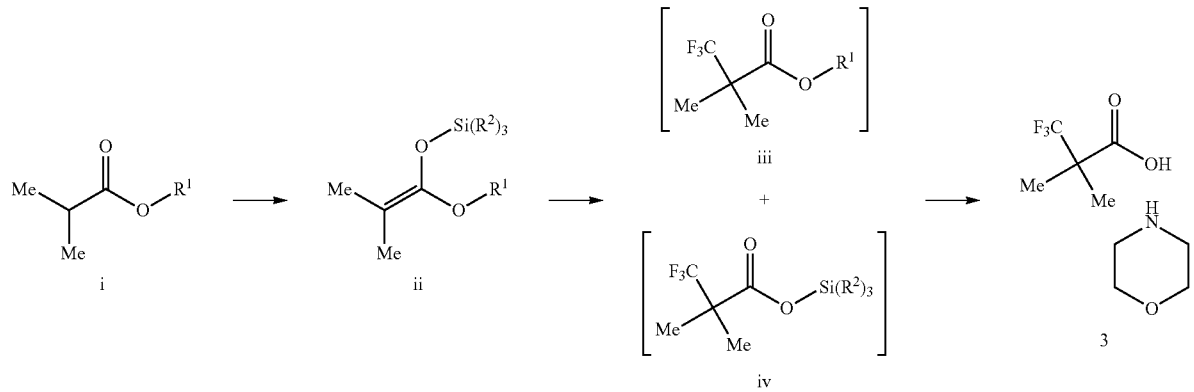

One aspect of the invention provides a method of making 3,3,3-trifluoro-2,2-dimethylpropionic acid or a salt thereof. A salt of 3,3,3-trifluoro-2,2-dimethylpropionic acid can be made using conventional methods in the art by reacting it with a suitable base, such as an amine base. The 3,3,3-trifluoro-2,2-dimethylpropionic acid can be de-salted using conventional methods in the art to prepare 3,3,3-trifluoro-2,2-dimethylpropionic acid as the free form. Isobutyrate ester i is converted to silyl keteneacetal ii using a base and a silylating reagent, wherein $R^1$ is alkyl and each $R^2$ is independently chosen from methyl, ethyl, isopropyl, tert-butyl, and phenyl. In some embodiments, $R^1$ is chosen from methyl, ethyl, propyl, butyl, and isoamyl. In some embodiments, $R^1$ is ethyl. In some embodiments, $R^1$ is trimethylsilyl. In some embodiments, $Si(R^2)_3$ is chosen from trimethylsilyl, triethylsilyl, triisopropylsilyl, tert-butyldimethylsilyl, and tert-butyldiphenylsilyl. In some embodiments, $Si(R^2)_3$ is tert-butyldimethylsilyl. In some embodiments, the base is lithium diisopropylamide. In some embodiments, this reaction is performed in 1,3-dimethyl-3,4,5,6-tetrahydro-2-pyrimidinone (DMPU) as a solvent. In some embodiments, the silylating reagent is chosen from trimethylsilyl chloride, triethylsilyl chloride, triisopropylsilyl chloride, tert-butyldimethylsilyl chloride, and tert-butyldiphenylsilyl chloride. In some embodiments, the silylating reagent is tert-butyldimethylsilyl chloride. Silyl keteneacetal ii is then converted to ester iii, silyl ester iv, or a mixture thereof. In some embodiments, this reaction is performed in the presence of a reagent of the formula $CF_3$—X, wherein X is a leaving group. In some embodiments, the reagent is $CF_3I$ or trifluoroacetic anhydride. In some embodiments, the reagent is $CF_3I$. In some embodiments, the reaction is performed in the presence of a ruthenium catalyst. In some embodiments, the ruthenium catalyst includes $[Ru(bpy)3]^{2+}$, wherein bpy is 2,2'-bipyridine. In some embodiments, the ruthenium catalyst is $[Ru(bpy)3]X_2$ wherein X is an anion, such as Cl⁻ or $PF_6^-$. In some embodiments, the ruthenium catalyst is Ru(bpy)$_3$Cl$_2$ hexahydrate (Ru(bpy)$_3$Cl$_2$ 6H$_2$O). In some embodiments, the reaction is performed in the presence of an iridium catalyst. In some embodiments, the iridium catalyst is [Ir(dtbbpy)(ppy)2]PF$_6$. In some embodiments, the catalyst is tetraphenylpyrylium tetrafluoroborate (TPP-BF$_4$). In some embodiments, this reaction is performed under photochemical conditions. In some embodiments the reaction is performed in the presence of light at a wavelength of 435-450 nm. In some embodiments the reaction is performed in the presence of light at a wavelength of 440-445 nm. Ester iii, silyl ester iv, or a mixture thereof is then converted to 3,3,3-trifluoro-2,2-dimethylpropionic acid (3). This can be performed under suitable hydrolysis or saponification conditions, or other conventional methods for converting an alkyl ester or a silyl ester into a carboxylic acid. In some embodiments, the hydrolysis is performed in the presence of sodium hydroxide. In some embodiments, the hydrolysis is performed in at least one solvent chosen from water, ethanol, THF, and 2-methyltetrahydrofuran.

Synthesis of Compound 1

One aspect of the invention provides methods of using the intermediates disclosed above in a process for preparing Compound 1. In some embodiments, Compound 1 can be synthesized according to Scheme 1.

Scheme 1: Synthesis of Compound 1
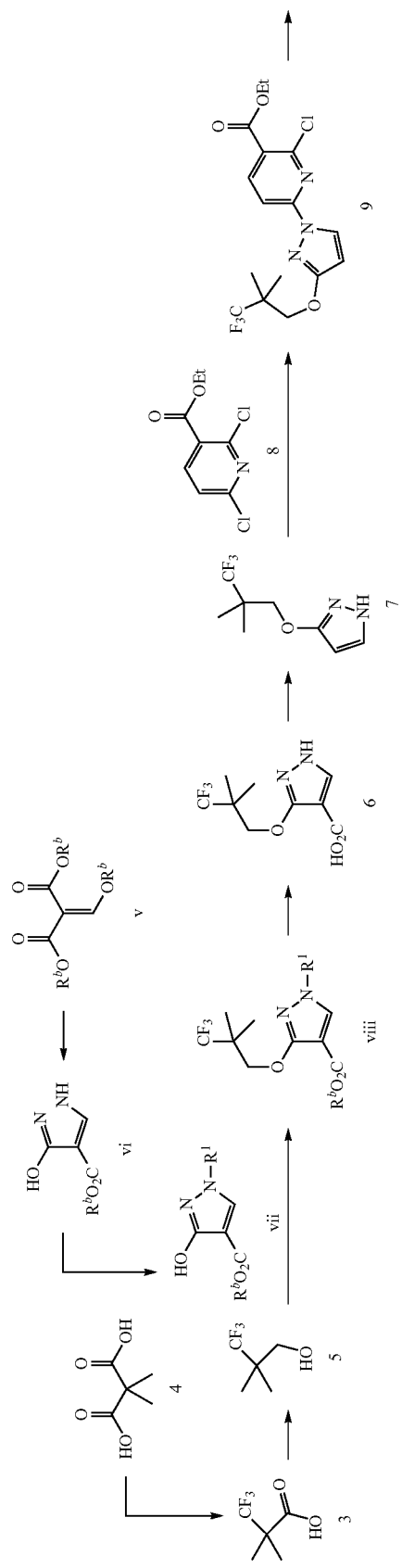

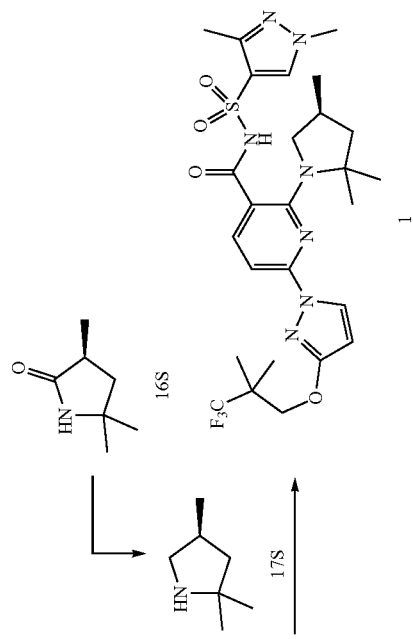
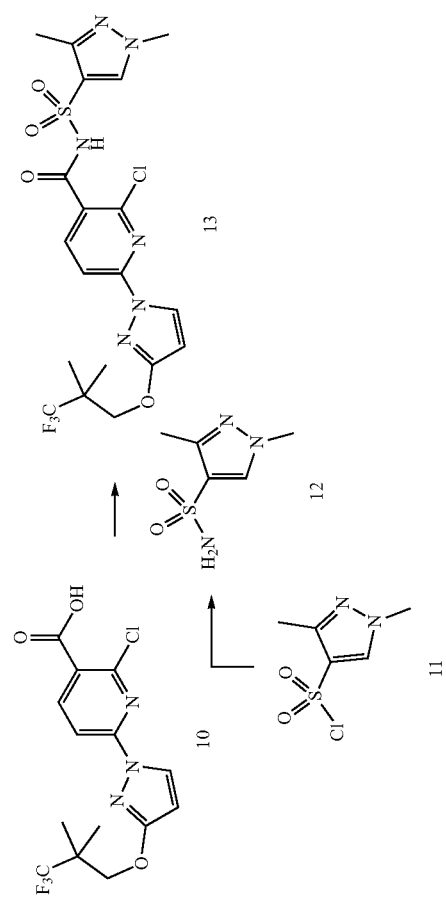

In some embodiments, $R^1$ is a protecting group. In some embodiments, $R^1$ is chosen from t-butyl carbamate (Boc), benzyl (Bn), tetrahydropyranyl (THP), 9-fluorenylmethyl carbamate (Fmoc), benzyl carbamate (Cbz), acetamide, trifluoroacetamide, triphenylmethylamine, benzylideneamine, and p-toluenesulfonamide. In certain embodiments, $R^1$ is chosen from t-butyl carbamate (Boc), benzyl (Bn), and tetrahydropyranyl (THP). In certain embodiments, $R^1$ is t-butyl carbamate (Boc). In some embodiments, $R^b$ is independently chosen from $C_1$-$C_4$ alkyl groups. In certain embodiments, $R^b$ is ethyl.

In some embodiments, Compound v

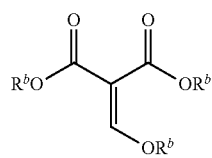

v is converted to Compound vi

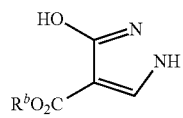

vi in the presence of hydrazine. In some embodiments, the reaction is performed in a solvent. In some embodiments, the solvent is ethanol. In some embodiments, $R^b$ is independently chosen from $C_1$-$C_4$ alkyl group. In certain embodiments, $R^b$ is ethyl.

In some embodiments, Compound vi

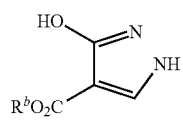

vi is converted to Compound vii

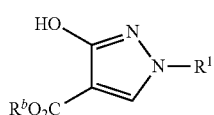

vii in the presence of di-tert-butyl dicarbonate. In some embodiments, the reaction is performed in the presence of a base. In some embodiments, the base is triethylamine. In some embodiments, the reaction is performed in a solvent. In some embodiments, the solvent is ethanol. In some embodiments, the Boc in Compound vii may be replaced by a group chosen from benzyl (Bn), tetrahydropyranyl (THP), 9-fluorenylmethyl carbamate (Fmoc), benzyl carbamate (Cbz), acetamide, trifluoroacetamide, triphenylmethylamine, benzylideneamine, and p-toluenesulfonamide. In some embodiments, $R^1$ is a protecting group. In some embodiments, $R^1$ is chosen from t-butyl carbamate (Boc), benzyl (Bn), tetrahydropyranyl (THP), 9-fluorenylmethyl carbamate (Fmoc), benzyl carbamate (Cbz), acetamide, trifluoroacetamide, triphenylmethylamine, benzylideneamine, and p-toluenesulfonamide. In certain embodiments, $R^1$ is chosen from t-butyl carbamate (Boc), benzyl (Bn), and tetrahydropyranyl (THP). In certain embodiments, $R^1$ is t-butyl carbamate (Boc). In some embodiments, $R^b$ is a $C_1$-$C_4$ alkyl group. In certain embodiments, $R^b$ is ethyl.

In some embodiments, Compound 4

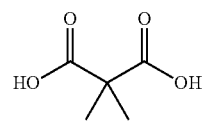

4 is converted to Compound 3

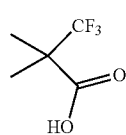

3 in the presence of $SF_4$. In some embodiments, the reaction is performed in a solvent. In some embodiments, the solvent is water.

In some embodiments, Compound 3

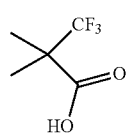

3 is converted to Compound 5

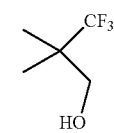

5 in the presence of a reagent. In some embodiments, the reagent is a reducing agent. In some embodiments, the reducing agent is chosen from boranes, borohydrides, and aluminum hydrides. In some embodiments, the reducing agent is chosen from sodium bis(2-methoxyethoxy)aluminum hydride (Vitride®), diisobutylaluminium hydride (DIBAL), and lithium aluminum hydride ($LiAlH_4$).

In other embodiments, Compound 3

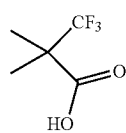

3 is converted to Compound 5

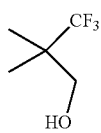

5 under catalytic hydrogenation conditions. In some embodiments, the conditions comprise hydrogen and a catalyst chosen from carbonylchlorohydrido{bis[2-(diphenylphosphino methyl)ethyl]amino}ethyl]amino}ruthenium(II) (Ru-MACHO), [2-(di-tert-butylphosphino methyl)-6-(diethylaminomethyl)pyridine]carbonylchlorohydridoruthe-nium (II) (Milstein catalyst), dichlorotriphenylphosphine[2-(diphenylphosphino)-N-(2-pyridinylmethyl) ethanamine] ruthenium(II) (Gusev Ru-PNN), dichlorotriphenylphosphine[bis(2-(ethylthio)ethyl)amine]ruthenium(II) (Gusev Ru-SNS), dichlorobis(2-(diphenyl phosphino)ethylamine)ruthenium (II), [Ru(acetylacetone)₃, 1,1,1-tris(diphenyl phosphinomethyl)ethane (triphos)], and [Ru(acetylacetone)₃, 1,1,1-tris(diphenylphosphino methyl)ethane (triphos), Zn]. In some embodiments, the conditions further comprising a base. In some embodiments, the base is chosen from potassium tertbutoxide and sodium methoxide.

In some embodiments, Compound 5

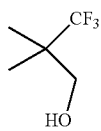

5 and Compound vii

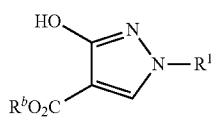

vii react to form Compound viii

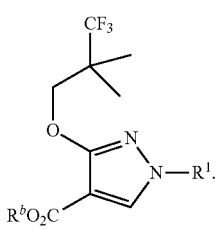

viii

In some embodiments, the reaction is performed in the presence of triphenylphosphine and an azodicarboxylate. In some embodiments, the azodicarboxylate is diethyl azodicarboxylate (DEAD) or diisopropyl azodicarboxylate (DIAD). In some embodiments, the reaction is performed in the presence of an azodicarboxylate and a trialkylphosphine or triarylphosphine. In some embodiments, R¹ is a protecting group. In some embodiments, R¹ is chosen from t-butyl carbamate (Boc), benzyl (Bn), tetrahydropyranyl (THP), 9-fluorenylmethyl carbamate (Fmoc), benzyl carbamate (Cbz), acetamide, trifluoroacetamide, triphenylmethylamine, benzylideneamine, and p-toluenesulfonamide. In certain embodiments, R¹ is chosen from t-butyl carbamate (Boc), benzyl (Bn), and tetrahydropyranyl (THP). In certain embodiments, R¹ is t-butyl carbamate (Boc). In some embodiments, R^b is a C₁-C₄ alkyl group. In certain embodiments, R^b is ethyl.

In some embodiments, Compound viii

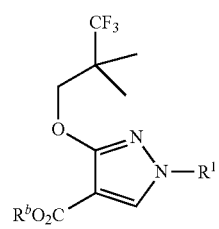

viii is converted to Compound 6

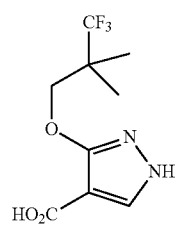

6 in the presence of an acid or base. In some embodiments, the base is chosen from KOtBu, KOH, and NaOH. In some embodiments, the acid is HCl. In some embodiments, the reaction is performed in a solvent. In some embodiments, the solvent is water and/or methanol and/or ethanol. In some embodiments, R¹ is a protecting group. In some embodiments, R¹ is chosen from t-butyl carbamate (Boc), benzyl (Bn), tetrahydropyranyl (THP), 9-fluorenylmethyl carbamate (Fmoc), benzyl carbamate (Cbz), acetamide, trifluoroacetamide, triphenylmethylamine, benzylideneamine, and p-toluenesulfonamide. In certain embodiments, R¹ is chosen from t-butyl carbamate (Boc), benzyl (Bn), and tetrahydropyranyl (THP). In certain embodiments, R¹ is t-butyl carbamate (Boc). In some embodiments, R^b is a C₁-C₄ alkyl group. In certain embodiments, R^b is ethyl.

In some embodiments, Compound 6

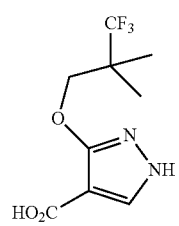

6 is converted to Compound 7

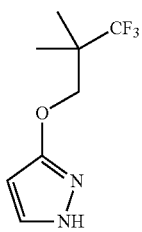

7 optionally in the presence of a reagent. In some embodiments, the reagent is a base. In some embodiments, the reagent is an acid. In some embodiments, the base is chosen from 1,8-diazabicyclo[5.4.0]undec-7-ene (DBU), aqueous sodium hydroxide, and potassium tert-butoxide. In some embodiments, the acid is chosen from aqueous HCl and acetic acid. In some embodiments, the reaction occurs thermally and not in the presence of a reagent. In some embodiments, the reaction is performed in a solvent. In some embodiments, the solvent is chosen from DMF, water, 2-methyltetrahydrofuran, DMSO, and toluene.

In some embodiments, Compound 7

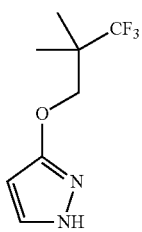

7 and Compound 8

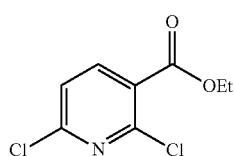

8 react to form Compound 9

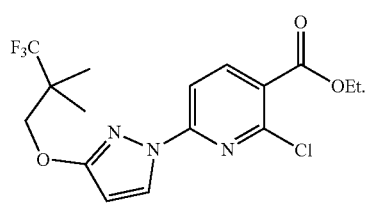

9

In some embodiments, the reaction is performed in the presence of 1,4-diazabicyclo[2.2.2] octane (DABCO). In some embodiments, the reaction is performed in the presence of a base. In some embodiments, the base is chosen from triethylamine, metal carbonates (e.g., cesium carbonate, potassium carbonate, or sodium carbonate), potassium tert-butoxide, potassium phosphate, DBU, and 1,1,3,3-tetramethylguanidine (TMG). In some embodiments, the base is 1,1,3,3-tetramethylguanidine (TMG) or potassium carbonate. In some embodiments, the base is DBU. In some embodiments, the reaction is performed in a solvent. In some embodiments, the solvent is chosen from DMF, acetonitrile, tetrahydrofuran, and DMSO.

In some embodiments, Compound 9

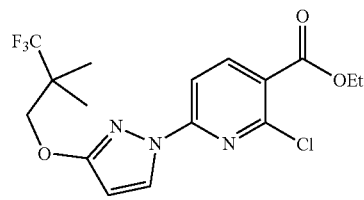

9 is converted to Compound 10

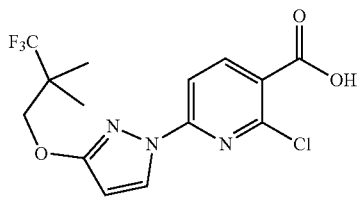

10 in the presence of a base. In some embodiments, the base is NaOH. In some embodiments, the reaction is performed in a solvent. In some embodiments, the solvent is water and/or ethanol. In some embodiments, the solvent is 2-MeTHF and/or ethanol.

In some embodiments, Compound 11

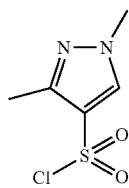

11 is converted to Compound 12

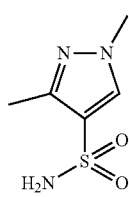

12 in the presence of ammonia. In some embodiments, the ammonia is in methanol.

In some embodiments, Compound 10

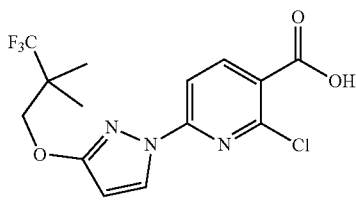

and Compound 12

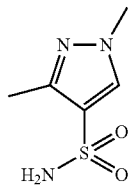

react to form Compound 13

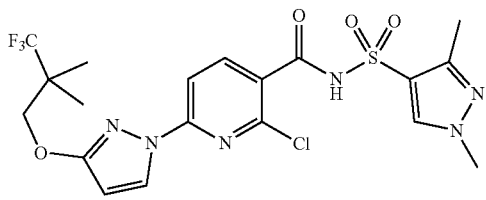

in the presence of a base. In some embodiments, the base is DBU. In some embodiments, the reaction is performed in a solvent. In some embodiments, the solvent is THF. In some embodiments, Compound 10 is first reacted with a coupling agent. In some embodiments, the coupling agent is carbonyldiimidazole (CDI).

In some embodiments, Compound 13

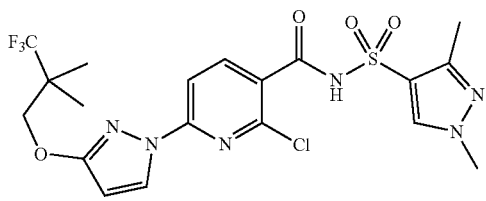

and Compound 17S

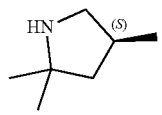

or a salt thereof, react to form Compound 1

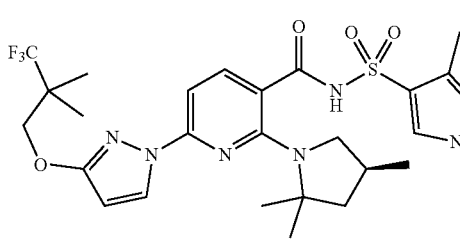

in the presence of a base. In some embodiments, the base is K$_2$CO$_3$. In some embodiments, a salt of Compound 17S is used. In some embodiments, the salt of Compound 17S is a hydrochloride salt. In some embodiments, the reaction is performed in a single solvent or a mixture of solvents. In some embodiments, the single solvent is selected from NMP, DMF, and DMSO. In some embodiments, the mixture of solvents comprises a first and a second solvent. The first solvent may be selected from NMP, DMF, and DMSO and the second solvent may be selected from DEE, i-BuOAc, n-BuOAc, and n-BuOH. In some embodiments, a mixture of NMP and n-BuOAc is used. In some embodiments, the solvent is a mixture of NMP and i-BuOAc. In some embodiments, the first solvent and second solvent are in a ratio of 10:1. In some embodiments, the first solvent and second solvent are in a ratio of about 5:1. In some embodiments, the first solvent and second solvent are in a ratio of about 4:1. In some embodiments, the first solvent and second solvent are in a ratio of about 2:1. In some embodiments, the first solvent and second solvent are in a ratio of about 1:1. In some embodiments, the first solvent and second solvent are in a ratio of about 1:2. In some embodiments, the first solvent and second solvent are in a ratio of about 1:4. In some embodiments, the first solvent and second solvent are in a ratio of about 1:5. In some embodiments, the first solvent and second solvent are in a ratio of about 1:10.

Synthesis of Pyrrolidine Intermediates

PCT/US2018/044963, incorporated herein by reference, discloses the following intermediates and methods of producing those intermediates that can be utilized in the processes disclosed herein:

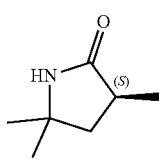

((S)-3,5,5-trimethylpyrrolidine-2-one),

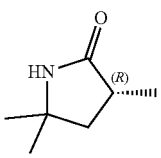

((R)-3,5,5-trimethylpyrrolidine-2-one),

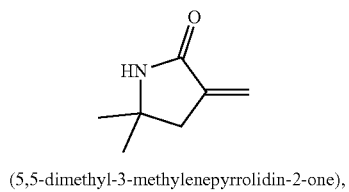

(5,5-dimethyl-3-methylenepyrrolidin-2-one),

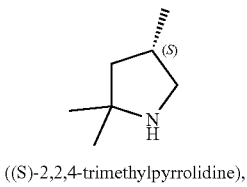

((S)-2,2,4-trimethylpyrrolidine),

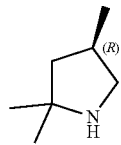

((R)-2,2,4-trimethylpyrrolidine), and pharmaceutically acceptable salts and/or derivatives thereof.

(S)-2,2,4-Trimethylpyrrolidine may be prepared by the process of Scheme 2, comprising:
- (a) reacting 2,2,6,6-tetramethyl-piperidin-4-one with chloroform and at least one base;
- (b) reacting the products of the reaction in (a) with an acid to produce 5,5-dimethyl-3-methylenepyrrolidin-2-one;
- (c) performing an enantioselective hydrogenation of 5,5-dimethyl-3-methylenepyrrolidin-2-one to produce (S)-3,5,5-trimethyl-pyrrolidin-2-one; and
- (d) reducing (S)-3,5,5-trimethyl-pyrrolidin-2-one to produce (S)-2,2,4-trimethylpyrrolidine.

(S)-3,5,5-trimethyl-pyrrolidin-2-one may be recrystallized to increase its chiral purity.

Scheme 2. Synthesis of (S)-2,2,4-trimethylpyrrolidine

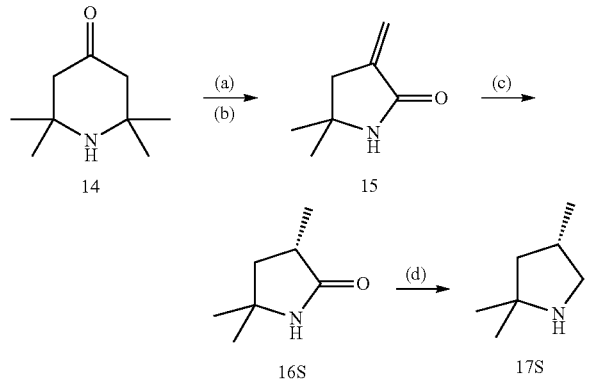

A salt of (S)-2,2,4-trimethylpyrrolidine may be prepared by:
- (a) reacting 2,2,6,6-tetramethyl-piperidin-4-one with chloroform and at least one base;
- (b) reacting the products of the reaction in (a) with an acid to produce 5,5-dimethyl-3-methylenepyrrolidin-2-one;
- (c) performing an enantioselective hydrogenation of 5,5-dimethyl-3-methylenepyrrolidin-2-one to produce (S)-3,5,5-trimethyl-pyrrolidin-2-one;
- (d) reducing (S)-3,5,5-trimethyl-pyrrolidin-2-one to produce (S)-2,2,4-trimethylpyrrolidine; and
- (e) treating (S)-2,2,4-trimethylpyrrolidine with acid to produce a salt of (S)-2,2,4-trimethylpyrrolidine.

(R)-2,2,4-trimethylpyrrolidine may be prepared by a process of Scheme 3, comprising:
- (a) reacting 2,2,6,6-tetramethyl-piperidin-4-one with chloroform and at least one base;
- (b) reacting the products of the reaction in (a) with an acid to produce 5,5-dimethyl-3-methylenepyrrolidin-2-one;
- (c) performing an enantioselective hydrogenation of 5,5-dimethyl-3-methylenepyrrolidin-2-one to produce (R)-3,5,5-trimethyl-pyrrolidin-2-one; and
- (d) reducing (R)-3,5,5-trimethyl-pyrrolidin-2-one to produce (R)-2,2,4-trimethylpyrrolidine.

Scheme 3. Synthesis of (R)-2,2,4-trimethylpyrrolidine

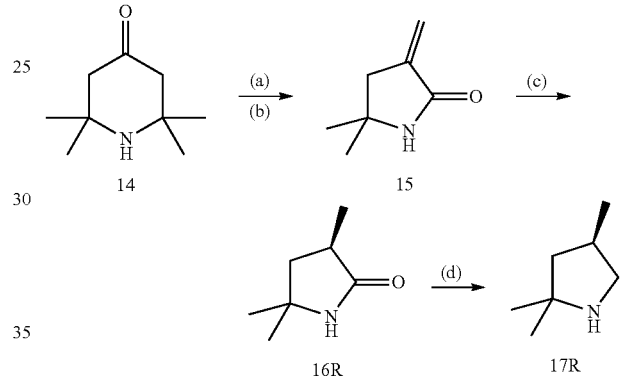

A salt of (R)-2,2,4-trimethylpyrrolidine may be prepared by a process comprising:
- (a) reacting 2,2,6,6-tetramethyl-piperidin-4-one with chloroform and at least one base;
- (b) reacting the products of the reaction in (a) with an acid to produce 5,5-dimethyl-3-methylenepyrrolidin-2-one;
- (c) performing an enantioselective hydrogenation of 5,5-dimethyl-3-methylenepyrrolidin-2-one to produce (R)-3,5,5-trimethyl-pyrrolidin-2-one;
- (d) reducing (R)-3,5,5-trimethyl-pyrrolidin-2-one to produce (R)-2,2,4-trimethylpyrrolidine; and
- (e) treating (R)-2,2,4-trimethylpyrrolidine with acid to produce a salt of (R)-2,2,4-trimethylpyrrolidine.

In Scheme 2 and Scheme 3, the piperidone ring of Compound 14 is contracted and acid is added to promote formation of predominantly Compound 15. In Scheme 2, the olefin group of Compound 15 is hydrogenated in the presence of chiral ligands to produce Compound 16S in (S) configuration. The carbonyl group of Compound 16S is reduced to form Compound 17S. The (S) configuration of Compound 16S is retained in Compound 17S. In Scheme 3, the olefin group of Compound 15 is hydrogenated in the presence of chiral ligands to produce Compound 16R in (R) configuration. The carbonyl group of Compound 16R is reduced to form Compound 17R. The (R) configuration of Compound 16R is retained in Compound 17R.

In some embodiments, Compound 14 is commercially available. In some embodiments, contraction of piperidone ring of Compound 14 to yield pyrrolidine of Compound 15 is carried out in the presence of NaOH and tri-butyl methyl ammonium chloride. In some embodiments, the reaction is further treated with hydrochloric acid to promote predominantly Compound 15.

In some embodiments, Compound 15 undergoes enantioselective hydrogenation in the presence of chiral ruthenium catalysts with phosphine ligands.

In some embodiments, Compound 16S or 16R is reduced with lithium aluminum hydride. In some embodiments, Compound 16S or 16R is reduced with lithium aluminum deuteride.

5,5-Dimethyl-3-methylenepyrrolidin-2-one may be prepared by a process of Scheme 4, comprising:
(a) reacting 2,2,6,6-tetramethyl-piperidin-4-one with chloroform and at least one base; and
(b) reacting the products of the reaction in (a) with an acid to produce 5,5-dimethyl-3-methylenepyrrolidin-2-one.

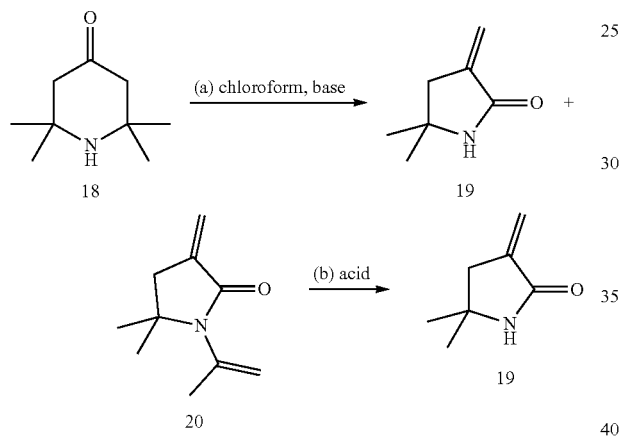

Without being bound to a particular theory, in the methods described herein, the reaction of 2,2,6,6-tetramethyl-piperidin-4-one (Compound 18 in Scheme 4) with chloroform and at least one base in the reaction in Step (a) generates 5,5-dimethyl-3-methylenepyrrolidin-2-one (Compound 19) and 5,5-dimethyl-3-methylene-1-(prop-1-en-2-yl)pyrrolidin-2-one (Compound 20) as shown in Scheme 4, and the acid treatment in the reaction in Step (b) converts Compound 20 (a co-product from the reaction in Step (a) along with Compound 19) to Compound 19, which can provide an improved yield of Compound 19. Optionally, the reaction in Step (b) is conducted without isolation of the products of the reaction in Step (a).

(S)-3,5,5-trimethylpyrrolidin-2-one may be prepared by the process of Scheme 5, comprising:
(a) reacting 2,2,6,6-tetramethyl-piperidin-4-one with chloroform and at least one base;
(b) reacting the products of the reaction in (a) with an acid to produce 5,5-dimethyl-3-methylenepyrrolidin-2-one; and
(c) performing an enantioselective hydrogenation of 5,5-dimethyl-3-methylenepyrrolidin-2-one to produce (S)-3,5,5-trimethyl-pyrrolidin-2-one.

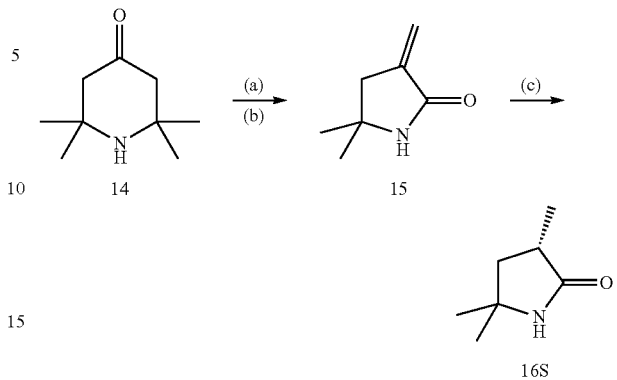

(R)-3,5,5-trimethylpyrrolidin-2-one may be prepared by the process of Scheme 6, comprising:
(a) reacting 2,2,6,6-tetramethyl-piperidin-4-one with chloroform and at least one base;
(b) reacting the products of the reaction in (a) with an acid to produce 5,5-dimethyl-3-methylenepyrrolidin-2-one; and
(c) performing enantioselective hydrogenation of 5,5-dimethyl-3-methylenepyrrolidin-2-one to produce (R)-3,5,5-trimethyl-pyrrolidin-2-one.

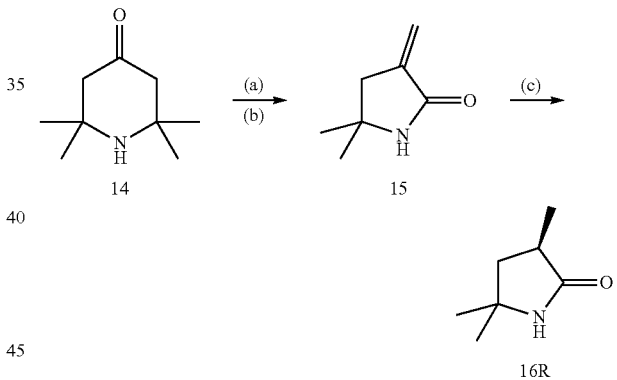

Step (a) Reaction of 2,2,6,6-tetramethyl-piperidin-4-one with chloroform and at least one base As noted above, 2,2,6,6-tetramethyl-piperidin-4-one may be reacted with chloroform and at least one base. In some embodiments, the at least one base is chosen from potassium t-butoxide, potassium hydroxide, and sodium hydroxide. In some embodiments, the at least one base is sodium hydroxide.

In some embodiments, 3 to 15 molar equivalents of the at least one base relative to the mole of 2,2,6,6-tetramethylpiperidin-4-one are added for the reaction in Step (a). In some embodiments, 5 to 12 molar equivalents of the at least one base are added. In some embodiments, 7.5 molar equivalents of the at least one base are added. In some embodiments, 10 molar equivalents of said at least one base are added. In some embodiments, 8 molar equivalents of sodium hydroxide are added.

In some embodiments, the at least one base in the reaction Step (a) is in solid form in at least one anhydrous solvent. In some embodiments, the at least one anhydrous solvent is chosen from dimethylsulfoxide and isopropyl alcohol.

In some embodiments, the at least one base in the reaction Step (a) is in the form of an aqueous solution having a concentration ranging from 20 wt % to 80 wt % relative to the total weight of the solution. In some embodiments, the at least one base is 20 wt % aqueous NaOH. In some embodiments, the at least one base is 30 wt % aqueous NaOH. In some embodiments, the at least one base is 40 wt % aqueous NaOH. In some embodiments, the at least one base is 50 wt % aqueous NaOH.

In some embodiments, chloroform in the reaction Step (a) is present in an amount ranging from 1 to 4 molar equivalents relative to the mole of 2,2,6,6-tetramethylpiperidin-4-one. In some embodiments, the chloroform is present in an amount ranging from 1.5 to 3.5 molar equivalents relative to the mole of 2,2,6,6-tetramethylpiperidin-4-one. In some embodiments, the chloroform is present in an amount of 1.75 molar equivalents relative to the mole of 2,2,6,6-tetramethylpiperidin-4-one.

In some embodiments, 2,2,6,6-tetramethyl-piperidin-4-one is reacted with chloroform, at least one base, and at least one solvent. In some embodiments, the at least one solvent is chosen from organic solvents. In some embodiments, the at least one solvent is immiscible with water. In some embodiments, the volume of the at least one solvent ranges from 0.1 to 10 volume equivalents relative to the volume of 2,2,6,6-tetramethylpiperidin-4-one. In some embodiments, the volume of the at least one solvent ranges from 1 to 4 volume equivalents relative to the volume of 2,2,6,6-tetramethylpiperidin-4-one. In some embodiments, the volume of the at least one solvent ranges from 1 to 3 volume equivalents relative to the volume of 2,2,6,6-tetramethylpiperidin-4-one. In some embodiments, the volume of the at least one solvent ranges from 1.5 to 2.5 volume equivalents relative to the volume of 2,2,6,6-tetramethylpiperidin-4-one. In some embodiments, the volume of the at least one solvent is 2 volume equivalents of the at least one solvent relative to the volume of 2,2,6,6-tetramethylpiperidin-4-one. In some embodiments, the at least one solvent is chosen from dichloromethane, heptane, chloroform, trifluorotoluene, tetrahydrofuran (THF), and n-methylpyrrolidone (NMP). In some embodiments, the at least one solvent is chosen from dichloromethane and heptane. In some embodiments, the at least one solvent is dichloromethane.

In some embodiments, the reaction Step (a) is performed without the at least one solvent.

In some embodiments, the reaction in Step (a) is performed without the use of phase transfer catalyst.

In some embodiments, in the reaction in Step (a), in addition to chloroform and at least one base, 2,2,6,6-tetramethyl-piperidin-4-one is reacted with at least one phase transfer catalyst. In some embodiments, the at least one phase transfer catalyst is chosen from tetraalkylammonium salts and crown ethers such as 18-crown-6 and 15-crown-5 phase transfer catalysts. In some embodiments, the at least one phase transfer catalyst is chosen from crown ethers, such as 18-crown-6 and 15-crown-5 phase transfer catalysts. In some embodiments, the at least one phase transfer catalyst is chosen from tetraalkylammonium salts. In some embodiments, the at least one phase transfer catalyst is chosen from tetraalkylammonium halides. In some embodiments, the at least one phase transfer catalyst is chosen from tributylmethylammonium chloride, tributylmethylammonium bromide, tetrabutylammonium bromide (TBAB), tetrabutylammonium chloride (TBAC), tetrabutylammonium iodide (TBAI), tetrabutylammonium hydroxide (TBAH), benzyltrimethylammonium chloride, tetraoctylammonium bromide (TOAB), tetraoctylammonium chloride (TOAC), tetraoctylammonium iodide (TOAI), trioctylmethylammonium chloride, and trioctylmethylammonium bromide.

In some embodiments, 0.01 molar equivalents to 0.2 molar equivalents of the at least one phase transfer catalyst relative to the mole of 2,2,6,6-tetramethylpiperidin-4-one is added to the reaction in (a). In some embodiments, 0.02 molar equivalents to 0.1 molar equivalents of said at least one phase transfer catalyst relative to the mole of 2,2,6,6-tetramethylpiperidin-4-one is added. In some embodiments, 0.03 molar equivalents to 0.06 molar equivalents of said at least one phase transfer catalyst relative to the mole of 2,2,6,6-tetramethylpiperidin-4-one is added. In some embodiments, 0.01 molar equivalents to 1 molar equivalent, such as to 0.2 molar equivalents, 0.4 molar equivalents, 0.6 molar equivalents, or 0.8 molar equivalents of said at least one phase transfer catalyst relative to the mole of 2,2,6,6-tetramethylpiperidin-4-one is added.

Step (b) Reaction of the products of the reaction in Step (a) with acid to produce 5,5-dimethyl-3-methylenepyrrolidin-2-one In some embodiments, the acid of the reaction in Step (b) is chosen from aqueous solutions of protic acids. In some embodiments, the protic acids are chosen from hydrochloric acid, methane sulfonic acid, triflic acid, and sulfuric acid. In some embodiments, the concentration of said aqueous solutions of protic acids range from 1M to 18M. In some embodiments, the concentration of said aqueous solutions of protic acids range from 2M to 10M. In some embodiments, the acid of the reaction in Step (b) is chosen from HCl having a concentration ranging from 2M to 3M. In some embodiments, the acid of the reaction in Step (b) is chosen from 2M HCl. In some embodiments, the acid of the reaction in Step (b) is chosen from 2.5M HCl. In some embodiments, the acid of the reaction in Step (b) is chosen from 3M HCl. In some embodiments, 0.5 to 10 molar equivalents of said acid relative to the mole of 2,2,6,6-tetramethylpiperidin-4-one are added to the reaction in Step (b). In some embodiments, 1 to 4 molar equivalents of said acid relative to the mole of 2,2,6,6-tetramethylpiperidin-4-one are added to the reaction in Step (b). In some embodiments, 1.5 molar equivalents of said acid relative to the mole of 2,2,6,6-tetramethylpiperidin-4-one are added to the reaction in Step (b).

In some embodiments, the yield of 5,5-dimethyl-3-methylenepyrrolidin-2-one produced from the reactions in Step (a) and Step (b) ranges from 40% to 70% relative to the mole of 2,2,6,6-tetramethylpiperidin-4-one. In some embodiments, the yield of 5,5-dimethyl-3-methylenepyrrolidin-2-one produced from the reactions in Step (a) and Step (b) ranges from 30% to 80% relative to the mole of 2,2,6,6-tetramethylpiperidin-4-one. In some embodiments, the yield of 5,5-dimethyl-3-methylenepyrrolidin-2-one produced from the reactions in Step (a) and Step (b) ranges from 50% to 70% relative to the mole of 2,2,6,6-tetramethylpiperidin-4-one. In some embodiments, the yield of 5,5-dimethyl-3-methylenepyrrolidin-2-one produced from the reactions in Step (a) and Step (b) ranges from 60% to 80% relative to the mole of 2,2,6,6-tetramethylpiperidin-4-one.

Step (c) Enantioselective hydrogenation of 5,5-dimethyl-3-methylenepyrrolidin-2-one to produce (S)- or (R)-3,5,5-trimethyl-pyrrolidin-2-one 5,5-dimethyl-3-methylenepyrrolidin-2-one can be hydrogenated to produce (S)- or (R)-3,5,5-trimethyl-pyrrolidin-2-one.

In some embodiments, the hydrogenation comprises reacting 5,5-dimethyl-3-methylenepyrrolidin-2-one with at least one catalyst and hydrogen gas to produce (S)-3,5,5-trimethyl-pyrrolidin-2-one. In some embodiments, the at least one catalyst is chosen from metals from the platinum group. As used herein, the term "platinum group" means ruthenium, rhodium, palladium, osmium, iridium, and platinum. In some embodiments, the at least one catalyst is chosen from ruthenium hydrogenation catalysts, rhodium hydrogenation catalysts, and iridium hydrogenation catalysts.

In some embodiments, the hydrogenation comprises reacting 5,5-dimethyl-3-methylenepyrrolidin-2-one with at least one catalyst and hydrogen gas to produce (R)-3,5,5-trimethyl-pyrrolidin-2-one. In some embodiments, the at least one catalyst is chosen from ruthenium hydrogenation catalysts, rhodium hydrogenation catalysts, and iridium hydrogenation catalysts.

The at least one catalyst may be heterogeneous or homogeneous. In some embodiments, the at least one catalyst is heterogeneous. In some embodiments, the at least one catalyst is homogenous. In some embodiments, the at least one catalyst comprises platinum. In some embodiments, the at least one catalyst comprises rhodium, ruthenium, or iridium. In some embodiments, the at least one catalyst employs at least one ligand. In some embodiments, the at least one ligand is chiral. In some embodiments, the at least one catalyst employs at least one phosphorus-containing ligand.

In some embodiments, the hydrogenation is enantioselective. Enantioselective hydrogenation can be done using a chiral ligand. In some embodiments, the at least one catalyst employs at least one chiral phosphorus-containing ligand. In some embodiments, the at least one chiral phosphorus-containing ligand is a chiral tertiary diphosphine. In some embodiments, the at least one catalyst employs at least one atropisomeric ligand, such as BINAP, Tol-BINAP, T-BINAP, H8-BINAP, Xyl-BINAP, DM-BINAP, or MeOBiphep. In some embodiments, the at least one catalyst employs at least one segphos-based ligand, such as segphos, dm-segphos, or dtbm-segphos. In some embodiments, the at least one catalyst employs at least one chiral ferrocenyl-based ligand, such as Josiphos, Walphos, Mandyphos, or Taniaphos. Non-limiting examples of BINAP include (R)-(+)-(1,1'-Binaphthalene-2,2'-diyl)bis(diphenylphosphine), (R)-(+)-2,2'-Bis(diphenylphosphino)-1,1'-binaphthalene ((R)-(+)-BINAP), (S)-(−)-(1,1'-Binaphthalene-2,2'-diyl)bis(diphenylphosphine), and (S)-(−)-2,2'-Bis(diphenylphosphino)-1,1'-binaphthalene ((S)-(−)-BINAP)). A non-limiting example of Tol-BINAP is (R)-(+)-2,2'-Bis(di-p-tolylphosphino)-1,1'-binaphthyl. Non-limiting examples of T-BINAP include (S)-(−)-2,2'-p-tolyl-phosphino)-1,1'-binaphthyl, (S)-Tol-BINAP. Examples of H8-BINAP include (R)-(+)-2,2'-Bis(diphenylphospino)-5,5',6,6',7,7',8,8'-octahydro-1,1'-binaphthyl, [(1R)-5,5',6,6',7,7',8,8'-octahydro-[1,1'-binaphthalene]-2,2'-diyl]bis[diphenylphosphine], and (S)-(−)-2,2'-Bis(diphenylphospino)-5,5',6,6',7,7',8,8'-octahydro-1,1'-binaphthyl, [(1S)-5,5',6,6',7,7',8,8'-octahydro-[1,1'-binaphthalene]-2,2'-diyl]bis[diphenylphosphine]. Non-limiting examples of DM-BINAP include (R)-(+)-1,1'-Binaphthalene-2,2'-diyl)bis[bis(3,5-dimethylphenyl)phosphine] and (R)-(+)-2,2'-Bis[di(3,5-xylyl)phosphino]-1,1'-binaphthyl. A non-limiting example of Xyl-BINAP is (R)-(+)-XylBINAP and (S)-(+)-XylBINAP available from Takasago International Corp. Non-limiting examples of MeOBiphep include (R)-(6,6'-Dimethoxybiphenyl-2,2'-diyl)bis[bis(3,5-di-tert-butyl-4-methoxyphenyl)phosphine], (S)-(6,6'-Dimethoxybiphenyl-2,2'-diyl)bis[bis(3,5-di-tert-butyl-4-methoxyphenyl)phosphine, (R)-(6,6'-Dimethoxybiphenyl-2,2'-diyl)bis[bis(3,5-di-tert-butylphenyl)phosphine], (S)-(6,6'-Dimethoxybiphenyl-2,2'-diyl)bis[bis(3,5-di-tert-butylphenyl)phosphine], (R)-(6,6'-Dimethoxybiphenyl-2,2'-diyl)bis{bis[3,5-diisopropyl-4-(dimethylamino)phenyl]phosphine}, (S)-(6,6'-Dimethoxybiphenyl-2,2'-diyl)bis{bis[3,5-diisopropyl-4-(dimethylamino)phenyl]phosphine}, (R)-(6,6'-Dimethoxybiphenyl-2,2'-diyl)bis[bis(3,5-dimethylphenyl)phosphine], (S)-(6,6'-Dimethoxybiphenyl-2,2'-diyl)bis[bis(3,5-dimethylphenyl)phosphine], (R)-(6,6'-Dimethoxybiphenyl-2,2'-diyl)bis[bis(4-methylphenyl)phosphine], (S)-(6,6'-Dimethoxybiphenyl-2,2'-diyl)bis[bis(4-methylphenyl)phosphine], (R)-(6,6'-Dimethoxybiphenyl-2,2'-diyl)bis[bis(3,4,5-trimethoxyphenyl)phosphine], (S)-(6,6'-Dimethoxybiphenyl-2,2'-diyl)bis[bis(3,4,5-trimethoxyphenyl)phosphine], (R)-(6,6'-Dimethoxybiphenyl-2,2'-diyl)bis(di-2-furylphosphine), (S)-(6,6'-Dimethoxybiphenyl-2,2'-diyl)bis(di-2-furylphosphine), (R)-(6,6'-Dimethoxybiphenyl-2,2'-diyl)bis(diisopropylphosphine), (S)-(6,6'-Dimethoxybiphenyl-2,2'-diyl)bis(diisopropylphosphine), (R)-(+)-(6,6'-Dimethoxybiphenyl-2,2'-diyl)bis(diphenylphosphine), and (S)-(−)-(6,6'-Dimethoxybiphenyl-2,2'-diyl)bis(diphenylphosphine). Non-limiting examples of segphos include (R)-(+)-5,5'-Bis(diphenylphosphino)-4,4'-bi-1,3-benzodioxole (or [4(R)-(4,4'-bi-1,3-benzodioxole)-5,5'-diyl]bis[diphenylphosphine]) and (S)-(−)-5,5'-Bis(diphenylphosphino)-4,4'-bi-1,3-benzodioxole. Non-limiting examples of dtbm-segphos include (R)-(−)-5,5'-Bis[di(3,5-di-tert-butyl-4-methoxyphenyl)phosphino]-4,4'-bi-1,3-benzodioxole (or [(4R)-(4,4'-bi-1,3-benzodioxole)-5,5'-diyl]bis[bis(3,5-di-tert-butyl-4-methoxyphenyl)phosphine]) and (S)-(+)-5,5'-Bis[di(3,5-di-tert-butyl-4-methoxyphenyl)phosphino]-4,4'-bi-1,3-benzodioxole. Examples of dm-segphos include (S)-(+)-5,5'-Bis[di(3,5-di-tert-butyl-4-methoxyphenyl)phosphino]-4,4'-bi-1,3-benzodioxole and (R)-(+)-5,5'-Bis[di(3,5-xylyl)phosphino]-4,4'-bi-1,3-benzodioxole (or [(4R)-(4,4'-bi-1,3-benzodioxole)-5,5'-diyl]bis[bis(3,5-dimethylphenyl)phosphine]). Non-limiting examples of chiral ferrocenyl-based ligands can be found in US 2015/0045556 (the chiral ligand descriptions of which are incorporated herein by reference). Non-limiting examples chiral ferrocenyl-based ligands include:

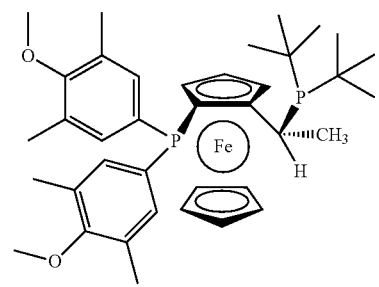

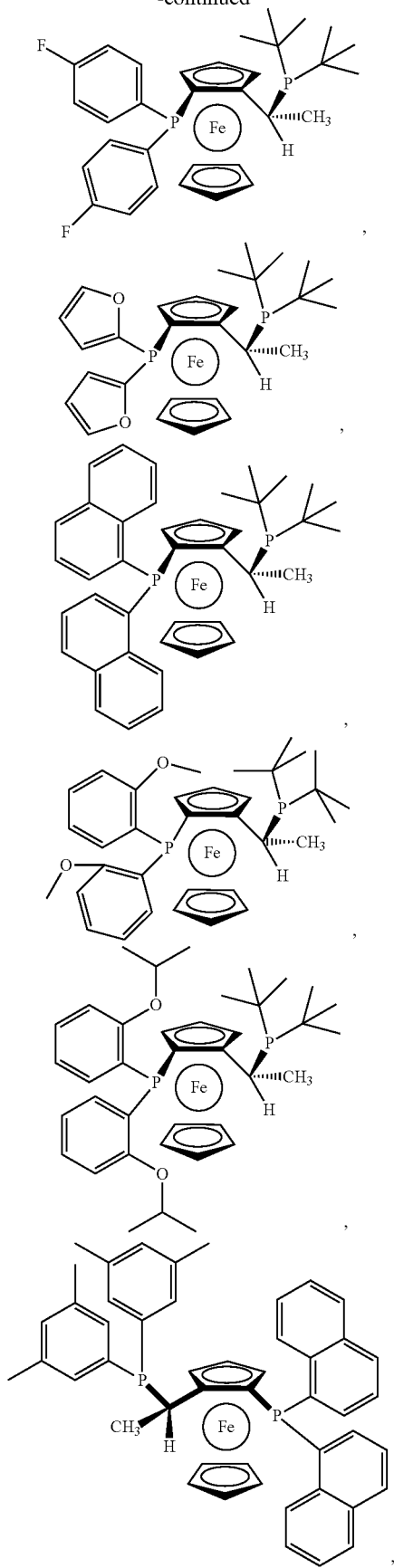
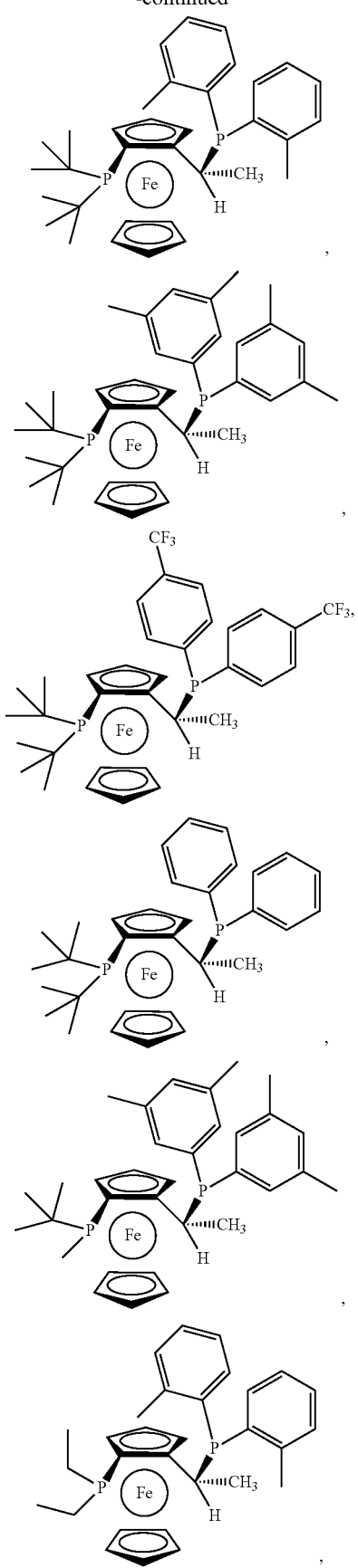

33
-continued
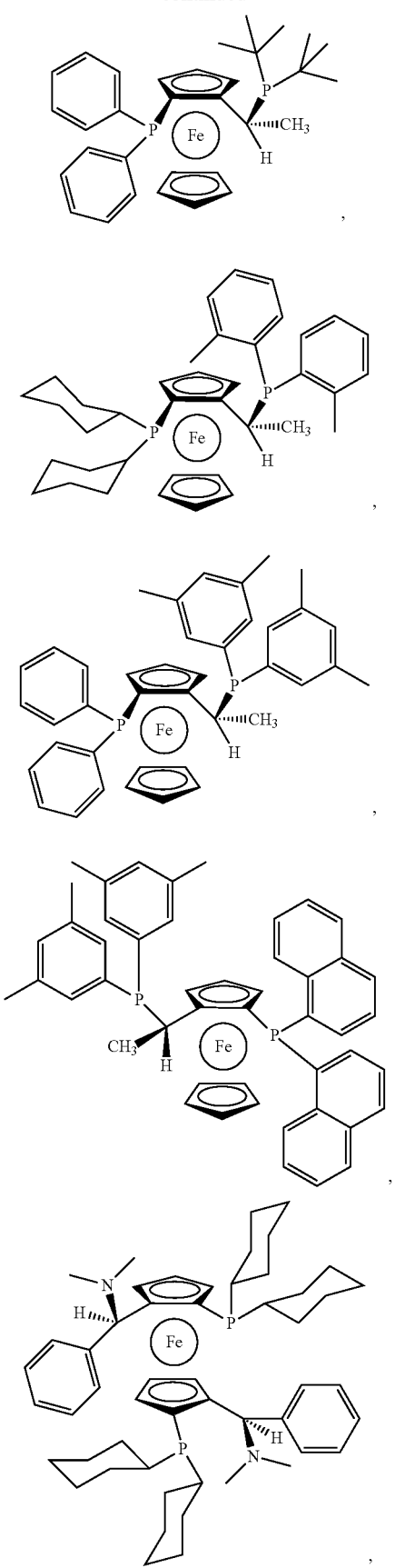
34
-continued
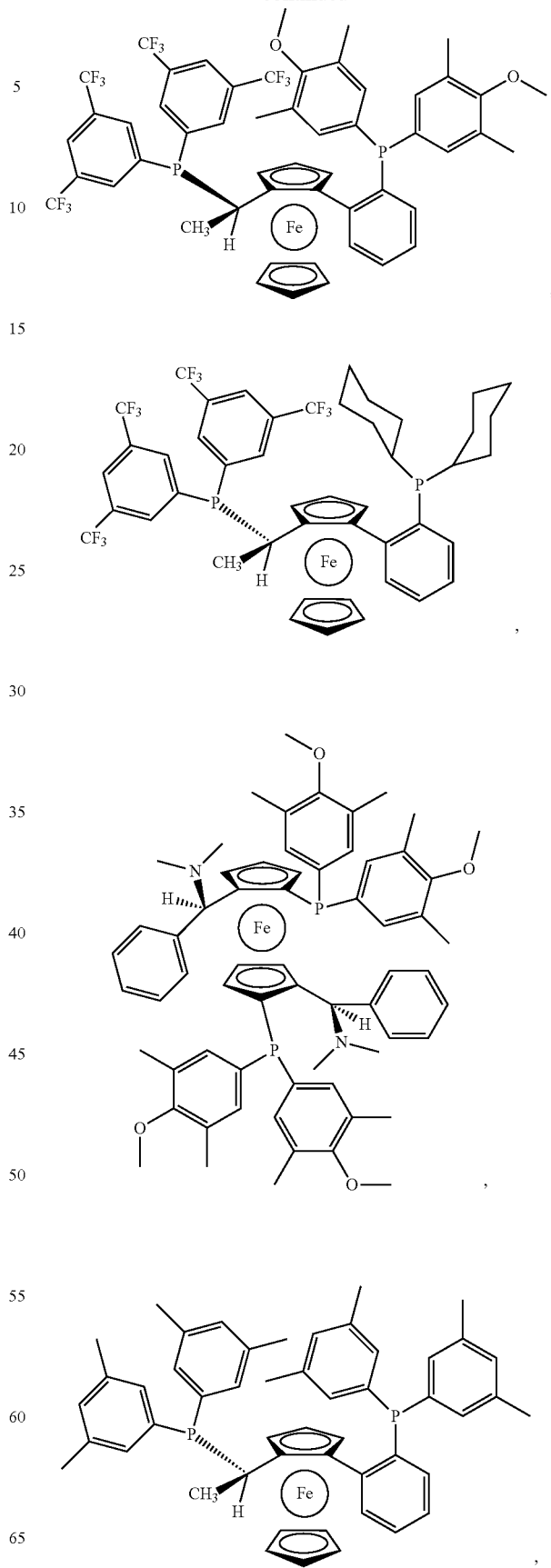

-continued

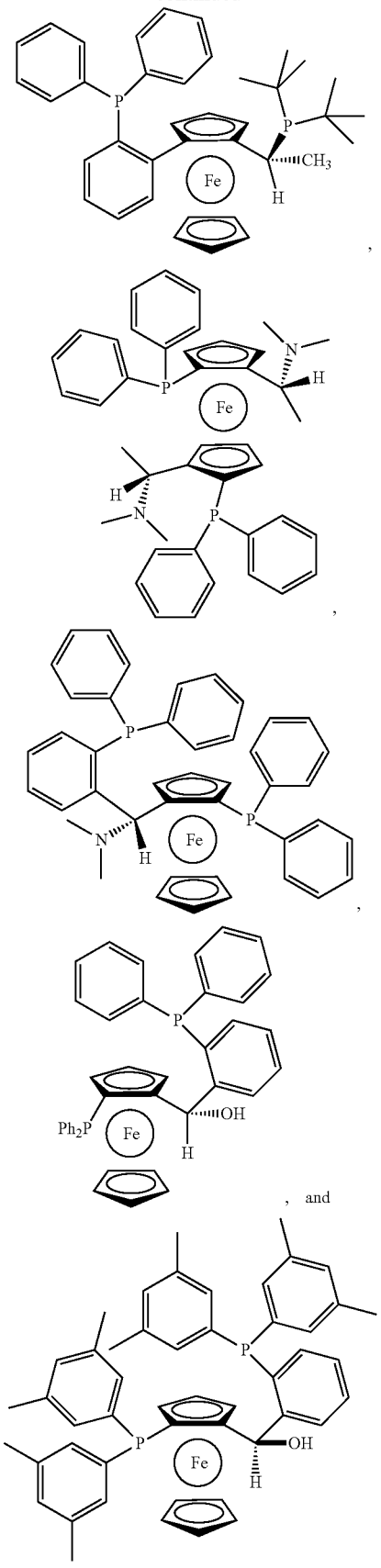

, and

In some embodiments, the hydrogenation is carried out in the presence of at least one chiral ligand. In some embodiments, the at least one chiral ligand is chosen from phosphine ligands, BINOL, TADDOL, BOX, DuPhos, DiPAMP, BINAP, Tol-BINAP, T-BINAP, H8-BINAP, DM-BINAP, Xyl-BINAP, MeOBiphep, DIOP, PHOX, PyBox, SALENs, SEGPHOS, DM-SEGPHOS, DTBM-SEGPHOS, JOSIPHOS, MANDYPHOS, WALPHOS, TANIAPHOS, sPHOS, xPHOS, SPANphos, Triphos, Xantphos, and Chiraphos ligands. In some embodiments, the at least one chiral ligand is a SEGPHOS ligand. In some embodiments, the at least one chiral ligand is a MANDYPHOS ligand. In some embodiments, the at least one chiral ligand is a MANDYPHOS SL-M004-1 available from, for example, Solvias. In some embodiments, the at least one chiral ligand is chosen from the following:

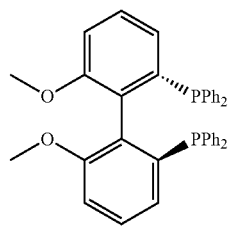

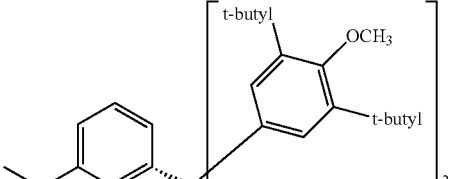

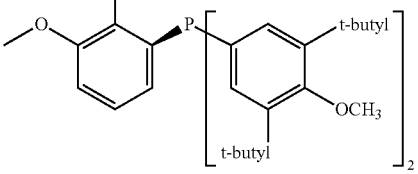

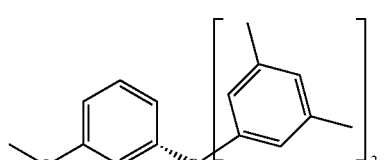

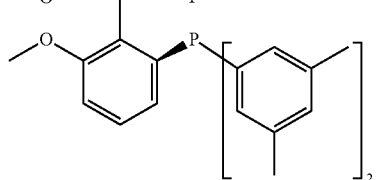

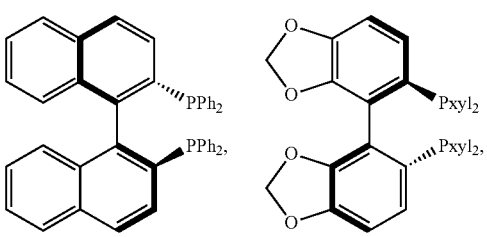

37
-continued
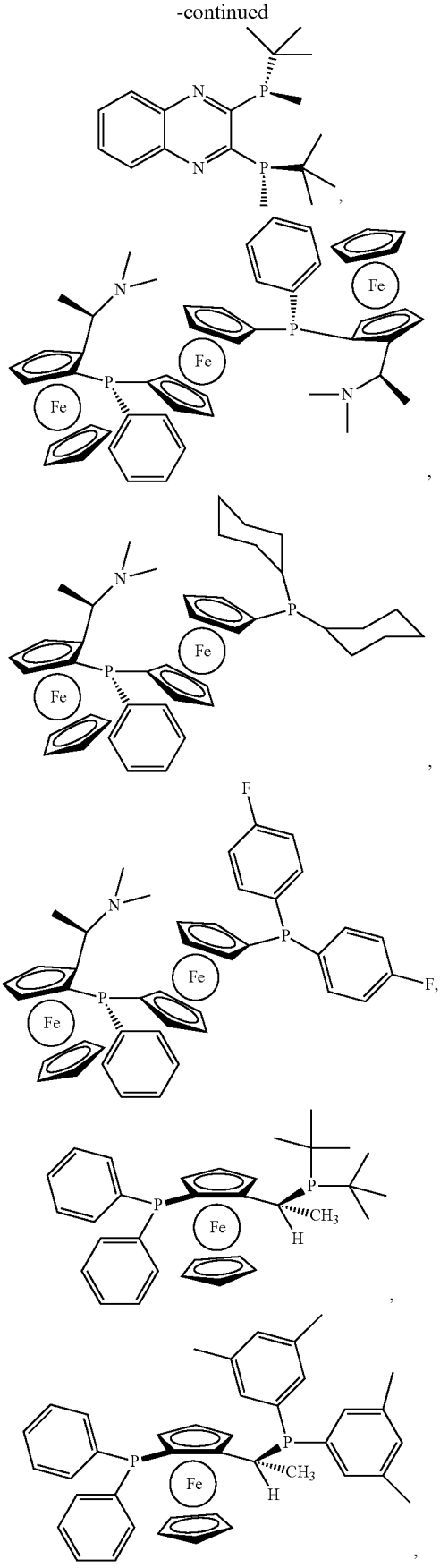
38
-continued
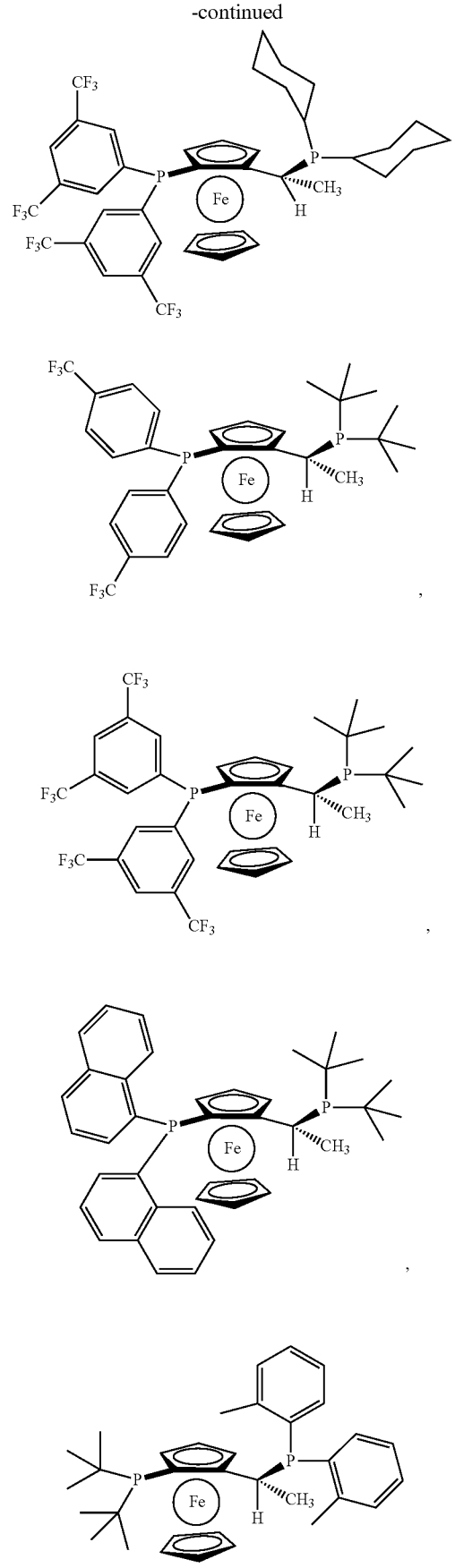

-continued
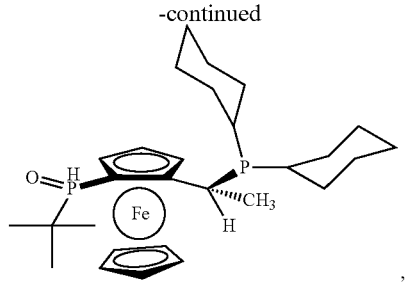
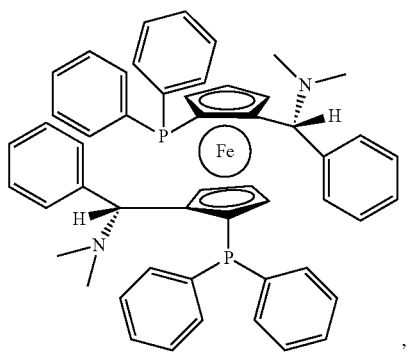
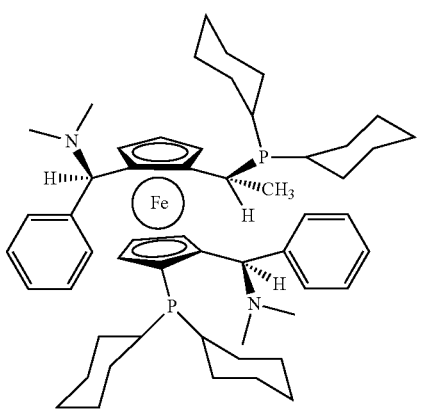
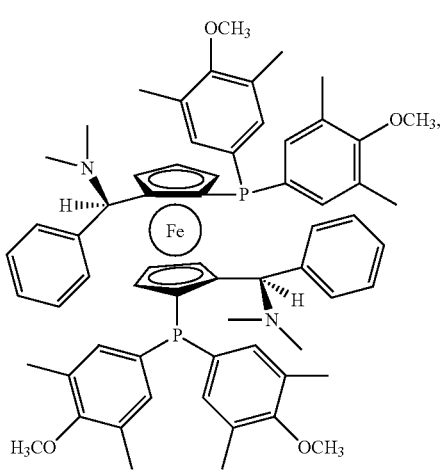
-continued
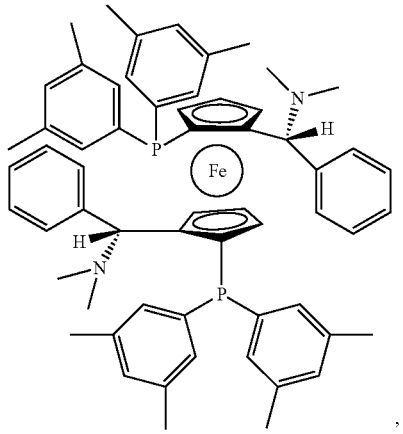
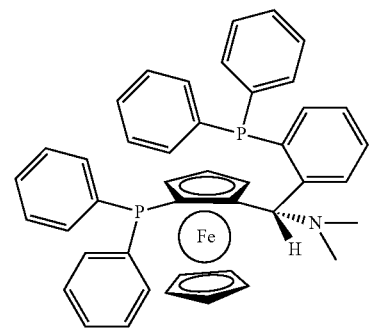
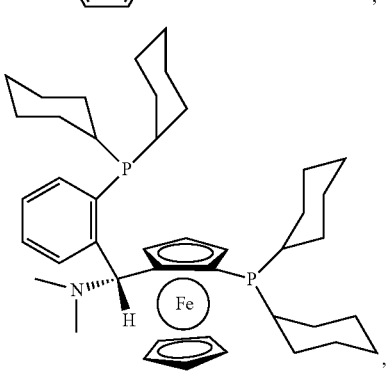
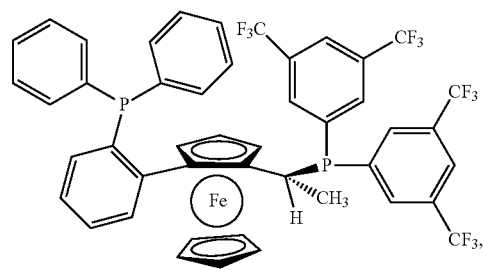
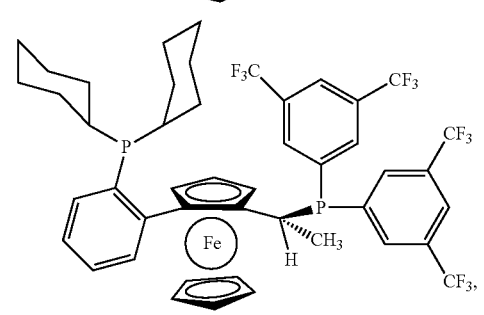

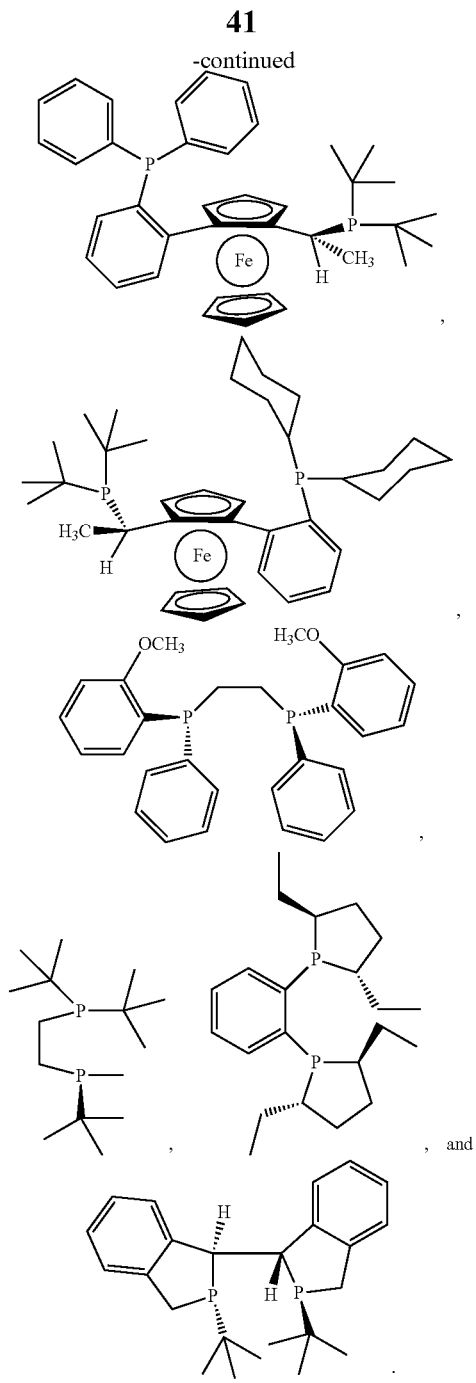
, and

In some embodiments, the hydrogenation is carried out in the presence of at least one transition metal. In some embodiments, the at least one transition metal is chosen from the platinum group metals. In some embodiments, the at least one transition metal is chosen from rhodium, ruthenium, rhenium, and palladium. In some embodiments, the at least one transition metal is ruthenium. In some embodiments, the at least one transition metal is rhodium.

In some embodiments, hydrogenation is carried out in the presence of at least one catalyst chosen from: [Rh(nbd)Cl]$_2$; [Rh(COD)$_2$OC(O)CF$_3$]; [Rh(COD)(Ligand A)BF$_4$; [Rh(COD)(Ligand B)BF$_4$; [Rh(COD)(Ligand C)BF$_4$; and [Rh(COD)(Ligand D)BF, wherein COD is 1,5-cyclooctadiene; Ligand A is:

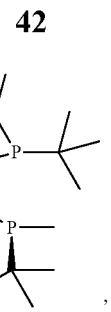

Ligand B is:

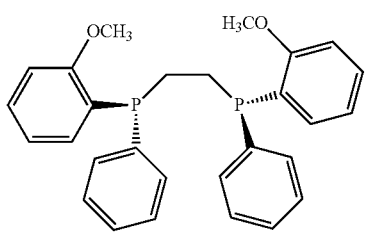

Ligand C is

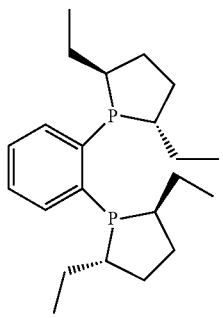

and Ligand D is

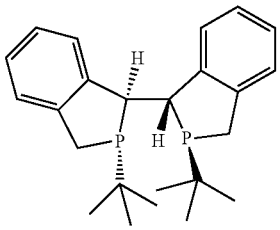

In some embodiments, hydrogenation is carried out in the presence of at least one catalyst chosen from: [Ru(COD)$_2$ Me-allyl)$_2$]BF$_4$, [RuCl(p-cymene){(R)-segphos}]Cl; [RuCl(p-cymene){(R)-binap}]Cl; Ru(OAc)$_2$[(R)-binap]; [NH$_2$Me$_2$][{RuCl[(R)-binap]}$_2$(µ-Cl)$_3$]; [RuCl(p-cymene){(R)-Xyl-binap}]Cl; [NH$_2$Me$_2$][{RuCl[(R)-Xyl-binap]}$_2$(µ-Cl)$_3$]; [RuCl(p-cymene){(R)—H8-binap}]Cl; [NH$_2$Me$_2$][{RuCl[(R)—H8-binap]}$_2$(µ-Cl)$_3$]; [NH$_2$Me$_2$][{RuCl[(R)-segphos]}$_2$(µ-Cl)$_3$]; [NH$_2$Me$_2$][{RuCl[(R)-dm-segphos]}$_2$(µ-Cl)$_3$]; [RuCl(p-cymene){(R)-dtbm-segphos}]Cl, wherein p-cymene is 1-methyl-4-(propan-2-yl)benzene, Me-allyl is 2-methylallyl, and OAC is acetate. In some embodiments, hydrogenation is carried out in the presence of [RuCl(p- cymene){(R)-segphos}]Cl. In some embodiments, hydrogenation is carried out in the presence of [Ru(COD)₂Me-allyl)₂]BF₄. In some embodiments, hydrogenation is carried out in the presence of [RuCl(p-cymene){(R)-segphos}]Cl; [RuCl(p-cymene){(R)-binap}]Cl; and/or [NH₂Me₂][{RuCl[(R)-segphos]}₂(µ-Cl)₃].

In some embodiments, the hydrogenation is carried out in the presence of at least one catalyst prepared in situ with a metal precursor and a ligand. In some embodiments, the at least one ligand is chosen from chiral ligands set forth above. In some embodiments, the at least one ligand is chosen from:

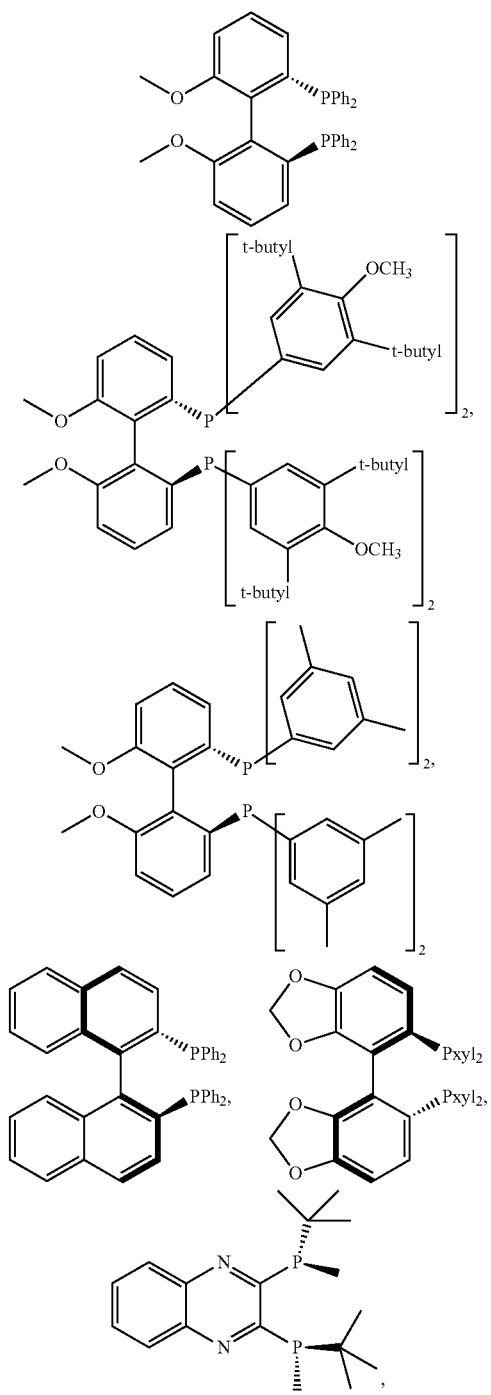

-continued

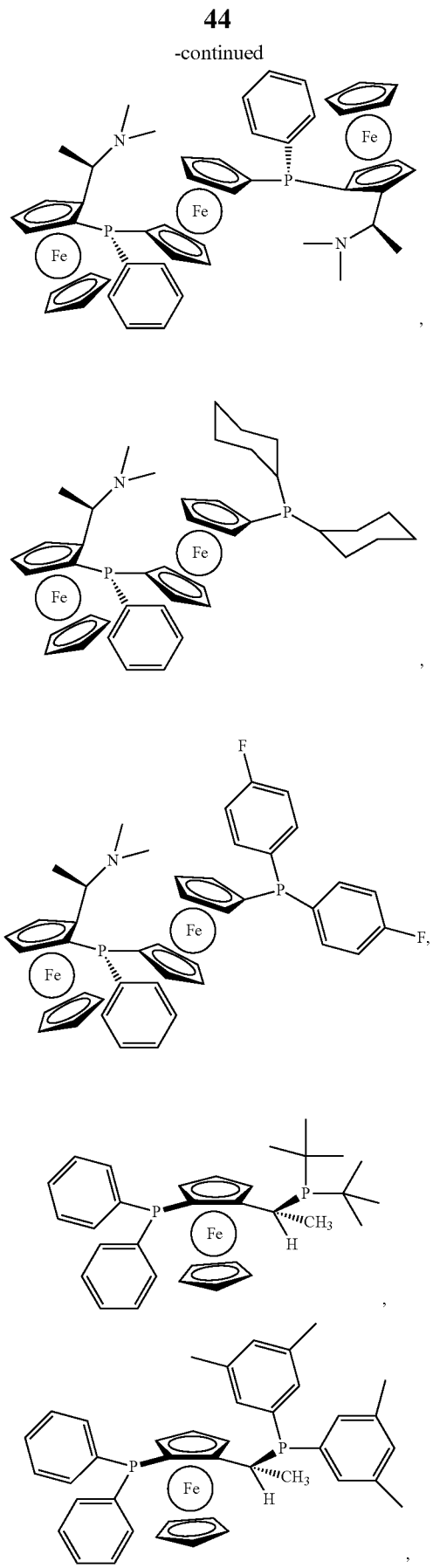

-continued
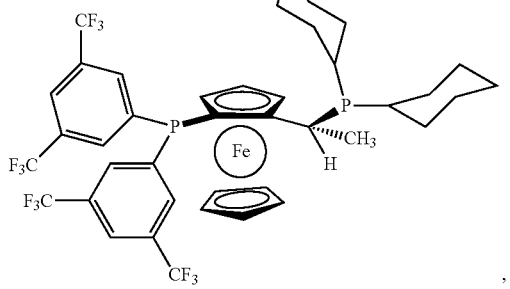
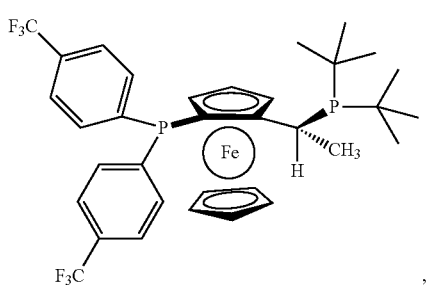
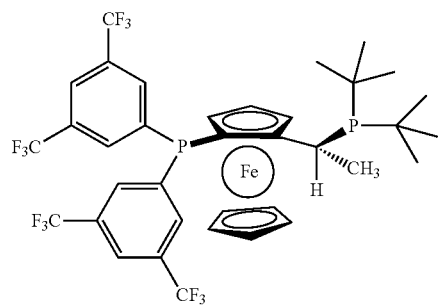
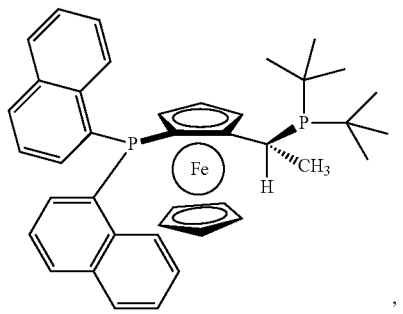
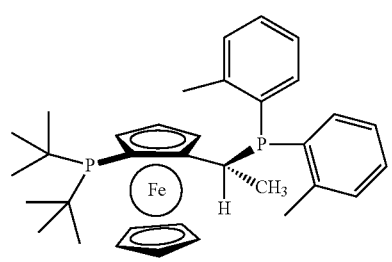
-continued
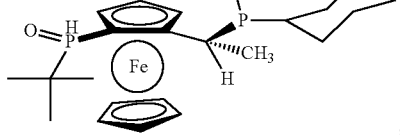
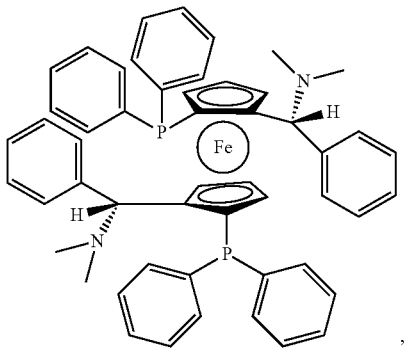
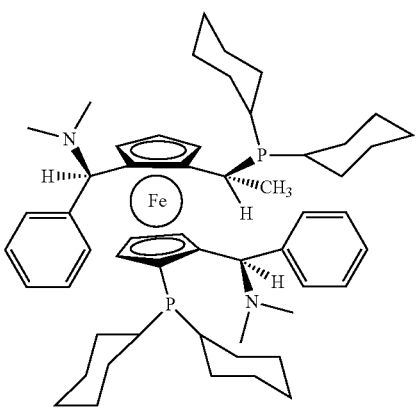
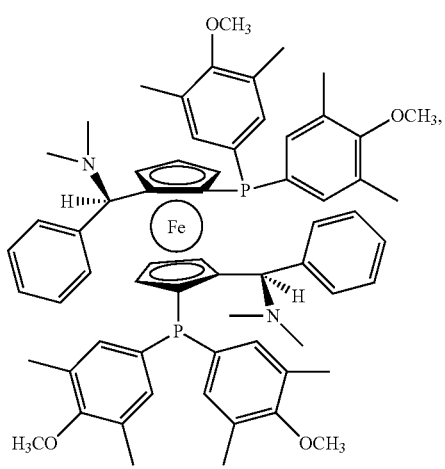

-continued

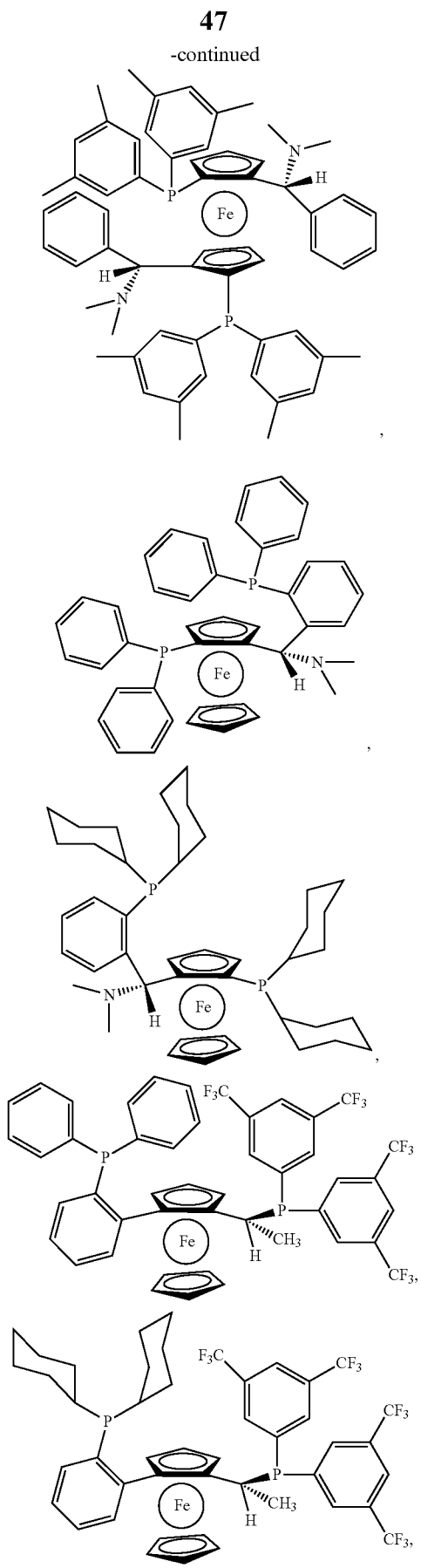

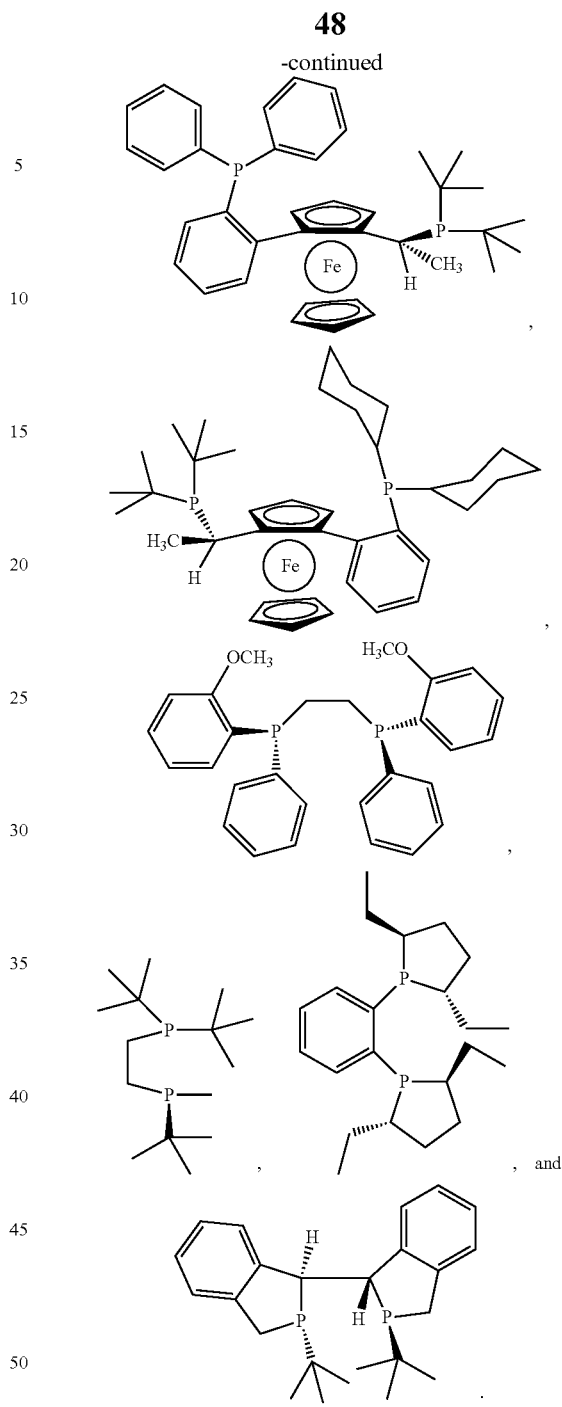

In some embodiments, at least one metal precursor is chosen from [Rh(nbd)Cl]$_2$; [Rh(COD)$_2$OC(O)CF$_3$]; [Rh(COD)(Ligand A)BF$_4$; [Rh(COD)(Ligand B)BF$_4$; [Rh(COD)(Ligand C)BF$_4$; [Rh(COD)(Ligand D)BF$_4$, [Ru(COD)(OC(O)CF$_3$)$_2$], [Ru(COD)Me-allyl)$_2$], [Rh(COD)(Ligand A)BF$_4$; [Rh(COD)(Ligand B)BF$_4$; [Rh(COD)(Ligand C)BF$_4$, and [Rh(COD)(Ligand D)BF.

In some embodiments, the hydrogenation is carried out at a temperature of 10° C. to 70° C. In some embodiments, hydrogenation is carried out at a temperature of 30° C. to 50° C. In some embodiments, hydrogenation is carried out at 45° C. In some embodiments, hydrogenation is carried out at 30° C.

Step (d) Reducing (S)- or (R)-3,5,5-trimethyl-pyrrolidin-2-one to produce free base or salts of (S)- or (R)-2,2,4-trimethylpyrrolidine, respectively In some embodiments, the process of producing intermediates comprises reducing (S)- or (R)-3,5,5-trimethyl-pyrrolidin-2-one to produce (S)- or (R)-2,2,4-trimethylpyrrolidine, respectively. In some embodiments, the reduction is performed in the presence of at least one reducing agent. In some embodiments, the at least one reducing agent is a hydride. In some embodiments, the hydride is chosen from lithium aluminum hydride, lithium aluminum deuteride, sodium bis(2-methoxyethoxy)aluminumhydride, and borane. In some embodiments, 1-2 equivalents of hydride are added. In some embodiments, the reducing agent is lithium aluminum hydride.

In some embodiments, the reduction is carried out at 40° C. to 100° C. In some embodiments, the reduction is carried out at 40° C. to 80° C. In some embodiments, the reduction is carried out at 50° C. to 70° C. In some embodiments, the reduction is carried out at 68° C.

In some embodiments, the reducing agent is hydrogen gas. In some embodiments, the reduction is carried out in the presence of one or more catalysts and hydrogen gas. In some embodiments, the reduction is carried out in the presence of one or more metallic catalysts and hydrogen gas. In some embodiments, the reduction is carried out under a catalytic hydrogenation condition in the presence of one or more catalysts and hydrogen gas. In some embodiments, the catalyst is chosen from Pt, Co, Sn, Rh, Re, and Pd. In some embodiments, the reduction is carried out in the presence of hydrogen gas and one or more catalysts chosen from Pt, Co, Sn, Rh, Re, and Pd. In some embodiments, the reduction is carried out in the presence of hydrogen gas and one or more monometallic or bimetallic catalysts chosen from Pt, Pd, Pt—Re, Pt—Co, Pt—Sn, Pd—Re, and Rh—Re. Any suitable amounts of such catalysts can be used for the reduction. In some embodiments, 0.1 wt %-5 wt % of such catalysts can be used. In some embodiments, such catalysts are used in one or more support materials selected from $TiO_2$, $SiO_2$, $Al_2O_3$ (e.g., theta-$Al_2O_3$ or gamma-$Al_2O_3$), and zeolite. In some embodiments, the reduction is carried out in the presence of hydrogen gas and one or more monometallic or bimetallic catalysts chosen from Pt—Sn in $TiO_2$ (or Pt—Sn/$TiO_2$), Pt—Re in $TiO_2$ (or Pt—Re/$TiO_2$), Pt in $TiO_2$ (or Pt/$TiO_2$), Rh in $TiO_2$ (or Rh/$TiO_2$), Rh—Re in $TiO_2$ (or Rh—Re/$TiO_2$), Pt—Sn in theta-$Al_2O_3$ (or Pt—Sn/theta-$Al_2O_3$), Pt—Sn in $SiO_2$ (or Pt—Sn/$SiO_2$), and Pt—Sn in $TiO_2$ (or Pt—Sn/$TiO_2$). In some embodiments, the reduction is carried out in the presence of hydrogen gas and one or more monometallic or bimetallic catalysts chosen from 4 wt % Pt-2 wt % Sn in $TiO_2$ (or 4 wt % Pt-2 wt % Sn/$TiO_2$), 4 wt % Pt-2 wt % Re in $TiO_2$ (or 4 wt % Pt-2 wt % Re/$TiO_2$), 4 wt % Pt in $TiO_2$ (or 4 wt % Pt/$TiO_2$), 4 wt % Rh in $TiO_2$ (or 4 wt % Rh/$TiO_2$), 4 wt % Rh-2% Re in $TiO_2$ (or 4 wt % Rh-2 wt % Re/$TiO_2$), 4 wt % Pt-2 wt % Sn in theta-$Al_2O_3$ (or 4 wt % Pt-2 wt % Sn/theta-$Al_2O_3$), 4 wt % Pt-2 wt % Sn in $SiO_2$ (or 4 wt % Pt-2 wt % Sn/$SiO_2$), 2 wt % Pt-0.5 wt % Sn in $SiO_2$ (or 2 wt % Pt-0.5 wt % Sn/$SiO_2$), 2 wt % Pt-0.5 wt % Sn in $TiO_2$ (or 2 wt % Pt-0.5 wt % Sn/$TiO_2$), and 2 wt % Pt-8 wt % Sn in $TiO_2$ (or 2 wt % Pt-8 wt % Sn/$TiO_2$).

In some embodiments, the reducing agent is quenched after reaction. In some embodiments, the reducing agent is quenched by sodium sulfate. In some embodiments, the reducing agent is quenched by water and then 15 wt % KOH in water.

In some embodiments, the product from the reduction step with a hydride is further treated with acid to produce a salt.

In some embodiments, the acid is chosen from hydrochloric acid, hydrobromic acid, phosphoric acid, sulfuric acid, oxalic acid, citric acid, a tartaric acid (e.g., L- or D-tartaric acid or dibenzoyl tartaric acid), a malic acid (e.g., L- or D-malic acid), a maleic acid (e.g., L- or D-maleic acid, 4-bromo-mandelic acid or 4-bromo-mandelic acid), a tartranilic acid (e.g., L- or D-tartranilic acid, (2,3)-2'-methoxy-tartranilic acid), a mandelic acid (e.g., L- or D-mandelic acid, 4-methyl-mandelic acid. O-acetyl mandelic acid or 2-chloromandelic acid), a tartaric acid (e.g., L- or D-mandelic acid, di-p-toluoyltartaric acid, di-p-anisoyltartaric acid), acetic acid, alpha-methoxy-phenyl acetic acid, a lactic acid (e.g., L- or D-lactic acid, 3-phenyllactic acid), a phenylalanine (e.g., N-acetyl-phenylalanine, Boc-homophenyl-alanine, or Boc-phenylalanine), a glutamic acid (e.g., L- or D-glutamic acid or pyroglutamic acid), phencyphos hydrate, chlocyphos, camphor sulfonic acid, camphoric acid, anisyphos, 2-phenylpropionic acid, N-acetyl-leucine, BINAP phosphate, N-acetyl-proline, α-hydroxyisovaleric acid, phenylsuccinic acid, and/or naproxen.

In some embodiments, the reduction and acid treatment reactions are performed without isolation of the reduction product. In some embodiments, (R)-3,5,5-trimethyl-pyrrolidin-2-one is reacted with a hydride and then with an acid to produce an (R)-2,2,4-trimethylpyrrolidine salt. In some embodiments, (S)-3,5,5-trimethyl-pyrrolidin-2-one is reacted with a hydride and then with an acid to produce an (S)-2,2,4-trimethylpyrrolidine salt.

In some embodiments, the reduction step product (e.g. (S)- or (R)-2,2,4-trimethylpyrrolidine) is isolated before the acid treatment step. In some embodiments, (S)-2,2,4-trimethylpyrrolidine is treated with an acid to produce a salt of (S)-2,2,4-trimethylpyrrolidine. In some embodiments, (R)-2,2,4-trimethylpyrrolidine is treated with an acid to produce a salt of (R)-2,2,4-trimethylpyrrolidine.

Unless otherwise indicated, structures depicted herein are also meant to include compounds that differ only in the presence of one or more isotopically enriched atoms. For example, Compounds 17S, 17R, 15, 16S, and 16R, wherein one or more hydrogen atoms are replaced with deuterium or tritium, or one or more carbon atoms are replaced by a $^{13}$C- or $^{14}$C-enriched carbon are within the scope of this invention. In some embodiments, Compounds 17S, 17R, 15, 16S, and 16R, wherein one or more hydrogen atoms are replaced with deuterium are prepared by the methods described herein. Such compounds are useful, for example, as analytical tools, probes in biological assays, or compounds with improved therapeutic profile.

Another aspect of the invention provides the following exemplary embodiments:

1. A method of preparing a compound of Formula (I):

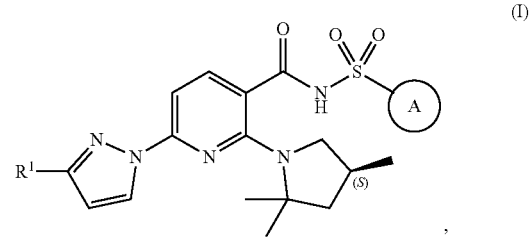

a pharmaceutically acceptable salt thereof, or a deuterated derivative of any of the foregoing, wherein:

$R^1$ is $CF_3$ or $CF_3$;

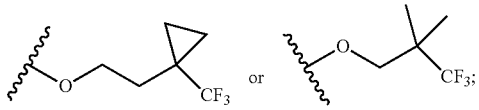

and

Ring A is phenyl or

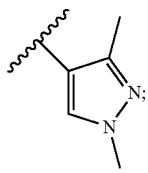

comprising:
(a) reacting 2,2,6,6-tetramethyl-piperidin-4-one or a salt thereof with chloroform and at least one base;
(b) reacting the products of the reaction in (a) with an acid to produce 5,5-dimethyl-3-methylenepyrrolidin-2-one or a salt thereof;
(c) performing an enantioselective hydrogenation of 5,5-dimethyl-3-methylenepyrrolidin-2-one or a salt thereof to produce (S)-3,5,5-trimethyl-pyrrolidin-2-one or a salt thereof;
(d) reducing (S)-3,5,5-trimethyl-pyrrolidin-2-one or a salt thereof to produce (S)-2,2,4-trimethylpyrrolidine;
(e) optionally treating (S)-2,2,4-trimethylpyrrolidine with acid to produce a salt of (S)-2,2,4-trimethylpyrrolidine; and
(f) reacting the (S)-2,2,4-trimethylpyrrolidine or salt thereof with a compound of Formula (F) or a salt thereof:

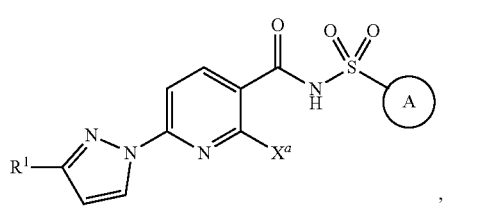

wherein:

$R^1$ is

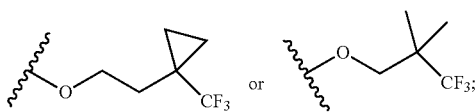

Ring A is phenyl or

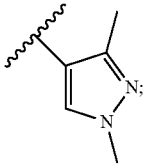 [SMILES: *c1cn(C)nc1C]

and $X^a$ is chosen from halogens, and wherein a compound of Formula (I), a pharmaceutically acceptable salt thereof, or a deuterated derivative of any of the foregoing is produced.

2. The method of embodiment 1, further comprising treating (S)-2,2,4-trimethylpyrrolidine with HCl to generate (S)-2,2,4-trimethylpyrrolidine hydrochloride.

3. The method of embodiment 1, wherein said at least one base added for the reaction in (a) is chosen from potassium t-butoxide, potassium hydroxide, and sodium hydroxide.

4. The method of embodiment 3, wherein from 3 to 15 molar equivalents of said at least one base relative to 2,2,6,6-tetramethylpiperidin-4-one or salt thereof are added for the reaction in (a).

5. The method of embodiment 4, wherein said at least one base is in the form of an aqueous solution having a concentration ranging from 20 wt % to 80 wt % relative to the total weight of said aqueous solution.

6. The method of embodiment 1, wherein said chloroform is present in an amount ranging from 1 to 4 molar equivalents relative to 2,2,6,6-tetramethylpiperidin-4-one or salt thereof.

7. The method of embodiment 6, wherein said 2,2,6,6-tetramethyl-piperidin-4-one or salt thereof is reacted with chloroform, at least one base, and at least one phase transfer catalyst.

8. The method of embodiment 7, wherein said at least one phase transfer catalyst is chosen from tetraalkylammonium salts and crown ethers.

9. The method of embodiment 8, wherein said at least one phase transfer catalyst is chosen from tetraalkylammonium halides.

10. The method of embodiment 9, wherein said at least one phase transfer catalyst is chosen from tributylmethylammonium chloride, tributylmethylammonium bromide, tetrabutylammonium bromide (TBAB), tetrabutylammonium chloride (TBAC), tetrabutylammonium iodide (TBAI), tetrabutylammonium hydroxide (TBAH), benzyltrimethylammonium chloride, tetraoctylammonium bromide (TOAB), tetraoctylammonium chloride (TOAC), tetraoctylammonium iodide (TOAI), trioctylmethylammonium chloride, and trioctylmethylammonium bromide.

11. The method of embodiment 10, wherein from 0.01 molar equivalents to 0.2 molar equivalents of said at least one phase transfer catalyst relative to 2,2,6,6-tetramethylpiperidin-4-one or salt thereof is added to the reaction in (a).

12. The method of any one of embodiments 1-11, wherein said acid of the reaction in (b) is chosen from aqueous solutions of protic acids.

13. The method of embodiment 12, wherein said protic acids are chosen from hydrochloric acid, methane sulfonic acid, triflic acid, and sulfuric acid.

14. The method of embodiment 12, wherein the concentration of said aqueous solutions of protic acids range from 1M to 18M.

15. The method of embodiment 12, wherein the concentration of said aqueous solutions of protic acids range from 2M to 10M.

16. The method of embodiment 12, wherein said acid of the reaction in (b) is chosen from HCl having a concentration ranging from 2M to 3M.

17. The method of embodiment 12, wherein 0.5 to 10 molar equivalents of said acid relative to 2,2,6,6-tetramethylpiperidin-4-one or salt thereof are added to the reaction in (b).

18. The method of embodiment 17, wherein 1 to 4 molar equivalents of said acid relative to 2,2,6,6-tetramethylpiperidin-4-one or salt thereof are added to the reaction in (b).

19. The method of embodiment 1, wherein said enantioselective hydrogenation in (c) comprises reacting 5,5-dimethyl-3-methylenepyrrolidin-2-one or a salt thereof with at least one catalyst and hydrogen gas to produce (S)-3,5,5-trimethyl-pyrrolidin-2-one or a salt thereof.

20. The method of embodiment 19, wherein said catalyst is chosen from ruthenium hydrogenation catalysts, rhodium hydrogenation catalysts, and iridium hydrogenation catalysts.

21. The method of embodiment 1, wherein said reducing reaction in (d) comprises reacting (S)-3,5,5-trimethyl-pyrrolidin-2-one or salt thereof with a reducing agent, such as hydride, to produce (S)-2,2,4-trimethylpyrrolidine.

22. The method of embodiment 21, wherein said reducing reaction comprises reacting 1-2 molar equivalents of the reducing agent, such as hydride, relative to (S)-3,5,5-trimethyl-pyrrolidin-2-one or salt thereof.

23. The method of embodiment 22, wherein said hydride is chosen from lithium aluminum hydride, sodium bis(2-methoxyethoxy)aluminumhydride, and borane.

24. The method of embodiment 22, wherein said reducing reaction comprises reacting a metal catalyst and a source of hydrogen or hydrogen gas.

25. The method of embodiment 1, wherein $X^a$ is —F or —Cl.

26. The method of any one of embodiments 1-25, wherein the reaction in (f) is performed in the presence of at least one base.

27. The method of embodiment 26, wherein the base is chosen from potassium carbonate and potassium phosphate.

28. The method of embodiment 27, wherein the reaction in (f) is performed in the presence of a metal carbonate in at least a first solvent chosen from N-methylpyrrolidine (NMP), DMF, and DMSO, and optionally in the presence of a second solvent selected from diethoxyethane (DEE), n-butylacetate (n-BuOAc), i-BuOAc, and n-BuOH.

29. The method of any one of embodiments 1-28, wherein said compound of Formula (I), pharmaceutically acceptable salt thereof, or deuterated derivative of any of the foregoing is Compound 2, a pharmaceutically acceptable salt thereof, or a deuterated derivative of any of the foregoing:

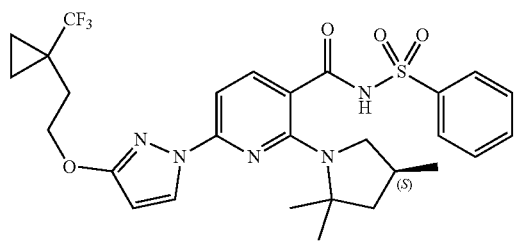

Compound 2

30. The method of embodiment 29, wherein the compound of Formula F or salt thereof is a compound of Formula (F-II) or a salt thereof:

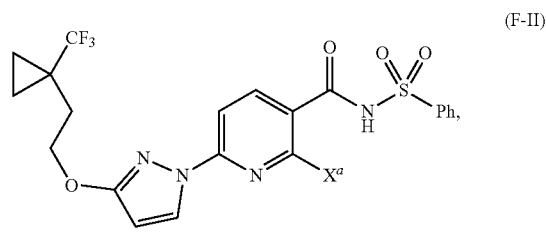

(F-II)

wherein $X^a$ is chosen from halogens.

31. The method of embodiment 30, further comprising reacting a compound of Formula (D-II) or a salt thereof:

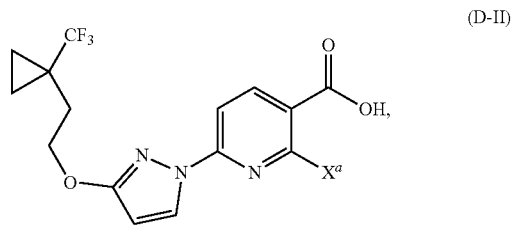

(D-II)

wherein $X^a$ is Cl, with benzenesulfonamide or a salt thereof to produce a compound of Formula (F-II) or a salt thereof:

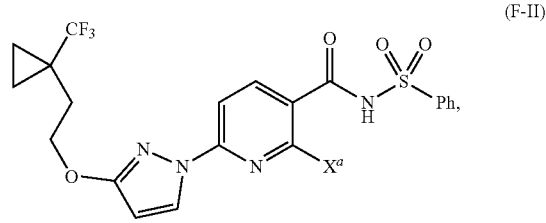

(F-II)

wherein $X^a$ is Cl.

32. The method of embodiment 30, wherein said a compound of Formula (D-II) or a salt thereof is reacted with a coupling reagent and resulting compound or salt is then reacted with benzenesulfonamide or a salt thereof in the presence of at least one base.

33. The method of embodiment 32, wherein said coupling reagent is 1,1'-carbonyldiimidazole (CDI) and said base is 1,8-diazabicyclo[5.4.0]undec-7-ene (DBU) or 1,1,3,3-tetramethylguanidine (TMG).

34. The method of embodiment 32, wherein the reactions are performed in at least one solvent chosen from tetrahydrofuran (THF) and 2-methyltetrahydrofuran (2-MeTHF).

35. The method of any one of embodiments 29-34, further comprising:
a) reacting Compound 39 or a salt thereof:

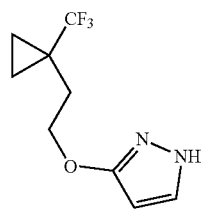

with a compound of Formula (B-I) or a salt thereof:

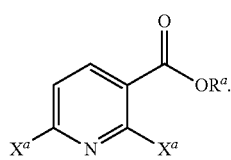

wherein
R$^a$ is chosen from C$_1$-C$_4$ alkyl groups; and
X$^a$ is —F or —Cl;
to produce a compound of Formula (C-II) or a salt thereof:

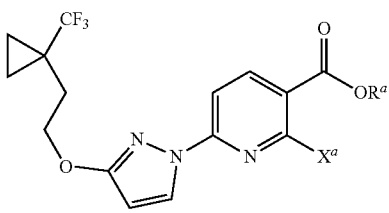

wherein
R$^a$ is chosen from C$_1$-C$_4$ alkyl groups; and
X$^a$ is —F or —Cl;
and
b) hydrolyzing the —C(O)OR$^a$ group of said compound of Formula (C-II) or salt thereof to produce a compound of Formula (D-II) or a salt thereof:

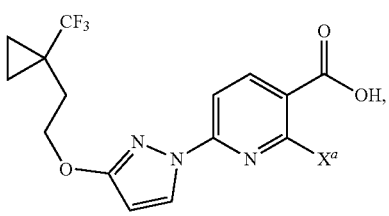

wherein
R$^a$ is chosen from C$_1$-C$_4$ alkyl groups; and
X$^a$ is —F or —Cl.

36. The method of embodiment 35, wherein R$^a$ is ethyl, and the hydrolysis of the —C(O)OR$^a$ group is performed in the presence of at least one base.

37. The method of embodiment 35, wherein R$^a$ is t-butyl, and the hydrolysis of the —C(O)OR$^a$ group is performed in the presence of an acid.

38. The method of any one of embodiments 35-37, wherein the reaction of Compound 39 or salt thereof with the compound of Formula (B-I) or salt thereof is performed in the presence of 1,4-diazabicyclo[2.2.2]octane (DABCO) and at least one base.

39. The method of embodiment 38, wherein the base is chosen from triethylamine, metal carbonates (e.g., cesium carbonate, potassium carbonate, or sodium carbonate), potassium tert-butoxide, potassium phosphate, DBU, and 1,1,3,3-tetramethylguanidine (TMG).

40. The method of any one of embodiments 34-39, further comprising decarboxylating Compound 49

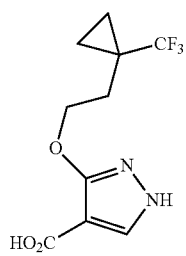

to produce Compound 39 or a salt thereof:

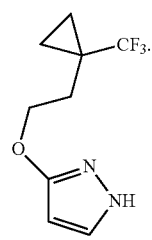

41. The method of embodiment 40, wherein the decarboxylation is performed in the presence of either at least one base or at least one acid.

42. The method of embodiment 41, wherein the base in the decarboxylation is chosen from 1,8-diazabicyclo[5.4.0]undec-7-ene (DBU), aqueous sodium hydroxide, and potassium tert-butoxide; or wherein the acid is chosen from aqueous HCl and acetic acid.

43. A method of preparing Compound 2:

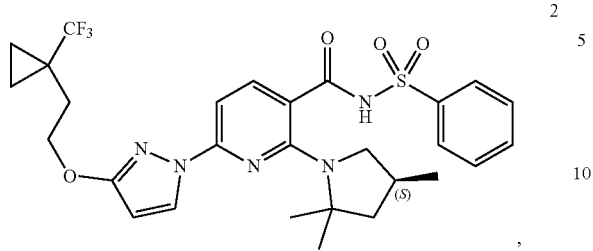

a pharmaceutically acceptable salt thereof, or deuterated derivative of any of the foregoing,
comprising:
  (a) reacting 2,2,6,6-tetramethyl-piperidin-4-one or a salt thereof with chloroform, at least one base chosen from potassium t-butoxide, potassium hydroxide, and sodium hydroxide, and at least one phase transfer catalyst chosen from tetrabutylmethylammonium chloride,
  (b) reacting the products of the reaction in (a) with HCl to produce 5,5-dimethyl-3-methylenepyrrolidin-2-one or a salt thereof,
  (c) performing an enantioselective hydrogenation of 5,5-dimethyl-3-methylenepyrrolidin-2-one or a salt thereof to produce (S)-3,5,5-trimethyl-pyrrolidin-2-one or a salt thereof;
  (d) reducing (S)-3,5,5-trimethyl-pyrrolidin-2-one or a salt thereof to produce (S)-2,2,4-trimethylpyrrolidine;
  (e) treating (S)-2,2,4-trimethylpyrrolidine with HCl to produce an HCl salt of (S)-2,2,4-trimethylpyrrolidine;
  (f) decarboxylating Compound 49:

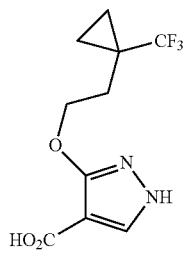

to form Compound 39 or a salt thereof:

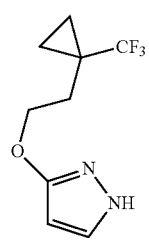

in the presence of at least one base chosen from 1,8-diazabicyclo[5.4.0]undec-7-ene (DBU), aqueous sodium hydroxide, and potassium tert-butoxide, or at least one acid chosen from aqueous HCl and acetic acid;
  (g) reacting Compound 39 or a salt thereof:

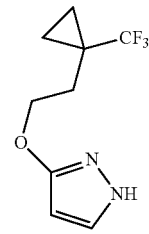

with a compound of Formula (B-I) or a salt thereof:

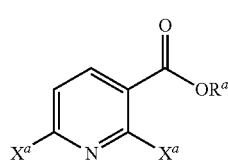

wherein $R^a$ is ethyl; and
each —$X^a$ is Cl;
  to produce a compound of Formula (C-II) or a salt thereof:

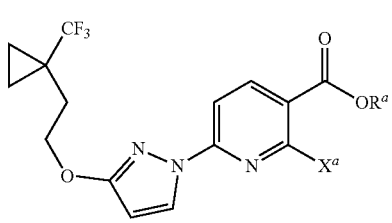

in the presence of a catalyst chosen from 1,4-diazabicyclo[2.2.2]octane (DABCO) and at least one base chosen from triethylamine, cesium carbonate, potassium carbonate, sodium carbonate, potassium tert-butoxide, potassium phosphate, DBU, and 1,1,3,3-tetramethylguanidine (TMG);
  (h) hydrolyzing the —C(O)OR$^a$ group of a compound of Formula (C-II) or a salt thereof to generate a compound of Formula (D-II) or a salt thereof:

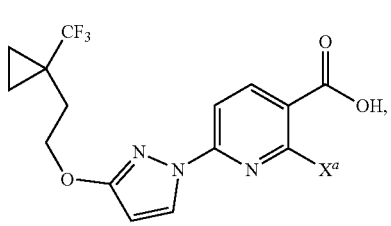

in the presence of at least one base chosen from NaOH and KOH;

(i) reacting the compound of Formula (D-II) or a salt thereof with 1,1'-carbonyldiimidazole (CDI), and subsequently reacting the product of the reaction of a compound of Formula (D-II) or a salt thereof with 1,1'-carbonyldiimidazole (CDI) with benzenesulfonamide or a salt thereof in the presence of at least one base chosen from 1,8-diazabicyclo[5.4.0]undec-7-ene (DBU), 1,4-diazabicyclo[2.2.2]octane (DABCO), 1,5,7-triazabicyclo[4.4.0]dec-5-ene (TBD), triethylamine, and 1,1,3,3-tetramethylguanidine (TMG), to generate a compound of Formula (F-II):

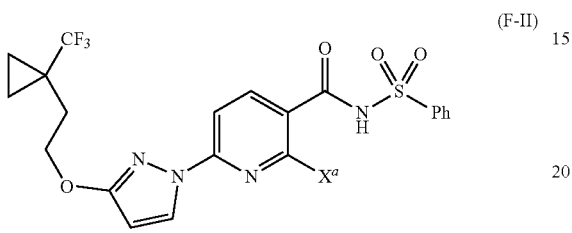

(F-II)

or a salt thereof, (j) reacting a compound of Formula (F-II) or a salt thereof with (S)-2,2,4-trimethylpyrrolidine or a salt thereof in the presence of K₂CO₃ to generate Compound 2 or a pharmaceutically acceptable salt thereof, or a deuterated derivative of any of the foregoing:

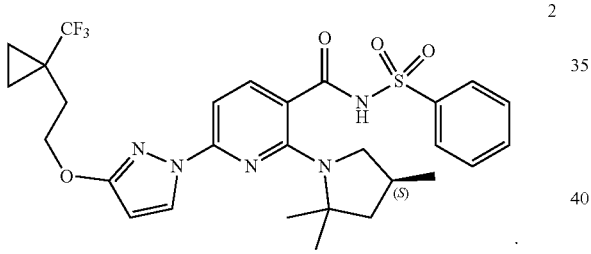

2

44. The method of embodiment 43, wherein in the reaction in (a), the chloroform is present in an amount ranging from 1.5 to 3.5 molar equivalents relative to 2,2,6,6-tetramethyl-piperidin-4-one or salt thereof, and wherein said at least one base is present in an amount ranging from 5 to 12 molar equivalents relative to 2,2,6,6-tetramethyl-piperidin-4-one or salt thereof, and wherein said tetrabutylmethylammonium chloride is present in an amount ranging from 0.02 molar equivalents to 0.1 molar equivalents relative to 2,2,6,6-tetramethyl-piperidin-4-one or salt thereof.

45. The method of embodiment 43, wherein in the reaction in (b), the products of the reaction in (a) are reacted with HCl in an amount ranging from 1 to 4 molar equivalents relative to 2,2,6,6-tetramethyl-piperidin-4-one or salt thereof.

46. The method of embodiment 43, wherein the reaction in (j) is performed in the presence of potassium carbonate or potassium phosphate and in at least one solvent chosen from N-methylpyrrolidine (NMP), DMF, DMSO, diethoxyethane, and n-butylacetate.

47. The method of embodiment 43, wherein the reaction in (i) is performed in at least one solvent chosen from tetrahydrofuran (THF) and 2-methyltetrahydrofuran (2-MeTHF).

48. The method of any one of embodiments 1-28, wherein the compound of Formula (I), pharmaceutically acceptable salt thereof, or deuterated derivative of any of the foregoing is Compound 1, a pharmaceutically acceptable salt thereof, or a deuterated derivative of any of the foregoing:

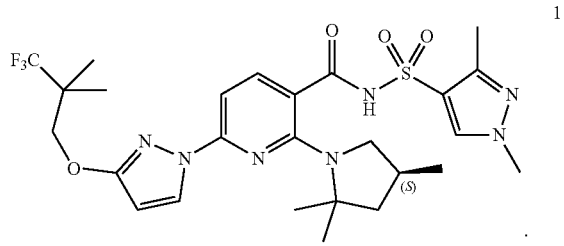

1

49. The method of embodiment 48, further comprising (g) reacting a compound of Formula (D-I):

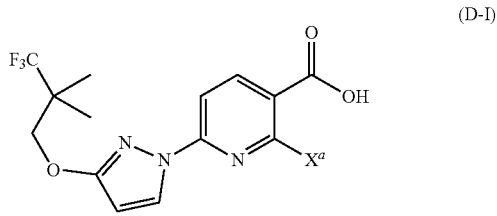

(D-I)

or a salt thereof
wherein each $X^a$ is —F or —Cl
with Compound 12 or a salt thereof:

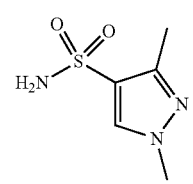

12 to produce a compound of Formula (F-I) or a salt thereof:

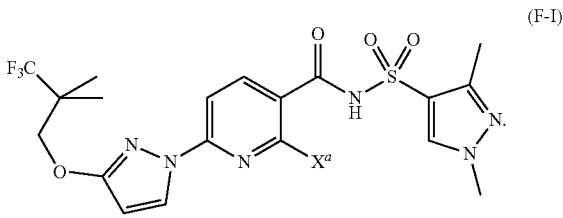

(F-I)

50. The method of embodiment 49, wherein said compound of Formula (D-I) or a salt thereof is reacted with a coupling reagent and resulting compound or salt is then reacted with Compound 12 or a salt thereof in the presence of at least one base.

51. The method of embodiment 50, wherein said coupling reagent is 1,1'-carbonyldiimidazole (CDI) and said base is 1,8-diazabicyclo[5.4.0]undec-7-ene (DBU).

52. The method of embodiment 50, wherein the reactions are performed in at least one solvent chosen from tetrahydrofuran (THF) and 2-methyltetrahydrofuran (2-MeTHF).

53. The method of any one of embodiments 47-52, further comprising:
reacting Compound 7 or a salt thereof

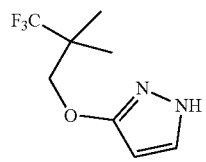

with a compound of Formula (B-I) or a salt thereof

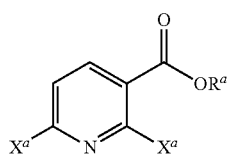

wherein each $R^a$ is independently chosen from $C_1$-$C_4$ alkyl; and each —$X^a$ is independently —F or —Cl; to produce a compound of Formula (C-I) or a salt thereof:

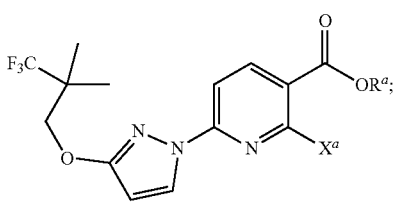

and
hydrolyzing the —C(O)OR$^a$ group of a compound of Formula (C-I) or a salt thereof to produce a compound of Formula (D-I) or a salt thereof.

54. The method of embodiment 53, wherein $R^a$ is ethyl, and the hydrolysis of the —C(O)OR$^a$ group is performed in the presence of at least one base.

55. The method of embodiment 53, wherein $R^a$ is methyl, and the hydrolysis of the —C(O)OR$^a$ group is performed in the presence of an acid.

56. The method of any one of embodiments 52-55, wherein the reaction of Compound 7 or a salt thereof with a compound of Formula (B-I) or a salt thereof is performed in the presence of 1,4-diazabicyclo[2.2.2]octane (DABCO) and at least one base.

57. The method of embodiment 56, wherein the base is chosen from triethylamine, cesium carbonate, potassium carbonate, sodium carbonate, potassium tert-butoxide, potassium phosphate, DBU, and 1,1,3,3-tetramethylguanidine (TMG).

58. The method of any one of embodiments 52-57, further comprising decarboxylating Compound 6:

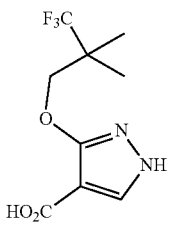

to form Compound 7 or a salt thereof:

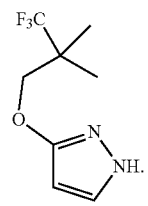

59. The method of embodiment 58, wherein the decarboxylation is performed in the presence of either at least one base or at least one acid.

60. The method of embodiment 59, wherein the base is chosen from 1,8-diazabicyclo[5.4.0]undec-7-ene (DBU), aqueous sodium hydroxide, and potassium tert-butoxide; or wherein the acid is chosen from aqueous HCl and acetic acid.

61. A method of preparing Compound 1, pharmaceutically acceptable salt thereof, or deuterated derivative of any of the foregoing:

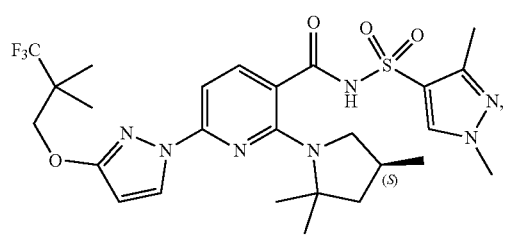

comprising:
(a) reacting 2,2,6,6-tetramethyl-piperidin-4-one or a salt thereof with chloroform, at least one base chosen from potassium t-butoxide, potassium hydroxide, and sodium hydroxide, and at least one phase transfer catalyst chosen from tetrabutylmethylammonium chloride,
(b) reacting the products of the reaction in (a) with HCl to produce 5,5-dimethyl-3-methylenepyrrolidin-2-one or a salt thereof,
(c) performing an enantioselective hydrogenation of 5,5-dimethyl-3-methylenepyrrolidin-2-one or a salt thereof to produce (S)-3,5,5-trimethyl-pyrrolidin-2-one or a salt thereof,
(d) reducing (S)-3,5,5-trimethyl-pyrrolidin-2-one or a salt thereof to produce (S)-2,2,4-trimethylpyrrolidine;
(e) treating (S)-2,2,4-trimethylpyrrolidine with HCl to produce a HCl salt of (S)-2,2,4-trimethylpyrrolidine;

(f) decarboxylating Compound 6 or a salt thereof:

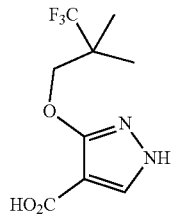
6 to form Compound 7 or a salt thereof:

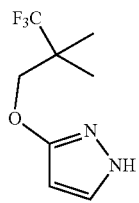
7 in the presence of a base chosen from 1,8-diazabicyclo[5.4.0]undec-7-ene (DBU), aqueous sodium hydroxide, and potassium tert-butoxide or at least one acid chosen from aqueous HCl and acetic acid;

(g) reacting Compound 7 or a salt thereof with a compound of Formula (B-I) or a salt thereof:

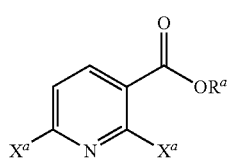
(B-I)

wherein $R^a$ is methyl; and
each —$X^a$ is Cl;
to generate a compound of Formula (C-I) or a salt thereof:

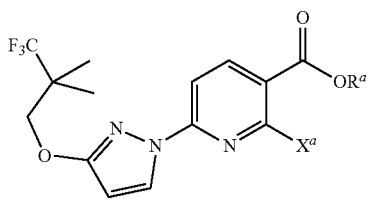
(C-I)

in the presence of a catalyst chosen from 1,4-diazabicyclo[2.2.2]octane (DABCO) and at least one base chosen from triethylamine, cesium carbonate, potassium carbonate, sodium carbonate, potassium tert-butoxide, potassium phosphate, DBU, and 1,1,3,3-tetramethylguanidine (TMG);

(h) hydrolyzing the —C(O)O$R^a$ group of a compound of Formula (C-I) or a salt thereof to generate a compound of Formula (D-I) or a salt thereof:

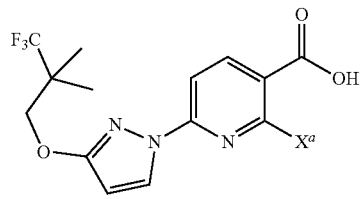
(D-I)

in the presence of at least one base chosen from NaOH and KOH;

(i) reacting a compound of Formula (D-I) or a salt thereof with 1,1'-carbonyldiimidazole (CDI) and subsequently reacting a product of the reaction of a compound of Formula (D-I) or a salt thereof with 1,1'-carbonyldiimidazole (CDI) with Compound 12 or a salt thereof:

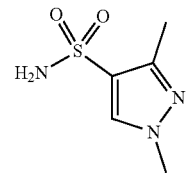
12 in the presence of at least one base chosen from 1,8-diazabicyclo[5.4.0]undec-7-ene (DBU) to yield Compound 13 or a salt thereof:

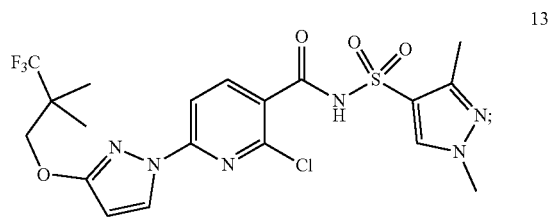 [SMILES: Cc1nn(C)cc1S(=O)(=O)NC(=O)c1ccc(-n2ccc(OCC(C)(C)C(F)(F)F)n2)nc1Cl]
13

(j) reacting Compound 13 or a salt thereof with (S)-2,2,4-trimethylpyrrolidine or a salt thereof in the presence of K$_2$CO$_3$ to generate Compound 1 or a pharmaceutically acceptable salt thereof, or a deuterated derivative of any of the foregoing:

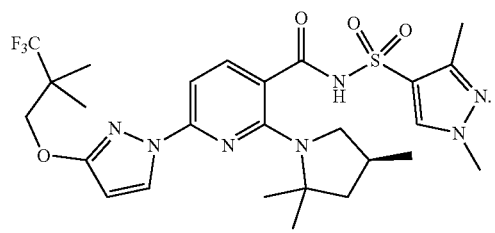
1

62. The method of embodiment 61, wherein in the reaction in (a), the chloroform is present in an amount ranging from 1.5 to 3.5 molar equivalents relative to 2,2,6,6-tetramethyl-piperidin-4-one or salt thereof, and wherein said at least one base is present in an amount ranging from 5 to 12 molar equivalents relative to 2,2,6,6-tetramethyl-piperidin-4-one or salt thereof, and wherein said tetrabutylmethylammonium chloride is present in an amount ranging from 0.02 molar equivalents to 0.1 molar equivalents relative to 2,2,6,6-tetramethyl-piperidin-4-one or salt thereof.

63. The method of embodiment 61, wherein in the reaction in (b) the products of the reaction in (a) are reacted with HCl in an amount ranging from 1 to 4 molar equivalents relative to 2,2,6,6-tetramethyl-piperidin-4-one or salt thereof.

64. The method of embodiment 62, wherein the reaction in (j) is performed in the presence of potassium carbonate or potassium phosphate and in at least one solvent chosen from N-methylpyrrolidine (NMP), DMF, DMSO, diethoxyethane, and n-butylacetate.

65. The method of embodiment 63, wherein the reaction in (i) is performed in at least one solvent chosen from tetrahydrofuran (THF) and 2-methyltetrahydrofuran (2-MeTHF).

66. A method of preparing a compound of Formula (Z-IIa) or a salt thereof:

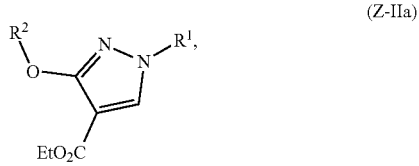
(Z-IIa)

comprising reacting a compound of Formula (Z-IIb) or a salt thereof

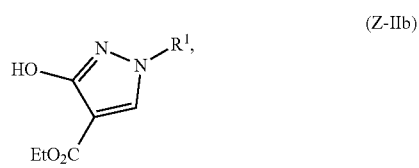
(Z-IIb)

wherein $R^1$ is a protecting group,
with a compound of Formula (B-iv) or a salt thereof

(B-iv)

wherein $R^2$ is chosen from

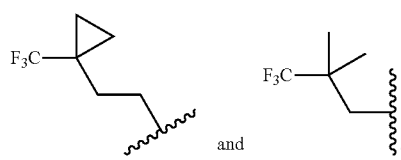

67. The method of embodiment 66, wherein said reaction comprises at least one base.

68. The method of embodiment 67, wherein the base is tetramethylguanidine.

69. The method of any one of embodiments 66 to 68, wherein $R^1$ is chosen from t-butyl carbamate (Boc), benzyl (Bn), tetrahydropyranyl (THP), 9-fluorenylmethyl carbamate (Fmoc), benzyl carbamate (Cbz), acetamide, trifluoroacetamide, triphenylmethylamine, benzylideneamine, and p-toluenesulfonamide.

70. The method of embodiment 69, wherein $R^1$ is chosen from t-butyl carbamate (Boc), benzyl (Bn), and tetrahydropyranyl (THP).

71. The method of embodiment 70, wherein $R^1$ is tetrahydropyranyl (THP).

72. The method of embodiment 70, wherein $R^1$ is t-butyl carbamate (Boc).

73. The method of any one of embodiments 66 to 72, wherein
$R^2$ is

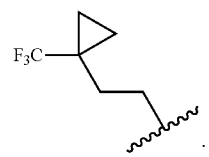

74. The method of any one of embodiments 66 to 72, wherein

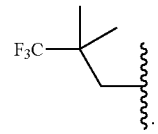 [SMILES: *CC(C)(C)C(F)(F)F]

$R^2$ is

75. A method of preparing Compound 49 or a salt thereof.

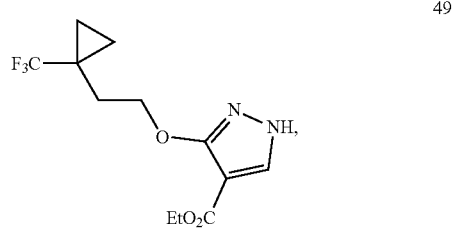 [SMILES: CCOC(=O)c1c[nH]nc1OCCC1(C(F)(F)F)CC1]
49 comprising deprotecting Compound 48 or a salt thereof

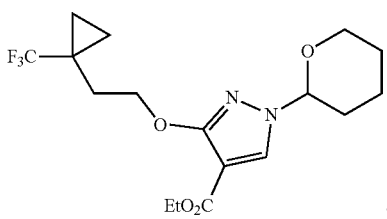
48

76. The method of embodiment 75, wherein said deprotecting comprises reacting a compound of Formula (B-I) or a salt thereof with an acid.

77. The method of embodiment 76, wherein the acid is methanesulfonic acid.

78. The method of embodiment 77, wherein Compound 48 or a salt thereof

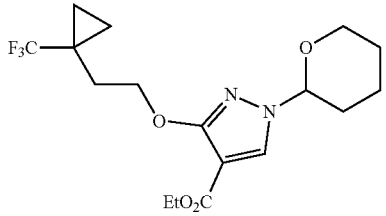

48 is prepared by a method comprising reacting Compound 45 or a salt thereof

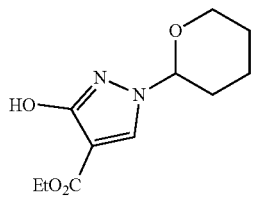

45 with Compound 47 or a salt thereof

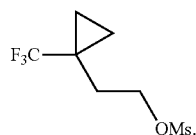

47

79. The method of embodiment 78, wherein said reaction comprises at least one base.
80. The method of embodiment 79, wherein the base is tetramethylguanidine.
81. The method of embodiment 78, wherein Compound 45 or a salt thereof

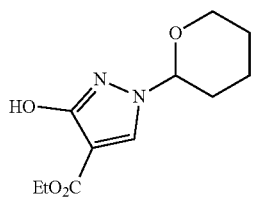

45 is prepared by a method comprising reacting Compound 35 or a salt thereof

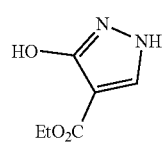

35 with dihydropyran.

82. The method of embodiment 81, wherein said reaction is performed in the presence of an acid.
83. The method of embodiment 82, wherein the acid is p-toluenesulfonic acid.
84. The method of embodiment 78, wherein Compound 47 or a salt thereof

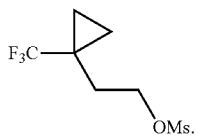

47 is prepared by a method comprising reacting Compound 46 or a salt thereof

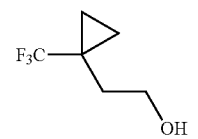

46 with methanesulfonylchloride.

85. Compound 45 or a salt thereof

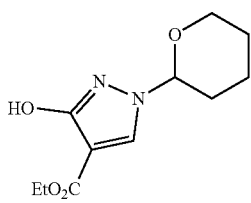

45

86. Compound 48 or a salt thereof

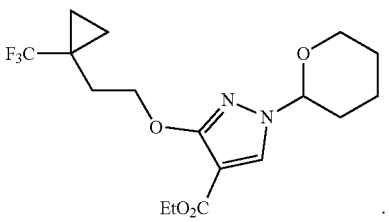

48

87. Compound 47 or a salt thereof

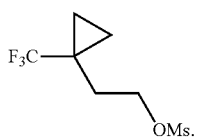

47

88. A compound of Formula viii:

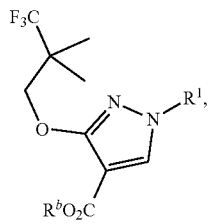

viii

Compound 6

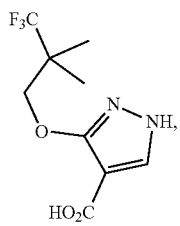

a salt of either of the foregoing, or a deuterated derivative of any of the foregoing, wherein $R^1$ is a protecting group; and $R^b$ is chosen from $C_1$-$C_4$ alkyl groups.

89. The compound, salt, or deuterated derivative according to embodiment 88, wherein $R^1$ is chosen from t-butyl carbamate (Boc), benzyl (Bn), tetrahydropyranyl (THP), 9-fluorenylmethyl carbamate (Fmoc), benzyl carbamate (Cbz), acetamide, trifluoroacetamide, triphenylmethylamine, benzylideneamine, and p-toluenesulfonamide.

90. The compound, salt, or deuterated derivative according to embodiment 88, wherein $R^1$ is chosen from t-butyl carbamate (Boc), benzyl (Bn), and tetrahydropyranyl (THP).

91. The compound, salt, or deuterated derivative according to embodiment 88, wherein $R^1$ is t-butyl carbamate (Boc).

92. The compound, salt, or deuterated derivative according to any one of embodiments 88 to 91, wherein $R^b$ is ethyl.

93. A method of preparing Compound 7 or a salt thereof:

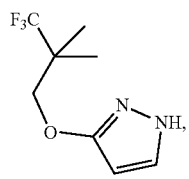

7 comprising decarboxylating Compound 6 or a salt thereof

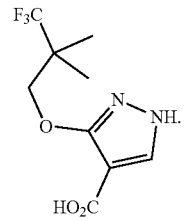

6

94. The method of embodiment 93, wherein said decarboxylating comprises reacting Compound 7 or a salt thereof with at least one base.

95. The method of embodiment 94, wherein the base is 1,8-diazabicyclo[5.4.0]undec-7-ene.

96. The method of embodiment 93, wherein said decarboxylation occurs thermally.

97. A method of preparing Compound 6 or a salt thereof:

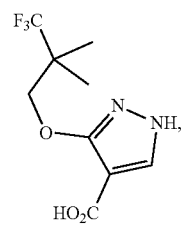

6 comprising hydrolyzing the —$CO_2R^b$ group of a compound of Formula viii or salt thereof:

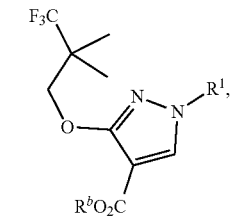

viii wherein $R^1$ is a protecting group; and $R^b$ is chosen from $C_1$-$C_4$ alkyl groups.

98. The method of embodiment 97, wherein $R^1$ is chosen from t-butyl carbamate (Boc), benzyl (Bn), tetrahydropyranyl (THP), 9-Fluorenylmethyl carbamate (Fmoc), benzyl carbamate (Cbz), acetamide, trifluoroacetamide, triphenylmethylamine, benzylideneamine, and p-toluenesulfonamide.

99. The method of embodiment 97, wherein $R^1$ is chosen from t-butyl carbamate (Boc), benzyl (Bn), and tetrahydropyranyl (THP).

100. The method of embodiment 97, wherein $R^1$ is benzyl (Bn).

101. The method according to any one of embodiments 97 to 101, wherein $R^b$ in Compound viii or salt thereof is ethyl.

102. The method of any one of embodiments 97 to 101, wherein said hydrolysis of the —$CO_2R^b$ group of a compound of Formula viii or salt thereof comprises reacting a compound of Formula viii or salt thereof with at least one base.

103. The method of embodiment 102, wherein the base is a metal hydroxide or a metal alkoxide.

104. The method of embodiment 103, wherein the base is KO$^t$Bu, NaOH, or KOH.

105. The method of any one of embodiments 97 to 104, further comprising aqueous extraction of Compound 6 or a salt thereof.

106. A method of preparing a compound of Formula viii or a salt thereof:

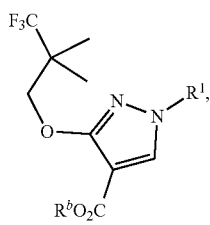

viii comprising reacting Compound 5 or a salt thereof:

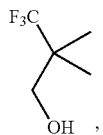

5 and a compound of Formula vii or a salt thereof

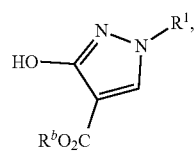

vii wherein R$^1$ is a protecting group and R$^b$ is chosen from C$_1$-C$_4$ alkyl groups.

107. The method of embodiment 106, wherein R$^1$ is chosen from t-butyl carbamate (Boc), benzyl (Bn), tetrahydropyranyl (THP), 9-fluorenylmethyl carbamate (Fmoc), benzyl carbamate (Cbz), acetamide, trifluoroacetamide, triphenylmethylamine, benzylideneamine, and p-toluenesulfonamide.

108. The method of embodiment 107, wherein R$^1$ is chosen from t-butyl carbamate (Boc), benzyl (Bn), and tetrahydropyranyl (THP).

109. The method of embodiment 107, wherein R$^1$ is t-butyl carbamate (Boc).

110. The method of any one of embodiments 106 to 109, wherein the reaction of Compound 5 or a salt thereof and a compound of Formula vii or a salt thereof is performed in the presence of triphenylphosphine and an azodicarboxylate.

111. The method of embodiment 110, wherein said azodicarboxylate is diethyl azodicarboxylate (DEAD) or diisopropyl azodicarboxylate (DIAD).

112. The method of any one of embodiments 106 to 111, further comprising preparing Compound 5 or a salt thereof:

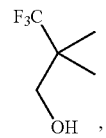

5 wherein said preparing Compound 5 or a salt thereof comprises reducing a compound of Formula (W-II) or a salt thereof:

(W-II)

wherein
R$^2$ is chosen from H and C$_1$-C$_4$ alkyl groups.

113. The method of embodiment 112, wherein said reduction comprises reacting a compound of Formula (W-II) or a salt thereof and a reagent chosen from boranes, borohydrides, and aluminum hydrides.

114. The method of embodiment 113, wherein the reagent is sodium bis(2-methoxyethoxy)aluminum hydride (Vitride®), diisobutylaluminium hydride (DIBAL), or LiAlH$_4$.

115. The method of embodiment 112, wherein the reduction of a compound of Formula (W-II) or a salt thereof to Compound 5 or a salt thereof occurs under catalytic hydrogenation conditions.

116. The method of embodiment 115, wherein the catalytic hydrogenation conditions comprise hydrogen and a catalyst chosen from carbonylchlorohydrido{bis[2-(diphenylphosphinomethyl)ethyl]amino}ethyl]amino}ruthenium(II) (Ru-MACHO), [2-(di-tert-butylphosphinomethyl)-6-(diethylaminomethyl)pyridine]carbonylchlorohydridoruthenium(II) (Milstein catalyst), dichlorotriphenylphosphine[2-(diphenylphosphino)-N-(2-pyridinylmethyl)ethanamine]ruthenium(II) (Gusev Ru-PNN), dichlorotriphenylphosphine[bis(2-(ethylthio)ethyl)amine]ruthenium (II) (Gusev Ru-SNS), dichlorobis(2-(diphenylphosphino)ethylamine)ruthenium (II), [Ru (acetylacetone)$_3$, 1,1,1-tris(diphenylphosphinomethyl)ethane (triphos)], and [Ru(acetylacetone)$_3$, 1,1,1-tris(diphenylphosphinomethyl)ethane (triphos), Zn].

117. The method of embodiment 115, further comprising at least one base.

118. The method of embodiment 117, wherein the base is chosen from potassium tertbutoxide and sodium methoxide.

119. The method of any one of embodiments 97 to 99, wherein R$^2$ is ethyl.

120. The method of embodiment 106, further comprising preparing a compound of Formula vii or a salt thereof:

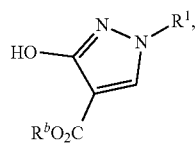

wherein R¹ is a protecting group and $R^b$ is independently chosen from $C_1$-$C_4$ alkyl group, and wherein said preparing a compound of Formula vii or a salt thereof comprises:

(a) reacting a compound of Formula v or a salt thereof:

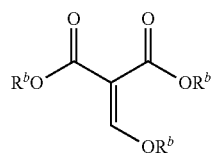

and a hydrazine to form a compound of Formula vi or a salt thereof:

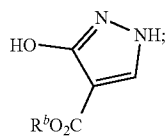

and (b) reacting a compound of Formula vi or a salt thereof and a reagent to form a compound of Formula vii or a salt thereof.

121. The method of embodiment 120, wherein the compound of Formula v or a salt thereof is diethyl 2-(ethoxymethylene)malonate (34) or a salt thereof:

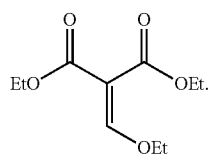

122. The method of embodiment 120, wherein R¹ is chosen from t-butyl carbamate (Boc), benzyl (Bn), tetrahydropyranyl (THP), 9-fluorenylmethyl carbamate (Fmoc), benzyl carbamate (Cbz), acetamide, trifluoroacetamide, phthalimide, triphenylmethylamine, benzylideneamine, and p-toluenesulfonamide.

123. The method of embodiment 122, wherein R¹ is chosen from t-butyl carbamate (Boc), benzyl (Bn), and tetrahydropyranyl (THP).

124. The method of embodiment 122, wherein R¹ is t-butyl carbamate (Boc).

125. A method of preparing 3,3,3-trifluoro-2,2-dimethylpropionic acid:

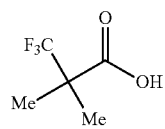

or a salt thereof, comprising (a) converting tert-butyl((1-ethoxy-2-methylprop-1-en-1-yl)oxy)dimethylsilane:

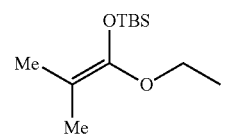

into
ethyl 3,3,3-trifluoro-2,2-dimethylpropanoate:

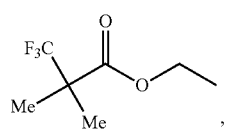

tert-butyldimethylsilyl 3,3,3-trifluoro-2,2-dimethylpropanoate:

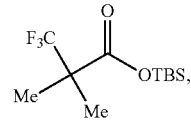

or a mixture thereof, under a photochemical condition with light at a wavelength of 435-450 nm; and (b) converting ethyl 3,3,3-trifluoro-2,2-dimethylpropanoate:

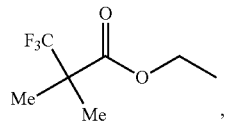

tert-butyldimethylsilyl 3,3,3-trifluoro-2,2-dimethylpropanoate:

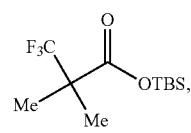

or a mixture thereof into 3,3,3-trifluoro-2,2-dimethylpropionic acid:

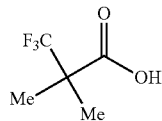

or a salt thereof.

126. A method of preparing 3,3,3-trifluoro-2,2-dimethyl-propionic acid:

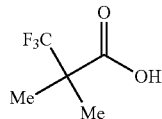

31 or a salt thereof, comprising step (a):

converting ethyl 3,3,3-trifluoro-2,2-dimethylpropanoate:

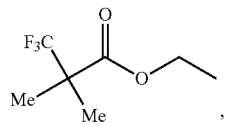

29 tert-butyldimethylsilyl 3,3,3-trifluoro-2,2-dimethylpropanoate:

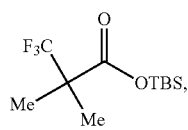

30 or a mixture thereof into 3,3,3-trifluoro-2,2-dimethyl-propionic acid:

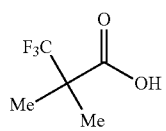

31 or a salt thereof.

127. The method of embodiment 125 or 126, wherein step (a) is performed in the presence of at least one base.
128. The method of embodiment 127, wherein the base is sodium hydroxide.
129. The method of any one of embodiments 126 to 128, comprising step (b): converting tert-butyl((1-ethoxy-2-methylprop-1-en-1-yl)oxy)dimethylsilane:

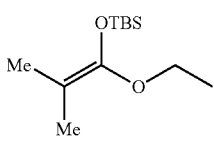

28 into ethyl 3,3,3-trifluoro-2,2-dimethylpropanoate:

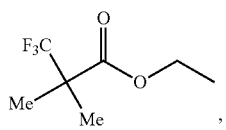

29 tert-butyldimethylsilyl 3,3,3-trifluoro-2,2-dimethylpropanoate:

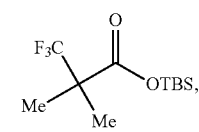

30 or a mixture thereof.

130. The method of embodiment 129, wherein step (b) is performed in the presence of $CF_3I$.
131. The method of embodiment 129 or 130, wherein step (b) is performed in the presence of a Ru catalyst.
132. The method of embodiment 131, wherein the Ru catalyst is $(bpy)_3Cl_2 \cdot 6H_2O$.
133. The method of any one of embodiments 129 to 132, wherein step (b) is performed under photochemical conditions.
134. The method of embodiment 133, wherein the photochemical conditions comprise light at a wavelength of 440-445 nm.
135. The method of any one of embodiments 129 to 134, comprising step (c): converting ethyl isobutyrate (27):

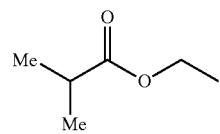

27 into tert-butyl((1-ethoxy-2-methylprop-1-en-1-yl)oxy)dimethylsilane (28):

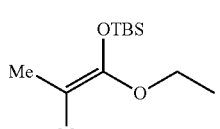

28

136. The method of embodiment 135, wherein step (c) is performed in the presence of tert-butyldimethylsilyl chloride.

137. The method of embodiment 135 or 136, wherein step (c) is performed in the presence of a second base.

138. The method of embodiment 137, wherein the second base is lithium diisopropylamide.

139. The method of embodiment 138, wherein step (c) is performed in the presence of 1,3-dimethyl-3,4,5,6-tetrahydro-2-pyrimidinone.

140. A method of preparing a compound of Formula (I):

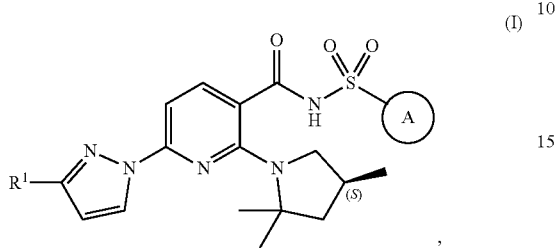

(I)

a pharmaceutically acceptable salt thereof, or a deuterated derivative of any of the foregoing, wherein:
R¹ is

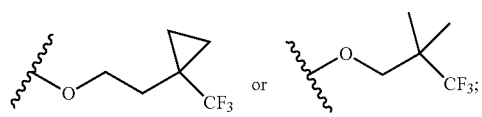

and
Ring A is phenyl or

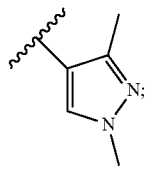 [SMILES: *c1cn(C)nc1C]

comprising the step of:
reacting a compound of Formula (D-III) or a salt thereof with a compound of Formula (G-I) or a salt thereof:

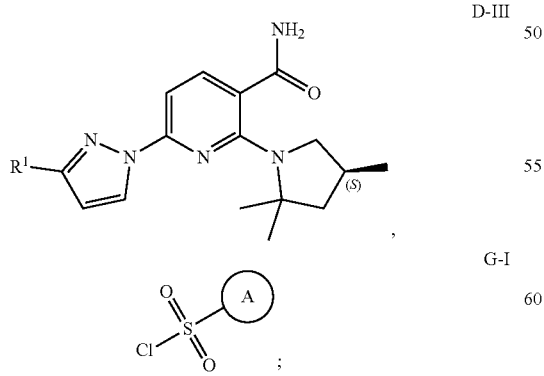

to produce a compound of Formula (I), a pharmaceutically acceptable salt thereof, or a deuterated derivative of any of the foregoing.

141. The method of embodiment 140, wherein the compound of Formula (D-III) or a salt thereof is produced by:
reacting (S)-6-bromo-2-(2,2,4-trimethylpyrrolidin-1-yl)nicotinamide (Compound 38):

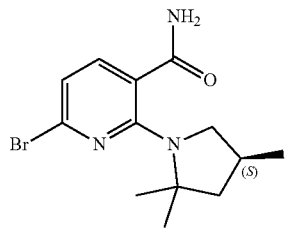

or salt thereof with Compound 7, Compound 39, or a salt thereof:

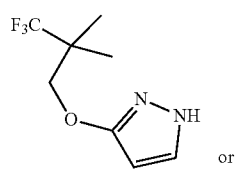

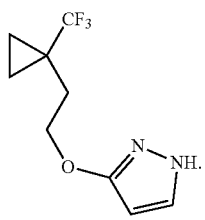

142. The method of embodiment 141, wherein Compound 38 or a salt thereof is produced by reacting (S)-2,2,4-trimethylpyrrolidine (Compound 17S):

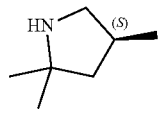

or salt thereof with 6-bromo-2-fluoronicotinamide (Compound 37) or a salt thereof:

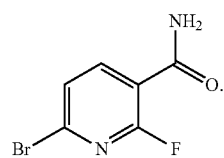

143. A method of preparing a compound of Formula (I):

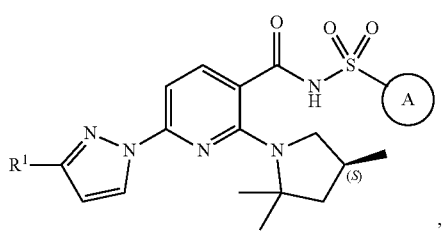
(I)

a pharmaceutically acceptable salt thereof, or a deuterated derivative of any of the foregoing, wherein:

R¹ is

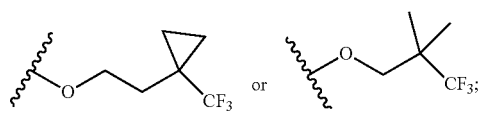

and

Ring A is phenyl or

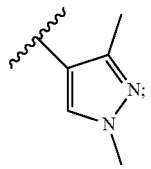 [SMILES: *c1cn(C)nc1C]

comprising the step of reacting a compound of Formula (D-IV)

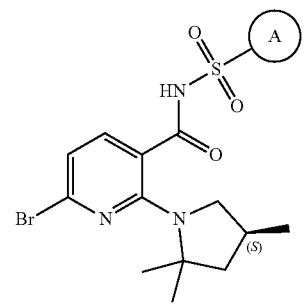
D-IV or a salt thereof with Compound 7:

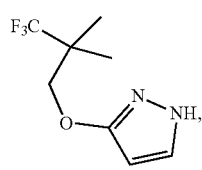
7 or Compound 39:

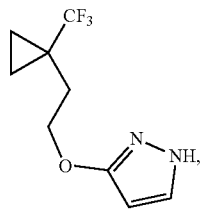
39 or a salt thereof to produce a compound of Formula (I), a pharmaceutically acceptable salt thereof, or a deuterated derivative of any of the foregoing.

144. The method of embodiment 143, wherein the compound of Formula (D-IV) or a salt thereof is produced by
reacting (S)-6-bromo-2-(2,2,4-trimethylpyrrolidin-1-yl)nicotinamide (Compound 38):

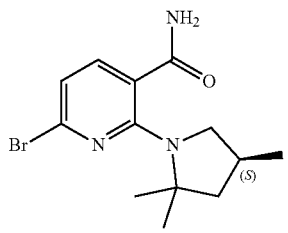
38 or a salt thereof with a compound of Formula (G-I):

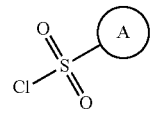
G-I or a salt thereof.

145. The method of embodiment 144, wherein Compound 38 is produced by reacting (S)-2,2,4-trimethylpyrrolidine (Compound 17S):

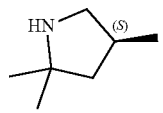
17S or salt thereof with 6-bromo-2-fluoronicotinamide (Compound 37) or a salt thereof:

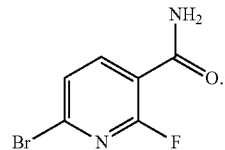
37

146. A method of preparing a compound of Formula (I):

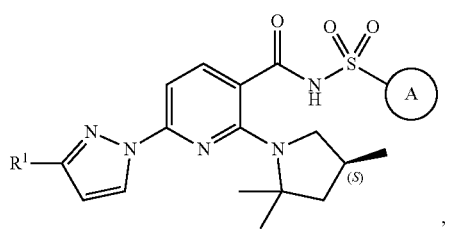

a pharmaceutically acceptable salt thereof, or a deuterated derivative of any of the foregoing, wherein:
R¹ is

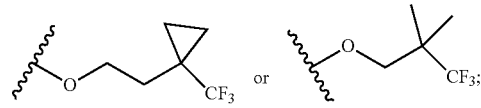

and
Ring A is phenyl or

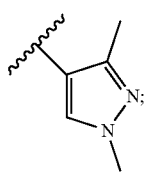

comprising:
(A) the steps of:
 (1) converting 6-bromo-2-fluoronicotinic acid or a salt thereof into to 6-bromo-2-fluoronicotinamide or a salt thereof,
 (2) reacting (S)-2,2,4-trimethylpyrrolidine or salt thereof with 6-bromo-2-fluoronicotinamide or a salt thereof:

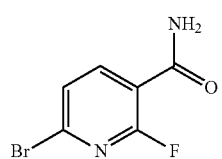

to produce (S)-6-bromo-2-(2,2,4-trimethylpyrrolidin-1-yl)nicotinamide or a salt thereof:

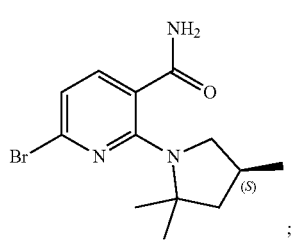

(3): reacting (S)-6-bromo-2-(2,2,4-trimethylpyrrolidin-1-yl)nicotinamide or salt thereof with Compound 7:

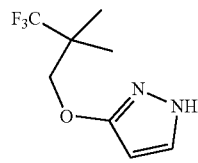

or
Compound 39:

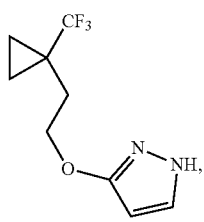

or a salt thereof to produce a compound of Formula (D-III) or a salt thereof:

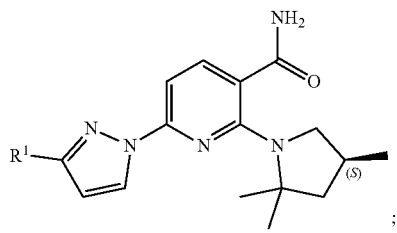

and
(4) reacting a compound of Formula (D-III) or a salt thereof with a compound of Formula (G-I) or a salt thereof:

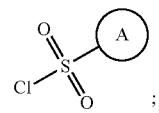

to produce a compound of Formula (I), a pharmaceutically acceptable salt thereof, or a deuterated derivative of any of the foregoing;
or
(B) the steps of:
 (1) converting 6-bromo-2-fluoronicotinic acid or a salt thereof into to 6-bromo-2-fluoronicotinamide or a salt thereof,
 (2) reacting (S)-2,2,4-trimethylpyrrolidine or salt thereof with 6-bromo-2-fluoronicotinamide or a salt thereof:

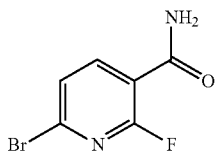
37 to produce (S)-6-bromo-2-(2,2,4-trimethylpyrrolidin-1-yl)nicotinamide or a salt thereof:

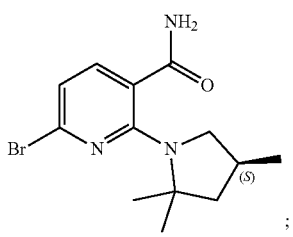
38

(3) reacting (S)-6-bromo-2-(2,2,4-trimethylpyrrolidin-1-yl)nicotinamide or a salt thereof with a compound of Formula (G-I):

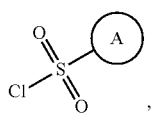
G-I or a salt thereof to produce a compound of Formula (D-IV) or a salt thereof:

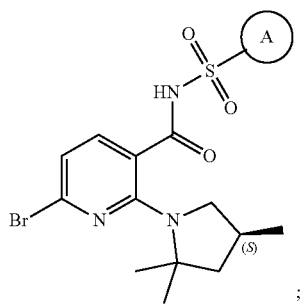
D-IV and (4) reacting a compound of Formula (D-IV) or a salt thereof with Compound 7:

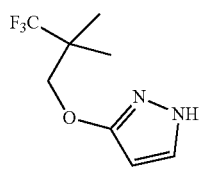
7 or
Compound 39:

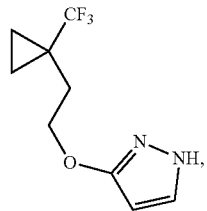
39 or a salt thereof to produce a compound of Formula (I), a pharmaceutically acceptable salt thereof, or a deuterated derivative of any of the foregoing.

147. The method of embodiment 146, wherein step of (A)(1) or step (B)(1) is performed in the presence of at least one coupling agent.

148. The method of embodiment 147, wherein the coupling agent is chosen from triphosgene, propanephosphonic acid anyhydride (T3P), HATU, EDCI, CDI, DCC, and ditertbutyl decarbonate (Boc$_2$O).

149. The method of embodiment 147, wherein step (A)(1) or step (B)(1) is performed in the presence of one or more of aqueous ammonia, anhydrous ammonia in an organic solvent, an ammonium salt, and Ammonia gas.

150. The method of embodiment 147, wherein step (A)(1) or step (B)(1) is performed in the presence of NH$_3$ in MeOH or NH$_4$HCO$_3$.

151. The method of any one of embodiments 142 or 146, wherein step (A)(2) is performed in the presence of at least one base.

152. The method of embodiment 151, wherein the base is chosen from metal carbonates, 1,8-diazabicyclo[5.4.0]undec-7-ene (DBU), 1,5-diazabicyclo[4.3.0]non-5-ene (DBN) and 1,1,3,3-tetramethylguanidine (TMG).

153. The method of embodiment 151, wherein the base is potassium carbonate.

154. The method of embodiment 151, wherein step (A)(2) is performed in the presence of at least one organic solvent.

155. The method of embodiment 154, wherein the organic solvent is acetonitrile.

156. The method of any one of embodiments 145 or 146, wherein step (B)(2) is performed in the presence of at least one base.

157. The method of embodiment 156, wherein the base is chosen from metal carbonates, 1,8-diazabicyclo[5.4.0]undec-7-ene (DBU), 1,5-diazabicyclo[4.3.0]non-5-ene (DBN) and 1,1,3,3-tetramethylguanidine (TMG).

158. The method of embodiment 156, wherein the base is potassium carbonate.

159. The method of embodiment 156, wherein the reaction is performed in the presence of at least one organic solvent.

160. The method of embodiment 159, wherein the organic solvent is acetonitrile.

161. The method of embodiment 141 or 146, wherein step (A)(3) is performed in the presence of at least one catalyst that is a carbon-nitrogen coupling catalyst (e.g., a copper catalyst or a palladium catalyst).

162. The method of embodiment 161, wherein the copper catalyst comprises a copper source such as a copper (I) halide (e.g., copper (I) iodide), or wherein the palladium catalyst is selected from [1,1'-bis(di-tertbutylphosphino)ferrocene]dichloropalladium(II), [(2-di-tert-butylphosphino-3,6-dimethoxy-2',4',6'-triisopropyl-1,1'-biphenyl)-2-(2'-amino-1,1'-biphenyl)]palladium(II) methanesulfonate, [(2-di-cyclohexylphosphino-3,6-dimethoxy-2',4',6'-triisopropyl-1,1'-biphenyl)-2-(2'-amino-1,1'-biphenyl)]palladium(II) methanesulfonate, tris(dibenzylideneacetone)dipalladium(0) (Pd$_2$dba$_3$)/2-di-tert-butylphosphino-2',4',6'-triisopropylbiphenyl), Pd$_2$dba$_3$/1,1'-bis(diisopropylphosphino)ferrocene, Pd$_2$dba$_3$/N-phenyl-2-(di-tert-butylphosphino)pyrrole, Pd$_2$dba$_3$/2-di-tert-butylphosphino-2'-methylbiphenyl, Pd$_2$dba$_3$/5-(di-tert-butylphosphino)-1', 3', 5'-triphenyl-1'H-[1,4']bipyrazole, Pd$_2$dba$_3$/2-(di-tert-butylphosphino)-1-(2-methoxyphenyl)-1H-pyrrole, Pd$_2$dba$_3$/2-dicyclohexylphosphino-2',6'-dimethoxybiphenyl, Pd$_2$dba$_3$/2-(di-tert-butylphosphino)-2',4',6'-triisopropyl-3,6-dimethoxy-1,1'-biphenyl, Pd$_2$dba$_3$/2-(dicyclohexylphosphino)$_{3,6}$-dimethoxy-2',4',6'-triisopropyl-1,1'-biphenyl, Pd$_2$dba$_3$/di-tert-butyl(2,2-diphenyl-1-methyl-1-cyclopropyl)phosphine, Pd$_2$dba$_3$/1-(dicyclohexylphosphino)-2,2-diphenyl-1-methylcyclopropane, and dichloro[1,3-bis(2,6-di-3-pentylphenyl)imidazol-2-ylidene](3-chloropyridyl)palladium(II).

163. The method of embodiment 161, wherein said step (A)(3) is performed in the presence of at least one said copper catalyst, wherein the copper catalyst comprises a copper source and a ligand such as an amine ligand (e.g. N,N'-dimethylethylenediamine, N,N'-dimethylcyclohexane-1,2-diamine), 1,10-phenanthroline, 8-hydroxyquinoline, L-proline, or 2-isobutyrylcyclohexanone.

164. The method of embodiment 163, wherein the amine ligand is N,N-dimethylcyclohexane-1,2-diamine.

165. The method of embodiment 141 or 146, wherein step (A)(3) is performed in the presence of at least one base.

166. The method of embodiment 165, wherein the base is potassium carbonate.

167. The method of embodiment 141 or 146, wherein step (A)(3) is performed in the presence of at least one organic solvent.

168. The method of embodiment 167, wherein the organic solvent is N,N-dimethylformamide (DMF).

169. The method of embodiment 143 or 146, wherein step (B)(4) is performed in the presence of at least one catalyst that is a carbon-nitrogen coupling catalyst (e.g., a copper catalyst or a palladium catalyst).

170. The method of embodiment 169, wherein the copper catalyst comprises a copper source such as copper (I) iodide, or wherein the palladium catalyst is selected from [1,1'-bis(di-tert-butylphosphino)ferrocene]dichloropalladium(II), [(2-di-tert-butylphosphino-3,6-dimethoxy-2',4',6'-triisopropyl-1,1'-biphenyl)-2-(2'-amino-1,1'-biphenyl)]palladium(II) methanesulfonate, [(2-di-cyclohexylphosphino-3,6-dimethoxy-2',4',6'-tri-isopropyl-1,1'-biphenyl)-2-(2'-amino-1,1'-biphenyl)]palladium(II) methanesulfonate, tris(dibenzylideneacetone)dipalladium(0) (Pd$_2$dba$_3$)/2-di-tert-butylphosphino-2',4',6'-triisopropylbiphenyl), Pd$_2$dba$_3$/1,1'-bis(diisopropylphosphino)ferrocene, Pd$_2$dba$_3$/N-phenyl-2-(di-tert-butylphosphino)pyrrole, Pd$_2$dba$_3$/2-di-tert-butylphosphino-2'-methylbiphenyl, Pd$_2$dba$_3$/5-(di-tert-butylphosphino)-1', 3', 5'-triphenyl-1'H-[1,4']bipyrazole, Pd$_2$dba$_3$/2-(di-tert-butylphosphino)-1-(2-methoxyphenyl)-1H-pyrrole, Pd$_2$dba$_3$/2-dicyclohexylphosphino-2',6'-dimethoxybiphenyl, Pd$_2$dba$_3$/2-(di-tert-butylphosphino)-2',4',6'-triisopropyl-3,6-dimethoxy-1,1'-biphenyl, Pd$_2$dba$_3$/2-(dicyclohexylphosphino)3,6-dimethoxy-2',4',6'-triisopropyl-1,1'-biphenyl, Pd$_2$dba$_3$/di-tert-butyl(2,2-diphenyl-1-methyl-1-cyclopropyl)phosphine, Pd$_2$dba$_3$/1-(dicyclohexylphosphino)-2,2-diphenyl-1-methylcyclopropane, and dichloro[1,3-bis(2,6-di-3-pentylphenyl)imidazol-2-ylidene](3-chloropyridyl)palladium(II).

171. The method of embodiment 169, wherein step (B)(4) is performed in the presence of at least one said copper catalyst, wherein the copper catalyst comprises a copper source and a ligand such as an amine ligand (e.g. N,N'-dimethylethylenediamine, N,N'-dimethylcyclohexane-1,2-diamine), 1,10-phenanthroline, 8-hydroxyquioline, L-proline, or 2-isobutyrylcyclohexanone.

172. The method of embodiment 171, wherein the amine ligand is N,N'-dimethylcyclohexane-1,2-diamine.

173. The method of embodiment 143 or 146, wherein step (B)(4) is performed in the presence of at least one base.

174. The method of embodiment 173, wherein the base is potassium carbonate.

175. The method of embodiment 143 or 146, wherein step (A)(4) is performed in the presence of at least one organic solvent.

176. The method of embodiment 175, wherein the organic solvent is N,N-dimethylformamide (DMF).

177. The method of embodiment 140 or 146, wherein step (A)(4) is performed in the presence of at least one base.

178. The method of embodiment 177, wherein the base in step (A)(4) is chosen from lithium tert-amoxide and potassium tert-butoxide.

179. The method of embodiment 140 or 146, wherein step (A)(4) is performed in the presence of at least one organic solvent.

180. The method of embodiment 179, wherein the organic solvent in step (A)(4) is tetrahydrofuran (THF) or 2-methyltetrahydrofuran.

181. The method of embodiment 144 or 146, wherein step (B)(3) is performed in the presence of at least one base.

182. The method of embodiment 181, wherein the base in step (B)(3) is chosen from lithium tert-amoxide and potassium tert-butoxide.

183. The method of embodiment 144 or 146, wherein step (B)(3) is performed in the presence of at least one organic solvent.

184. The method of embodiment 183, wherein the organic solvent in step (B)(3) is tetrahydrofuran (THF) or 2-methyltetrahydrofuran.

185. The method of any one of embodiments 140-184, wherein said compound of Formula (I), pharmaceutically acceptable salt thereof, or deuterated derivative of any of the foregoing is Compound 2, a pharmaceutically acceptable salt thereof, or a deuterated derivative of any of the foregoing:

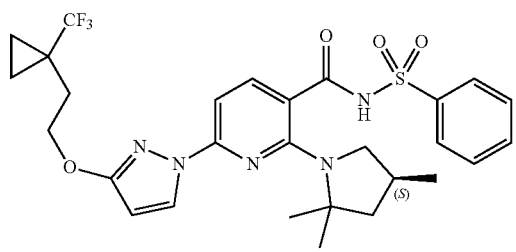

186. The method of any one of embodiments 140-184, wherein the compound of Formula (I), pharmaceutically acceptable salt thereof, or deuterated derivative of any of the foregoing is Compound 1, a pharmaceutically acceptable salt thereof, or a deuterated derivative of any of the foregoing:

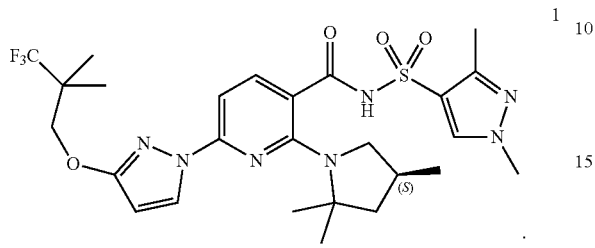
1

187. A compound chosen from:

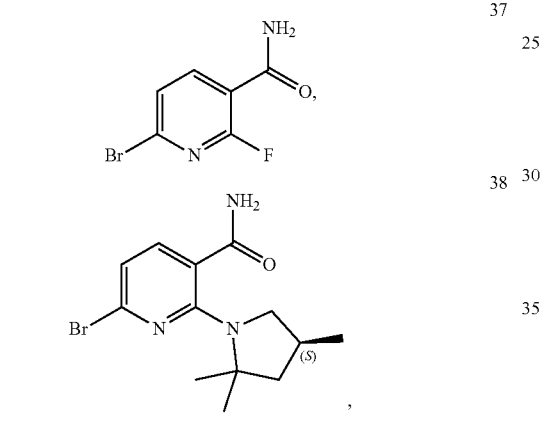

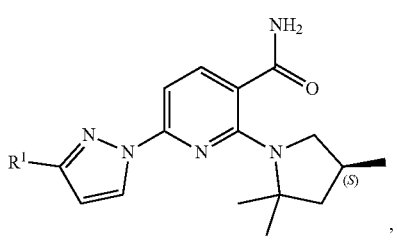

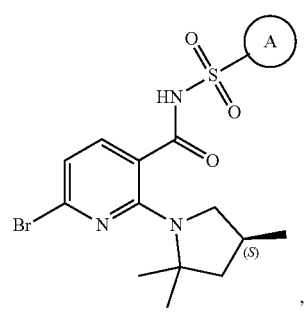

wherein —$R^1$ is and

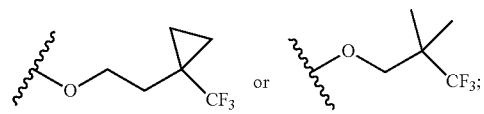

Ring A is phenyl or

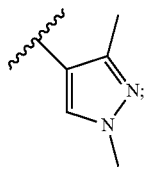 [SMILES: *c1cn(C)nc1C]

or a salt thereof, or a deuterated derivative of any of the foregoing.

188. A compound of Formula viii:

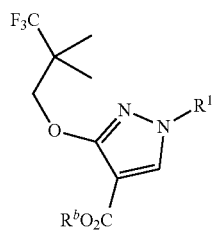
viii or Compound 6

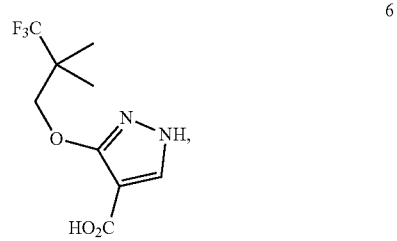 [SMILES: CC(C)(COc1n[nH]cc1C(=O)O)C(F)(F)F]
6 or a salt of a compound of Formula viii or Compound 6, or a deuterated derivative of any of the foregoing, wherein
$R^1$ is a protecting group; and
$R^b$ is chosen from $C_1$-$C_4$ alkyl groups.

189. The compound, salt, or deuterated derivative according to embodiment 188, wherein $R^1$ is chosen from t-butyl carbamate (Boc), benzyl (Bn), tetrahydropyranyl (THP), 9-fluorenylmethyl carbamate (Fmoc), benzyl carbamate (Cbz), acetamide, trifluoroacetamide, triphenylmethylamine, benzylideneamine, and p-toluenesulfonamide.

190. The compound, salt, or deuterated derivative according to embodiment 188, wherein $R^1$ is chosen from t-butyl carbamate (Boc), benzyl (Bn), and tetrahydropyranyl (THP).

191. The compound, salt, or deuterated derivative according to embodiment 188, wherein $R^1$ is t-butyl carbamate (Boc).

192. The compound, salt, or deuterated derivative according to any one of embodiments 188-191, wherein $R^b$ is ethyl.

193. A method of preparing Compound 7 or a salt thereof:

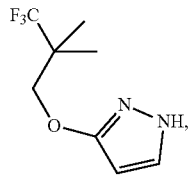

7 comprising decarboxylating Compound 6 or a salt thereof 6

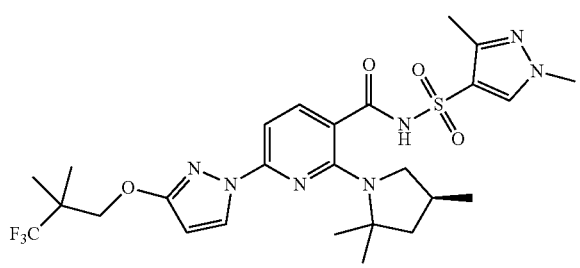

6

194. The method of embodiment 193, wherein said decarboxylating comprises reacting Compound 7 or a salt thereof with a base.

195. The method of embodiment 194, wherein the base is 1,8-diazabicyclo[5.4.0]undec-7-ene.

196. The method of embodiment 195, wherein said decarboxylation occurs thermally.

197. A method of producing Compound 1:

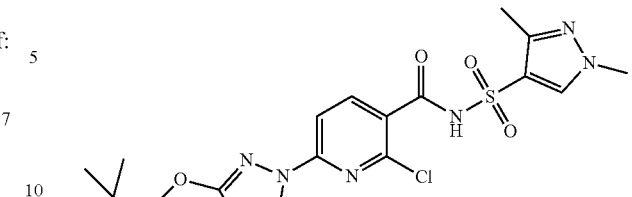

1 or a pharmaceutically acceptable salt thereof, comprising reacting Compound 13:

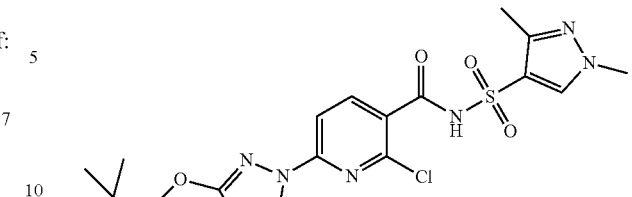

13 or a salt thereof, with Compound 17S:

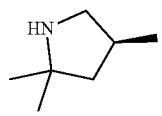

17S or a salt thereof, in the presence of $K_2CO_3$, a first solvent, and a second solvent.

198. A method of producing Compound 2:

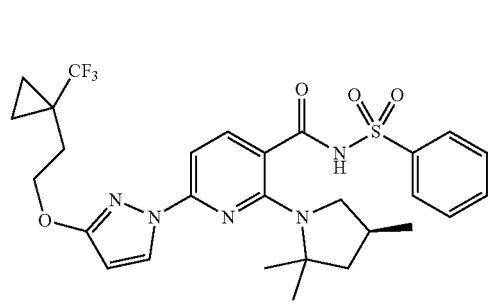

2 or a pharmaceutically acceptable salt thereof, comprising reacting Compound 54:

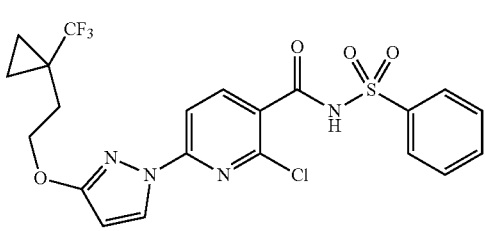

54 or a salt thereof, with Compound 17S:

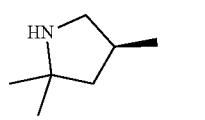

17S or a salt thereof, in the presence of $K_2CO_3$, a first solvent, and a second solvent.

199. The method of embodiment 197 or 198, wherein the first solvent chosen from N-methylpyrrolidine (NMP), DMF, and DMSO.

200. The method of embodiment 197 or 198, wherein the second solvent is chosen from diethoxyethane (DEE), n-butylacetate (n-BuOAc), i-BuOAc, and n-BuOH.

201. The method of embodiment 197 or 198, wherein the first solvent is NMP, and the second solvent is n-BuOAc.

202. A process of preparing Compound 2 or a pharmaceutically acceptable salt thereof, or a deuterated derivative of any of the foregoing:

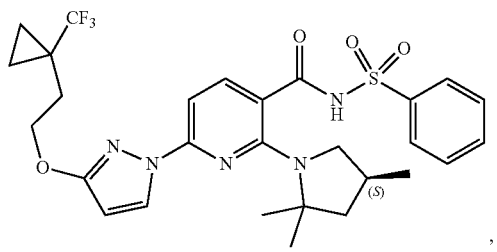

2

, comprising the step of reacting a compound of Formula (F-II) or a salt thereof:

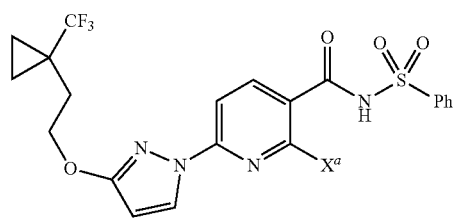

(F-II)

with (S)-2,2,4-trimethylpyrrolidine (Compound 17S) or a salt thereof in the presence of $K_2CO_3$ to generate Compound 2 or a pharmaceutically acceptable salt thereof, or a deuterated derivative of any of the foregoing;
wherein the compound of Formula (F-II) or salt thereof has been prepared by the steps comprising:
(i) decarboxylating Compound 49:

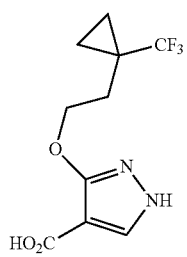

49 to form Compound 39 or a salt thereof:

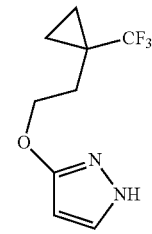

39 in the presence of at least one base chosen from 1,8-diazabicyclo[5.4.0]undec-7-ene (DBU), aqueous sodium hydroxide, and potassium tert-butoxide, or at least one acid chosen from aqueous HCl and acetic acid;
(ii) reacting Compound 39 or a salt thereof:

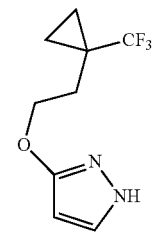

39 with a compound of Formula (B-I) or a salt thereof:

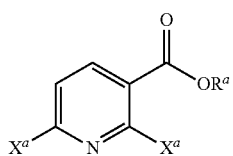

(B-I)

wherein $R^a$ is ethyl, and each —$X^a$ is Cl, to produce a compound of Formula (C-II) or a salt thereof:

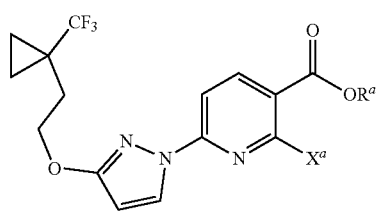

(C-II)

in the presence of a catalyst chosen from 1,4-diazabicyclo[2.2.2]octane (DABCO) and at least one base chosen from triethylamine, cesium carbonate, potassium carbonate, sodium carbonate, potassium tert-butoxide, potassium phosphate, DBU, and 1,1,3,3-tetramethylguanidine (TMG);
(iii) hydrolyzing the —C(O)OR$^a$ group of a compound of Formula (C-II) or a salt thereof in the presence of at least one base chosen from NaOH and KOH to generate a compound of Formula (D-II) or a salt thereof:

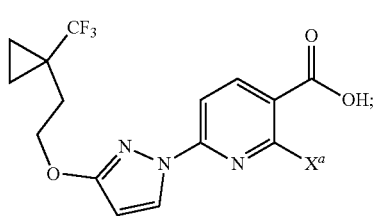

(D-II)

(iv) reacting the compound of Formula (D-II) or a salt thereof with 1,1'-carbonyldiimidazole (CDI), and subsequently reacting the product of the reaction of a compound of Formula (D-II) or a salt thereof with 1,1'-carbonyldiimidazole (CDI) with benzenesulfonamide or a salt thereof in the presence of at least one base chosen from 1,8-diazabicyclo[5.4.0]undec-7-ene (DBU), 1,4-diazabicyclo[2.2.2]octane (DABCO), 1,5,7-triazabicyclo[4.4.0]dec-5-ene (TBD), triethylamine, and 1,1,3,3-tetramethylguanidine (TMG), to generate a compound of Formula (F-II) or a salt thereof;

and wherein Compound 17S or salt thereof has been prepared by the steps comprising:

(i) reacting 2,2,6,6-tetramethyl-piperidin-4-one or a salt thereof with chloroform, at least one base chosen from potassium t-butoxide, potassium hydroxide, and sodium hydroxide, and at least one phase transfer catalyst chosen from tetrabutylmethylammonium chloride, (ii) reacting the products of the reaction in (a) with HCl to produce 5,5-dimethyl-3-methylenepyrrolidin-2-one or a salt thereof, (iii) performing an enantioselective hydrogenation of 5,5-dimethyl-3-methylenepyrrolidin-2-one or a salt thereof to produce (S)-3,5,5-trimethyl-pyrrolidin-2-one or a salt thereof;

(iv) reducing (S)-3,5,5-trimethyl-pyrrolidin-2-one or a salt thereof to produce Compound 17S;

(v) optionally treating (S)-2,2,4-trimethylpyrrolidine with HCl to produce an HCl salt of Compound 17S.

203. A process of preparing Compound 1 or a pharmaceutically acceptable salt thereof, or a deuterated derivative of any of the foregoing:

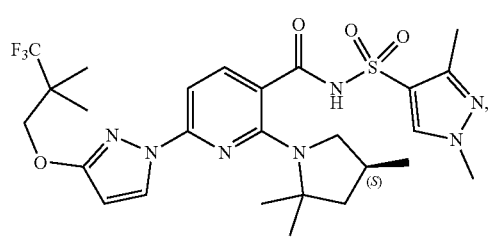

1 comprising the step of reacting Compound 13 or a salt thereof:

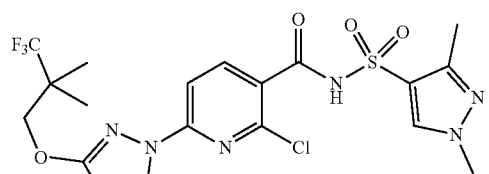

13 with (S)-2,2,4-trimethylpyrrolidine (Compound 17S) or a salt thereof in the presence of $K_2CO_3$ to generate Compound 1 or a pharmaceutically acceptable salt thereof, or a deuterated derivative of any of the foregoing;

wherein Compound 13 or salt thereof has been prepared by the steps comprising:

(i) decarboxylating Compound 6:

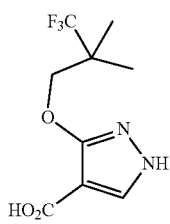

6 to form Compound 7 or a salt thereof:

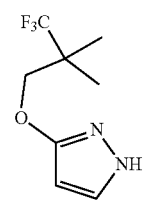

7 in the presence of a base chosen from 1,8-diazabicyclo[5.4.0]undec-7-ene (DBU), aqueous sodium hydroxide, and potassium tert-butoxide or at least one acid chosen from aqueous HCl and acetic acid;

(ii) reacting Compound 7 or a salt thereof with a compound of Formula (B-I) or a salt thereof:

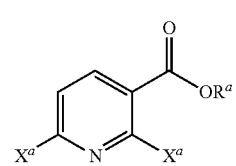

(B-I)

wherein $R^a$ is methyl, and each $—X^a$ is —Cl, to generate a compound of Formula (C-I) or a salt thereof:

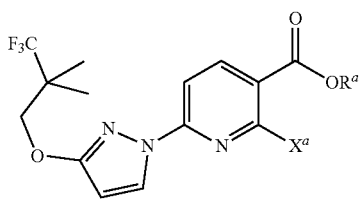

(C-I)

in the presence of a catalyst chosen from 1,4-diazabicyclo[2.2.2]octane (DABCO) and at least one base chosen from triethylamine, cesium carbonate, potassium carbonate, sodium carbonate, potassium tert-butoxide, potassium phosphate, DBU, and 1,1,3,3-tetramethylguanidine (TMG);

(iii) hydrolyzing the —C(O)OR$^a$ group of a compound of Formula (C-I) or a salt thereof in the presence of at least one base chosen from NaOH and KOH to generate a compound of Formula (D-I) or a salt thereof:

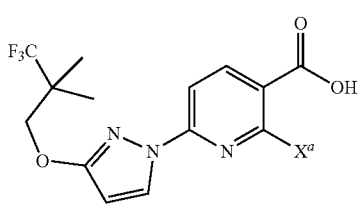

(D-I)

(iv) reacting a compound of Formula (D-I) or a salt thereof with 1,1'-carbonyldiimidazole (CDI) and subsequently reacting a product of the reaction of a compound of Formula (D-I) or a salt thereof with 1,1'-carbonyldiimidazole (CDI) with Compound 12 or a salt thereof:

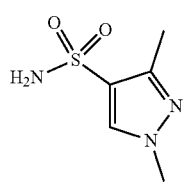

12 in the presence of at least one base chosen from 1,8-diazabicyclo[5.4.0]undec-7-ene (DBU) to yield Compound 13 or a salt thereof.

204. The process of embodiment 203, wherein Compound 17S or salt thereof has been prepared by the steps comprising:

(i) reacting 2,2,6,6-tetramethyl-piperidin-4-one or a salt thereof with chloroform, at least one base chosen from potassium t-butoxide, potassium hydroxide, and sodium hydroxide, and at least one phase transfer catalyst chosen from tetrabutylmethylammonium chloride, (ii) reacting the products of the reaction in (a) with HCl to produce 5,5-dimethyl-3-methylenepyrrolidin-2-one or a salt thereof, (iii) performing an enantioselective hydrogenation of 5,5-dimethyl-3-methylenepyrrolidin-2-one or a salt thereof to produce (S)-3,5,5-trimethyl-pyrrolidin-2-one or a salt thereof;

(iv) reducing (S)-3,5,5-trimethyl-pyrrolidin-2-one or a salt thereof to produce Compound 17S;

(v) optionally treating (S)-2,2,4-trimethylpyrrolidine with HCl to produce an HCl salt of Compound 17S.

205. The method of embodiment 203 or 204, wherein Compound 6:

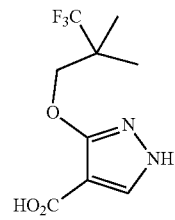

6 or a salt thereof, has been prepared by the step of hydrolyzing the —CO$_2$R$^b$ group of a compound of Formula viii:

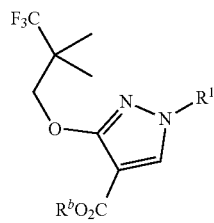

viii or salt thereof, wherein R$^1$ is a protecting group, and R$^b$ is chosen from C$_1$-C$_4$ alkyl groups.

206. The method of embodiment 205, wherein the compound of Formula viii:

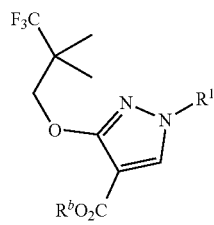

viii or a salt thereof, has been prepared by the step of reacting Compound 5 or a salt thereof:

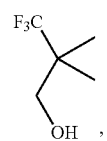

5 and a compound of Formula vii or a salt thereof

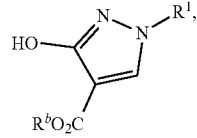

vii wherein R¹ is a protecting group and $R^b$ is chosen from $C_1$-$C_4$ alkyl groups.

207. The method of embodiment 206, wherein Compound 5:

5 or a salt thereof, has been prepared by the step of reducing a compound of Formula (W-II):

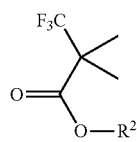

(W-II)

(W-II) or a salt thereof, wherein R² is chosen from H and $C_1$-$C_4$ alkyl groups 208. The method of embodiment 207, wherein the compound of Formula (W-II) is 3,3,3-trifluoro-2,2-dimethylpropionic acid (Compound 31):

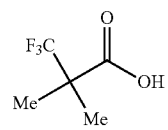

31 or a salt thereof,
and wherein Compound 31 has been prepared by the steps comprising:

(a) converting tert-butyl((1-ethoxy-2-methylprop-1-en-1-yl)oxy)dimethylsilane (Compound 28):

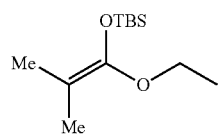

28 into ethyl 3,3,3-trifluoro-2,2-dimethylpropanoate (Compound 29):

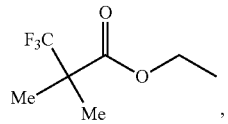

29 tert-butyldimethylsilyl 3,3,3-trifluoro-2,2-dimethylpropanoate (Compound 30):

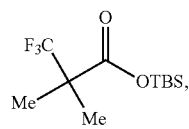

30 or a mixture thereof, under a photochemical condition with light at a wavelength of 435-450 nm; and (b) converting Compound 29, Compound 30, or a mixture thereof into Compound 31 or a salt thereof.

209. The method of any of embodiments 197-201, wherein the ratio of the first solvent to the second solvent is selected from 10:1, 5:1, 4:1, 2:1, 1:1, 1:2, 1:4, 1:5, and 1:10.

EXAMPLES

General Experimental Procedures

The definitions of certain abbreviations for the Examples below are summarized below:

Boc anhydride [(Boc)₂O: di-tert-butyl dicarbonate]
CDI: carbonyl diimidazole
DABCO: 1,4-diazabicyclo[2.2.2]octane
DBU: 1,8-diazabicyclo(5.4.0)undec-7-ene
DCC: N,N'-Dicyclohexylcarbodiimide
DCM: dichloromethane
DEE: 1,2-diethoxyethane
DIAD: diisopropyl azodicarboxylate
DIEA (DIPEA; N,N-diisopropylethylamine)
DMA: N,N-Dimethylacetamide
DMF: N,N-dimethylformamide
DMSO: dimethyl sulfoxide
EDCI: N-(3-Dimethylaminopropyl)-N'-ethylcarbodiimide hydrochloride
Et₂O: diethyl ether
EtOH: ethanol
HATU: 1-[Bis(dimethylamino)methylene]-1H-1,2,3-triazolo[4,5-b]pyridinium 3-oxid hexafluorophosphate
IPA: isoproanol
MeOH: methanol
NMP: N-methyl-2-pyrrolidone
MTBE: methyl tert-butyl ether
TBS-$C_1$: tert-Butyldimethylsilyl chloride
TFA: trifluoroacetic acid
THF: tetrahydrofuran)
p-TsOH: p-Toluenesulfonic Acid
TPPO-DIAD complex: a complex of triphenylphosphine oxide with diisopropyl azodicarboxylate Reagents and starting materials were obtained by commercial sources unless otherwise stated and were used without purification. Proton, carbon, and fluorine NMR spectra were acquired on either of a Bruker Biospin DRX 400 MHz FTNMR spectrometer operating at a ¹H resonant frequency of 400 MHz, ¹³C resonant frequency of 100 MHz, or a $^{19}$F resonant frequency of 376 MHz, or on a 300 MHz NMR spectrometer. One dimensional proton, carbon, and fluorine spectra were acquired using a broadband observe (BBFO) probe with 20 Hz sample rotation at 0.1834 and 0.9083 Hz/Pt digital resolution respectively. All proton carbon, and fluorine spectra were acquired with temperature control at 30° C. using standard, previously published pulse sequences and routine processing parameters. Low-resolution mass spectra were reported as [M+H]$^+$ species obtained using a single quadrupole mass spectrometer equipped with an electrospray ionization (ESI) source capable of achieving a mass accuracy of 0.1 Da and a minimum resolution of 1000 (no units on resolution) across the detection range. Optical purity of methyl (2S)-2,4-dimethyl-4-nitro-pentanoate was determined using chiral gas chromatography (GC) analysis on an Agilent 7890A/MSD 5975C instrument, using a Restek Rt-βDEXcst (30 m×0.25 mm×0.25 um_df) column, with a 2.0 mL/min flow rate (H$_2$ carrier gas), at an injection temperature of 220° C. and an oven temperature of 120° C., 15 minutes.

Example 1: Synthesis of
(4S)-2,2,4-trimethylpyrrolidine hydrochloride

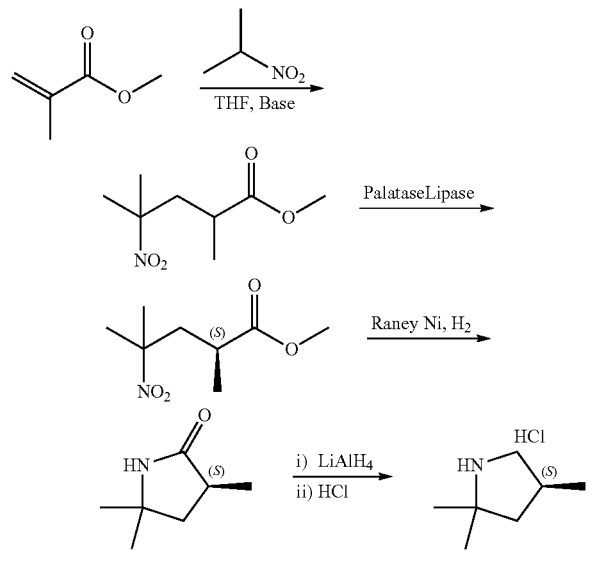

Step 1: methyl-2,4-dimethyl-4-nitro-pentanoate

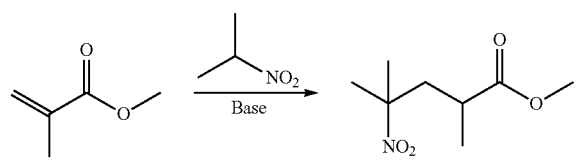

Tetrahydrofuran (THF, 4.5 L) was added to a 20 L glass reactor and stirred under N$_2$ at room temperature. 2-Nitropropane (1.5 kg, 16.83 mol) and 1,8-diazabicyclo[5.4.0]undec-7-ene (DBU) (1.282 kg, 8.42 mol) were then charged to the reactor, and the jacket temperature was increased to 50° C. Once the reactor contents were close to 50° C., methyl methacrylate (1.854 kg, 18.52 mol) was added slowly over 100 minutes. The reaction temperature was maintained at or close to 50° C. for 21 hours. The reaction mixture was concentrated in vacuo then transferred back to the reactor and diluted with methyl tert-butyl ether (MTBE) (14 L). 2 M HCl (7.5 L) was added, and this mixture was stirred for 5 minutes then allowed to settle. Two clear layers were visible—a lower yellow aqueous phase and an upper green organic phase. The aqueous layer was removed, and the organic layer was stirred again with 2 M HCl (3 L). After separation, the HCl washes were recombined and stirred with MTBE (3 L) for 5 minutes. The aqueous layer was removed, and all of the organic layers were combined in the reactor and stirred with water (3 L) for 5 minutes. After separation, the organic layers were concentrated in vacuo to afford a cloudy green oil. Crude product was treated with MgSO$_4$ and filtered to afford methyl-2,4-dimethyl-4-nitro-pentanoate as a clear green oil (3.16 kg, 99% yield).

$^1$H NMR (400 MHz, Chloroform-d) δ 3.68 (s, 3H), 2.56-2.35 (m, 2H), 2.11-2.00 (m, 1H), 1.57 (s, 3H), 1.55 (s, 3H), 1.19 (d, J=6.8 Hz, 3H).

Step 2: Synthesis of methyl
(2S)-2,4-dimethyl-4-nitro-pentanoate

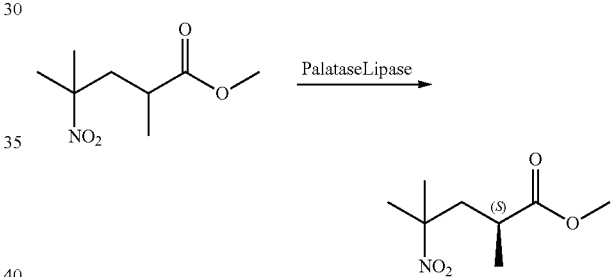

A reactor was charged with purified water (2090 L; 10 vol) and then potassium phosphate monobasic (27 kg, 198.4 moles; 13 g/L for water charge). The pH of the reactor contents was adjusted to pH 6.5 (±0.2) with 20% (w/v) potassium carbonate solution. The reactor was charged with racemic methyl-2,4-dimethyl-4-nitro-pentanoate (209 kg; 1104.6 moles), and Palatase 20000 L lipase (13 L, 15.8 kg; 0.06 vol).

The reaction mixture was adjusted to 32±2° C. and stirred for 15-21 hours, and pH 6.5 was maintained using a pH stat with the automatic addition of 20% potassium carbonate solution. When the racemic starting material was converted to >98% ee of the S-enantiomer, as determined by chiral GC, external heating was switched off. The reactor was then charged with MTBE (35 L; 5 vol), and the aqueous layer was extracted with MTBE (3 times, 400-1000 L). The combined organic extracts were washed with aqueous Na$_2$CO$_3$ (4 times, 522 L, 18% w/w 2.5 vol), water (523 L; 2.5 vol), and 10% aqueous NaCl (314 L, 1.5 vol). The organic layer was concentrated in vacuo to afford methyl (2S)-2,4-dimethyl-4-nitro-pentanoate as a mobile yellow oil (>98% ee, 94.4 kg; 45% yield).

Step 3: Synthesis of (3S)-3,5,5-trimethylpyrrolidin-2-one

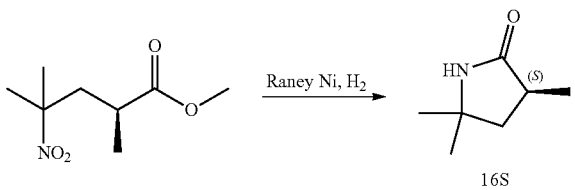

A 20 L reactor was purged with N₂. The vessel was charged sequentially with DI water-rinsed, damp Raney® Ni (2800 grade, 250 g), methyl (2S)-2,4-dimethyl-4-nitro-pentanoate (1741 g, 9.2 mol), and ethanol (13.9 L, 8 vol). The reaction was stirred at 900 rpm, and the reactor was flushed with H₂ and maintained at ~2.5 bar. The reaction mixture was then warmed to 60° C. for 5 hours. The reaction mixture was cooled and filtered to remove Raney nickel, and the solid cake was rinsed with ethanol (3.5 L, 2 vol). The ethanolic solution of the product was combined with a second equal sized batch and concentrated in vacuo to reduce to a minimum volume of ethanol (~1.5 volumes). Heptane (2.5 L) was added, and the suspension was concentrated again to ~1.5 volumes. This was repeated 3 times; the resulting suspension was cooled to 0-5° C., filtered under suction, and washed with heptane (2.5 L). The product was dried under vacuum for 20 minutes then transferred to drying trays and dried in a vacuum oven at 40° C. overnight to afford (3S)-3,5,5-trimethylpyrrolidin-2-one as a white solid (2.042 kg, 16.1 mol, 87%). ¹H NMR (400 MHz, Chloroform-d) δ 6.39 (s, 1H), 2.62 (ddq, J=9.9, 8.6, 7.1 Hz, 1H), 2.17 (dd, J=12.4, 8.6 Hz, 1H), 1.56 (dd, J=12.5, 9.9 Hz, 1H), 1.31 (s, 3H), 1.25 (s, 3H), 1.20 (d, J=7.1 Hz, 3H).

Step 4: Synthesis of (4S)-2,2,4-trimethylpyrrolidine hydrochloride

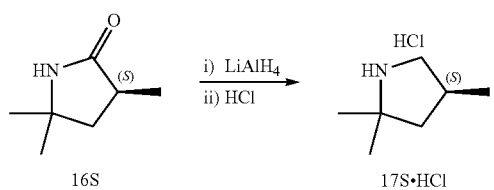

A glass lined 120 L reactor was charged with lithium aluminum hydride pellets (2.5 kg, 66 mol) and dry THF (60 L) and warmed to 30° C. The resulting suspension was charged with (S)-3,5,5-trimethylpyrrolidin-2-one (7.0 kg, 54 mol) in THF (25 L) over 2 hours while maintaining the reaction temperature at 30 to 40° C. After complete addition, the reaction temperature was increased to 60-63° C. and maintained overnight. The reaction mixture was cooled to 22° C., then cautiously quenched with the addition of ethyl acetate (EtOAc) (1.0 L, 10 moles), followed by a mixture of THF (3.4 L) and water (2.5 kg, 2.0 eq), and then a mixture of water (1.75 kg) with 50% aqueous sodium hydroxide (750 g, 2 equiv water with 1.4 equiv sodium hydroxide relative to aluminum), followed by 7.5 L water. After the addition was complete, the reaction mixture was cooled to room temperature, and the solid was removed by filtration and washed with THF (3×25 L). The filtrate and washings were combined and treated with 5.0 L (58 moles) of aqueous 37% HCl (1.05 equiv.) while maintaining the temperature below 30° C. The resultant solution was concentrated by vacuum distillation to a slurry. Isopropanol (8 L) was added and the solution was concentrated to near dryness by vacuum distillation. Isopropanol (4 L) was added, and the product was slurried by warming to about 50° C. MTBE (6 L) was added, and the slurry was cooled to 2-5° C. The product was collected by filtration and rinsed with 12 L MTBE and dried in a vacuum oven (55° C./300 torr/N₂ bleed) to afford (4S)-2,2,4-trimethylpyrrolidine·HCl as a white solid (6.21 kg, 75% yield). ¹H NMR (400 MHz, DMSO-d6) δ 9.34 (br d, 2H), 3.33 (dd, J=11.4, 8.4 Hz, 1H), 2.75 (dd, J=11.4, 8.6 Hz, 1H), 2.50-2.39 (m, 1H), 1.97 (dd, J=12.7, 7.7 Hz, 1H), 1.42 (s, 3H), 1.38 (dd, J=12.8, 10.1 Hz, 1H), 1.31 (s, 3H), 1.05 (d, J=6.6 Hz, 3H).

Example 2: Synthesis of 5,5-dimethyl-3-methylenepyrrolidin-2-one

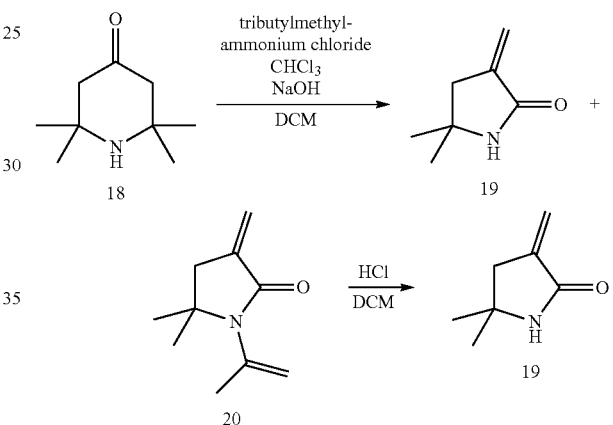

Example 2A 2,2,6,6-tetramethylpiperidin-4-one (50.00 g, 305.983 mmol, 1.000 equiv), tributylmethyl ammonium chloride (2.89 g, 3.0 mL, 9.179 mmol, 0.030 equiv), chloroform (63.92 g, 43.2 mL, 535.470 mmol, 1.750 equiv), and DCM (dichloromethane) (100.0 mL, 2.00 vol) were charged to a 1000 mL three-neck round bottom flask equipped with an overhead stirrer. The reaction mixture was stirred at 300 rpm, and 50 wt % NaOH (195.81 g, 133.2 mL, 2,447.863 mmol, 8.000 equiv) was added dropwise (via addition funnel) over 1.5 h while maintaining the temperature below 25° C. with intermittent ice/acetone bath. The reaction mixture was stirred at 500 rpm for 18 h, and monitored by GC (3% unreacted piperidinone after 18 h). The suspension was diluted with DCM (100.0 mL, 2.00 vol) and H₂O (300.0 mL, 6.00 vol), and the phases were separated. The aqueous phase was extracted with DCM (100.0 mL, 2.00 vol). The organic phases were combined and 3 M hydrochloric acid (16.73 g, 153.0 mL, 458.974 mmol, 1.500 equiv) was added. The mixture was stirred at 500 rpm for 2 h. The conversion was complete after approximately 1 h. The aqueous phase was saturated with NaCl, H₂O (100.0 mL, 2.00 vol) was added to help reduce the emulsion, and the phases were separated. The aqueous phase was extracted with DCM (100.0 mL, 2.00 vol) twice. H₂O (100.0 mL, 2.00 vol) was added to help with emulsion separation. The organic phases were combined, dried (MgSO₄), and concentrated to afford 32.6 g (85%) of crude 5,5-dimethyl-3-methylenepyrrolidin-2-one (19) as a pale orange clumpy solid. The crude was recrystallized from hot (90° C.) iPrOAc (71.7 mL, 2.2 vol. of crude), cooled to 80° C., and ~50 mg of crystalline 5,5-dimethyl-3-methylenepyrrolidin-2-one (19) was added for seeding. Crystallization started at 77° C., the mixture was slowly cooled to ambient temperature, and aged for 2 h. The solid was collected by filtration, washed with 50/50 iPrOAc/heptane (20.0 mL, 0.40 vol) twice, and dried overnight in the vacuum oven at 40° C. to afford the desired product (23.70 g, 189.345 mmol, 62% yield) as a white sand colored crystalline solid.

$^1$H NMR (400 MHz, CDCl₃, 7.26 ppm) δ 7.33 (bs, 1H), 5.96-5.95 (m, 1H), 5.31-5.30 (m, 1H), 2.6 (t, J=2.5 Hz, 2H), 1.29 (s, 6H).

Example 2B

Step 1: Under a nitrogen atmosphere, 2,2,6,6-tetramethylpiperidin-4-one (257.4 kg, 1658.0 mol, 1.00 eq.), tri-butyl methyl ammonium chloride (14.86 kg, 63.0 mol, 0.038 eq.), chloroform (346.5 kg, 2901.5 mol, 1.75 eq.) and DCM (683.3 kg) were added to a 500 L enamel reactor. The reaction was stirred at 85 rpm and cooled to 15~17° C. The solution of 50 wt % sodium hydroxide (1061.4 kg, 13264.0 mol, 8.00 eq.) was added dropwise over 40 h while maintaining the temperature between 15-25° C. The reaction mixture was stirred and monitored by GC.

Step 2: The suspension was diluted with DCM (683.3 kg) and water (1544.4 kg). The organic phase was separated. The aqueous phase was extracted with DCM (683.3 kg). The organic phases were combined, cooled to 10° C. and then 3 M hydrochloric acid (867.8 kg, 2559.0 mol, 1.5 eq.) was added. The mixture was stirred at 10-15° C. for 2 h. The organic phase was separated. The aqueous phase was extracted with DCM (683.3 kg×2). The organic phases were combined, dried over Na₂SO₄ (145.0 kg) for 6 h. The solid was filtered off and washed with DCM (120.0 kg). The filtrate was stirred with active charcoal (55 kg) for 6 h. The resulting mixture was filtered and the filtrate was concentrated under reduced pressure (30-40° C., −0.1 MPa). Then isopropyl acetate (338 kg) was added and the mixture was heated to 87-91° C., stirred for 1 h. Then the solution was cooled to 15° C. in 18 h and stirred for 1 h at 15° C. The solid was collected by filtration, washed with 50% isopropyl acetate/hexane (80.0 kg×2) and dried overnight in the vacuum oven at 50° C. to afford 5,5-dimethyl-3-methylenepyrrolidin-2-one as an off white solid, 55% yield.

Example 3: Synthesis of (S)-3,5,5-trimethyl-pyrrolidin-2-one from 5,5-dimethyl-3-methylenepyrrolidin-2-one

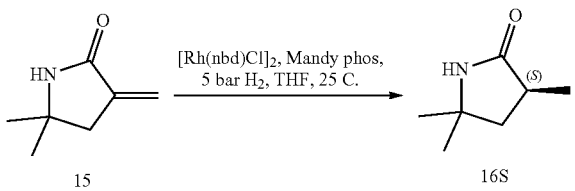

Example 3A—Use of Rh Catalyst

Step 1—Preparation of Rh Catalyst Formation

In a 3 L Schlenk flask, 1.0 l of tetrahydrofuran (THF) was degassed with an argon stream. Mandyphos Ligand SL-M004-1 (1.89 g) and [Rh(nbd)Cl]₂ (98%, 0.35 g) (chloronorbornadiene rhodium(I) dimer) were added. The resulting orange catalyst solution was stirred for 30 min at room temperature to form a catalyst solution.

Step 2

A 50 L stainless steel autoclave was charged with 5,5-dimethyl-3-methylenepyrrolidin-2-one (6.0 kg) and THF (29 L). The autoclave was sealed and the resulting suspension was flushed with nitrogen (3 cycles at 10 bar), and then released of pressure. Next the catalyst solution from Step 1 was added. The autoclave was flushed with nitrogen without stirring (3 cycles at 5 bar) and hydrogen (3 cycles at 5 bar). The pressure was set to 5 bar and a 50 L reservoir was connected. After 1.5 h with stirring at 1000 rpm and no hydrogen uptake the reactor was flushed again with nitrogen (3 cycles at 10 bar) with stirring and additional catalyst solution was added. The autoclave was again flushed to hydrogen with the above described procedure (3×5 bar N2, 3×5 bar H2) and adjusted to 5 bar. After 2 h, the pressure was released, the autoclave was flushed with nitrogen (3 cycles at 5 bar) and the product solution was discharged into a 60 L inline barrel. The autoclave was charged again with THF (5 L) and stirred with 1200 rpm for 5 min. The wash solution was added to the reaction mixture.

Step 3

The combined solutions were transferred into a 60 L reactor. The inline barrel was washed with 1 L THF which was also added into the reactor. 20 L THF were removed by evaporation at 170 mbar and 40° C. 15 L heptane were added. The distillation was continued and the removed solvent was continuously replaced by heptane until the THF content in the residue was 1% w/w (determined by NMR). The reaction mixture was heated to 89° C. (turbid solution) and slowly cooled down again (ramp: 14° C./h). Several heating and cooling cycles around 55 to 65° C. were made. The off-white suspension was transferred to a stirred pressure filter and filtered (ECTFE-pad, d=414 mm, 60 my, Filtration time=5 min). 10 L of the mother liquor was transferred back into the reactor to wash the crystals from the reactor walls and the obtained slurry was also added to the filter. The collected solid was washed with 2×2.5 l heptane, discharged and let dry on the rotovap at 40° C. and 4 mbar to obtain the product, (S)-3,5,5-trimethyl-pyrrolidin-2-one; 5.48 Kg (91%), 98.0% ee.

Example 3B—Use of Ru Catalyst

The reaction was performed in a similar manner as described above in Example 3A except the use of a Ru catalyst instead of a Rh catalyst.

Compound (15) (300 g) was dissolved in THF (2640 g, 10 Vol) in a vessel. In a separate vessel, a solution of [RuCl(p-cymene){(R)-segphos}]Cl (0.439 g, 0.0002 eq) in THF (660 g, 2.5 Vol) was prepared. The solutions were premixed in situ and passed through a Plug-flow reactor (PFR). The flow rate for the Compound (15) solution was at 1.555 mL/min and the Ru catalyst solution was at 0.287 mL/min.

Residence time in the PFR was 4 hours at 30° C., with hydrogen pressure of 4.5 MPa. After completion of reaction, the THF solvent was distilled off to give a crude residue. Heptane (1026 g, 5 vol) was added and the resulting mixture was heated to 90° C. The mixture was seeded with 0.001 eq. of Compound 16S seeds. The mixture was cooled to −15° C. at 20° C./h. After cooling, heptane (410 g, 2 vol) was added and the solid product was recovered by filtration. The resulting product was dried in a vacuum oven at 35° C. to give (S)-3,5,5-trimethyl-pyrrolidin-2-one (281.77 g, 98.2% ee, 92% yield).

Example 3C—Analytical Measurements

Analytical chiral HPLC method for the determination of the conversion, chemoselectivity, and enantiomeric excess of the products from Example 3A and 3B was made under the following conditions Instrument: Agilent Chemstation 1100
Column: Phenomenex Lux 5u Cellulose-2, 4.6 mm×250 mm×5 um, LHS6247
Solvent: Heptane/iPrOH (90:10)
Flow: 1.0 ml/min
Detection: UV (210 nm)
Temperature: 25° C.
Sample concentration: 30 μl of reaction solution evaporated, dissolved in 1 mL heptane/iPrOH (80/20)
Injection volume: 10.0 μL, Run time 20 min
Retention times:
  5,5-dimethyl-3-methylenepyrrolidin-2-one: 13.8 min
  (S)-3,5,5-trimethyl-pyrrolidin-2-one: 10.6 min
  (R)-3,5,5-trimethyl-pyrrolidin-2-one: 12.4 min Example 4: Synthesis of (S)-3,5,5-trimethyl-pyrrolidin-2-one from 5,5-dimethyl-3-methylenepyrrolidin-2-one

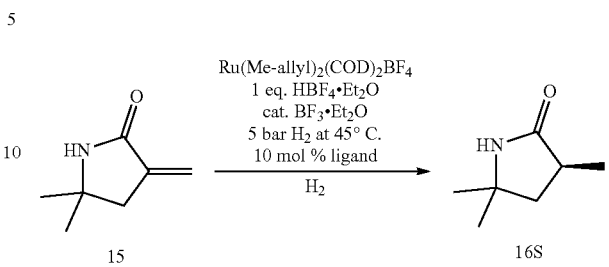

Mandyphos (0.00479 mmol, 0.12 eq) was weighed into a GC vial. In a separate vial Ru(Me-allyl)$_2$(COD) (16.87 mg, 0.0528 mmol) was weighed and dissolved in DCM (1328 μL). In another vial HBF$_4$·Et$_2$O (6.6 μL) and BF$_3$·Et$_2$O (2.0 μL) were dissolved in DCM (240 μL). To the GC vial containing the ligand was added, under a flow of argon, the Ru(Me-allyl)$_2$(COD) solution (100 μL; 0.00399 mmol, 0.1 eq) and the HBF$_4$·Et$_2$O/BF$_3$·Et$_2$O solution (20 μL; 1 eq HBF$_4$·Et$_2$O and catalytic BF$_3$·Et$_2$O). The resulting mixtures were stirred under a flow of argon for 30 minutes.

5,5-dimethyl-3-methylenepyrrolidin-2-one (5 mg, 0.0399 mmol) in EtOH (1 mL) was added. The vials were placed in the hydrogenation apparatus. The apparatus was flushed with H$_2$ (3 x) and charged with 5 bar H$_2$. After standing for 45 minutes, the apparatus was placed in an oil bath at temperature of 45° C. The reaction mixtures were stirred overnight under H$_2$. 200 μL of the reaction mixture was diluted with MeOH (800 μL) and analyzed for conversion and ee.

1H NMR (400 MHz, Chloroform-d) δ 6.39 (s, 1H), 2.62 (ddq, J=9.9, 8.6, 7.1 Hz, 1H), 2.17 (ddd, J=12.4, 8.6, 0.8 Hz, 1H), 1.56 (dd, J=12.5, 9.9 Hz, 1H), 1.31 (s, 3H), 1.25 (s, 3H), 1.20 (d, J=7.1 Hz, 3H).

TABLE 1

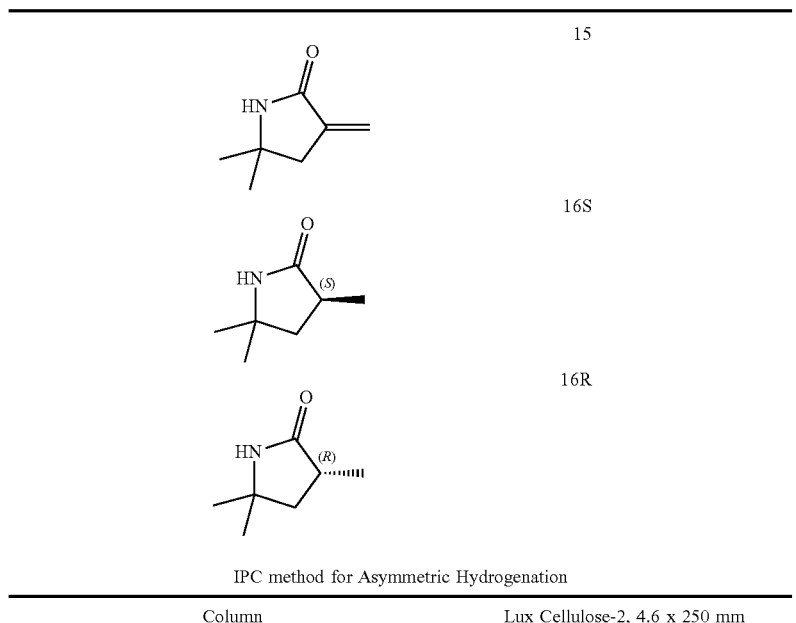

IPC method for Asymmetric Hydrogenation

| Column | Lux Cellulose-2, 4.6 x 250 mm |
|---|---|
| Isocratic | 90% Heptane/10% IPA |
| Flow rate | 1.0 mL/min |
| Column Temperature | 30° C. |
| UV detector wavelength | 210 nm, bw = 4; Ref = off |

TABLE 1-continued

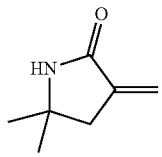

15

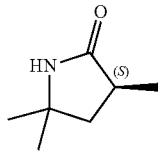

16S

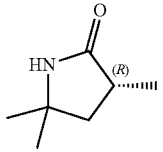

16R

IPC method for Asymmetric Hydrogenation

| | |
|---|---|
| Injection volume | 10 µL |
| Run time | 15 minutes |
| Nominal concentration | 0.4 mg/mL |
| Diluent | Heptane/IPA (8/2) |
| Retention times | Compound 16S = 10.6 min |
| | Compound 16R = 11.8 min |
| | Compound 15 = 12.6 min |
| Compound 16S/Compound 16R Resolution | 2.8 |
| Compound 16R/Compound 15 Resolution | 2.0 |

Example 5. Synthesis of (S)-2,2,4-trimethylpyrrolidine hydrochloride from (S)-3,5,5-trimethyl-pyrrolidin-2-one

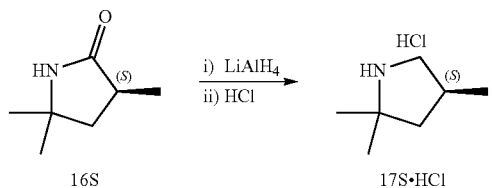

Example 5A

Anhydrous THF (100 ml) was charged to a dry 750 ml reactor and the jacket temperature was set to 50° C. Once the vessel contents were at 50° C. LiAlH₄ pellets (10 g, 263 mmol, 1.34 eq.) were added. The mixture was stirred for 10 minutes, then a solution of (S)-3,5,5-trimethyl-pyrrolidin-2-one (16S) (25 g, 197 mmol) in anhydrous THF (100 ml) was added dropwise over 45 minutes, maintaining the temperature between 50-60° C. Once the addition was complete the jacket temperature was increased to 68° C. and the reaction stirred for 18.5 hrs. The reaction mixture was cooled to 30° C. then saturated sodium sulfate solution (20.9 ml) was added dropwise over 30 minutes, keeping the temperature below 40° C. Vigorous evolution of hydrogen was observed and the reaction mixture thickened but remained mixable. The mixture thinned towards the end of the addition. The mixture was cooled to 20° C., diluted with iPrOAc (100 ml) and stirred for an additional 10 minutes. The suspension was then drained and collected through the lower outlet valve, washing through with additional iPrOAc (50 ml). The collected suspension was filtered through a celite pad on a sintered glass funnel under suction and washed with iPrOAc (2×50 ml).

The filtrate was transferred back to the cleaned reactor and cooled to 0° C. under nitrogen. 4M HCl in dioxane (49.1 ml, 197 mmol, 1 eq.) was then added dropwise over 15 minutes, maintaining the temperature below 20° C. A white precipitate formed. The reactor was then reconfigured for distillation, the jacket temperature was increased to 100° C., and distillation of solvent was carried out. Additional i-PrOAc (100 mL) was added during concentration, after >100 mL distillate had been collected. Distillation was continued until ~250 mL total distillate was collected, then a Dean-Stark trap was attached and reflux continued for 1 hour. No water was observed to collect. The reaction mixture was cooled to 20° C. and filtered under suction under nitrogen. The filtered solid was washed with i-PrOAc (100 mL), dried under suction in nitrogen, then transferred to a glass dish and dried in a vacuum oven at 40° C. with a nitrogen bleed. (S)-2,2,4-Trimethylpyrrolidine hydrochloride (17S·HCl) was obtained as a white solid (24.2 g, 82%).

GC analysis (purity): >99.5%
GC chiral purity: 99.5%
Water content (by KF): 0.074%
Residual solvent (by ¹H-NMR): 0.41%

Example 5B

To a glass lined 120 L reactor was charged LiAlH₄ pellets (2.5 kg 66 mol, 1.2 equiv.) and dry THF (60 L) and warmed to 30° C. To the resulting suspension was charged (S)-3,5,5-trimethylpyrrolidin-2-one (7.0 kg, 54 mol) in THF (25 L) over 2 hours while maintaining the reaction temperature at 30 to 40° C. After complete addition, the reaction temperature was increased to 60-63° C. and maintained overnight. The reaction mixture was cooled to 22° C. and sampled to check for completion, then cautiously quenched with the addition of EtOAc (1.0 L, 10 moles, 0.16 eq) followed by a mixture of THF (3.4 L) and water (2.5 kg, 2.0 eq) then followed by a mixture of water (1.75 kg) with 50% aqueous sodium hydroxide (750 g, 2 eq water with 1.4 eq sodium hydroxide relative to aluminum), followed by 7.5 L water (6 eq "Fieser" quench). After the addition was completed, the reaction mixture was cooled to room temperature, and the solid was removed by filtration and washed with THF (3×25 L). The filtrate and washings were combined and treated with 5.0 L (58 moles) of aqueous 37% HCl (1.05 equiv.) while maintaining the temperature below 30° C.

The resultant solution was concentrated by vacuum distillation to a slurry in two equal part lots on the 20 L Buchi evaporator. Isopropanol (8 L) was charged and the solution reconcentrated to near dryness by vacuum distillation. Isopropanol (4 L) was added and the product slurried by warming to about 50° C. Distillation from Isopropanol continued until water content by KF is ≤0.1%. Methyl tertbutyl ether (6 L) was added and the slurry cooled to 2-5° C. The product was collected by filtration and rinsed with 12 L methyl tert-butyl ether and pulled dry with a strong nitrogen flow and further dried in a vacuum oven (55° C./300 torr/$N_2$ bleed) to afford (S)-2,2,4-trimethylpyrrolidine·HCl as a white, crystalline solid (6.21 kg, 75% yield). $^1$H NMR (400 MHz, DMSO-d6) δ 9.34 (s, 2H), 3.33 (dd, J=11.4, 8.4 Hz, 1H), 2.75 (dd, J=11.4, 8.6 Hz, 1H), 2.50-2.39 (m, 1H), 1.97 (dd, J=12.7, 7.7 Hz, 1H), 1.42 (s, 3H), 1.38 (dd, J=12.8, 10.1 Hz, 1H), 1.31 (s, 3H), 1.05 (d, J=6.6 Hz, 3H).

Example 5C

With efficient mechanical stirring, a suspension of LiAlH$_4$ pellets (100 g 2.65 mol; 1.35 eq.) in THF (1 L; 4 vol. eq.) warmed at a temperature from 20° C.-36° C. (heat of mixing). A solution of (S)-3,5,5-trimethylpyrrolidin-2-one (250 g; 1.97 mol) in THF (1 L; 4 vol. eq.) was added to the suspension over 30 min. while allowing the reaction temperature to rise to ~60° C. The reaction temperature was increased to near reflux (~68° C.) and maintained for about 16 h. The reaction mixture was cooled to below 40° C. and cautiously quenched with drop-wise addition of a saturated aqueous solution of Na$_2$SO$_4$ (209 mL) over 2 h. After the addition was completed, the reaction mixture was cooled to ambient temperature, diluted with i-PrOAc (1 L), and mixed thoroughly. The solid was removed by filtration (Celite pad) and washed with i-PrOAc (2×500 mL). With external cooling and N$_2$ blanket, the filtrate and washings were combined and treated with drop-wise addition of anhydrous 4 M HCl in dioxane (492 mL; 2.95 mol; 1 equiv.) while maintaining the temperature below 20° C. After the addition was completed (20 min), the resultant suspension was concentrated by heating at reflux (74-85° C.) and removing the distillate. The suspension was backfilled with i-PrOAc (1 L) during concentration. After about 2.5 L of distillate was collected, a Dean-Stark trap was attached and any residual water was azeotropically removed. The suspension was cooled to below 30° C. when the solid was collected by filtration under a N$_2$ blanket. The solid is dried under N$_2$ suction and further dried in a vacuum oven (55° C./300 torr/N$_2$ bleed) to afford 261 g (89% yield) of (S)-2,2,4-trimethylpyrrolidine·HCl as a white, crystalline solid. $^1$H NMR (400 MHz, DMSO-d6) δ 9.34 (s, 2H), 3.33 (dd, J=11.4, 8.4 Hz, 1H), 2.75 (dd, J=11.4, 8.6 Hz, 1H), 2.50-2.39 (m, 1H), 1.97 (dd, J=12.7, 7.7 Hz, 1H), 1.42 (s, 3H), 1.38 (dd, J=12.8, 10.1 Hz, 1H), 1.31 (s, 3H), 1.05 (d, J=6.6 Hz, 3H). $^1$H NMR (400 MHz, CDCl$_3$) δ 9.55 (d, J=44.9 Hz, 2H), 3.52 (ddt, J=12.1, 8.7, 4.3 Hz, 1H), 2.94 (dq, J=11.9, 5.9 Hz, 1H), 2.70-2.51 (m, 1H), 2.02 (dd, J=13.0, 7.5 Hz, 1H), 1.62 (s, 3H), 1.58-1.47 (m, 4H), 1.15 (d, J=6.7 Hz, 3H).

Example 5D

A 1 L four-neck round bottom flask was degassed three times. A 2M solution of LiAlH$_4$ in THF (100 mL) was charged via cannula transfer. (S)-3,5,5-trimethylpyrrolidin-2-one (19.0 g) in THF (150 mL) was added dropwise via an addition funnel over 1.5 hours at 50-60° C., washing in with THF (19 mL). Upon completion of the addition, the reaction was stirred at 60° C. for 8 hours and allowed to cool to room temperature overnight. GC analysis showed <1% starting material remained.

Deionized water (7.6 mL) was added slowly to the reaction flask at 10-15° C., followed by 15% potassium hydroxide (7.6 mL). Isopropyl acetate (76 mL) was added, the mixture was stirred for 15 minutes and filtered, washing through with isopropyl acetate (76 mL).

The filtrate was charged to a clean and dry 500 mL four neck round bottom flask and cooled to 0-5° C. 36% Hydrochloric acid (15.1 g, 1.0 eq.) was added keeping the temperature below 20° C. Distillation of the solvent, backfilling with isopropyl acetate (190 mL), was carried out to leave a residual volume of ~85 mL. Karl Fischer analysis=0.11% w/w H$_2$O. MTBE (methyl tertiary butyl ether) (19 mL) was added at 20-30° C. and the solids were filtered off under nitrogen at 15-20° C., washing with isopropyl acetate (25 mL) and drying under vacuum at 40-45° C. to give crude (S)-2,2,4-trimethylpyrrolidine hydrochloride as a white crystalline solid (17.4 g, 78% yield). GC purity=99.5%. Water content=0.20% w/w. Chiral GC gave an ee of 99.0% (S). Ruthenium content=0.004 ppm. Lithium content=0.07 ppm.

A portion of the dried crude (S)-2,2,4-trimethylpyrrolidine hydrochloride (14.3 g) was charged to a clean and dry 250 mL four-neck round bottom flask with isopropanol (14.3 mL) and the mixture held at 80-85° C. (reflux) for 1 hour to give a clear solution. The solution was allowed to cool to 50° C. (solids precipitated on cooling) then MTBE (43 mL) was added and the suspension held at 50-55° C. (reflux) for 3 hours. The solids were filtered off at 10° C., washing with MTBE (14 mL) and dried under vacuum at 40° C. to give recrystallised (S)-2,2,4-trimethylpyrrolidine hydrochloride (17S·HCl) as a white crystallised solid (13.5 g, 94% yield on recrystallisation, 73% yield). GC purity=99.9%. Water content=0.11% w/w. Chiral GC gave an ee of 99.6 (S). Ruthenium content=0.001 ppm. Lithium content=0.02 ppm.

Example 5E

A reactor was charged with lithium aluminum hydride (LAH) (1.20 equiv.) and 2-MeTHF (2-methyltetrahydrofuran) (4.0 vol), and heated to internal temperature of 60° C. while stirring to disperse the LAH. A solution of (S)-3,5,5-trimethylpyrrolidin-2-one (1.0 equiv) in 2-MeTHF (6.0 vol) was prepared and stirred at 25° C. to fully dissolve the (S)-3,5,5-trimethylpyrrolidin-2-one. The (S)-3,5,5-trimethylpyrrolidin-2-one solution was added slowly to the reactor while keeping the off-gassing manageable, followed by rinsing the addition funnel with 2-MeTHF (1.0 vol) and adding it to the reactor. The reaction was stirred at an internal temperature of 60±5° C. for no longer than 6 h. The internal temperature was set to 5±5° C. and the agitation rate was increased. A solution of water (1.35 equiv.) in 2-MeTHF (4.0 v) was prepared and added slowly to the reactor while the internal temperature was maintained at or below 25° C. Additional water (1.35 equiv.) was charged slowly to the reactor while the internal temperature was maintained at or below 25° C. Potassium hydroxide (0.16 equiv.) in water (0.40 vol) was added to the reactor over no less than 20 min while the temperature was maintained at or below 25° C. The resulting solids were removed by filtration, and the reactor and cake were washed with 2-MeTHF (2×2.5 vol). The filtrate was transferred back to a jacketed vessel, agitated, and the temperature was adjusted to 15±5° C. Concentrated aqueous HCl (35-37%, 1.05 equiv.) was added slowly to the filtrate while maintaining the temperature at or below 25° C. and was stirred no less than 30 min. Vacuum was applied and the solution was distilled down to a total of 4.0 volumes while maintaining the internal temperature at or below 55° C., then 2-MeTHF (6.00 vol) was added to the vessel. The distillation was repeated until Karl Fischer analysis (KF)<0.20% w/w H2O. Isopropanol was added (3.00 vol), and the temperature was adjusted to 70° C. (65-75° C.) to achieve a homogenous solution, and stirred for no less than 30 minutes at 70° C. The solution was cooled to 50° C. (47-53° C.) over 1 hour and stirred for no less than 1 h, while the temperature was maintained at 50° C. (47-53° C.). The resulting slurry was cooled to −10° C. (−15 to −5° C.) linearly over no less than 12 h. The slurry was stirred at −10° C. for no less than 2 h. The solids were isolated via filtration or centrifugation and were washed with a solution of 2-MeTHF (2.25 vol) and IPA (isopropanol) (0.75 vol). The solids were dried under vacuum at 45±5° C. for not less than 6 h to yield (S)-2,2,4-trimethylpyrrolidine hydrochloride (17S·HCl).

Example 6: Phase Transfer Catalyst (PTC) Screens for the Synthesis of 5,5-dimethyl-3-methylenepyrrolidin-2-one

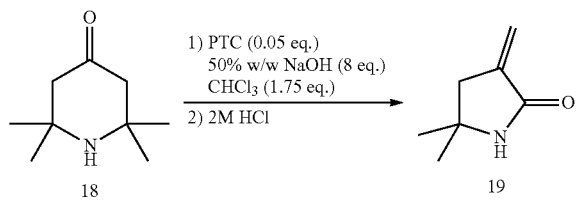

2,2,6,6-tetramethylpiperidin-4-one (500.0 mg, 3.06 mmol, 1.0 eq.), PTC (0.05 eq.), and chloroform (0.64 g, 0.4 mL, 5.36 mmol, 1.75 eq.) were charged into a vial equipped with a magnetic stir bar. The vial was cooled in an ice bath and a solution of 50 wt % sodium hydroxide (0.98 g, 24.48 mmol, 8.0 eq.) was added dropwise over 2 min. The reaction mixture was stirred until completion as assessed by GC analysis. The reaction mixture was diluted with DCM (2.0 mL, 4.0 v) and H₂O (3.0 mL, 6.0 v). The phases were separated and the aqueous phase was extracted with DCM (1.0 mL, 2.0 v). The organic phases were combined and 2 M hydrochloric acid (0.17 g, 2.3 mL, 4.59 mmol, 1.5 eq.) was added. The reaction mixture was stirred until completion and assessed by HPLC. The aqueous phase was saturated with NaCl and the phases were separated. The aqueous phase was extracted with DCM (1.0 mL, 2.0 v) twice, the organic phases were combined, and 50 mg of biphenyl in 2 mL of MeCN was added as an internal HPLC standard. Solution yield was assessed by HPLC. Reaction results are summarized in Table 2.

TABLE 2

| Reactions | Conditions | Result |
| --- | --- | --- |
| 6A | 18-crown-6 (0.05 eq.) | Complete in 2 h, 75% solution yield |
| 6B | TBAB (0.05 eq.) | Complete in 2 h, 83% solution yield |
| 6C | TBAC (0.05 eq.) | Complete in 4 h, 67% solution yield |
| 6D | Tetrabutylammonium hydroxide (0.05 eq.) | Complete in 4 h, 74% solution yield |
| 6E | 15-crown-5 (0.05 eq.) | Complete in 4 h, 78% solution yield |
| 6F | No PTC | Incomplete after 4 days |
| 6G | benzyltrimethylammonium chloride (0.05 eq.) | Complete in 7 h, 72% solution yield |
| 6H | Triton B (0.05 eq.) | Almost complete in 7 h (1% starting material leftover), 69% solution yield |
| 6I | Tributylmethylammonium chloride (0.05 eq.) | Complete in 4 h, 75% solution yield |
| 6J | Aliquat 336 (0.05 eq.) | Complete in 6 h, 76% solution yield |

Example 7: Solvent Screens for the Synthesis of 5,5-dimethyl-3-methylenepyrrolidin-2-one

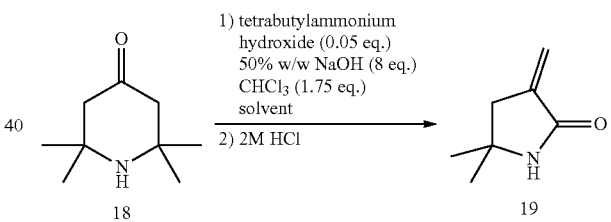

2,2,6,6-tetramethylpiperidin-4-one (500.0 mg, 3.06 mmol, 1.0 eq.), tetrabutylammonium hydroxide (0.12 g, 0.153 mmol, 0.050 eq), chloroform (0.64 g, 0.4 mL, 5.36 mmol, 1.75 eq.), and solvent (2 vol. or 4 vol., as shown in Table 3 below) were charged into a vial equipped with a magnetic stir bar. The vial was cooled in an ice bath and a solution of 50 wt % sodium hydroxide (0.98 g, 24.48 mmol, 8.0 eq.) was added drop wise over 2 min. The reaction mixture was stirred until completion and assessed by GC analysis. The reaction mixture was diluted with DCM (2.0 mL, 4.0 v) and H₂O (3.0 mL, 6.0 v). The phases were separated and the aqueous phase was extracted with DCM (1.0 mL, 2.0 v). The organic phases were combined and 2 M hydrochloric acid (0.17 g, 2.3 mL, 4.59 mmol, 1.5 eq.) was added. The reaction mixture was stirred until completion, assessed by HPLC. The aqueous phase was saturated with NaCl and the phases were separated. The aqueous phase was extracted with DCM (1.0 mL, 2.0 v) twice, the organic phases were combined, and 50 mg of biphenyl in 2 mL of MeCN was added as an internal IPLC standard. Solution yield was assessed by HPLC. Reaction results are summarized in Table 3.

TABLE 3

| Reactions | Solvent | Result |
|---|---|---|
| 7A | CHCl₃ (4 vol.) | Complete overnight, 59% solution yield |
| 7B | DCM (4 vol.) | Incomplete overnight |
| 7C | CHCl₃ (2 vol.) | Complete in 6.5 h, 67% solution yield |
| 7D | THF (4 vol.) | Incomplete overnight |
| 7E | trifluorotoluene (4 vol.) | Incomplete overnight |
| 7F | NMP (N-methyl pyrrolidone) (4 vol.) | Incomplete overnight |
| 7G | DCM (2 vol.) | Complete overnight, 79% solution yield |
| 7H | THF (2 vol.) | Almost complete overnight (3% starting material), 66% solution yield |
| 7I | trifluorotoluene (2 vol.) | Almost complete overnight (1% starting material), 77% solution yield |
| 7J | heptane (2 vol.) | Almost complete at 6 h (5% starting material), complete over the weekend, 72% solution yield |

Example 8: Base Screens for the Synthesis of 5,5-dimethyl-3-methylenepyrrolidin-2-one

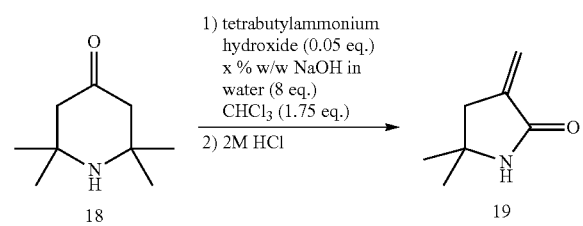

2,2,6,6-tetramethylpiperidin-4-one (500.0 mg, 3.06 mmol, 1.0 eq.), tetrabutylammonium hydroxide (0.12 g, 0.153 mmol, 0.050 eq), and chloroform (0.64 g, 0.4 mL, 5.36 mmol, 1.75 eq.) were charged into a vial equipped with a magnetic stir bar. The vial was cooled in an ice bath, and a solution of an amount wt % sodium hydroxide as shown in Table 4 below in water (0.98 g, 24.48 mmol, 8.0 eq.) was added drop wise over 2 min. The reaction mixture was stirred until completion and assessed by GC analysis. The reaction mixture was diluted with DCM (2.0 mL, 4.0 v) and H₂O (3.0 mL, 6.0 v). The phases were separated and the aqueous phase is extracted with DCM (1.0 mL, 2.0 v). The organic phases were combined and 2 M hydrochloric acid (0.17 g, 2.3 mL, 4.59 mmol, 1.5 eq.) was added. The reaction mixture was stirred until completion, assessed by HPLC. The aqueous phase was saturated with NaCl and the phases were separated. The aqueous phase was extracted with DCM (1.0 mL, 2.0 v) twice, the organic phases were combined, and 50 mg of biphenyl in 2 mL of MeCN was added as an internal HPLC standard. Solution yield was assessed by HPLC. Reaction results are summarized in Table 4.

TABLE 4

| Reactions | Conditions | Result |
|---|---|---|
| 8A | 50 wt % NaOH (8 eq.) | Almost complete overnight (3% starting material), 81% solution yield |
| 8B | 40 wt % NaOH (8 eq.) | Incomplete overnight (9% starting material), 73% solution yield |
| 8C | 30 wt % NaOH (8 eq.) | Incomplete overnight |
| 8D | solid NaOH (8 eq.) 10 µL water | Complete in 2 h, 38% solution yield |

Example 9: Various Amounts of Phase Transfer Catalyst (PTC) for the Synthesis of 5,5-dimethyl-3-methylenepyrrolidin-2-one

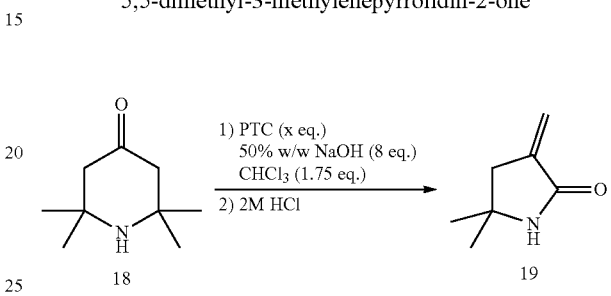

In this experiment, various amounts of PTCs were tested as described below: Tetrabutylammonium hydroxide (0.01 eq.), TBAB (0.01 eq.), Tributylmethylammonium chloride (0.01 eq.), Tetrabutylammonium hydroxide (0.02 eq.), TBAB (0.02 eq.), Tributylmethylammonium chloride (0.02 eq.), Tetrabutylammonium hydroxide (0.03 eq.), TBAB (0.03 eq.), Tributylmethylammonium chloride (0.03 eq.).

2,2,6,6-tetramethylpiperidin-4-one (500.0 mg, 3.06 mmol, 1.0 eq.), PTC (0.12 g, 0.153 mmol, 0.050 eq), and chloroform (1.75 eq.) were charged into a vial equipped with a magnetic stir bar. The vial was cooled in an ice bath, and a solution of 50 wt % sodium hydroxide (0.98 g, 24.48 mmol, 8.0 eq.) was added drop wise over 2 min. The reaction mixture was stirred until completion, assessed by GC analysis. The reaction mixture was diluted with DCM (2.0 mL, 4.0 v) and H₂O (3.0 mL, 6.0 v). The phases were separated and the aqueous phase was extracted with DCM (1.0 mL, 2.0 v). The organic phases were combined and 2 M hydrochloric acid (0.17 g, 2.3 mL, 4.59 mmol, 1.5 eq.) was added. The reaction mixture was stirred until completion, assessed by HPLC. The aqueous phase was saturated with NaCl and the phases were separated. The aqueous phase was extracted with DCM (1.0 mL, 2.0 v) twice, the organic phases were combined, and 50 mg of biphenyl in 2 mL of MeCN was added as an internal HPLC standard. Solution yield was assessed by HPLC. The reaction results are summarized in Table 5.

TABLE 5

| Reactions | Conditions | Result |
|---|---|---|
| 9A | Tetrabutylammonium hydroxide (0.01 eq.) | Slow, incomplete over the weekend |
| 9B | TBAB (0.01 eq.) | Slow, incomplete over the weekend |
| 9C | Tributylmethylammonium chloride (0.01 eq.) | Incomplete over 2 days |
| 9D | Tetrabutylammonium hydroxide (0.02 eq.) | Almost complete overnight (2% starting material), 82% solution yield |

TABLE 5-continued

| Reactions | Conditions | Result |
|---|---|---|
| 9E | TBAB (0.02 eq.) | Almost complete overnight (2% starting material), 71% solution yield |
| 9F | Tributylmethylammonium chloride (0.02 eq.) | Incomplete overnight (4% starting material), 72% solution yield |
| 9G | Tetrabutylammonium hydroxide (0.03 eq.) | Almost complete overnight (3% starting material), 76% solution yield |
| 9H | TBAB (0.03 eq.) | Almost complete overnight (3% starting material), 76% solution yield |
| 9I | Tributylmethylammonium chloride (0.03 eq.) | Almost complete overnight (2% starting material), 78% solution yield |

Example 10: Preparation of 2,2,6,6-tetramethylpiperidin-4-one hydrochloride (14·HCl)

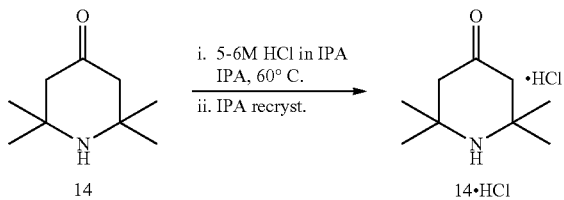

2,2,6,6-tetramethyl-4-piperidinone (14) (30 g, 193.2 mmol, 1.0 eq) was charged to a 500 mL nitrogen purged three necked round bottomed flask equipped with condenser. IPA (300 mL, 10 vol) was added to the flask and the mixture heated to 60° C. until dissolved.

To the solution at 60° C. was added 5-6 M HCl in IPA (40 mL, 214.7 mmol, 1.1 eq) over 10 min and the resulting suspension stirred at 60° C. for 30 min then allowed to cool to ambient temperature. The suspension was stirred at ambient temperature overnight, then filtered under vacuum and washed with IPA (3×60 mL, 3×2 vol). The cream colored solid was dried on the filter under vacuum for 10 min.

The wet cake was charged to a 1 L nitrogen purged three necked round bottomed flask equipped with condenser. IPA (450 mL, 15 vol) was added to the flask and the suspension heated to 80° C. until dissolved. The mixture was allowed to cool slowly to ambient temperature over 3 h and the resulting suspension stirred overnight at ambient temperature.

The suspension was filtered under vacuum, washed with IPA (60 mL, 2 vol) and dried on the filter under vacuum for 30 min. The resulting product was dried in a vacuum oven at 40° C. over the weekend to give 2,2,6,6-tetramethylpiperidin-4-one hydrochloride (14·HCl) a white crystalline solid, 21.4 g, 64% yield.

Example 11: Synthesis of (S)-2,2,4-trimethylpyrrolidine hydrochloride (17S·HCl) from (S)-3,5,5-trimethyl-pyrrolidin-2-one (16S)

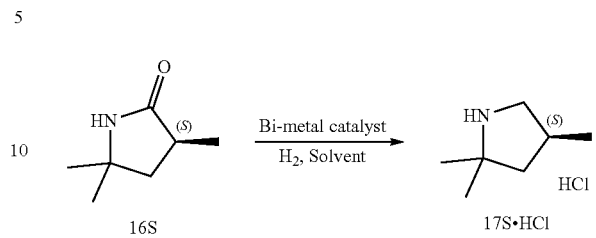

Each reactor was charged with (S)-3,5,5-trimethyl-pyrrolidin-2-one (16S) in THF, $H_2$, and the catalyst shown in the below table. The reactor was heated to 200° C. and pressurized to 60 bar, and allowed to react for 12 hours. GC analysis showed that (S)-2,2,4-trimethylpyrrolidine was produced in the columns denoted by "+."

| Catalyst | Product obtained (+) |
|---|---|
| 4% Pt-2% Re/TiO$_2$ | + |
| 4% Rh-2% Re/TiO$_2$ | + |
| 4% Rh/TiO$_2$ | + |
| 4% Pd/TiO$_2$ | + |
| 4% Pt/TiO$_2$ | + |
| 4% Pt-2% Sn/TiO$_2$ | + |
| 4% Pt-2% Co/TiO$_2$ | + |

A 2.5% solution of (S)-3,5,5-trimethyl-pyrrolidin-2-one (16S) in THF was flowed at 0.05 mL/min into a packed bed reactor prepacked with 2% Pt-0.5% Sn/SiO$_2$ catalyst immobilized on silica gel. H$_2$ gas was also flowed into the packed bed reactor at 20 mL/min. The reaction was carried out at 130° C. under 80 bar pressure with a WHSV (Weigh Hourly Space Velocity) of 0.01-0.02 h$^{-1}$. The product feed was collected in a batch tank and converted to (S)-2,2,4-trimethylpyrrolidine HCl in batch mode: 36% Hydrochloric acid (1.1 eq.) was added keeping the temperature below 20° C. Distillation of the solvent, backfilling with isopropyl acetate (4 v), was carried out to leave a residual volume of 5 v. Karl Fischer analysis <0.2% w/w H$_2$O. MTBE (methyl tertiary butyl ether) (lv) was added at 20-30° C. and the solids were filtered off under nitrogen at 15-20° C., washing with isopropyl acetate (1.5 v) and drying under vacuum at 40-45° C. to give (S)-2,2,4-trimethylpyrrolidine hydrochloride (17S·HCl) as a white crystalline solid (74.8% yield, 96.1% ee).

Alternate Synthesis

A 2.5% solution of (S)-3,5,5-trimethyl-pyrrolidin-2-one (16S) in THF was flowed at 0.05 mL/min into a packed bed reactor prepacked with 4% Pt-2% Sn/TiO$_2$ catalyst immobilized on silica gel. H$_2$ gas was also flowed into the packed bed reactor at 20 mL/min. The reaction was carried out at 200° C. under 50 bar pressure with a WHSV (Weigh Hourly Space Velocity) of 0.01-0.02 h$^{-1}$. The product feed was collected in a batch tank and converted to (S)-2,2,4-trimethylpyrrolidine HCl in batch mode: 36% Hydrochloric acid (1.1 eq.) was added keeping the temperature below 20° C. Distillation of the solvent, backfilling with isopropyl acetate (4 v), was carried out to leave a residual volume of 5 v. Karl Fischer analysis <0.2% w/w H$_2$O. MTBE (methyl tertiary butyl ether) (lv) was added at 20-30° C. and the solids were filtered off under nitrogen at 15-20° C., washing with isopropyl acetate (1.5 v) and drying under vacuum at 40-45° C. to give (S)-2,2,4-trimethylpyrrolidine hydrochloride (17S·HCl) as a white crystalline solid (88.5% yield, 29.6% ee).

Alternate Synthesis

A 2.5% solution of (S)-3,5,5-trimethyl-pyrrolidin-2-one (16S) in THE was flowed at 0.05 mL/min into a packed bed reactor prepacked with 2% Pt-0.5% Sn/TiO$_2$ catalyst immobilized on silica gel. H$_2$ gas was also flowed into the packed bed reactor at 20 mL/min. The reaction was carried out at 150° C. under 50 bar pressure with a WHSV (Weigh Hourly Space Velocity) of 0.01-0.02 h$^{-1}$. The product feed was collected in a batch tank and converted to (S)-2,2,4-trimethylpyrrolidine HCl in batch mode: 36% Hydrochloric acid (1.1 eq.) was added keeping the temperature below 20° C. Distillation of the solvent, backfilling with isopropyl acetate (4 v), was carried out to leave a residual volume of 5 v. Karl Fischer analysis <0.2% w/w H$_2$O. MTBE (methyl tertiary butyl ether) (1v) was added at 20-30° C. and the solids were filtered off under nitrogen at 15-20° C., washing with isopropyl acetate (1.5 v) and drying under vacuum at 40-45° C. to give (S)-2,2,4-trimethylpyrrolidine hydrochloride (17S·HCl) as a white crystalline solid (90.9% yield, 98.0% ee).

Alternate Synthesis

A 2.5% solution of (S)-3,5,5-trimethyl-pyrrolidin-2-one (16S) in THE was flowed at 0.03 mL/min into a packed bed reactor prepacked with 2% Pt-8% Sn/TiO$_2$ catalyst immobilized on silica gel. H$_2$ gas was also flowed into the packed bed reactor at 40 mL/min. The reaction was carried out at 180° C. under 55 bar pressure with a residence time of 6 min. The product feed was collected in a batch tank and converted to (S)-2,2,4-trimethylpyrrolidine HCl in batch mode: 36% Hydrochloric acid (1.1 eq.) was added keeping the temperature below 20° C. Distillation of the solvent, backfilling with isopropyl acetate (4 v), was carried out to leave a residual volume of 5 v. Karl Fischer analysis <0.2% w/w H$_2$O. MTBE (methyl tertiary butyl ether) (1v) was added at 20-30° C. and the solids were filtered off under nitrogen at 15-20° C., washing with isopropyl acetate (1.5 v) and drying under vacuum at 40-45° C. to give (S)-2,2,4-trimethylpyrrolidine hydrochloride (17S·HCl) as a white crystalline solid (90.4% yield, 96.8% ee).

Example 12: Preparation of N-(1,3-dimethylpyrazol-4-yl)sulfonyl-6-[3-(3,3,3-trifluoro-2,2-dimethylpropoxy)pyrazol-1-yl]-2-[(4S)-2,2,4-trimethylpyrrolidin-1-yl]pyridine-3-carboxamide (Compound 1)

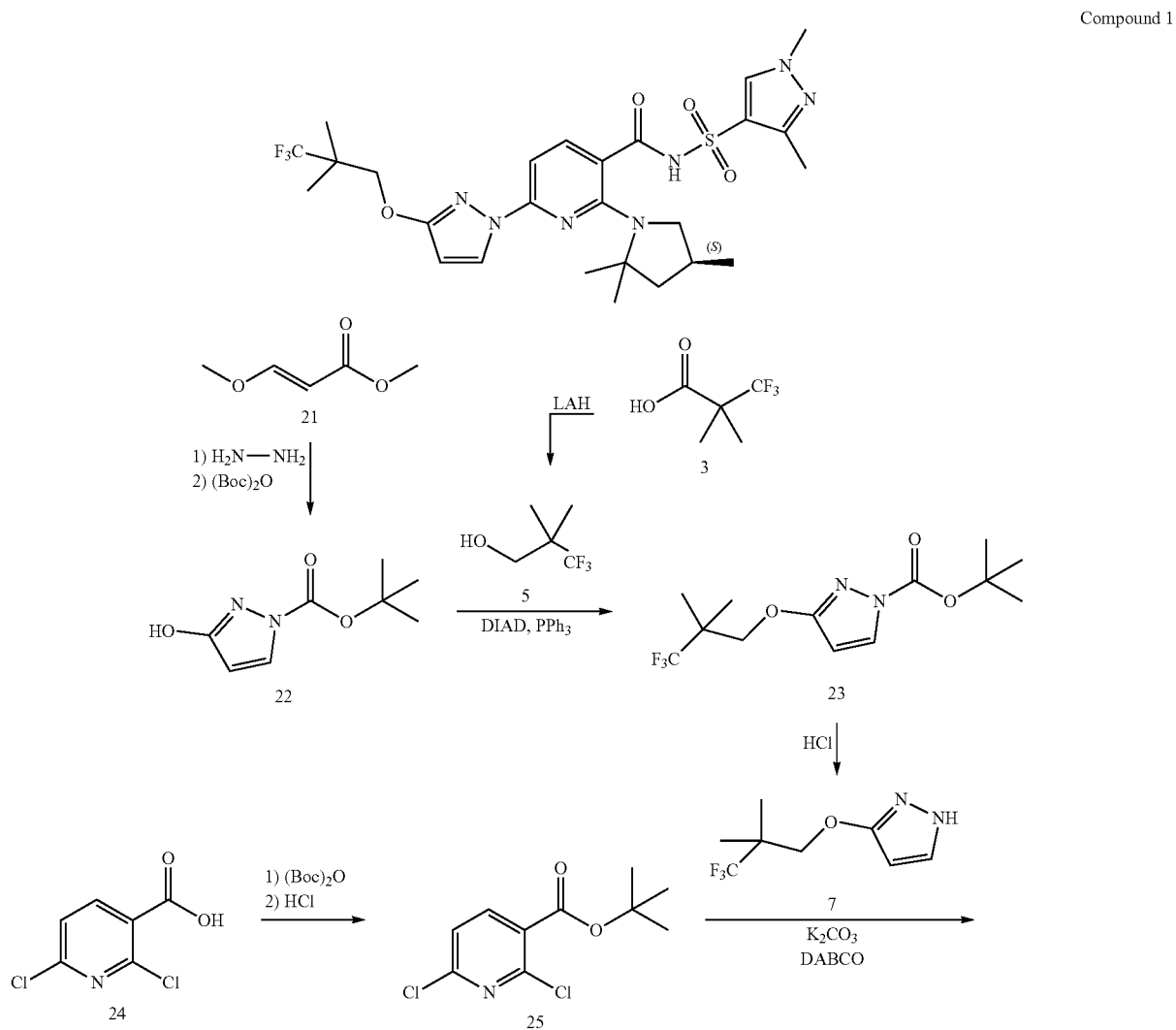

-continued
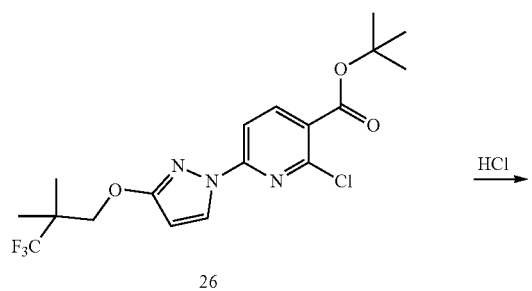
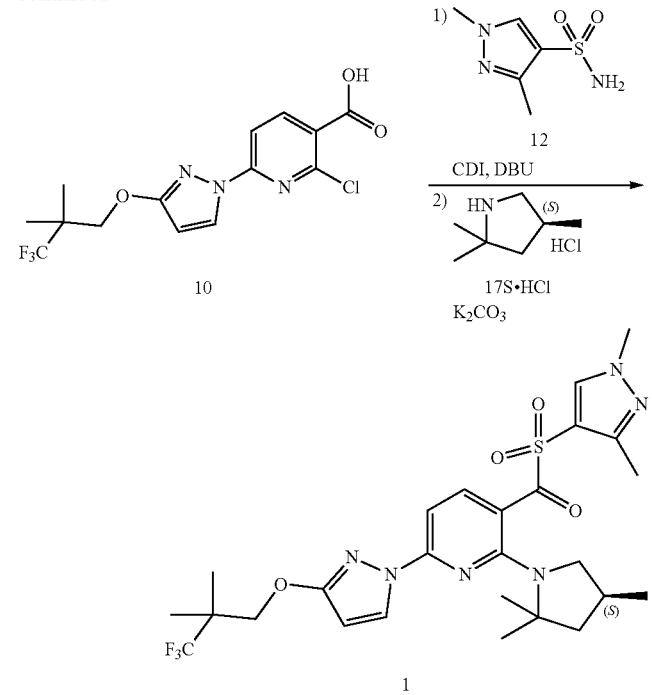
I. Preparation of Starting Materials
A. Synthesis of 3,3,3-Trifluoro-2,2-dimethylpropionic acid (31), morpholine salt
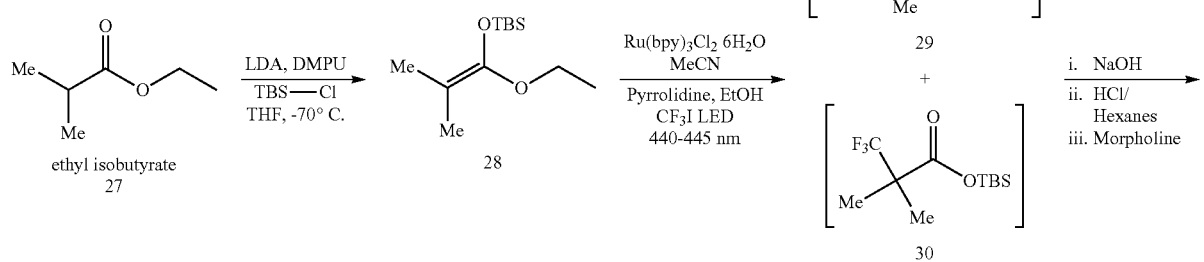
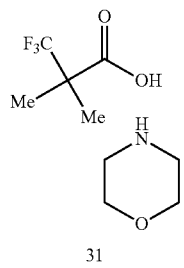

Step 1: tert-Butyl((1-ethoxy-2-methylprop-1-en-1-yl)oxy)dimethylsilane (28)

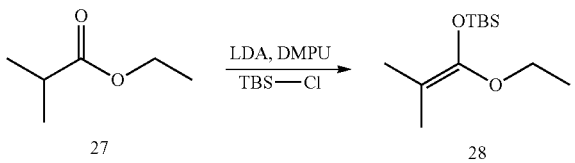

A 2 L 3-necked round-bottom flask, equipped with a J-Kem thermocouple and an overhead stirrer, was purged with nitrogen for >20 minutes. Hexyllithium solution (2.3 M in hexanes; 1.05 equiv; 0.260 L, 597 mmol) was transferred into the flask via cannula. The flask was then cooled to −65° C. in a dry ice/isopropyl alcohol bath and diisopropylamine (1.05 equiv; 0.842 L; 597 mmol) was added via an addition funnel, and the internal temperature was maintained at −40±5° C. Once the diisopropylamine addition was complete, tetrahydrofuran (THF) (0.423 L; 6.4 vol) was added to the reactor and the reaction was warmed to room temperature and stirred for 15 minutes. The solution was then cooled to −60° C. and ethyl isobutyrate (1.0 equiv; 0.754 L; 568 mmol) was added dropwise maintaining the temperature below −45° C. 1,3-Dimethyl-3,4,5,6-tetrahydro-2(1H)-pyrimidinone (DMPU) (0.9 equiv; 0.616 L; 511 mmol) was then added dropwise to the reaction flask and the temperature was maintained below −45° C. In a separate flask, tert-butyldimethylsilyl chloride (TBSCl) (1.05 equiv; 89.9 g; 597 mmol) was dissolved in THF (2.2 vol w.r.t. TBSCl) and then added to the 2 L reactor. The internal temperature was maintained at ≤−30° C. during the addition of the TBSCl solution. The resulting reaction mixture was allowed to warm to room temperature and stirred overnight under inert atmosphere. The reaction solution was transferred to a 2 L one-neck round-bottom flask. Additional THF (50 mL, ×2) was used to rinse and transfer. The solution was concentrated in vacuo to remove most of the THF. Hexanes were added to the concentrated tert-butyl((1-ethoxy-2-methylprop-1-en-1-yl)oxy)dimethylsilane (500 mL). The organic phase was washed with three times with water (500 mL×3), to remove salts. The organic layer was dried over $Na_2SO_4$ (100 g). The solution was filtered and the waste cake washed with additional hexanes (100 mL). The resulting hexanes solution of tert-butyl((1-ethoxy-2-methylprop-1-en-1-yl)oxy)dimethylsilane was concentrated in vacuo. A quantitative 1H-NMR assay was performed with benzyl benzoate as an internal standard. The quantitative NMR assay indicated that 108.6 grams of tert-butyl((1-ethoxy-2-methylprop-1-en-1-yl)oxy)dimethylsilane (83% yield) was present, and that 1.2 mol % of ethyl isobutyrate relative to tert-butyl((1-ethoxy-2-methylprop-1-en-1-yl)oxy)dimethylsilane was also present. The resulting tert-butyl((1-ethoxy-2-methylprop-1-en-1-yl)oxy)dimethylsilane solution was used without further purification for the photochemical reaction of Step 2.

Step 2: 3,3,3-Trifluoro-2,2-dimethylpropionic acid (31), morpholine salt

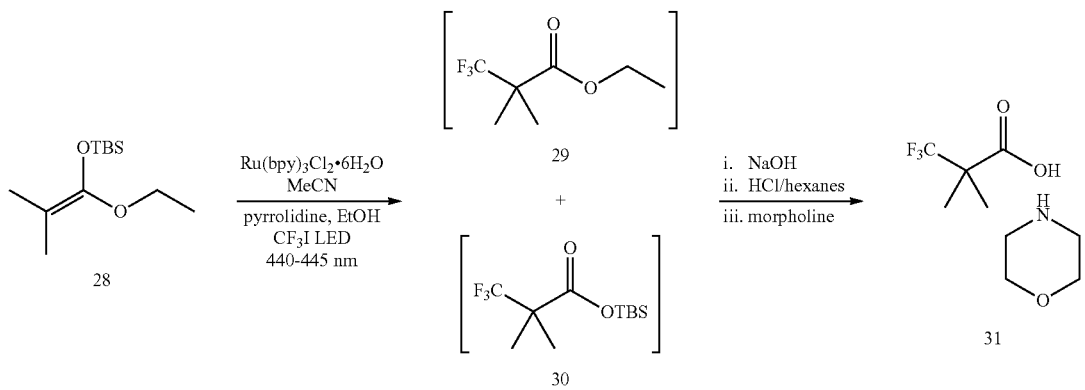

Stock solution A: The concentrated tert-butyl((1-ethoxy-2-methylprop-1-en-1-yl)oxy)dimethylsilane (198 g; 0.86 mol) was dissolved in acetonitrile (895 g; 1.14 L; 5.8 vol) to give a cloudy, yellow solution that was then filtered. The density of the clear, filtered solution was measured to be 0.81 g/mL and the molar concentration was calculated to be 0.6 M. This is referred to as stock solution A (substrate).

Stock solution B: The catalyst and reagent solution was prepared by dissolving $Ru(bpy)_3C_{12}$ hexahydrate in acetonitrile, followed by adding ethanol and pyrrolidine to give a red-colored solution (density measured: 0.810 g/mL). The molar concentration of the catalyst was calculated to be 0.00172 M. The molar concentration of the solution with respect to EtOH/pyrrolidine was calculated to be ~2.3 M. See Table 6.

TABLE 6

| Stock Soln | Component | mmol | Mass (g) | w/w % | Density | Molar Conc. (M) |
|---|---|---|---|---|---|---|
| A | tert-butyl((1-ethoxy-2-methyl-prop-1-en-1-yl)oxy)dimethyl-silane | 860 | 264 (75 wt %) | 17.1 | 0.81 | ~0.6 |
|   | Acetonitrile | — | 895 | 82.9 | | |
| B- | $Ru(byp)_3Cl_2$ | 1.35 | 1.01 | 0.16 | 0.81 | ~2.3 |
|   | Ethanol | 1790 | 82.5 | 13.1 | | |
|   | Pyrrolidine | 1790 | 127 | 20.1 | | |
|   | Acetonitrile |  | 421 | 66.7 | | |

(i) Photochemical Trifluoromethylation $CF_3I$ gas was delivered to the reactor directly from the lecture bottle using a regulator and mass flow controller.

Stock solutions A and B were pumped at 6.7 g/min and 2.07 g/min, respectively, to mix in a static mixer. The resulting solution was then combined with CF$_3$I in a static mixer. The CF$_3$I was metered into the reactor via a mass flow controller at 2.00 g/min (2 equiv). Liquid chromatography (LC) assay indicated that 1.0% of the tert-butyl((1-ethoxy-2-methyl-prop-1-en-1-yl)oxy)dimethylsilane was left unreacted. Details of the reaction parameters are shown in the table below. The reaction stream was passed through the 52 mL photoreactor while being irradiated with the 800 W 440-445 LED light source. The first 5 minutes of eluent was discarded. Thereafter the eluent was collected for a total of 3.05 hours. A total of ~2.3 L of solution was collected during the reaction (~1.06 mol). See Table 7.

TABLE 7

| Stock soln | Concentration | Equivalents |
|---|---|---|
| A (substrate) | 17.1% w/w | 1.0 equiv |
| B (reagents, catalyst) | [EtOH] = 13.1 w/w % <br> [Pyrrolidine] = 20.1 w/w % <br> [Ru(bpy)$_3$Cl$_2$] = 0.16 w/w % | EtOH: 1.2 equiv; <br> Pyrrolidline: 1.2 equiv. <br> Ru(bpy)$_3$Cl$_2$: 0.09 mol % |
| CF$_3$I | Gas | 2.0 equiv. |

(ii) Saponification & Salt Formation

The saponication of the crude solution (4.1 L, from 1.60 mol tert-butyl((1-ethoxy-2-methylprop-1-en-1-yl)oxy)dimethylsilane) was carried out in a 5 L 4-necked round-bottomed flask in 2 roughly equal size batches using 15 wt % NaOH (aq) (total~320 g NaOH) at 50° C. for 2-4 h. Upon completion of the reaction determined by gas chromatography (GC) analysis, the re-combined batches were cooled to room temperature and hexanes (500 mL) and toluene (500 mL) were added to give a clear phase separation. The top organic layer was washed with half-brine (1 L) and combined with the first portion of the product-containing aqueous solution (4.5 L). The combined aqueous stream was washed with hexanes (500 mL) and concentrated to 2-3 L to remove a majority of volatile acetonitrile. To the aqueous phase was added concentrated HCl (1 L, 12 N) and the resulting mixture was extracted with hexanes (4×1 L). The combined hexanes extracts were washed with half brine (2×500 mL) and concentrated to give an oil (216 g). The oil was dissolved in THF (580 mL), and morpholine (120 mL, 1.0 equiv) was added slowly via an addition funnel. Upon completion of addition, the batch was seeded (0.5-1 g) with morpholine salt, and the seeds were held and allowed to thicken over 30 min. Hexanes (1660 mL) were added over ~ 2 h, and the mixture was aged for another 3 h. The batch was filtered, washed with hexanes (~500 mL) in portions and dried under vacuum/dry air flush to give 3,3,3-trifluoro-2,2-dimethylpropionic acid, morpholine salt as a white solid (283 g, 73%). $^1$H NMR (400 MHz, CD$_3$OD) δ 3.84-3.86 (m, 4H), 3.15-3.18 (m, 4H), 1.33 (s, 6H); $^{19}$F NMR (376 MHz, CD$_3$OD) δ −75.90 (s, 3F).

B. Synthesis of 3,3,3-Trifluoro-2,2-dimethyl-propan-1-ol (5)

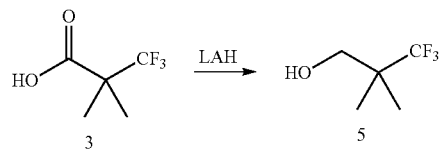

A 1 L 3 neck round bottom flask was fitted with a mechanical stirrer, a cooling bath, an addition funnel, and a J-Kem temperature probe. The vessel was charged with lithium aluminum hydride (LAH) pellets (6.3 g, 0.1665 mol) under a nitrogen atmosphere. The vessel was then charged with tetrahydrofuran (200 mL) under a nitrogen atmosphere. The mixture was allowed to stir at room temperature for 0.5 hours to allow the pellets to dissolve. The cooling bath was then charged with crushed ice in water and the reaction temperature was lowered to 0° C. The addition funnel was charged with a solution of 3,3,3-trifluoro-2,2-dimethyl-propanoic acid (20 g, 0.1281 mol) in tetrahydrofuran (60 mL) and the clear pale yellow solution was added drop wise over 1 hour. After the addition was complete the mixture was allowed to slowly warm to room temperature and stirring was continued for 24 hours. The suspension was cooled to 0° C. with a crushed ice-water in the cooling bath and then quenched by the very slow and drop wise addition of water (6.3 ml), followed by sodium hydroxide solution (15 weight %; 6.3 mL) and then finally with water (18.9 mL). The reaction temperature of the resulting white suspension was recorded at 5° C. The suspension was stirred at −5° C. for 30 minutes and then filtered through a 20 mm layer of Celite. The filter cake was washed with tetrahydrofuran (2×100 mL). The filtrate was dried over sodium sulfate (150 g) and then filtered. The filtrate was concentrated under reduced pressure to provide a clear colorless oil (15 g) containing a mixture of the product 3,3,3-trifluoro-2,2-dimethyl-propan-1-ol in THF (73% weight of product~10.95 g, and 27 wt. % THF as determined by 1H-NMR). The distillate from the rotary evaporation was distilled at atmospheric pressure using a 30 cm Vigreux column to provide 8.75 g of a residue containing 60% weight of THF and 40% weight of product (~3.5 g), which corresponds to 14.45 g (79% yield). 1H NMR (400 MHz, DMSO-d6) δ 4.99 (t, J=5.7 Hz, 1H), 3.38 (dd, J=5.8, 0.9 Hz, 2H), 1.04 (d, J=0.9 Hz, 6H).

C. Synthesis of tert-Butyl 3-oxo-2,3-dihydro-1H-pyrazole-1-carboxylate (22)

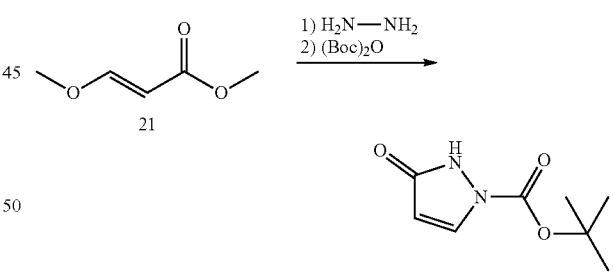

A 50 L Syrris controlled reactor was started and the jacket was set to 20° C., stirring at 150 rpm, reflux condenser (10° C.) and nitrogen purge. MeOH (2.860 L) and methyl (E)-3-methoxyprop-2-enoate (2.643 kg, 22.76 mol) were added and the reactor was capped. The reaction was heated to an internal temperature of 40° C. and the system was set to hold jacket temp at 40° C. Hydrazine hydrate (1300 g of 55% w/w, 22.31 mol) was added portion wise via addition funnel over 30 min. The reaction was heated to 60° C. for 1 h. The reaction mixture was cooled to 20° C. and triethylamine (2.483 kg, 3.420 L, 24.54 mol) was added portion wise, maintaining reaction temp <30° C. A solution of Boc anhydride (di-tert-butyl dicarbonate) (4.967 kg, 5.228 L, 22.76 mol) in MeOH (2.860 L) was added portion wise maintaining temperature <45° C. The reaction mixture was stirred at 20° C. for 16 h. The reaction solution was partially concentrated to remove MeOH, resulting in a clear light amber oil. The resulting oil was transferred to the 50 L reactor, stirred and added water (7.150 L) and heptane (7.150 L). The additions caused a small amount of the product to precipitate. The aqueous layer was drained into a clean container and the interface and heptane layer were filtered to separate the solid (product). The aqueous layer was transferred back to the reactor, and the collected solid was placed back into the reactor and mixed with the aqueous layer. A dropping funnel was added to the reactor and loaded with acetic acid (1.474 kg, 1.396 L, 24.54 mol), then began dropwise addition of acid. The jacket was set to 0° C. to absorb the quench exotherm. After addition (pH=5), the reaction mixture was stirred for 1 h. The solid was collected by filtration and washed with water (7.150 L) and washed a second time with water (3.575 L) and pulled dry. The crystalline solid was scooped out of the filter into a 20 L rotovap bulb and heptane (7.150 L) was added. The mixture was slurried at 45° C. for 30 mins, and then 1-2 volumes of solvent was distilled off. The slurry in the rotovap flask was filtered and the solids washed with heptane (3.575 L) and pulled dry. The solid was further dried in vacuo (50° C., 15 mbar) to give tert-butyl 5-oxo-1H-pyrazole-2-carboxylate (2921 g, 71%) as coarse solid. $^1$H NMR (400 MHz, DMSO-d6) δ 10.95 (s, 1H), 7.98 (d, J=2.9 Hz, 1H), 5.90 (d, J=2.9 Hz, 1H), 1.54 (s, 9H).

II. Preparation of Compound I

Step A: tert-Butyl 3-(3,3,3-trifluoro-2,2-dimethyl-propoxy)pyrazole-1-carboxylate (23)

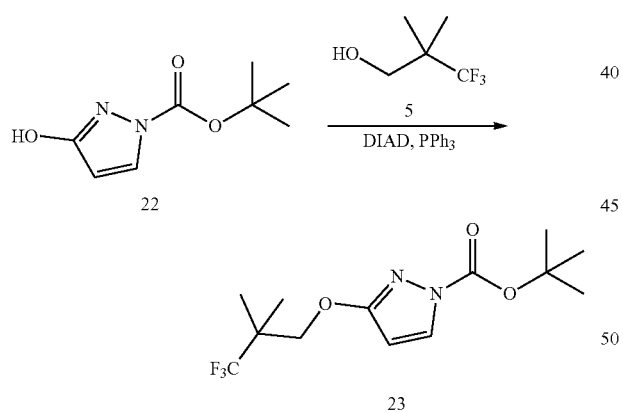

A mixture of 3,3,3-trifluoro-2,2-dimethyl-propan-1-ol (10 g, 70.36 mmol) and tert-butyl 3-hydroxypyrazole-1-carboxylate (12.96 g, 70.36 mmol) in toluene (130 mL) was treated with triphenyl phosphine (20.30 g, 77.40 mmol) followed by isopropyl N-isopropoxycarbonyliminocarbamate (14.99 mL, 77.40 mmol) and the mixture was stirred at 110° C. for 16 hours. The yellow solution was concentrated under reduced pressure, diluted with heptane (100 mL) and the precipitated triphenylphosphine oxide was removed by filtration and washed with heptane/toluene 4:1 (100 mL). The yellow filtrate was evaporated and the residue purified by silica gel chromatography with a linear gradient of ethyl acetate in hexane (0-40%) to give tert-butyl 3-(3,3,3-trifluoro-2,2-dimethyl-propoxy)pyrazole-1-carboxylate (12.3 g, 57%) as an off white solid. ESI-MS m/z calc. 308.13477, found 309.0 (M+1)+; Retention time: 1.84 minutes. $^1$H NMR (400 MHz, DMSO-d6) δ 8.10 (d, J=3.0 Hz, 1H), 6.15 (d, J=3.0 Hz, 1H), 4.18 (s, 2H), 1.55 (s, 9H), 1.21 (s, 6H).

Step B: 3-(3,3,3-trifluoro-2,2-dimethyl-propoxy)-1H-pyrazole (7)

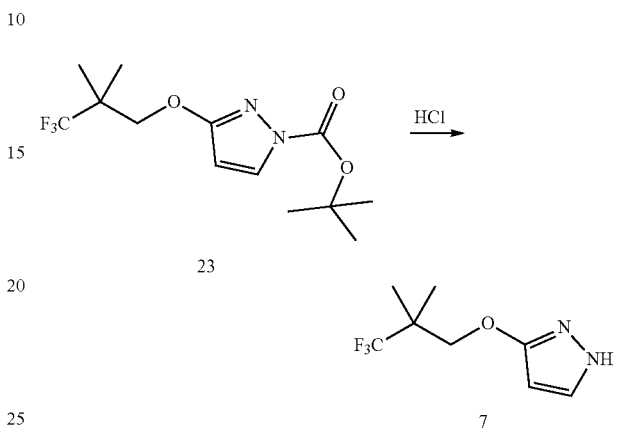

tert-Butyl 3-(3,3,3-trifluoro-2,2-dimethyl-propoxy)pyrazole-1-carboxylate (13.5 g, 43.79 mmol) was treated with 4 M hydrogen chloride in dioxane (54.75 mL, 219.0 mmol) and the mixture was stirred at 45° C. for 1 hour. The reaction mixture was evaporated to dryness and the residue was extracted with 1 M aqueous NaOH (100 ml) and methyl tert-butyl ether (100 ml), washed with brine (50 ml) and extracted with methyl tert-butyl ether (50 ml). The combined organic phases were dried, filtered and evaporated to give 3-(3,3,3-trifluoro-2,2-dimethyl-propoxy)-1H-pyrazole (9.0 g, 96%) as an off white solid. ESI-MS m/z calc. 208.08235, found 209.0 (M+1)+; Retention time: 1.22 minutes. $^1$H NMR (400 MHz, DMSO-d6) δ 11.91 (s, 1H), 7.52 (d, J=2.2 Hz, 1H), 5.69 (t, J=2.3 Hz, 1H), 4.06 (s, 2H), 1.19 (s, 6H).

Step C: tert-Butyl 2,6-dichloropyridine-3-carboxylate (25)

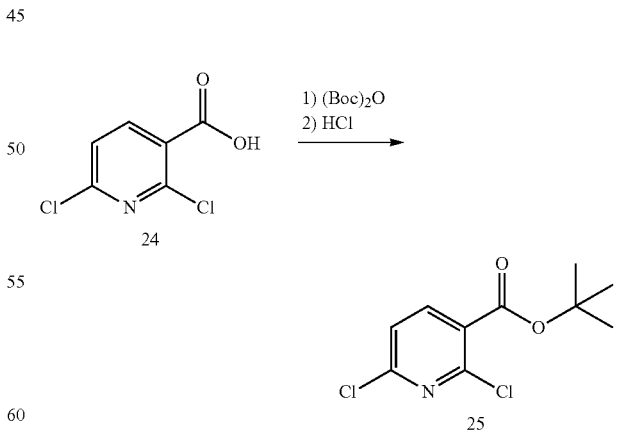

A solution of 2,6-dichloropyridine-3-carboxylic acid (10 g, 52.08 mmol) in THF (210 mL) was treated successively with di-tert-butyl dicarbonate (17 g, 77.89 mmol) and 4-(dimethylamino)pyridine (3.2 g, 26.19 mmol) and left to stir overnight at room temperature. At this point, HCl 1N (400 mL) was added and the mixture was stirred vigorously for about 10 minutes. The product was extracted with ethyl acetate (2×300 mL) and the combined organics layers were washed with water (300 mL) and brine (150 mL) and dried over sodium sulfate and concentrated under reduced pressure to give 12.94 g (96% yield) of tert-butyl 2,6-dichloropyridine-3-carboxylate as a colorless oil. ESI-MS m/z calc. 247.01668, found 248.1 (M+1)+; Retention time: 2.27 minutes. $^1$H NMR (300 MHz, CDCl$_3$) ppm 1.60 (s, 9H), 7.30 (d, J=7.9 Hz, 1H), 8.05 (d, J=8.2 Hz, 1H).

Step D: tert-Butyl 2-chloro-6-[3-(3,3,3-trifluoro-2,2-dimethyl-propoxy)pyrazol-1-yl]pyridine-3-carboxylate (26)

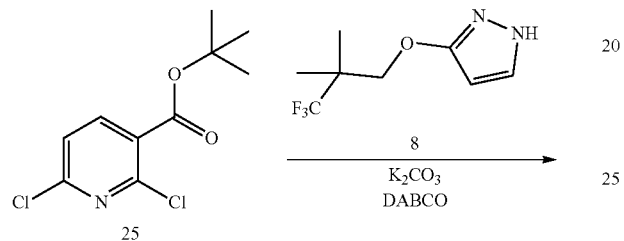

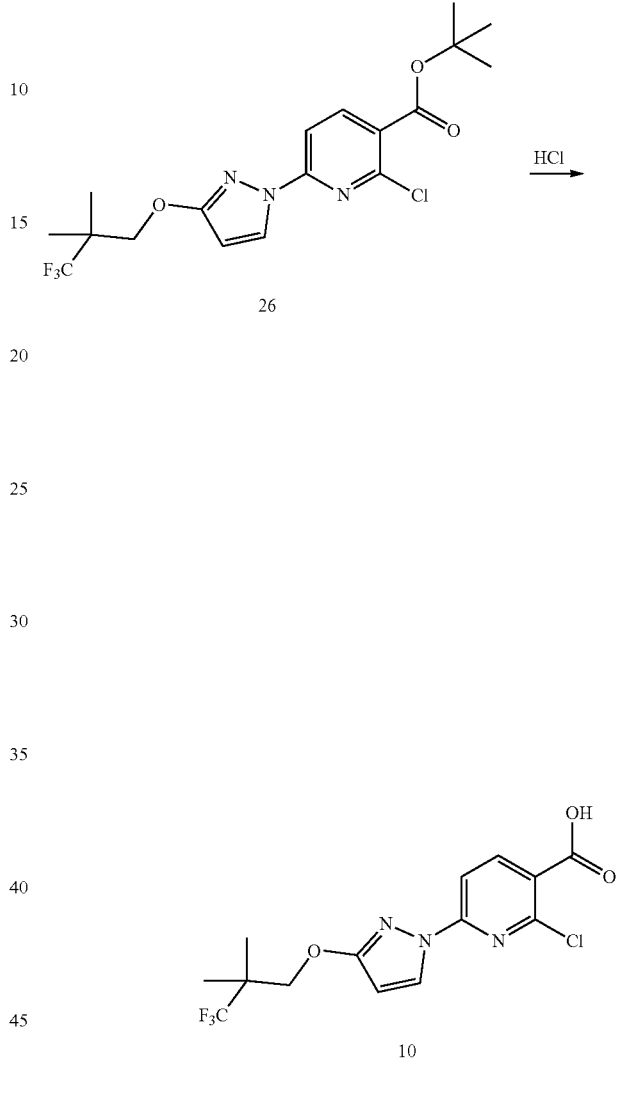

Step E: 2-chloro-6-[3-(3,3,3-trifluoro-2,2-dimethyl-propoxy)pyrazol-1-yl]pyridine-3-carboxylic acid (10)

To a solution of tert-butyl 2,6-dichloropyridine-3-carboxylate (10.4 g, 41.9 mmol) and 3-(3,3,3-trifluoro-2,2-dimethyl-propoxy)-1H-pyrazole (9.0 g, 41.93 mmol) in DMF (110 mL) were added potassium carbonate (7.53 g, 54.5 mmol) and 1,4-diazabicyclo[2.2.2]octane (706 mg, 6.29 mmol) and the mixture was stirred at room temperature for 16 hours. The cream suspension was cooled in a cold water bath and cold water (130 mL) was slowly added. The thick suspension was stirred at room temperature for 1 hour, filtered and washed with plenty of water to give tert-butyl 2-chloro-6-[3-(3,3,3-trifluoro-2,2-dimethyl-propoxy)pyrazol-1-yl]pyridine-3-carboxylate (17.6 g, 99%) as an off white solid. ESI-MS m/z calc. 419.12234, found 420.0 (M+1)+; Retention time: 2.36 minutes. $^1$H NMR (400 MHz, DMSO-d6) δ 8.44 (d, J=2.9 Hz, 1H), 8.31 (d, J=8.4 Hz, 1H), 7.76 (d, J=8.4 Hz, 1H), 6.26 (d, J=2.9 Hz, 1H), 4.27 (s, 2H), 1.57 (s, 9H), 1.24 (s, 6H).

tert-Butyl 2-chloro-6-[3-(3,3,3-trifluoro-2,2-dimethyl-propoxy)pyrazol-1-yl]pyridine-3-carboxylate (17.6 g, 40.25 mmol) was suspended in isopropanol (85 mL) treated with hydrochloric acid (34 mL of 6 M, 201 mmol) and heated to reflux for 3 hours (went almost complete into solution at reflux and started to precipitate again). The suspension was diluted with water (51 mL) at reflux and left to cool to room temperature under stirring for 2.5 h. The solid was collected by filtration, washed with isopropanol/water 1:1 (50 mL), plenty of water and dried in a drying cabinet under vacuum at 45-50° C. with a nitrogen bleed overnight to give 2-chloro-6-[3-(3,3,3-trifluoro-2,2-dimethyl-propoxy)pyrazol-1-yl]pyridine-3-carboxylic acid (13.7 g, 91%) as an off white solid. ESI-MS m/z calc. 363.05975, found 364.0 (M+1)+; Retention time: 1.79 minutes. $^1$H NMR (400 MHz, DMSO-d6) δ 13.61 (s, 1H), 8.44 (d, J=2.9 Hz, 1H), 8.39 (d, J=8.4 Hz, 1H), 7.77 (d, J=8.4 Hz, 1H), 6.25 (d, J=2.9 Hz, 1H), 4.28 (s, 2H), 1.24 (s, 6H).

Step F: 2-Chloro-N-(1,3-dimethylpyrazol-4-yl)
sulfonyl-6-[3-(3,3,3-trifluoro-2,2-dimethyl-propoxy)
pyrazol-1-yl]pyridine-3-carboxamide (13)

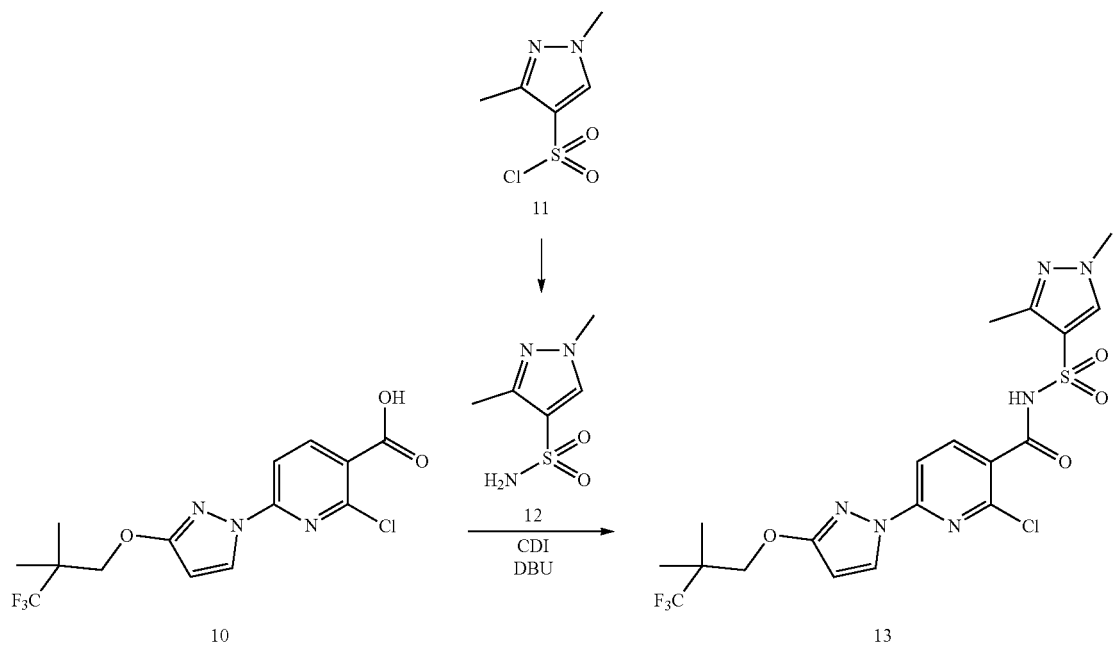

2-Chloro-6-[3-(3,3,3-trifluoro-2,2-dimethyl-propoxy) pyrazol-1-yl]pyridine-3-carboxylic acid (100 mg, 0.2667 mmol) and CDI (512 mg, 3.158 mmol) were combined in THF (582.0 μL) and the mixture was stirred at room temperature. Meanwhile, 1,3-dimethylpyrazole-4-sulfonyl chloride (62 mg, 0.3185 mmol) was combined with ammonia (in methanol) in a separate vial, instantly forming a white solid. After stirring for an additional 20 min, the volatiles were removed by evaporation, and 1 mL of dichloromethane was added to the solid residue, and was also evaporated. DBU (100 μL, 0.6687 mmol) was then added and the mixture stirred at 60° C. for 5 minutes, followed by addition of THF (1 mL) which was subsequently evaporated. The contents of the vial containing the CDI activated carboxylic acid in THF were then added to the vial containing the newly formed sulfonamide and DBU, and the reaction mixture was stirred for 4 hours at room temperature. The reaction mixture was diluted with 10 mL of ethyl acetate, and washed with 10 mL solution of citric acid (1 M). The aqueous layer was extracted with ethyl acetate (2×10 mL) and the combined organics were washed with brine, dried over sodium sulfate, and concentrated to give 2-chloro-N-(1,3-dimethylpyrazol-4-yl)sulfonyl-6-[3-(3,3,3-trifluoro-2,2-dimethyl-propoxy) pyrazol-1-yl]pyridine-3-carboxamide as white solid (137 mg, 99%) that was used in the next step without further purification. ESI-MS m/z calc. 520.09076, found 521.1 (M+1)+; Retention time: 0.68 minutes.

Step G: N-(1,3-dimethylpyrazol-4-yl)sulfonyl-6-[3-
(3,3,3-trifluoro-2,2-dimethyl-propoxy)pyrazol-1-yl]-
2-[(4S)-2,2,4-trimethylpyrrolidin-1-yl]pyridine-3-
carboxamide (Compound 1)

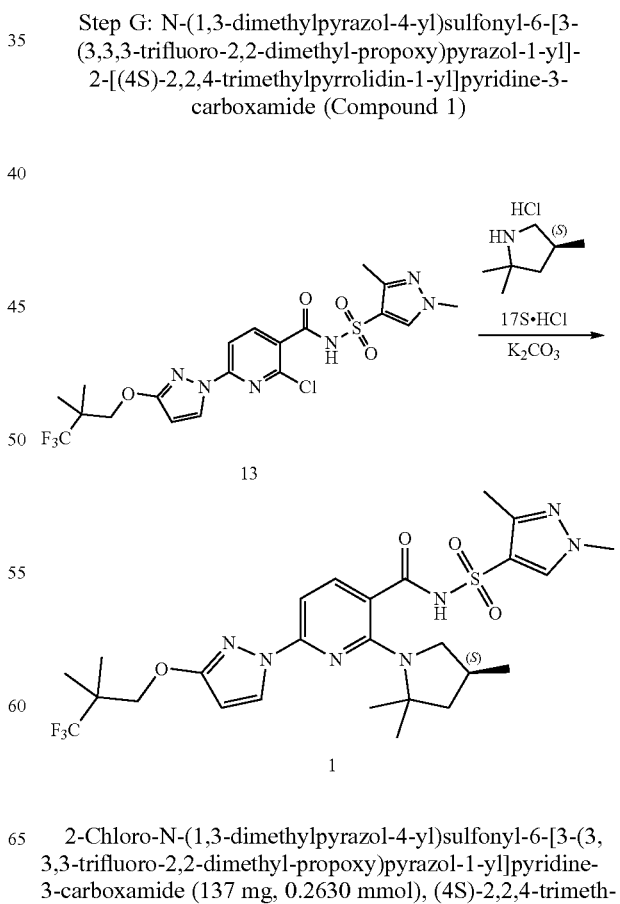

2-Chloro-N-(1,3-dimethylpyrazol-4-yl)sulfonyl-6-[3-(3,3,3-trifluoro-2,2-dimethyl-propoxy)pyrazol-1-yl]pyridine-3-carboxamide (137 mg, 0.2630 mmol), (4S)-2,2,4-trimethylpyrrolidine (Hydrochloride salt) (118 mg, 0.7884 mmol), and potassium carbonate (219 mg, 1.585 mmol) were combined in DMSO (685.0 μL) and the mixture was heated at 130° C. for 16 hours. The reaction was cooled to room temperature, and 1 mL of water was added. After stirring for 15 minutes, the contents of the vial were allowed to settle, and the liquid portion was removed via pipet and the remaining solids were dissolved with 20 mL of ethyl acetate and were washed with 1 M citric acid (15 mL). The layers were separated and the aqueous layer was extracted two additional times with 15 mL of ethyl acetate. The organics were combined, washed with brine, dried over sodium sulfate and concentrated. The resulting solid was further purified by silica gel chromatography eluting with a gradient of methanol in dichloromethane (0-10%) to give N-(1,3-dimethylpyrazol-4-yl)sulfonyl-6-[3-(3,3,3-trifluoro-2,2-dimethyl-propoxy)pyrazol-1-yl]-2-[(4S)-2,2,4-trimethylpyrrolidin-1-yl]pyridine-3-carboxamide (72 mg, 41%) as a white solid. ESI-MS m/z calc. 597.2345, found 598.3 (M+1)+; Retention time: 2.1 minutes. $^1$H NMR (400 MHz, DMSO) δ 12.36 (s, 1H), 8.37 (s, 1H), 8.22 (d, J=2.8 Hz, 1H), 7.74 (d, J=8.2 Hz, 1H), 6.93 (d, J=8.2 Hz, 1H), 6.17 (d, J=2.8 Hz, 1H), 4.23 (s, 2H), 3.81 (s, 3H), 2.56 (d, J=10.4 Hz, 1H), 2.41 (t, J=8.7 Hz, 1H), 2.32 (s, 3H), 2.18 (dd, J=12.4, 6.1 Hz, 1H), 1.87 (dd, J=11.7, 5.5 Hz, 1H), 1.55 (d, J=11.2 Hz, 6H), 1.42 (t, J=12.0 Hz, 1H), 1.23 (s, 6H), 0.81 (d, J=6.2 Hz, 3H).

Alternative Step F: 2-chloro-N-((1,3-dimethyl-1H-pyrazol-4-yl)sulfonyl)-6-(3-(3,3,3-trifluoro-2,2-dimethylpropoxy)-1H-pyrazol-1-yl)nicotinamide (13)

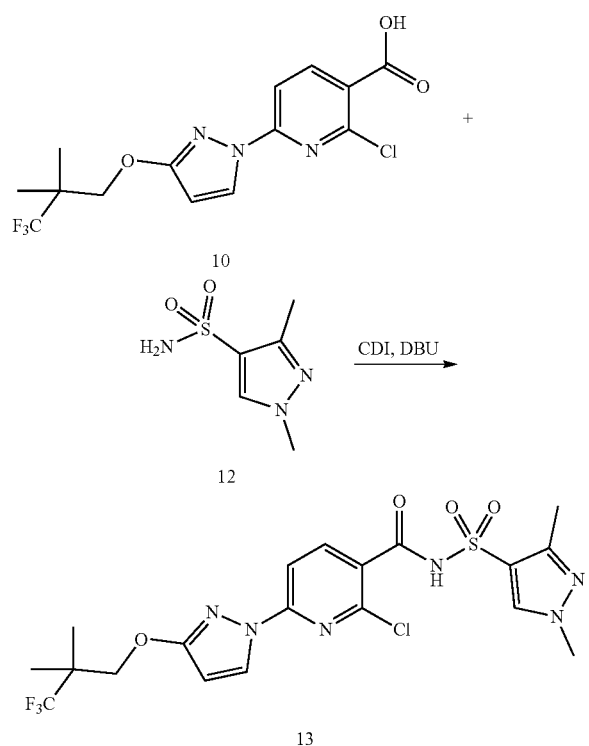

To a suspension of 2-chloro-6-[3-(3,3,3-trifluoro-2,2-dimethyl-propoxy)pyrazol-1-yl]pyridine-3-carboxylic acid (20.0 g, 53.89 mmol) in THF (78.40 mL) was added solid carbonyldiimidazole (approximately 10.49 g, 64.67 mmol) portion wise and the resulting solution was stirred at room temperature (slight exotherm from 18-21° C. was observed). After 1 h, solid 1,3-dimethylpyrazole-4-sulfonamide (approximately 11.33 g, 64.67 mmol) was added, followed by DBU (approximately 9.845 g, 9.671 mL, 64.67 mmol) in two equal portions over 1 min (exotherm from 19 to 35° C.). The reaction mixture was stirred at room temperature for 16 h. The reaction mixture was diluted with ethyl acetate (118 mL) and then HCl (approximately 107.8 mL of 2 M, 215.6 mmol). The phases were separated and the aqueous phase was extracted with ethyl acetate (78 mL). The combined organics were washed with water (39.2 mL), then brine (40 mL), dried over sodium sulfate and concentrated. The resulting foam was crystallized from a 1:1 isopropanol:heptane mixture (80 mL) to afford 2-chloro-N-((1,3-dimethyl-1H-pyrazol-4-yl)sulfonyl)-6-(3-(3,3,3-trifluoro-2,2-dimethyl-propoxy)-1H-pyrazol-1-yl)nicotinamide (26.1 g, 93%) as a white solid. ESI-MS m/z calc. 520.0, found 520.9 (M+1)+; Retention time: 1.83 minutes.

First Alternative Step G: N-(1,3-dimethylpyrazol-4-yl)sulfonyl-6-[3-(3,3,3-trifluoro-2,2-dimethyl-propoxy)pyrazol-1-yl]-2-[(4S)-2,2,4-trimethylpyrrolidin-1-yl]pyridine-3-carboxamide (Compound 1)

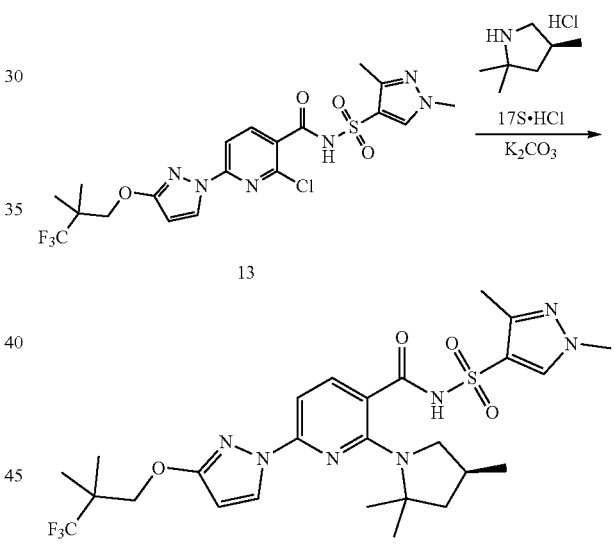

2-Chloro-N-(1,3-dimethylpyrazol-4-yl)sulfonyl-6-[3-(3,3,3-trifluoro-2,2-dimethyl-propoxy)pyrazol-1-yl]pyridine-3-carboxamide (20.0 g, 38.39 mmol), (4S)-2,2,4-trimethylpyrrolidine (Hydrochloride salt) (approximately 14.36 g, 95.98 mmol), and K$_2$CO$_3$ (approximately 26.54 g, 192.0 mmol) were combined in DMSO (80.00 mL) and 1,2-diethoxyethane (20.00 mL) in a 500-mL flask with reflux condenser. The reaction mixture was heated at 120° C. for 16 h then cooled to room temperature. The reaction was diluted with DCM (200.0 mL) and HCl (approximately 172.8 mL of 2 M, 345.5 mmol); aqueous pH~1. The phases were separated, and the aqueous phase was extracted with DCM (100.0 mL). The organic phases were combined, washed with water (100.0 mL) (3 x), and dried (Na2SO4) to afford an amber solution. The solution was filtered through a DCM-packed silica gel bed (80 g; 4 g/g) and washed with 20% EtOAc/DCM (5×200 mL). The combined filtrate/ washes were concentrated to afford 22.2 g of an off-white powder. The powder was slurried in MTBE (140 mL) for 30 min. The solid was collected by filtration (paper/sintered-glass) to afford 24 g after air-drying. The solid was transferred to a drying dish and vacuum-dried (40° C./200 torr/N2 bleed) overnight to afford 20.70 g (90%) of a white powder. ESI-MS m/z calc. 597.2345, found 598.0 (M+1)+; Retention time: 2.18 minutes. $^1$H NMR (400 MHz, Chloroform-d) δ 13.85 (s, 1H), 8.30 (d, J=8.6 Hz, 1H), 8.23 (d, J=2.8 Hz, 1H), 8.08 (s, 1H), 7.55 (d, J=8.5 Hz, 1H), 5.98 (d, J=2.8 Hz, 1H), 4.24 (s, 2H), 3.86 (s, 3H), 3.44 (dd, J=10.3, 8.4 Hz, 1H), 3.09 (dd, J=10.3, 7.8 Hz, 1H), 2.67-2.52 (m, 1H), 2.47 (s, 3H), 2.12 (dd, J=12.3, 7.8 Hz, 1H), 1.70 (dd, J=12.4, 9.6 Hz, 1H), 1.37 (s, 3H), 1.33 (s, 3H), 1.27 (s, 6H), 1.20 (d, 3H).

III. Alternate Synthesis of 3-(3,3,3-Trifluoro-2,2-dimethyl-propoxy)-1H-pyrazole (7)

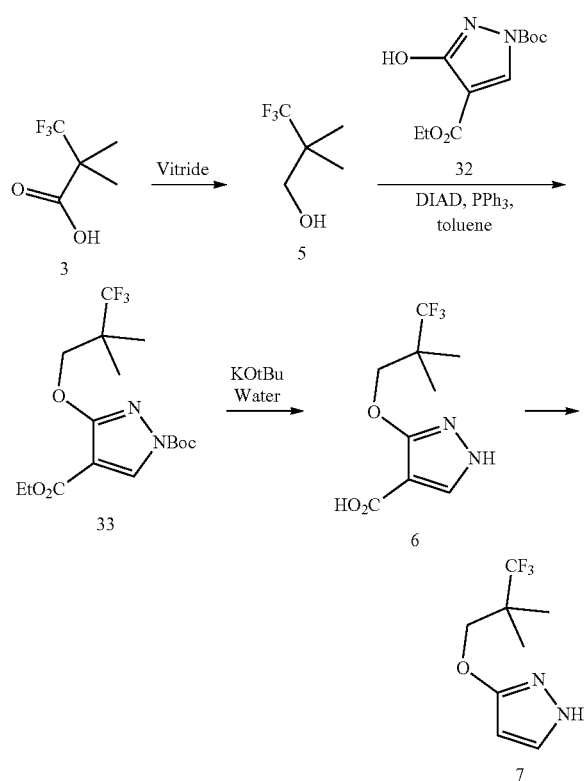

A. Preparation of 1-(tert-Butyl) 4-ethyl 3-hydroxy-1H-pyrazole-1,4-dicarboxylate (32)

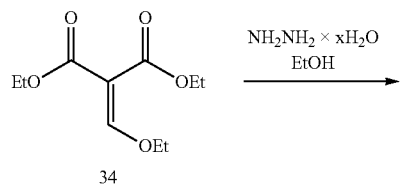

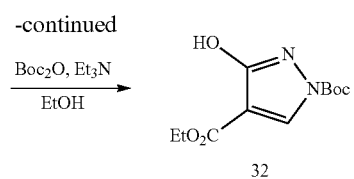

A reactor was charged with diethyl 2-(ethoxymethylene)malonate (4.32 g, 20 mmol, 1 equiv) and hydrazine (1.18 mL, 55% w/w, 1.04 equiv) was added, and the temperature rose from 16° C. to 23° C. The mixture was heated to reflux for 2 h, and an aliquot was removed and diluted with 1:1 MeCN/water and evaluated. Additional aliquots were removed at t=6 h and t=6.5 h. After approximately 8.5 h, a timer for heating was set to 12 h. After heating was complete, an additional aliquot was evaluated using HPLC. The reaction mixture crystallized on cooling, so the mixture was heated back to reflux for 6 h, with additional aliquots being removed to monitor reaction progress, and then allowed to cool to ambient temperature. The reaction mixture crystallized upon cooling, and the mixture was heated to 40° C. Et$_3$N (139 μL) was added, followed by addition of Boc$_2$O (4.37 g) in EtOH (4.4 mL) via addition funnel. The mixture became homogeneous. After 15 min (halfway through addition), crystallization started. The addition was complete after 30 min total of addition. After 50 min, an HPLC aliquot was sampled. After an additional 15 min, the reaction mixture was allowed to cool to ambient temperature. After 2 h 40 min, water (20 mL) was added. After an additional 1 hour, the solids were collected by filtration and washed with 2:1 EtOH/water (2×9 mL). The solid was dried in a vacuum oven at 50° C. with an N$_2$ bleed. After drying, 1-(tert-butyl) 4-ethyl 3-hydroxy-1H-pyrazole-1,4-dicarboxylate was obtained (3.04 g).

B. Preparation of 3-(3,3,3-Trifluoro-2,2-dimethyl-propoxy)-1H-pyrazole (7)

Step 1: 3,3,3-Trifluoro-2,2-dimethylpropan-1-ol (5)

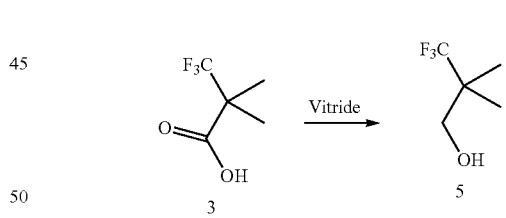

A reactor was charged with toluene (300 mL) and 3,3,3-trifluoro-2,2-dimethylpropanoic acid (30 g, 192.2 mmol) and was capped and purged under nitrogen. The reaction was set to control the internal temperature to 40° C. A solution of Vitride® (65% in toluene, approximately 119.6 g of 65% w/w, 115.4 mL of 65% w/w, 384.4 mmol) was set up for addition via syringe, and addition was begun at 40° C., with the target addition temp between 40 and 50° C. The reaction was stirred at 40° C. for 90 min. The reaction was cooled to 10° C. the remaining Vitride® was quenched with slow the addition of water (6 mL). A solution of 15% aq NaOH (30 mL) was added in portions, and solids precipitated half way through the base addition. Water (60.00 mL) was added. The mixture was warmed to 30° C. and held for at least 15 mins. The mixture was then cooled to 20° C. The aqueous layer was removed. The organic layer was washed with water (60 mL×3), and then washed with brine (60 mL). The washed organic layer was dried under $Na_2SO_4$, followed with $MgSO_4$. The mix was filtered through Celite, and the cake was washed with toluene (60.00 mL) and pulled dry. The product 3,3,3-trifluoro-2,2-dimethyl-propan-1-ol (22.5 g, 82%) was obtained as clear colorless solution.

Step 2: 1-(tert-Butyl) 4-ethyl 3-(3,3,3-trifluoro-2,2-dimethylpropoxy)-1H-pyrazole-1,4-dicarboxylate (33)

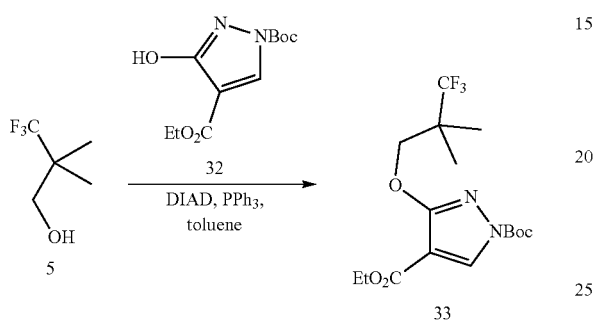

A reactor was charged with 1-(tert-butyl) 4-ethyl 3-hydroxy-1H-pyrazole-1,4-dicarboxylate (5.13 g, 20.02 mmol), 3,3,3-trifluoro-2,2-dimethylpropan-1-ol (2.85 g, 20.1 mmol), triphenylphosphine (5.25 g, 20.0 mmol), and toluene (30 mL). It was stirred at ambient temperature, and DIAD (4 mL, 20 mmol) was added via pipette. The slurry became homogeneous and the temperature of the reaction rose from 16 C to 36 C. The reaction was heated to 105 C for 85 minutes, and then was cooled to ambient temperature. The material crystallized upon cooling and was seeded with triphenylphosphine oxide. While stirring at ambient temperature, heptane (20 mL) was added. The mixture was filtered and the solid was washed twice with toluene/heptane (3:2 ratio, 10 mL). The filtrate was concentrated and further dried in a vacuum oven at 50° C. with an $N_2$ bleed to yield 1-(tert-butyl) 4-ethyl 3-(3,3,3-trifluoro-2,2-dimethylpropoxy)-1H-pyrazole-1,4-dicarboxylate as a gummy solid, which was used without further purification.

Step 3: 3-(3,3,3-trifluoro-2,2-dimethylpropoxy)-1H-pyrazole-4-carboxylic acid (6)

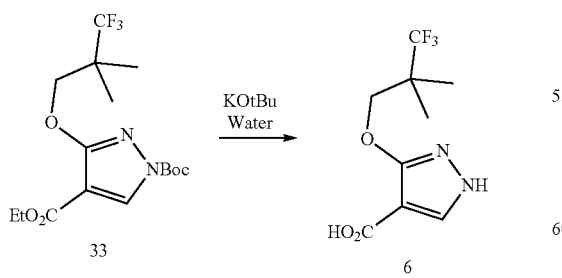

A solution of 1-(tert-butyl) 4-ethyl 3-(3,3,3-trifluoro-2,2-dimethylpropoxy)-1H-pyrazole-1,4-dicarboxylate from the previous step and 2-methyltetrahydrofuran (2-Me-THF, 62 mL) was prepared and KOt-Bu (12.35 g, 110.1 mmol) was added in one portion. The temperature of the reaction rose to 40 C and the mixture became a thick slurry. The temperature of the reaction was maintained at 40 C and water (500 μL, 27.75 mmol) was added, and then the temperature of the reaction rose to 47 C. After 3.5 hours the reaction was allowed to cool to ambient temperature and water (40 mL) was added, and the aqueous phase was extracted with 2-Me-THF (1×20 mL). The aqueous phase was acidified to pH=2-3 with concentrated HCl (8.4 mL, 12M, 100.8 mmol), and crystallization occurred. Isopropanol (5 mL 10% v/v in water) was added. The solid was collected by filtration and washed with isopropanol (3×15 mL 10% v/v in water). The solid was dried in a vacuum oven at 50° C. with an $N_2$ bleed to yield 3-(3,3,3-trifluoro-2,2-dimethylpropoxy)-1H-pyrazole-4-carboxylic acid (4.0 g, 79%) as a solid.

Step 4: 3-(3,3,3-trifluoro-2,2-dimethyl-propoxy)-1H-pyrazole (7)

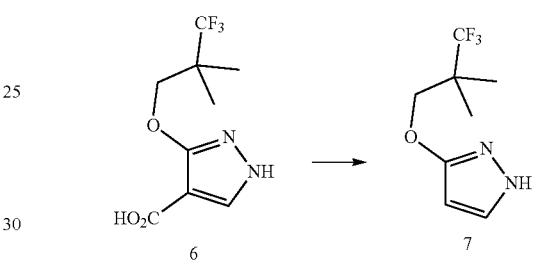

3-(3,3,3-trifluoro-2,2-dimethylpropoxy)-1H-pyrazole-4-carboxylic acid (50 mg, 1.0 equiv), DBU (6 μL, 0.2 equiv.), and dimethylacetamide (0.15 mL) were mixed and heated to 80 C for three hours, and then to 100° C. for two hours. At that time, the reaction as monitored by HPLC showed almost complete conversion to 3-(3,3,3-trifluoro-2,2-dimethylpropoxy)-1H-pyrazole.

IV. Alternate procedure for the preparation of 2-chloro-6-[3-(3,3,3-trifluoro-2,2-dimethyl-propoxy)pyrazol-1-yl]pyridine-3-carboxylic acid (10)

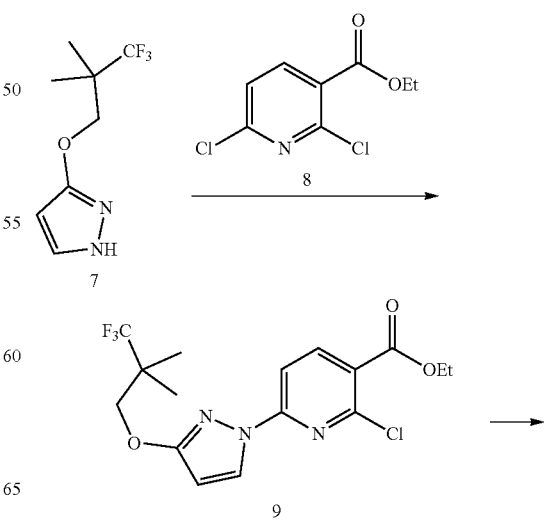

Step B: 2-chloro-6-(3-(3,3,3-trifluoro-2,2-dimethyl-propoxy)-1h-pyrazol-1-yl)nicotinic acid

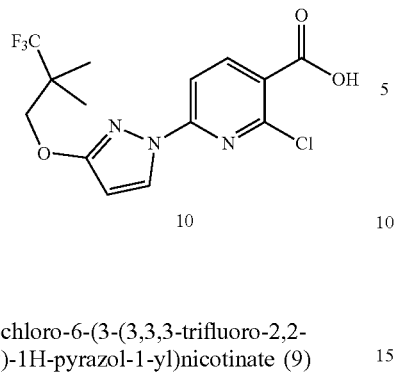

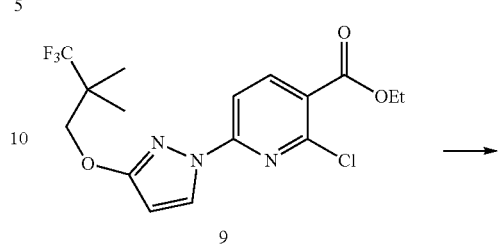

Step A: Ethyl 2-chloro-6-(3-(3,3,3-trifluoro-2,2-dimethylpropoxy)-1H-pyrazol-1-yl)nicotinate (9)

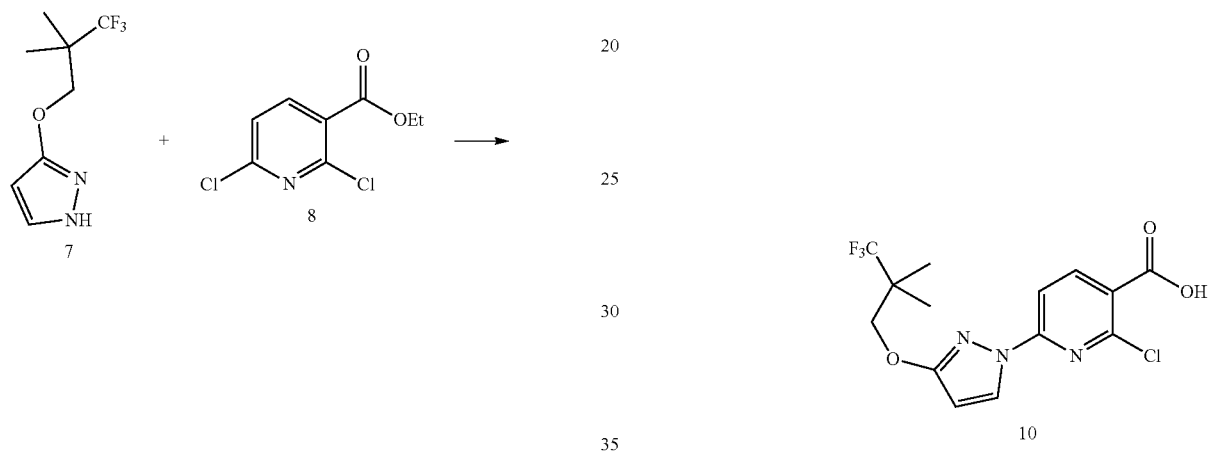

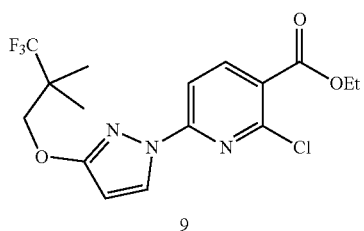

A solution of ethyl 2,6-dichloronicotinate (256 g, 1.16 mol) and 3-(3,3,3-trifluoro-2,2-dimethyl-propoxy)-1H-pyrazole (242 g, 1.16 mol) in DMF (1.53 L) was treated with potassium carbonate (209 g, 1.51 mol) and 1,4-diazabicyclo[2.2.2]octane (DABCO) (19.6 g, 174 mmol). The resultant suspension was stirred allowed to exotherm from 14 to 25° C. and then maintained at 20-25° C. with external cooling for 3 days. The suspension was cooled to below 10° C. when water (2.0 L) was added in a thin stream while maintaining the temperature below 25° C. After the addition was complete, the suspension was stirred for an additional 1 h. The solid was collected by filtration (sintered-glass/polypad) and the filter-cake was washed with water (2×500-mL) and dried with suction for 2 h to afford water-damp ethyl 2-chloro-6-(3-(3,3,3-trifluoro-2,2-dimethylpropoxy)-1H-pyrazol-1-yl)nicotinate (512 g; 113% yield) as white powder which was used without further steps in the subsequent reaction.

The water-damp ethyl 2-chloro-6-(3-(3,3,3-trifluoro-2,2-dimethylpropoxy)-1H-pyrazol-1-yl)nicotinate (455 g, 1.16 mol; assumed 100% yield from previous step) in EtOH (1.14 L) and THF (455 mL) was stirred at ambient temperature (17° C.) when 1 M NaOH (1.16 L, 1.16 mol) was added. The reaction mixture exothermed to 30° C. and was further warmed at 40° C. for 2 h. The solution was quenched with 1 M HCl (1.39 L, 1.39 mol) which resulted in an immediate precipitation which became thicker as the acid was added. The creamy suspension was allowed to cool to room temperature and was stirred overnight. The solid was collected by filtration (sintered-glass/poly pad). The filter-cake was washed with water (2×500-mL). The filter-cake was dried by suction for 1 h but remained wet. The damp solid was transferred to a 10-L Buchi flask for further drying (50° C./20 torr), but was not effective. Further effort to dry by chasing with i-PrOH was also ineffective. Successful drying was accomplished after the damp solid was backfilled with i-PrOAc (3 L), the suspension was heated at 60° C. (homogenization), and re-concentrated to dryness (50° C./20 torr) to afford dry 2-chloro-6-(3-(3,3,3-trifluoro-2,2-dimethyl-propoxy)-1h-pyrazol-1-yl)nicotinic acid (408 g; 97% yield for two steps) as a fine, white powder. The product was further dried in a vacuum oven (50° C./10 torr/N2 bleed) for 2 h but marginal weight loss was observed. 1H NMR (400 MHz, DMSO-d6) δ 13.64 (s, 1H), 8.49-8.36 (m, 2H), 7.77 (d, J=8.4 Hz, 1H), 6.26 (d, J=2.8 Hz, 1H), 4.28 (s, 2H), 1.24 (s, 6H). 19F NMR (376 MHz, DMSO-d6) δ −75.2. KF analysis: 0.04% water.

Example 13: Preparation of N-(Benzenesulfonyl)-6-[3-[2-[1-(trifluoromethyl)cyclopropyl]ethoxy]pyrazol-1-yl]-2-[(4S)-2,2,4-trimethylpyrrolidin-1-yl]pyridine-3-carboxamide (Compound 2)

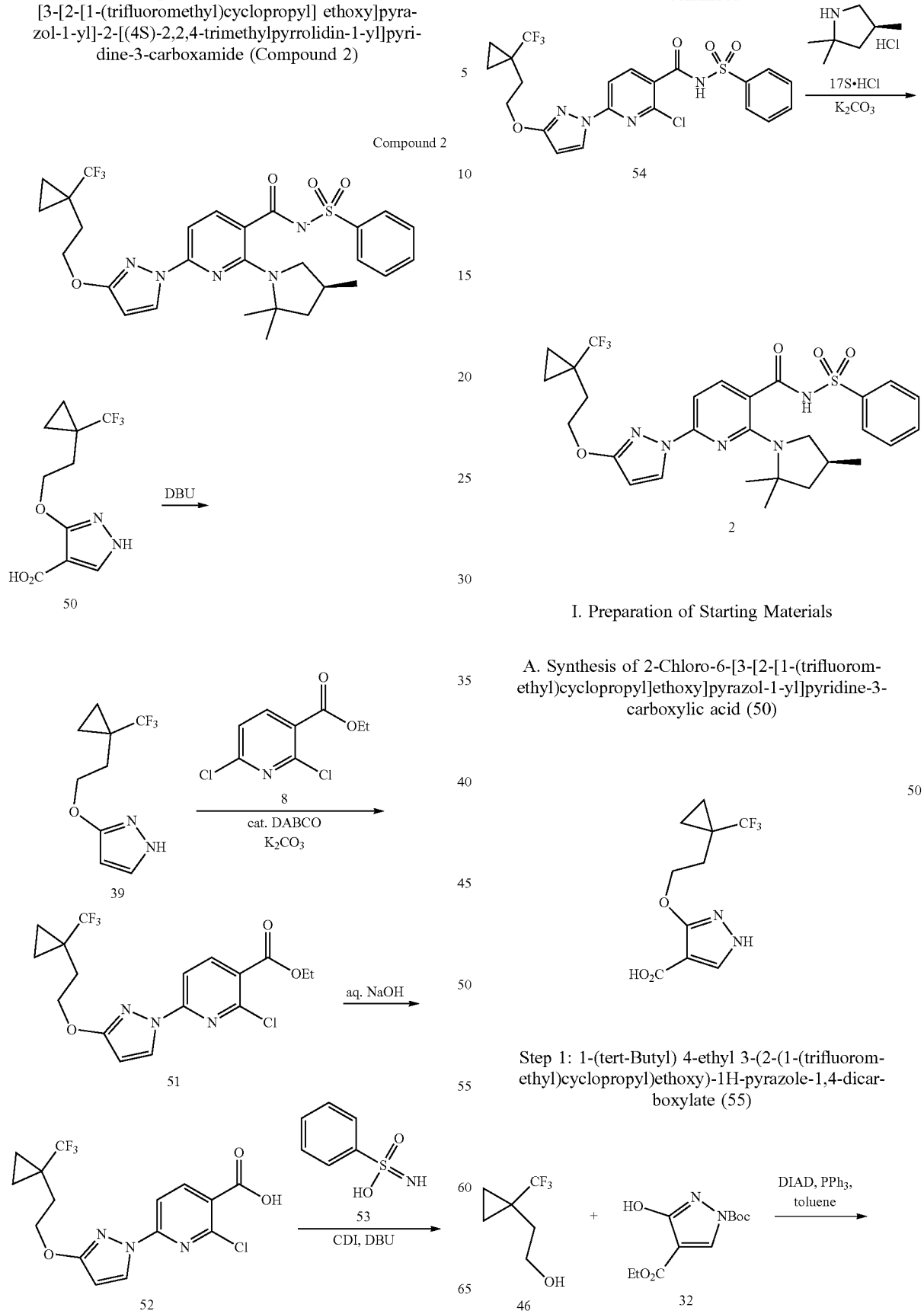

I. Preparation of Starting Materials

A. Synthesis of 2-Chloro-6-[3-[2-[1-(trifluoromethyl)cyclopropyl]ethoxy]pyrazol-1-yl]pyridine-3-carboxylic acid (50)

Step 1: 1-(tert-Butyl) 4-ethyl 3-(2-(1-(trifluoromethyl)cyclopropyl)ethoxy)-1H-pyrazole-1,4-dicarboxylate (55)

-continued

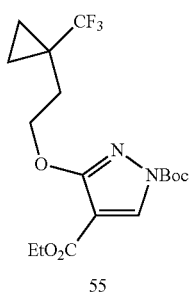

55

A 5 L reactor was started with the jacket set to 40° C., stirring at 450 rpm, reflux condenser at room temperature and nitrogen purge. The vessel was charged with toluene (1.0 L, 10.0 vol), 2-[1-(trifluoromethyl)cyclopropyl]ethanol (100.0 g, 648.8 mmol, 1.0 equiv), and 1-(tert-butyl) 4-ethyl 3-hydroxy-1H-pyrazole-1,4-dicarboxylate (166.3 g, 648.8 mmol), and the mixture was stirred. The reaction mixture was charged with triphenyl phosphine (195.7 g, 746.1 mmol, 1.15 equiv), then the reactor was set to maintain an internal temperature of 40° C. Diisopropyl azoldicarboxylate (150.9 g, 746.1 mmol, 1.15 equiv) was added into an addition funnel and was added to the reaction while maintaining the reaction temperature between 40 and 50° C. (addition was exothermic, exotherm addition controlled), and stirred for a total of 2.5 hours. Once the reaction was deemed complete by HPLC, heptane was added (400 mL, 4 vol), the solution was cooled to 20° C. over 60 minutes, and the bulk of triphenylphosphine oxide-DIAD complex (TPPO-DIAD) crystallized out. Once at room temp, the mixture was filtered, and the solid was washed with heptane (400 mL, 4.0 vol) and pulled dry. The filtrate was used in the next step as a solution in toluene-heptane without further purification.

Step 2: Ethyl 3-(2-(1-(trifluoromethyl)cyclopropyl)ethoxy)-1H-pyrazole-4-carboxylate (49)

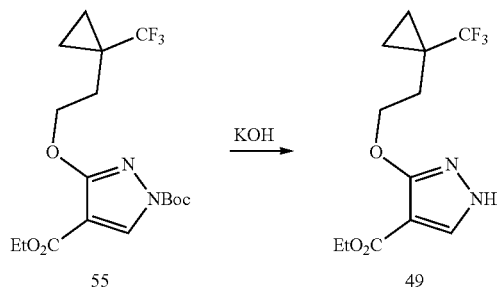 [SMILES: CCOC(=O)c1cn(C(=O)OC(C)(C)C)nc1OCCC1(C(F)(F)F)CC1 ; "KOH" ; CCOC(=O)c1c[nH]nc1OCCC1(C(F)(F)F)CC1]

A 500 mL reactor was started with the jacket set to 40° C., stirring at 450 rpm, reflux condenser at room temp, and nitrogen purge. The vessel was charged with a toluene solution consisting of approximately 160 mmol, 65.0 g of 1-(tert-butyl) 4-ethyl 3-(2-(1-(trifluoromethyl)cyclopropyl)ethoxy)-1H-pyrazole-1,4-dicarboxylate in 3 vol of toluene (prepared by concentrating a 25% portion of filtrate from previous reaction down to 4 volumes in a rotovap). The reaction was set to maintain an internal temperature at 40° C. and KOH (33.1 g, 1.5 eq. of aqueous 45% KOH solution) was added in one portion, resulting in a mild exothermic addition, while $CO_2$ was generated upon removal of the protecting group. The reaction proceeded for 1.5 hr, monitored by HPLC, with the product partially crystallizing during the reaction. Heptane (160 mL, 2.5 vol) was added to the reaction mixture and the reaction was cooled to room temperature over 30 minutes. The resulting mixture was filtered, and the solid was washed with heptane (80.00 mL, 1.25 vol), pulled dry, then dried in vacuo (55° C., vacuum). 52.3 g of ethyl 3-(2-(1-(trifluoromethyl)cyclopropyl)ethoxy)-1H-pyrazole-4-carboxylate was obtained as a crude, colorless solid that was used without further purification.

Step 3: 3-(2-(1-(trifluoromethyl)cyclopropyl)ethoxy)-1H-pyrazole-4-carboxylic acid (50)

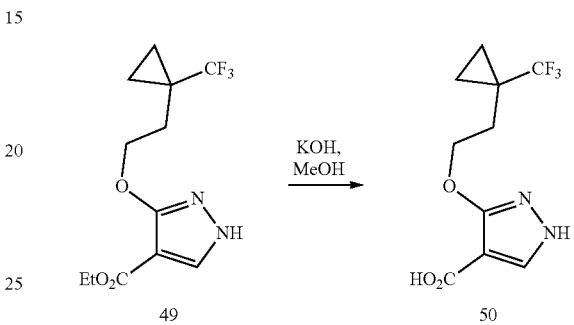

A 500 mL reactor was started with the jacket set to 40° C., stirring at 450 rpm, reflux condenser at room temp, and nitrogen purge. The vessel was charged with methanol (150.0 mL, 3.0 vol), a solution of ethyl 3-(2-(1-(trifluoromethyl)cyclopropyl)ethoxy)-1H-pyrazole-4-carboxylate (50.0 g, 171.1 mmol, 1.0 equiv), and the reaction was stirred to suspend the solids. The reactor was set to maintain internal temperature at 40° C. To the mixture was added KOH (96 g of aqueous 45% KOH, 1.71 mol, 10.0 equiv) in portions maintaining the internal temperature <50° C. Once addition was complete, the reaction was set to maintain temperature at 50° C., and the reaction proceeded for 23 hours, monitored by HPLC. Once complete the reaction was cooled to 10° C. then partially concentrated on a rotary evaporator to remove most of the MeOH. The resulting solution was diluted with water (250 mL, 5.0 vol) and 2-Me-THF (150 mL, 3.0 vol), and transferred to the reactor, stirred at room temp, then stopped, and layers were allowed to separate. The layers were tested, with remaining TPPO-DIAD complex in the organic layer and product in the aqueous layer. The aqueous layer was washed again with 2-Me-THF (100 mL, 2.0 vol), the layers separated, and the aqueous layer returned to the reactor vessel. The stirrer was started and set to 450 rpm, and the reactor jacket was set to 0° C. The pH was adjusted to pH acidic by addition of 6M aqueous HCl (427 mL, 15 equiv) portion wise, maintaining the internal temperature between 10 and 30° C. The product began to crystallize close to pH neutral and was accompanied with strong off-gassing, and so the acid was added slowly, and then further added to reach pH 1 once the off-gassing had ended. To the resulting suspension was added 2-Me-THF (400 mL, 8.0 vol), and the product was allowed to dissolve into the organic layer. Stirring was stopped, the layers were separated, and the aqueous layer was returned to the reactor, stirred and re-extracted with 2-Me-THF (100 mL, 2.0 vol). The organic layers were combined in the reactor and stirred at room temperature, washed with brine (100 mL, 2 vols), dried over $Na_2SO_4$, filtered through celite, and the solid was washed with 2-Me-THF (50 mL, 1.0 vol). The filtrate was transferred to a clean rotovap flask, stirred, warmed to 50° C. and heptane (200 mL, 4.0 vol) added, and then partially concentrated with the addition of heptane (300 mL, 6.0 vol) and then seeded with 50 mg of 3-(2-(1-(trifluoromethyl) cyclopropyl)ethoxy)-1H-pyrazole-4-carboxylic acid), and the product crystallized during solvent removal. The distillation was stopped when the bulk of the 2-Me-THF had distilled off. The bath heater was turned off, the vacuum removed, and the mixture was allowed to stir and cool to room temperature. The mixture was filtered (slow speed) and the solid was washed with heptane (100 mL, 2.0 vol), and the solid was collected and dried in vacuo (50° C., rotovap). 22.47 g of 3-(2-(1-(trifluoromethyl)cyclopropyl) ethoxy)-1H-pyrazole-4-carboxylic acid was obtained as an off-white solid. $^1$H NMR (400 MHz, DMSO-$d_6$) δ 12.45 (s, 2H), 8.01 (s, 1H), 4.26 (t, J=7.0 Hz, 2H), 2.05 (t, J=7.0 Hz, 2H), 0.92 (m, 4H).

B. Alternate synthesis of ethyl 3-(2-(1-(trifluoromethyl)cyclopropyl)ethoxy)-1H-pyrazole-4-carboxylate (49)

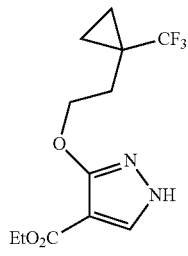

Step 1: Ethyl 3-hydroxy-1-(tetrahydro-2H-pyran-2-yl)-1H-pyrazole-4-carboxylate (45)

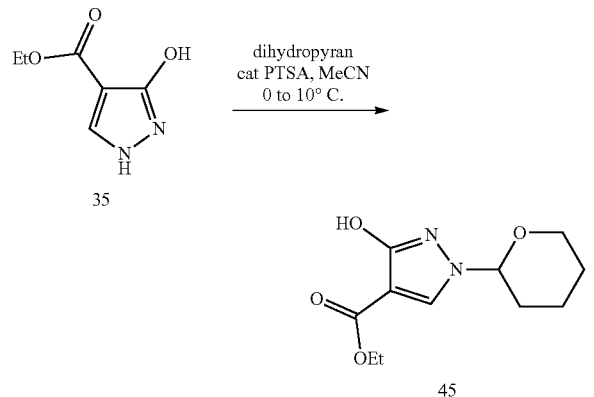

Ethyl 3-hydroxy-1H-pyrazole-4-carboxylate (45 g, 288.2 mmol, 1 equiv) was added to MeCN (270.0 mL, 6 vol) and the mixture was cooled to 0° C. (rxn mixture temp). 2,3-Dihydropyran (27 mL, 295.9 mmol, 1.03 eq) was added. After re-equilibrating the temperature for 5 min, p-TsOH hydrate (1.9 g, 9.989 mmol, 0.035 eq) was added as a solid in one portion. The temperature rose from −2.5 to 3° C. over ca 20 min before going back down. After 2 h the mixture was allowed to warm to 10° C. After 2 h, HPLC indicated complete conversion. The solid was collected by filtration and washed with MeCN (2×50 mL). Ethyl 3-hydroxy-1-(tetrahydro-2H-pyran-2-yl)-1H-pyrazole-4-carboxylate (45) was dried in a vacuum oven at 50° C. with a $N_2$ bleed to afford 60.28 g of ethyl 3-hydroxy-1-(tetrahydro-2H-pyran-2-yl)-1H-pyrazole-4-carboxylate (45) (87%) as an off-white solid.

Step 2: 2-(1-(trifluoromethyl)cyclopropyl)ethyl methanesulfonate (47)

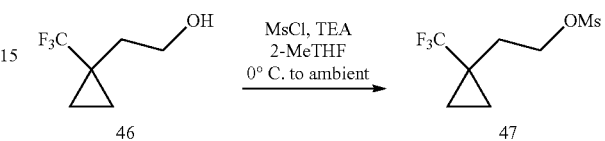

2-(1-(Trifluoromethyl)cyclopropyl)ethan-1-ol (46) (40 g, 259.5 mmol, 1 eq) in 2-MeTHF (160 mL, 4 vol). TEA (40 mL, 287.0 mmol, 1.1 eq) was added and the mixture cooled to 0° C. (rxn mixture temp). Mesyl chloride (MsCl) (21 mL, 271.3 mmol, 1.05 eq) in 2-MeTHF (90 mL, 2.25 vol) was added dropwise via addition funnel (−4° C.). The temperature was maintained at ≤3° C. After complete addition (temp reached 1° C. during addition), the temperature was maintained at 0° C. for 1 h. The chiller was turned off and the mixture was allowed to warm to ambient. After additional 2 h, 90 mL of water was added. The organic layer was washed with 90 mL of 20% aq w/v $KHCO_3$. The organic layer was dried ($Na_2SO_4$), filtered, and concentrated. The crude product was further dried in vacuum oven at 50 C with a $N_2$ bleed to afford 58.2 g of 2-(1-(trifluoromethyl)cyclopropyl)ethyl methanesulfonate (47) as an off-white/yellow oil.

Step 3: Ethyl 1-(tetrahydro-2H-pyran-2-yl)-3-(2-(1-(trifluoromethyl)cyclopropyl)ethoxy)-1H-pyrazole-4-carboxylate (48)

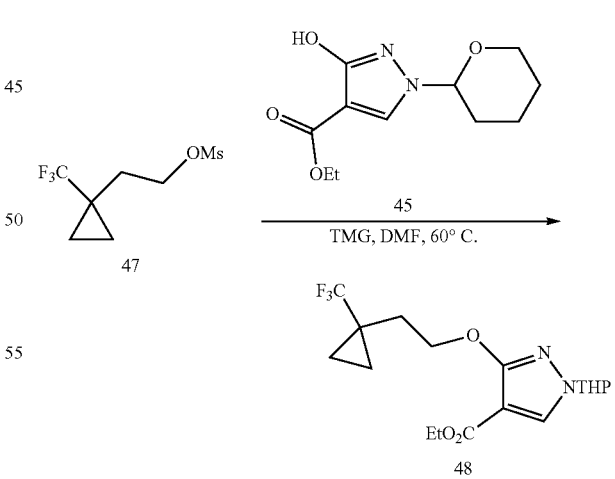

2-(1-(Trifluoromethyl)cyclopropyl)ethyl methanesulfonate (47) (50 g, 215.3 mmol, 1.04 eq) and ethyl 3-hydroxy-1-(tetrahydro-2H-pyran-2-yl)-1H-pyrazole-4-carboxylate (45) (50 g, 208.1 mmol, 1 eq) in DMF (250.0 mL, 5 vol) were added to a vessel. 1,1,3,3-Tetramethylguanidine (29 mL, 231.1 mmol, 1.1 eq) was added and the mixture was heated to 60° C. (rxn mixture temp). After heating for 12 h, HPLC showed complete reaction. 500 mL of water was added followed by 375 mL of isopropyl acetate (IPAc). The organic layer washed with 125 ml of water. The organic layer was filtered, concentrated, and dried further in a vacuum oven at 50° C. with a N₂ bleed to afford 82.8 g ethyl 1-(tetrahydro-2H-pyran-2-yl)-3-(2-(1-(trifluoromethyl)cyclopropyl)ethoxy)-1H-pyrazole-4-carboxylate (48) (containing residual solvents) as a yellow oil.

Step 4: Ethyl 3-(2-(1-(trifluoromethyl)cyclopropyl)ethoxy)-1H-pyrazole-4-carboxylate (49)

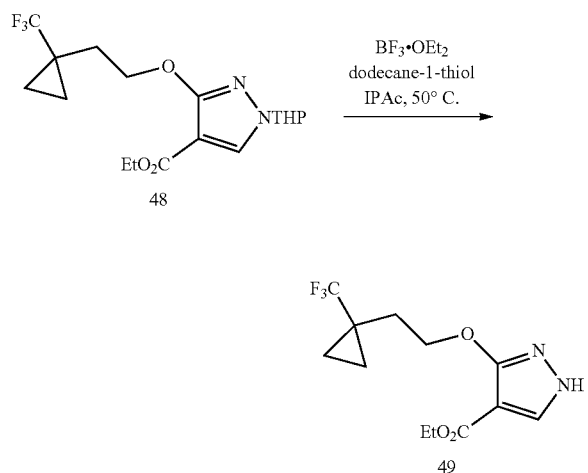

Ethyl 1-(tetrahydro-2H-pyran-2-yl)-3-(2-(1-(trifluoromethyl)cyclopropyl)ethoxy)-1H-pyrazole-4-carboxylate (48) (60 g, 159.4 mmol, 1 eq) was mixed with 600 mL of IPAc (10 vol). Dodecane-1-thiol (96 mL, 401 mmol, 2.5 eq) was added and the mixture was heated to 50° C. BF₃·OEt₂ (50 mL, 405 mmol, 2.5 eq) was added dropwise via addition funnel over 40 min. After 1.5 h HPLC indicated complete reaction. After cooling the mixture to ambient, 180 mL of 10% aq w/v NaOH was added via addition funnel. There was a temperature rise from 24 to 30° C. during addition. The aqueous layer was weakly basic (pH 7-8 to pH paper). The organic layer was dried (Na₂SO₄), filtered, and concentrated. 600 mL of heptane was added and the mixture was concentrated. Crystallization occurred during concentration with heptane. 300 mL of heptane was added and the slurry stirred at ambient for several hours. The solid was collected by filtration and washed with heptane (2×60 mL). Ethyl 3-(2-(1-(trifluoromethyl)cyclopropyl)ethoxy)-1H-pyrazole-4-carboxylate (49) was dried in a vacuum oven at 50 C with N₂ bleed.

II. Synthesis of N-(Benzenesulfonyl)-6-[3-[2-[1-(trifluoromethyl)cyclopropyl]ethoxy]pyrazol-1-yl]-2-[(4S)-2,2,4-trimethylpyrrolidin-1-yl]pyridine-3-carboxamide (Compound 2)

Step 1: 3-(2-(1-(Trifluoromethyl)cyclopropyl)ethoxy)-1H-pyrazole (39)

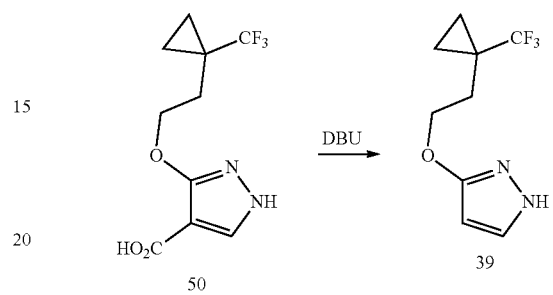

A mixture of toluene (490.0 mL), 3-(2-(1-(trifluoromethyl)cyclopropyl)ethoxy)-1H-pyrazole-4-carboxylic acid (70.0 g, 264.9 mmol), and DMSO (70.00 mL) was placed in a reactor and heated to 100° C. with stirring. DBU (approximately 20.16 g, 19.80 mL, 132.4 mmol) was added to the reactor over 15 min. The mixture was stirred for 20 h to complete the reaction and then cooled to 20° C. The mixture was washed with water (350.0 mL), then 0.5N aq HCl (280.0 mL), then water (2×140.0 mL), and lastly with brine (210.0 mL). The organic layer was dried with Na₂SO₄, and then activated charcoal (5 g, Darco 100 mesh) was added to the stirred slurry. The dried mixture was filtered through celite, and the solid was washed with toluene (140.0 mL) and then pulled dry. The filtrate was concentrated in a rotovap (50° C., vac) to afford 3-[2-[1-(trifluoromethyl)cyclopropyl]ethoxy]-1H-pyrazole (30.89 g, 53%) as an amber oil. ¹H NMR (400 MHz, DMSO-d₆) δ 11.87 (s, 1H), 7.50 (d, J=2.4 Hz, 1H), 5.63 (d, J=2.4 Hz, 1H), 4.23-4.06 (m, 2H), 2.01 (t, J=7.1 Hz, 2H), 1.00-0.77 (m, 4H).

Step 2: Ethyl 2-chloro-6-[3-[2-[1-(trifluoromethyl)cyclopropyl]ethoxy]pyrazol-1-yl]pyridine-3-carboxylate (51)

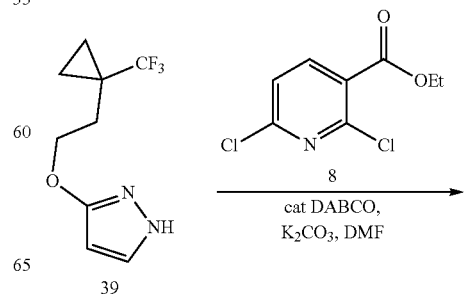

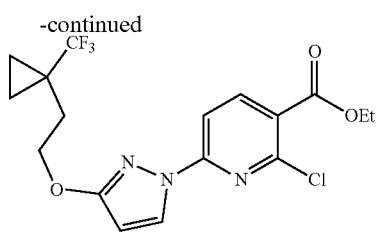

51

A mixture of DMF (180.0 mL), ethyl 2,6-dichloropyridine-3-carboxylate (approximately 29.97 g, 136.2 mmol), 3-[2-[1-(trifluoromethyl)cyclopropyl]ethoxy]-1H-pyrazole (30.0 g, 136.2 mmol), and K$_2$CO$_3$, (325 mesh, approximately 24.48 g, 177.1 mmol) was added to a stirred reactor at 20° C. DABCO (approximately 2.292 g, 20.43 mmol) was then added to the reactor, and the mixture was stirred at 20° C. for 1 hour, and then the temperature was increased to 30° C., and the mixture stirred for 24 hours to complete the reaction. The mixture was cooled to 20° C.; then water (360 mL) was added slowly. The mixture was then drained from the reactor and the solid was isolated by filtration. The solid was then washed with water (2×150 mL), and then the solid was dried under vacuum at 55° C. to afford ethyl 2-chloro-6-[3-[2-[1-(trifluoromethyl)cyclopropyl]ethoxy]pyrazol-1-yl]pyridine-3-carboxylate (51.37 g, 93%) as a fine, beige colored solid. $^1$H NMR (400 MHz, DMSO-d$_6$) δ 8.44 (d, J=2.9 Hz, 1H), 8.41 (d, J=8.5 Hz, 1H), 7.75 (d, J=8.5 Hz, 1H), 6.21 (d, J=2.9 Hz, 1H), 4.34 (m, 4H), 2.09 (t, J=7.1 Hz, 2H), 1.34 (t, J=7.1 Hz, 3H), 1.00-0.84 (m, 4H).

Step 3: 2-Chloro-6-[3-[2-[1-(trifluoromethyl)cyclopropyl]ethoxy]pyrazol-1-yl]pyridine-3-carboxylic acid (52)

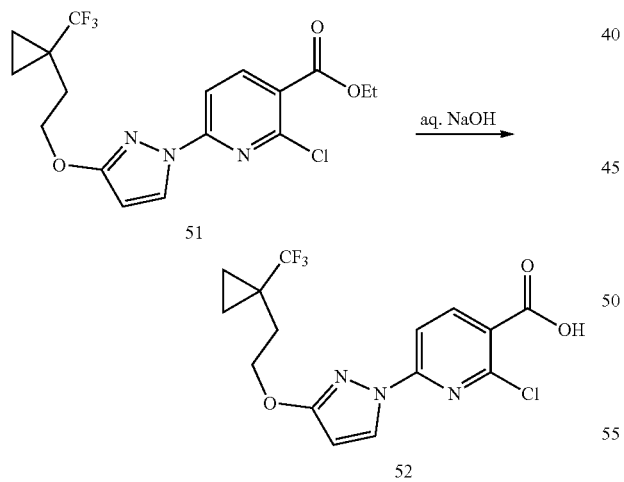

A solution of ethyl 2-chloro-6-[3-[2-[1-(trifluoromethyl)cyclopropyl]ethoxy]pyrazol-1-yl]pyridine-3-carboxylate (50.0 g, 123.8 mmol) in THF (300.0 mL) was prepared in a reactor at 20° C. EtOH (150.0 mL) was added, followed by aqueous NaOH (approximately 59.44 g of 10% w/w, 148.6 mmol). The mixture was stirred for 1 hour to complete the reaction; then aq 1N HCl (750.0 mL) was slowly added. The resulting suspension was stirred for 30 min at 10° C., and then the solid was isolated by filtration. The solid was washed with water (150 mL then 2×100 mL) and then pulled dry by vacuum. The solid was then further dried under vacuum with heating to afford 2-chloro-6-[3-[2-[1-(trifluoromethyl)cyclopropyl]ethoxy]pyrazol-1-yl]pyridine-3-carboxylic acid (42.29 g, 91%). $^1$H NMR (400 MHz, DMSO-d6) δ 13.63 (s, 1H), 8.48-8.35 (m, 2H), 7.73 (d, J=8.4 Hz, 1H), 6.20 (d, J=2.9 Hz, 1H), 4.35 (t, J=7.1 Hz, 2H), 2.09 (t, J=7.1 Hz, 2H), 1.01-0.82 (m, 4H).

Step 4: N-(Benzenesulfonyl)-2-chloro-6-[3-[2-[1-(trifluoromethyl)cyclopropyl] ethoxy]pyrazol-1-yl] pyridine-3-carboxamide (54)

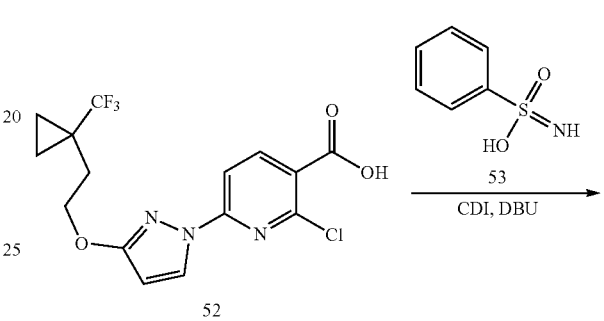

54

A solution of 2-chloro-6-[3-[2-[1-(trifluoromethyl)cyclopropyl]ethoxy]pyrazol-1-yl]pyridine-3-carboxylic acid (0.15 g, 0.3992 mmol) and carbonyl diimidazole (77 mg, 0.4790 mmol) in THF (2.0 mL) was stirred for one hour, and benzenesulfonamide (81 mg, 0.5190 mmol) and DBU (72 μL, 0.4790 mmol) were added. The reaction was stirred for 16 hours, acidified with 1 M aqueous citric acid, and extracted with ethyl acetate. The combined extracts were dried over sodium sulfate and evaporated. The residue was purified by silica gel chromatography eluting with a gradient of methanol in dichloromethane (0-5%) to give N-(benzenesulfonyl)-2-chloro-6-[3-[2-[1-(trifluoromethyl)cyclopropyl]ethoxy]pyrazol-1-yl]pyridine-3-carboxamide (160 mg, 78%). ESI-MS m/z calc. 514.07, found 515.1 (M+1)+; Retention time: 0.74 minutes.

Step 5: N-(Benzenesulfonyl)-6-[3-[2-[1-(trifluoromethyl)cyclopropyl]ethoxy]pyrazol-1-yl]-2-[(4S)-2,2,4-trimethylpyrrolidin-1-yl]pyridine-3-carboxamide (Compound 2)

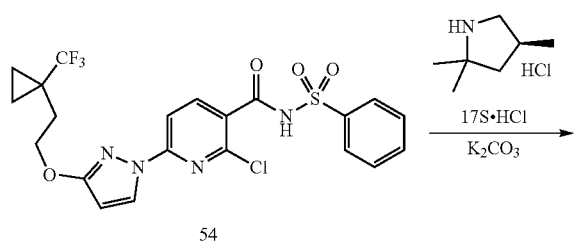

A mixture of N-(benzenesulfonyl)-2-chloro-6-[3-[2-[1-(trifluoromethyl)cyclopropyl] ethoxy]pyrazol-1-yl]pyridine-3-carboxamide (160 mg, 0.3107 mmol), (4S)-2,2,4-trimethylpyrrolidine hydrochloride salt (139 mg, 0.9321 mmol), and potassium carbonate (258 mg, 1.864 mmol) in DMSO (1.5 mL) was stirred at 130° C. for 17 hours. The reaction mixture was acidified with 1 M aqueous citric acid and extracted with ethyl acetate. The combined extracts were dried over sodium sulfate and evaporated to yield a crude product that was purified by reverse-phase HPLC utilizing a gradient of 10-99% acetonitrile in 5 mM aqueous HCl to yield N-(benzenesulfonyl)-6-[3-[2-[1-(trifluoromethyl)cyclopropyl]ethoxy]pyrazol-1-yl]-2-[(4S)-2,2,4-trimethylpyrrolidin-1-yl]pyridine-3-carboxamide (87 mg, 47%). ESI-MS m/z calc. 591.21, found 592.3 (M+1)+; Retention time: 2.21 minutes. $^1$H NMR (400 MHz, DMSO-d6) δ 12.48 (s, 1H), 8.19 (d, J=2.8 Hz, 1H), 8.04-7.96 (m, 2H), 7.81 (d, J=8.2 Hz, 1H), 7.77-7.70 (m, 1H), 7.70-7.62 (m, 2H), 6.92 (d, J=8.2 Hz, 1H), 6.10 (d, J=2.8 Hz, 1H), 4.31 (t, J=7.0 Hz, 2H), 2.42 (t, J=10.5 Hz, 1H), 2.28 (dd, J=10.2, 7.0 Hz, 1H), 2.17-2.01 (m, 3H), 1.82 (dd, J=11.9, 5.5 Hz, 1H), 1.52 (d, J=9.4 Hz, 6H), 1.36 (t, J=12.1 Hz, 1H), 1.01-0.92 (m, 2H), 0.92-0.85 (m, 2H), 0.65 (d, J=6.3 Hz, 3H). pKa: 4.95±0.06.

Alternative Step 5: N-(Benzenesulfonyl)-6-[3-[2-[1-(trifluoromethyl)cyclopropyl] ethoxy]pyrazol-1-yl]-2-[(4S)-2,2,4-trimethylpyrrolidin-1-yl]pyridine-3-carboxamide (Compound 2)

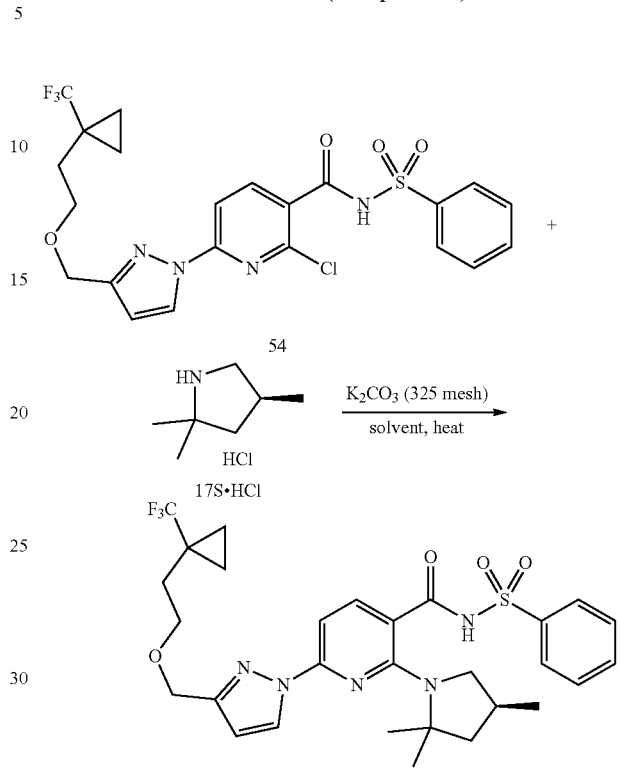

A mixture of Compound 54 (1 equiv), Compound 17S·HCl (2.2 equiv) and K$_2$CO$_3$ (325 mesh, 3.2 equiv) in NMP and the co-solvent (total solvent used: 5.5 mL/g; solvent mixtures all consist of 4.5:1 NMP:co-solvent) was heated to 120° C. with stirring. Starting material (Compound 54) remaining was measured by HPLC (shown in the table below).

| Scale (g Compound 54) | Solvent | Reaction time | Starting Material (Compound 54) Remaining (% area) |
|---|---|---|---|
| 15 g | NMP-DEE | 24 hour | 3.10 |
| 5 g | NMP | 70 hour | 4.34 |
| 10 g | NMP-n-BuOAc | 24 hour | 3.12 |

The NMP-DEE and NMP-n-BuOAc reactions yielded Compound 2 with no detectable byproducts determined by HPLC. The reaction carried out in NMP alone had a slight amount of byproduct and required a significantly longer reaction time.

Step 5: N-(Benzenesulfonyl)-6-[3-[2-[1-(trifluoromethyl)cyclopropyl]ethoxy]pyrazol-1-yl]-2-[(4S)-2,2,4-trimethylpyrrolidin-1-yl]pyridine-3-carboxamide (Compound 2), potassium salt 100 mg of N-(benzenesulfonyl)-6-[3-[2-[1-(trifluoromethyl)cyclopropyl]ethoxy]pyrazol-1-yl]-2-[(4S)-2,2,4-trimethylpyrrolidin-1-yl]pyridine-3-carboxamide was dissolved in 1 mL of acetonitrile. 10.0 mL of 0.1N KOH solution in water was stirred at room temperature, to which the Compound 2 acetonitrile solution was added slowly. Precipitate was observed during addition of acetonitrile solution, and solids formed on the stir bar. The mixture was stirred for several hours, during which time the clump broke up into smaller agglomerates. After stirring overnight (approximately 18 hours), solids were isolated by filtration, analyzed by XRPD, and determined to be crystalline Form B of a potassium salt of N-(benzenesulfonyl)-6-[3-[2-[1-(trifluoromethyl)cyclopropyl]ethoxy]pyrazol-1-yl]-2-[(4S)-2,2,4-trimethylpyrrolidin-1-yl]pyridine-3-carboxamide.

Example 14: Alternative Syntheses of Compound 1 and Compound 2

Compound 1 and Compound 2 can also be prepared as described below in using 6-bromo-2-fluoronicotinamide (Compound 37).

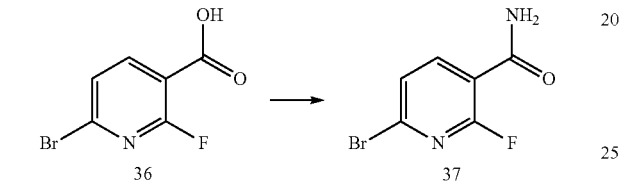

To a mixture of 6-bromo-2-fluoro-pyridine-3-carboxylic acid (40.55 g, 184.3 mmol) and 2-methyltetrahydrofuran (2-MeTHF) (326.6 mL) was added di-tertbutyl dicarbonate (Boc$_2$O) (approximately 52.29 g, 55.04 mL, 239.6 mmol) and N-methylmorpholine (approximately 18.66 g, 20.28 mL, 184.5 mmol) (resulted in gas evolution). The mixture was stirred at ambient temperature (20-25° C.) for approximately 24 h then water (162 mL) was added. The organic layer was isolated then washed with 5% aq w/v KHCO$_3$ (65 mL), then dried (Na$_2$SO$_4$), filtered, and concentrated. Isopropanol was added then removed under vacuum three times (320 mL then 2×160 mL) to afford a solid that was triturated with isopropanol (60 mL), isolated by filtration and washed with isopropanol (2×20 mL), and then dried to give 6-bromo-2-fluoronicotinamide (36.11 g, 89% yield). $^1$H NMR (400 MHz, DMSO-d$_6$) δ 8.12 (dd, J=9.4, 7.8 Hz, 1H), 7.95 (s, 1H), 7.88 (s, 1H), 7.74 (dd, J=7.8, 1.3 Hz, 1H); $^{19}$F NMR (376 MHz, DMSO-d$_6$) δ −65.33 (d, J=9.4 Hz).

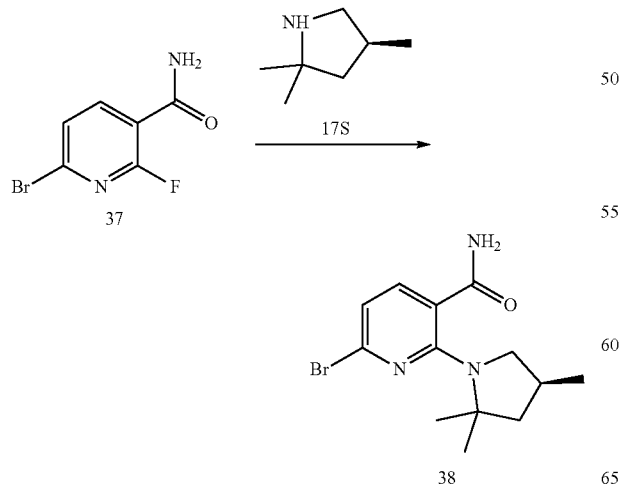

A mixture of 6-bromo-2-fluoronicotinamide (37), (S)-2,2,4-trimethylpyrrolidine (17S) or salt thereof, potassium carbonate and acetonitrile is heated until the reaction is complete. A work-up is performed to afford (S)-6-bromo-2-(2,2,4-trimethylpyrrolidin-1-yl)nicotinamide (38).

Alternative A: Synthesis of N-(1,3-dimethylpyrazol-4-yl)sulfonyl-6-[3-(3,3,3-trifluoro-2,2-dimethylpropoxy)pyrazol-1-yl]-2-[(4S)-2,2,4-trimethylpyrrolidin-1-yl]pyridine-3-carboxamide (Compound 1)

N-(1,3-dimethylpyrazol-4-yl)sulfonyl-6-[3-(3,3,3-trifluoro-2,2-dimethyl-propoxy)pyrazol-1-yl]-2-[(4S)-2,2,4-trimethylpyrrolidin-1-yl]pyridine-3-carboxamide (Compound 1) can also be prepared as shown in Scheme 7 or Scheme 8 using (S)-6-bromo-2-(2,2,4-trimethylpyrrolidin-1-yl)nicotinamide (38).

Scheme 7

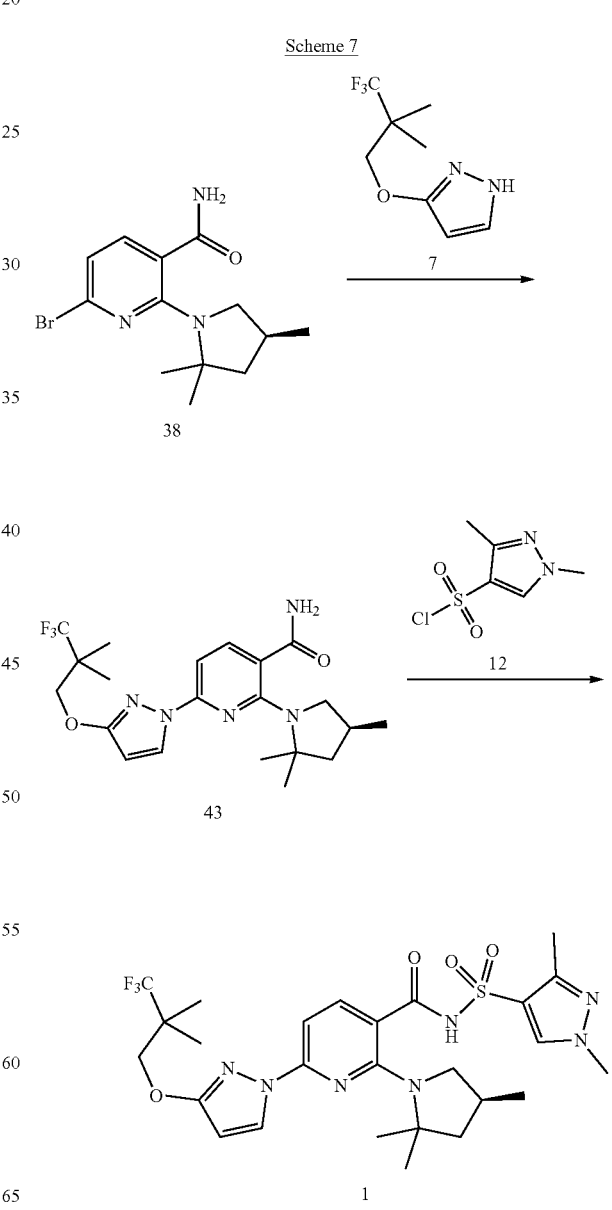

Step A: (S)-6-(3-(3,3,3-trifluoro-2,2-dimethyl-propoxy)-1H-pyrazol-1-yl)-2-(2,2,4-trimethylpyrrolidin-1-yl)nicotinamide (43)

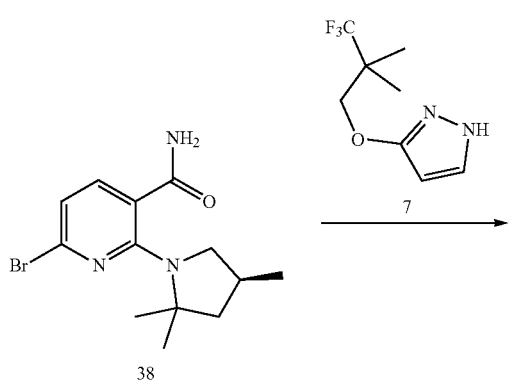

A mixture of (S)-6-bromo-2-(2,2,4-trimethylpyrrolidin-1-yl)nicotinamide (38), 3-(3,3,3-trifluoro-2,2-dimethyl-propoxy)-1H-pyrazole (7), copper (I) iodide, N,N'-dimethylcyclohexane-1,2-diamine and potassium carbonate is heated in DMF until the reaction is completed. A work-up is performed to afford (S)-6-(3-(3,3,3-trifluoro-2,2-dimethyl-propoxy)-1H-pyrazol-1-yl)-2-(2,2,4-trimethylpyrrolidin-1-yl)nicotinamide (43).

Alternative Step A: (S)-6-(3-(3,3,3-trifluoro-2,2-dimethylpropoxy)-1H-pyrazol-1-yl)-2-(2,2,4-trimethylpyrrolidin-1-yl)nicotinamide (43)

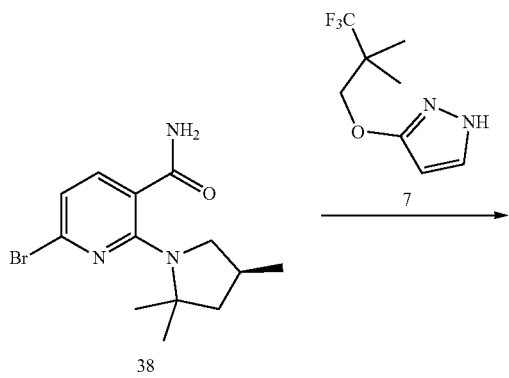

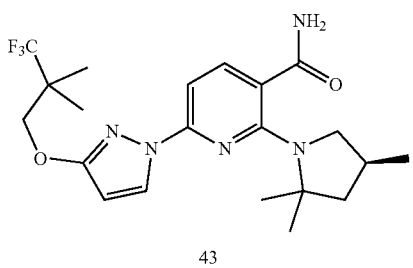

A mixture of (S)-6-bromo-2-(2,2,4-trimethylpyrrolidin-1-yl)nicotinamide (38), 3-(3,3,3-trifluoro-2,2-dimethyl-propoxy)-1H-pyrazole (7), and [(2-di-tert-butylphosphino-2',4',6'-triisopropyl-1,1'-biphenyl)-2-(2'-amino-1,1'-biphenyl)] palladium(II) methanesulfonate is stirred in methyl ethyl ketone at ambient temperature. 1-methyl-2,3,4,6,7,8-hexahydropyrimido[1,2-a]pyrimidine is added and the mixture heated to 80° C. until the reaction is completed. A work-up is performed to afford (S)-6-(3-(3,3,3-trifluoro-2,2-dimethylpropoxy)-1H-pyrazol-1-yl)-2-(2,2,4-trimethylpyrrolidin-1-yl)nicotinamide (43).

Step B: N-(1,3-dimethylpyrazol-4-yl)sulfonyl-6-[3-(3,3,3-trifluoro-2,2-dimethyl-propoxy)pyrazol-1-yl]-2-[(4S)-2,2,4-trimethylpyrrolidin-1-yl]pyridine-3-carboxamide (Compound 1)

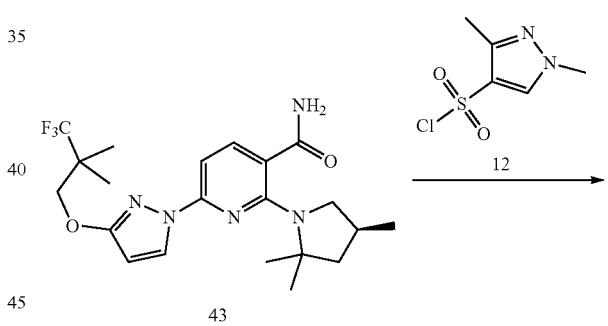

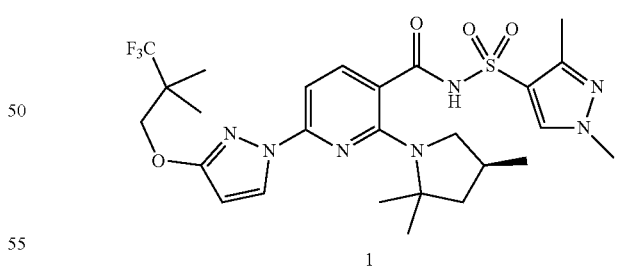

A mixture of (S)-6-(3-(3,3,3-trifluoro-2,2-dimethyl-propoxy)-1H-pyrazol-1-yl)-2-(2,2,4-trimethylpyrrolidin-1-yl)nicotinamide (43), lithium tert-amoxide and 2-methyl tetrahydrofuran is treated with 1,3-dimethyl-1H-pyrazole-4-sulfonyl chloride (12). The mixture is stirred until the reaction is complete then a work-up is performed to afford N-(1,3-dimethylpyrazol-4-yl)sulfonyl-6-[3-(3,3,3-trifluoro-2,2-dimethyl-propoxy)pyrazol-1-yl]-2-[(4S)-2,2,4-trimethylpyrrolidin-1-yl]pyridine-3-carboxamide (Compound 1).

Scheme 8

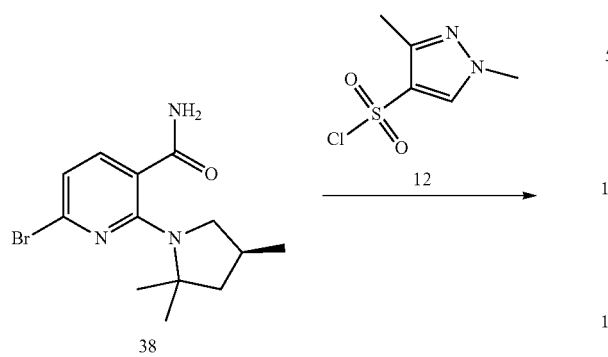

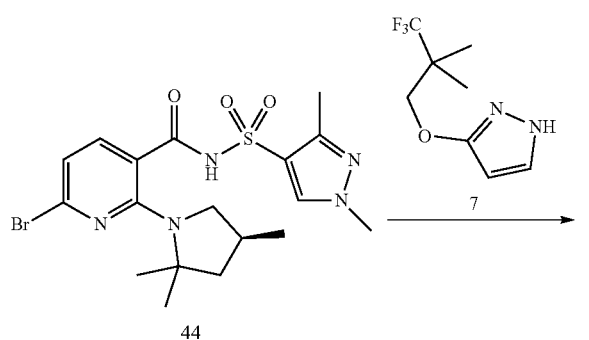

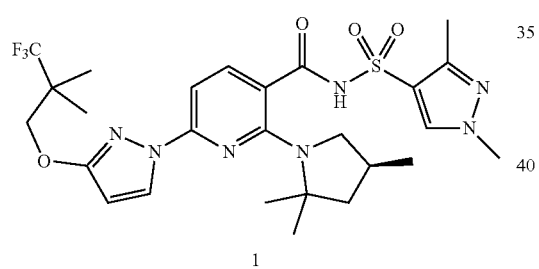

Step A: (S)-6-bromo-N-((1,3-dimethyl-1H-pyrazol-4-yl)sulfonyl)-2-(2,2,4-trimethylpyrrolidin-1-yl)nicotinamide (44)

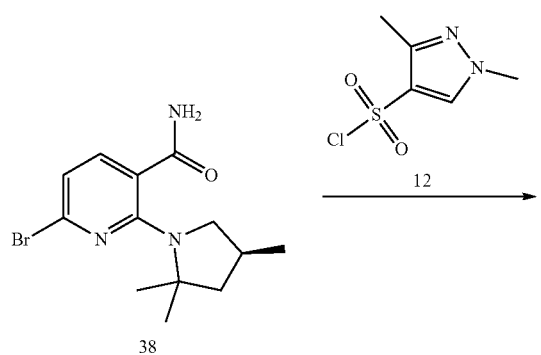

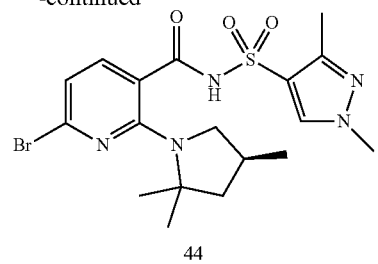

A mixture of (S)-6-bromo-2-(2,2,4-trimethylpyrrolidin-1-yl)nicotinamide (38), lithium tert-amoxide and 2-methyl tetrahydrofuran is treated with 1,3-dimethyl-1H-pyrazole-4-sulfonyl chloride. The mixture is stirred until the reaction is complete then a work-up is performed to afford (S)-6-bromo-N-((1,3-dimethyl-1H-pyrazol-4-yl)sulfonyl)-2-(2,2,4-trimethylpyrrolidin-1-yl)nicotinamide (44).

Step B: N-(1,3-dimethylpyrazol-4-yl)sulfonyl-6-[3-(3,3,3-trifluoro-2,2-dimethyl-propoxy)pyrazol-1-yl]-2-[(4S)-2,2,4-trimethylpyrrolidin-1-yl]pyridine-3-carboxamide (Compound 1)

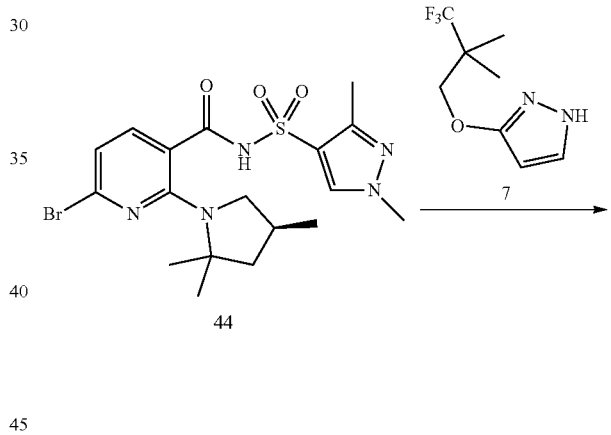

A mixture of (S)-6-bromo-N-((1,3-dimethyl-1H-pyrazol-4-yl)sulfonyl)-2-(2,2,4-trimethylpyrrolidin-1-yl)nicotinamide, 3-(3,3,3-trifluoro-2,2-dimethylpropoxy)-1H-pyrazole (44), copper (I) iodide, N,N'-dimethylcyclohexane-1,2-diamine and potassium carbonate is heated in DMF until the reaction is completed. A work-up is performed to afford N-(1,3-dimethylpyrazol-4-yl)sulfonyl-6-[3-(3,3,3-trifluoro-2,2-dimethyl-propoxy)pyrazol-1-yl]-2-[(4S)-2,2,4-trimethylpyrrolidin-1-yl]pyridine-3-carboxamide (Compound 1).

Alternative Step B: N-(1,3-dimethylpyrazol-4-yl)sulfonyl-6-[3-(3,3,3-trifluoro-2,2-dimethyl-propoxy)pyrazol-1-yl]-2-[(4S)-2,2,4-trimethylpyrrolidin-1-yl]pyridine-3-carboxamide (Compound 1)

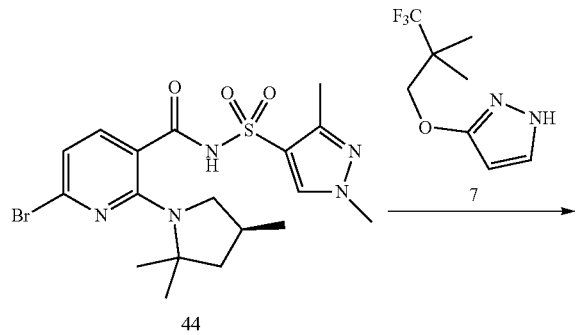

A mixture of (S)-6-bromo-N-((1,3-dimethyl-1H-pyrazol-4-yl)sulfonyl)-2-(2,2,4-trimethylpyrrolidin-1-yl)nicotinamide (44), 3-(3,3,3-trifluoro-2,2-dimethylpropoxy)-1H-pyrazole (7), and [(2-di-tert-butylphosphino-2',4',6'-triisopropyl-1,1'-biphenyl)-2-(2'-amino-1,1'-biphenyl)]palladium(II) methanesulfonate is stirred in methyl ethyl ketone at ambient temperature. 1-methyl-2,3,4,6,7,8-hexahydropyrimido[1,2-a]pyrimidine is added and the mixture heated to 80° C. until the reaction is completed. A work-up is performed to afford N-(1,3-dimethylpyrazol-4-yl)sulfonyl-6-[3-(3,3,3-trifluoro-2,2-dimethyl-propoxy)pyrazol-1-yl]-2-[(4S)-2,2,4-trimethylpyrrolidin-1-yl]pyridine-3-carboxamide (Compound 1).

Alternative B: Synthesis of N-(Benzenesulfonyl)-6-[3-[2-[1-(trifluoromethyl)cyclopropyl] ethoxy]pyrazol-1-yl]-2-[(4S)-2,2,4-trimethylpyrrolidin-1-yl]pyridine-3-carboxamide (Compound 2)

(S)—N-(phenylsulfonyl)-6-(3-(2-(1-(trifluoromethyl)cyclopropyl)ethoxy)-1H-pyrazol-1-yl)-2-(2,2,4-trimethylpyrrolidin-1-yl)nicotinamide can also be prepared as shown in Scheme 9 or Scheme 10 using (S)-6-bromo-2-(2,2,4-trimethylpyrrolidin-1-yl)nicotinamide.

Scheme 9

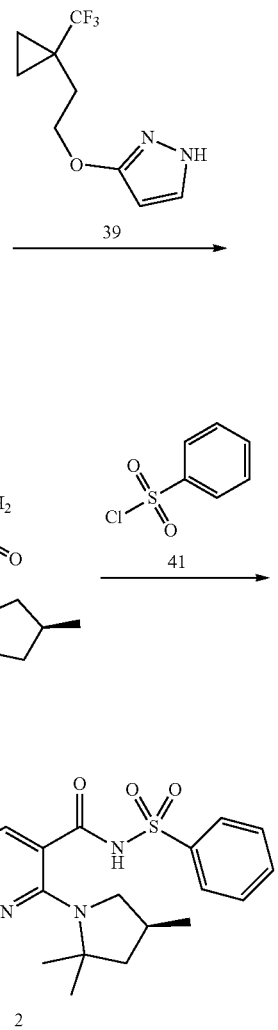

Step A: (S)-6-(3-(2-(1-(trifluoromethyl)cyclopropyl)ethoxy)-1H-pyrazol-1-yl)-2-(2,2,4-trimethylpyrrolidin-1-yl)nicotinamide

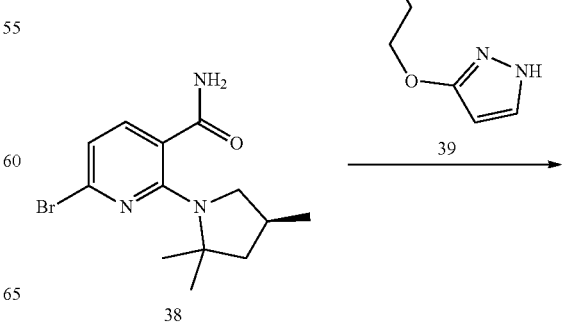

-continued

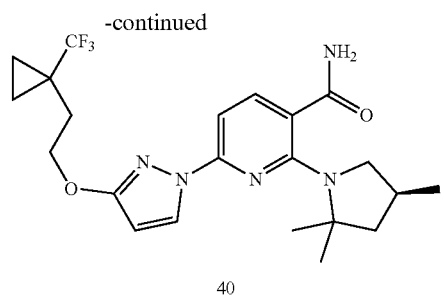

40

A mixture of (S)-6-bromo-2-(2,2,4-trimethylpyrrolidin-1-yl)nicotinamide, 3-(2-(1-(trifluoromethyl)cyclopropyl)ethoxy)-1H-pyrazole, copper (I) iodide, N,N'-dimethylcyclohexane-1,2-diamine and potassium carbonate is heated in DMF until the reaction is completed. A work-up is performed to afford (S)-6-(3-(2-(1-(trifluoromethyl)cyclopropyl)ethoxy)-1H-pyrazol-1-yl)-2-(2,2,4-trimethylpyrrolidin-1-yl)nicotinamide.

Alternative Step A: (S)-6-(3-(2-(1-(trifluoromethyl)cyclopropyl)ethoxy)-1H-pyrazol-1-yl)-2-(2,2,4-trimethylpyrrolidin-1-yl)nicotinamide

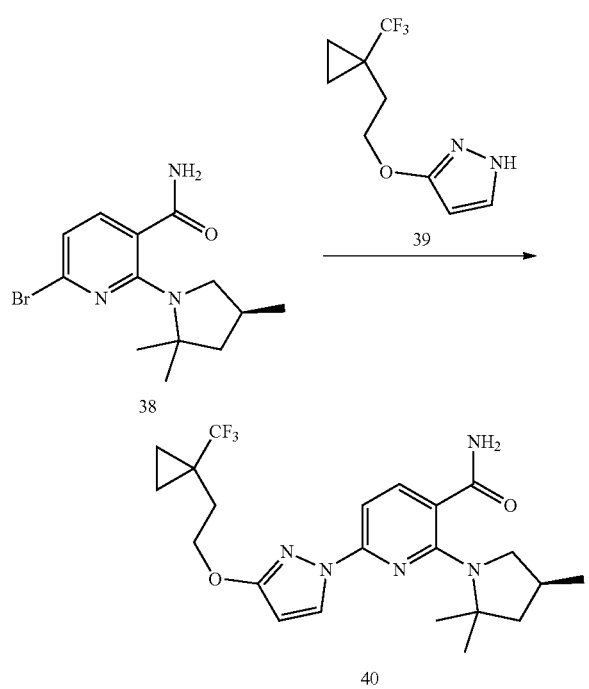

A mixture of (S)-6-bromo-2-(2,2,4-trimethylpyrrolidin-1-yl)nicotinamide, 3-(2-(1-(trifluoromethyl)cyclopropyl)ethoxy)-1H-pyrazole, and [(2-di-tert-butylphosphino-2',4',6'-triisopropyl-1,1'-biphenyl)-2-(2'-amino-1,1'-biphenyl)] palladium(II) methanesulfonate is stirred in methyl ethyl ketone at ambient temperature. 1-methyl-2,3,4,6,7,8-hexahydropyrimido[1,2-a]pyrimidine is added and the mixture heated to 80° C. until the reaction is completed. A work-up is performed to afford (S)-6-(3-(2-(1-(trifluoromethyl)cyclopropyl)ethoxy)-1H-pyrazol-1-yl)-2-(2,2,4-trimethylpyrrolidin-1-yl)nicotinamide.

Step B: N-(Benzenesulfonyl)-6-[3-[2-[1-(trifluoromethyl)cyclopropyl]ethoxy]pyrazol-1-yl]-2-[(4S)-2,2,4-trimethylpyrrolidin-1-yl]pyridine-3-carboxamide (Compound 2)

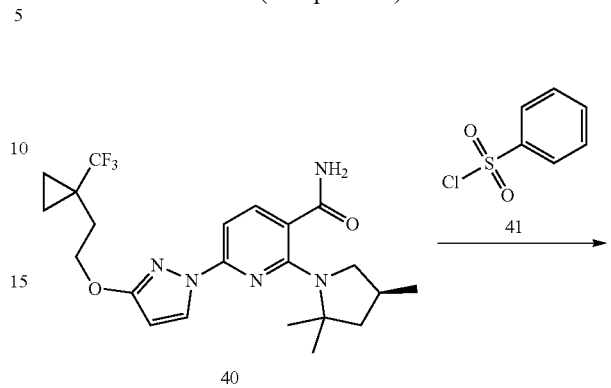

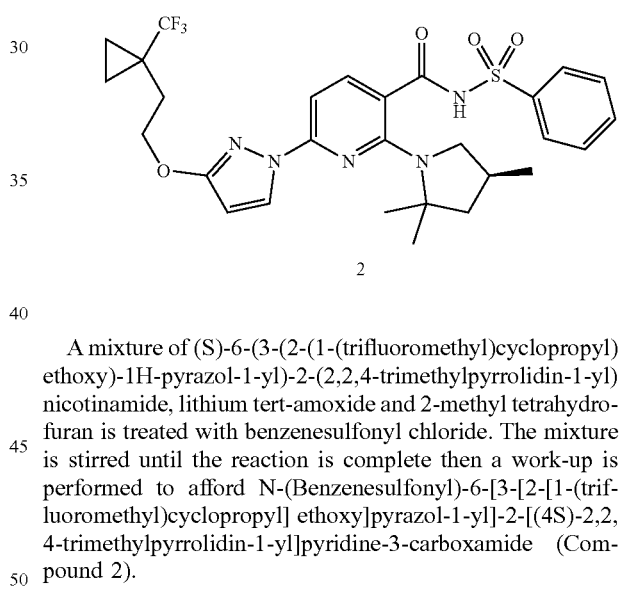

A mixture of (S)-6-(3-(2-(1-(trifluoromethyl)cyclopropyl)ethoxy)-1H-pyrazol-1-yl)-2-(2,2,4-trimethylpyrrolidin-1-yl)nicotinamide, lithium tert-amoxide and 2-methyl tetrahydrofuran is treated with benzenesulfonyl chloride. The mixture is stirred until the reaction is complete then a work-up is performed to afford N-(Benzenesulfonyl)-6-[3-[2-[1-(trifluoromethyl)cyclopropyl] ethoxy]pyrazol-1-yl]-2-[(4S)-2,2,4-trimethylpyrrolidin-1-yl]pyridine-3-carboxamide (Compound 2).

Scheme 10

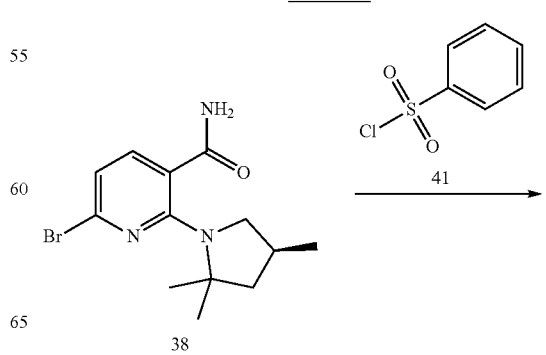

161
-continued

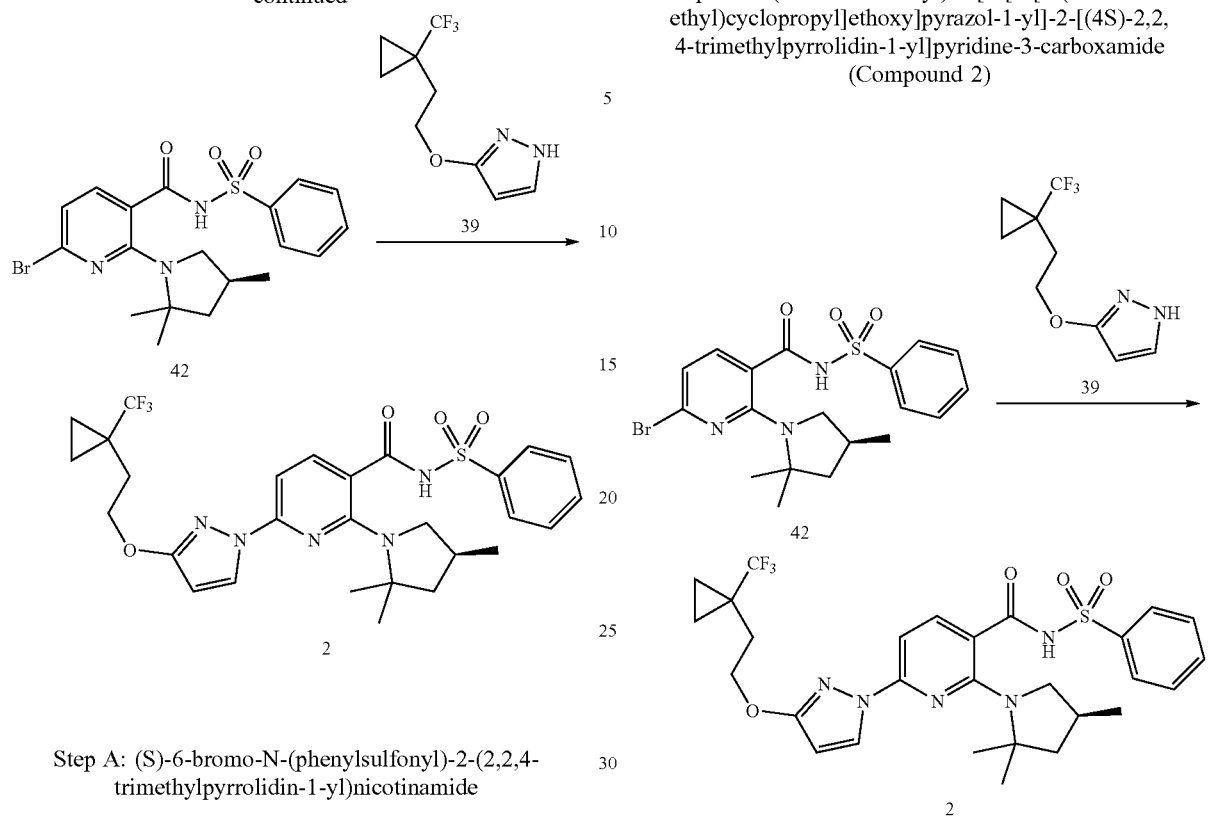

Step A: (S)-6-bromo-N-(phenylsulfonyl)-2-(2,2,4-trimethylpyrrolidin-1-yl)nicotinamide A mixture of (S)-6-bromo-2-(2,2,4-trimethylpyrrolidin-1-yl)nicotinamide, lithium tert-amoxide and 2-methyl tetrahydrofuran is treated with benzenesulfonyl chloride. The mixture is stirred until the reaction is complete then a work-up is performed to afford (S)-6-bromo-N-(phenylsulfonyl)-2-(2,2,4-trimethylpyrrolidin-1-yl)nicotinamide.

162

Step B: N-(Benzenesulfonyl)-6-[3-[2-[1-(trifluoromethyl)cyclopropyl]ethoxy]pyrazol-1-yl]-2-[(4S)-2,2,4-trimethylpyrrolidin-1-yl]pyridine-3-carboxamide (Compound 2)

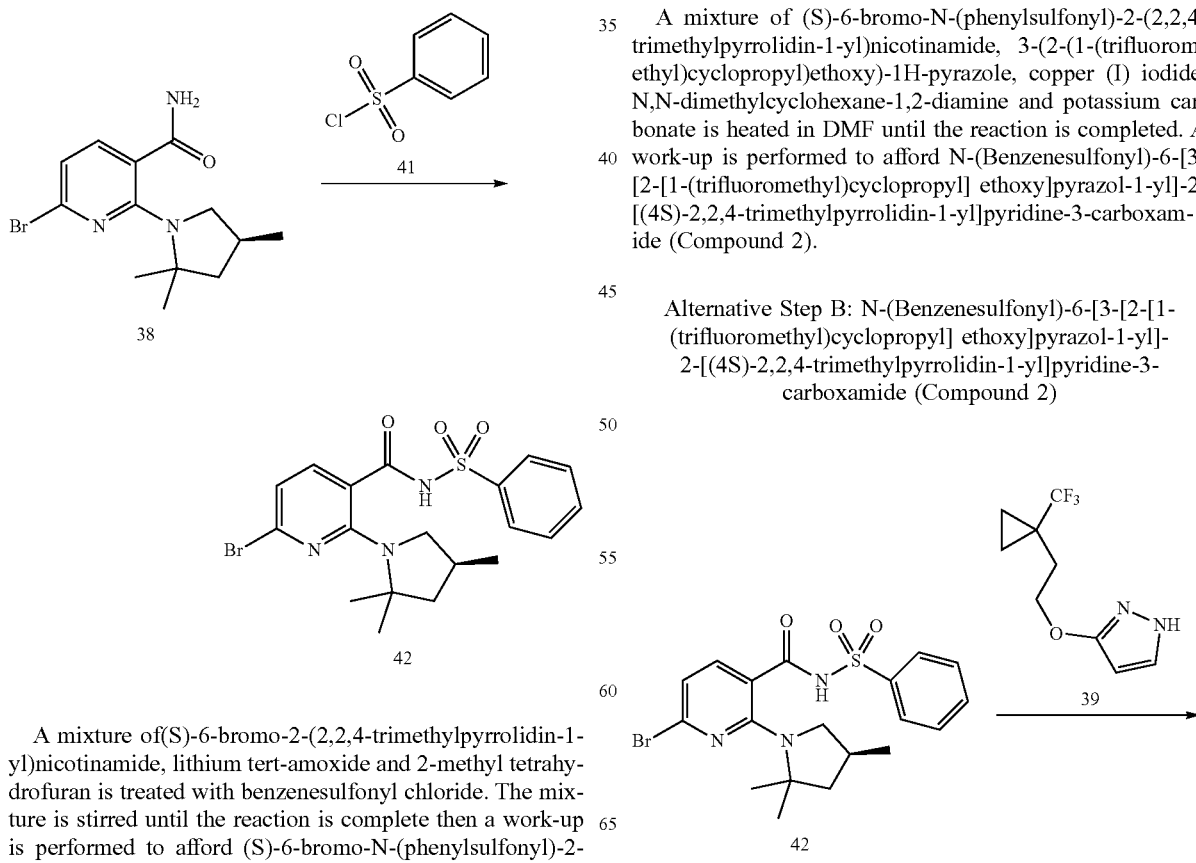

A mixture of (S)-6-bromo-N-(phenylsulfonyl)-2-(2,2,4-trimethylpyrrolidin-1-yl)nicotinamide, 3-(2-(1-(trifluoromethyl)cyclopropyl)ethoxy)-1H-pyrazole, copper (I) iodide, N,N-dimethylcyclohexane-1,2-diamine and potassium carbonate is heated in DMF until the reaction is completed. A work-up is performed to afford N-(Benzenesulfonyl)-6-[3-[2-[1-(trifluoromethyl)cyclopropyl] ethoxy]pyrazol-1-yl]-2-[(4S)-2,2,4-trimethylpyrrolidin-1-yl]pyridine-3-carboxamide (Compound 2).

Alternative Step B: N-(Benzenesulfonyl)-6-[3-[2-[1-(trifluoromethyl)cyclopropyl] ethoxy]pyrazol-1-yl]-2-[(4S)-2,2,4-trimethylpyrrolidin-1-yl]pyridine-3-carboxamide (Compound 2)

163 -continued

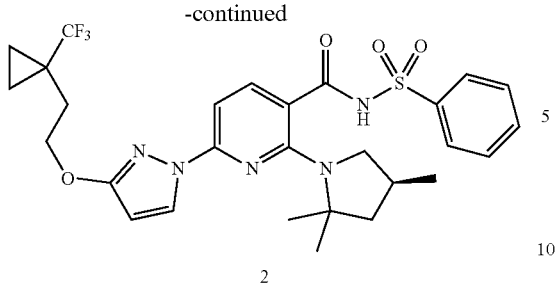

2

A mixture of (S)-6-bromo-N-(phenylsulfonyl)-2-(2,2,4-trimethylpyrrolidin-1-yl)nicotinamide, 3-(2-(1-(trifluoromethyl)cyclopropyl)ethoxy)-1H-pyrazole, and [(2-di-tert-butylphosphino-2',4',6'-triisopropyl-1,1'-biphenyl)-2-(2'-amino-1,1'-biphenyl)]palladium(II) methanesulfonate is stirred in methyl ethyl ketone at ambient temperature. 1-methyl-2,3,4,6,7,8-hexahydropyrimido[1,2-a]pyrimidine is added and the mixture heated to 80° C. until the reaction is completed. A work-up is performed to afford N-(benzenesulfonyl)-6-[3-[2-[1-(trifluoromethyl)cyclopropyl]ethoxy]pyrazol-1-yl]-2-[(4S)-2,2,4-trimethylpyrrolidin-1-yl]pyridine-3-carboxamide (Compound 2). All publications and patents referred to in this disclosure are incorporated herein by reference to the same extent as if each individual publication or patent application were specifically and individually indicated to be incorporated by reference. Should the meaning of the terms in any of the patents or publications incorporated by reference conflict with the meaning of the terms used in this disclosure, the meaning of the terms in this disclosure are intended to be controlling. Furthermore, the foregoing discussion discloses and describes merely exemplary embodiments of the present disclosure. One skilled in the art will readily recognize from such discussion and from the accompanying drawings and claims, that various changes, modifications, and variations can be made therein without departing from the spirit and scope of the disclosure as defined in the following claims.

The invention claimed is:

1. A compound of Formula viii:

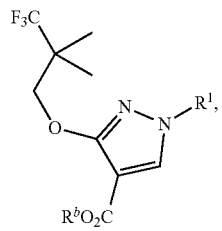

Compound 6

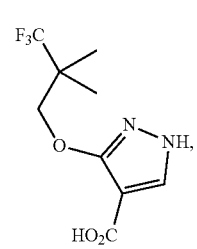

a salt or deuterated derivative thereof, wherein $R^1$ is a protecting group; and $R^b$ is $C_1$-$C_4$ alkyl.

2. The compound, salt, or deuterated derivative according to claim 1, wherein $R^1$ is t-butyl carbamate (Boc), benzyl (Bn), tetrahydropyranyl (THP), 9-fluorenylmethyl carbamate (Fmoc), benzyl carbamate (Cbz), acetamide, trifluoroacetamide, triphenylmethylamine, benzylideneamine, and p-toluenesulfonamide.

3. The compound, salt, or deuterated derivative according to claim 1, wherein $R^1$ is t-butyl carbamate (Boc), benzyl (Bn), and tetrahydropyranyl (THP).

4. The compound, salt, or deuterated derivative according to claim 1, wherein $R^1$ is t-butyl carbamate (Boc).

SEQUENCE LISTING

Sequence total quantity: 1
SEQ ID NO: 1    moltype = DNA   length = 22
FEATURE         Location/Qualifiers
source          1..22
                mol_type = genomic DNA
                organism = Homo sapiens
SEQUENCE: 1
agggagaatg atgatgaagt ac                                              22

5. The compound, salt, or deuterated derivative according to claim 1, wherein $R^b$ is ethyl.

* * * * *